US012735730B2

(12) United States Patent
Manchester et al.

(10) Patent No.: US 12,735,730 B2
(45) Date of Patent: Sep. 15, 2026

(54) **ENGINEERED STRAINS OF *Corynebacteria***

(71) Applicant: Archer Daniels Midland Company, Decatur, IL (US)

(72) Inventors: Shawn Manchester, Decatur, IL (US); Peter Enyeart, Decatur, IL (US)

( * ) Notice: Subject to any disclaimer, the term of this patent is extended or adjusted under 35 U.S.C. 154(b) by 1161 days.

(21) Appl. No.: 17/274,093

(22) PCT Filed: Sep. 6, 2019

(86) PCT No.: PCT/US2019/049893
§ 371 (c)(1),
(2) Date: Mar. 5, 2021

(87) PCT Pub. No.: WO2020/051420
PCT Pub. Date: Mar. 12, 2020

(65) Prior Publication Data

US 2024/0254526 A1 Aug. 1, 2024

Related U.S. Application Data

(60) Provisional application No. 62/728,384, filed on Sep. 7, 2018.

(51) Int. Cl.

| | |
|---|---|
| ***C12P 13/08*** | (2006.01) |
| ***C12N 1/205*** | (2026.01) |
| ***C12N 15/77*** | (2006.01) |
| ***C12R 1/15*** | (2006.01) |

(52) U.S. Cl.
CPC .............. *C12P 13/08* (2013.01); *C12N 1/205* (2021.05); *C12N 15/77* (2013.01); *C12N 2800/101* (2013.01); *C12R 2001/15* (2021.05)

(58) Field of Classification Search
CPC ......... C12P 13/08; C12N 1/205; C12N 15/77; C12N 2800/101; C12R 2001/15
See application file for complete search history.

(56) References Cited

U.S. PATENT DOCUMENTS

| | | | | |
|---|---|---|---|---|
| 6,221,636 | B1 | 4/2001 | Hayakawa et al. | |
| 2010/0273222 | A1* | 10/2010 | Moon | C12P 13/08 435/252.32 |
| 2017/0159045 | A1* | 6/2017 | Serber | G01N 35/00871 |

FOREIGN PATENT DOCUMENTS

| | | | |
|---|---|---|---|
| WO | 01/49854 | A2 | 7/2001 |
| WO | WO-2017100376 | A2 | 6/2017 |

OTHER PUBLICATIONS

Bott and Brocker, "Two-component signal transduction in Corynebacterium glutamicum and other corynebacteria: on the way towards stimuli and targets" Appl Microbiol Biotechnol 94:1131-1150 (Year: 2012).*

Baumgart et al., "Impact of LytR-CpsA-Psr Proteins on Cell Wall Biosynthesis in Corynebacterium glutamicum." Journal of Bacteriology. 198:22, 3045-3059. (Year: 2016).*

Radmacher and Eggeling, "The three tricarboxylate synthase activities of Corynebacterium glutamicum and increase of L-lysine synthesis." Appl Microbiol Biotechnol. 76:587-595. (Year: 2007).*

Becker et al. "From zero to hero—Design-based systems metabolic engineering of Corynebacterium glutamicum for L-lysine production." Metabolic Enginering, 13, 159-168. (Year: 2011).*

Rech et al., "Properties of the Periplasmic ModA Molybdate-binding Protein of *Escherichia coli.*" JBC, 271:5, 2557-2562. (Year: 1996).*

Bellorini et al., Evaluation Report on the Analytical Methods submitted in connection with the Application for Authorisation of a Feed Additive according to Regulation (EC) No. 1831/2003. Report FAD-2018-0, Project report, European Commission, Aug. 7, 2018, URL:https://ec.europa.eu//frc/en/eurl/feed-additivies/evaluation-reports/fad-2018-0012.

Ezerskis, "Evaluation Report on the Analytical Methods submitted in connection with the Application for Authorisation of a Feed Additive, L-lysine monohydrochloride and concentrated liquid L-lysine produced by Corynebacterium glutamicum NRRL-B-67535," Dec. 13, 2018, https://ec.europa.eu/jrc/sites/jrcsh/files/finrep_fad-2018-0037-lysine.pdf.

International Search Report for PCT/US2019/049893, mailed Oct. 29, 2019.

Written Opinion for PCT/US2019/049893, mailed Oct. 29, 2019.

* cited by examiner

*Primary Examiner* — Suzanne M Noakes
*Assistant Examiner* — Ciara A McKnight
(74) *Attorney, Agent, or Firm* — Banner & Witcoff, Ltd.

(57) ABSTRACT

This disclosure provides engineered strains of Corynebacteria for the cost-effective production of lysine, tools and methods used to produce the engineered strains, and methods of using the engineered strains to produce lysine.

4 Claims, 4 Drawing Sheets

Specification includes a Sequence Listing.

```
SEQ ID NO:3   1    MNDSRNRGRKVTRKAGPPEAGQENHLDTPVFQAPDASSNQSAVKAETAGNDNRDAAQGAQGSQDSQGSQNAQGSQNRESG  80
WP_011014791  1    MNDSRNRGRKVTRKAGPPEAGQENHLDTPVFQAPDASSNQSAVKAETAGNDNRDAAQGAQGSQDSQGSQnAQGSQNRESG  80
WP_096456687  1    MNDSRNRGRKVTRKAGPPEAGQENHVETPVFQAPDASSNQSTVKAETAGNDNRDSSQGSQ----AQGSQ-AKESGDAKSG  75
WP_023635875  1    MTEPRNRSRKVTRKAGPPET-----TEAPAFQAPDTSVEVSA-KDEA---EKKTSGEGSSN----QEAS-SKGNR----G  62

SEQ ID NO:3   81   NNNRNRSNNNRRGGRGRRGSGNANEGANNNSGNQNRQGGNRGNRGGGRRNVVKSMQGADLTQRLPEPPKAPANGLRIYAL  160
WP_011014791  81   NNNRNRSNNNRRGGRGRRGSGNANEGANNNSGNQNRQGGNRGNRGGGRRNVVKSMQGADLTQRLPEPPKAPANGLRIYAL  160
WP_096456687  76   NNNRNRSSNNRRGGRGRRGSGNANEGSNNNGGNR----GNRGNRGGGRRNVVKSMQGADLTQRLPEPPKAPSNGLRIYAL  151
WP_023635875  63   RSNSGRAGNGTRNGRSRRG-----------GNPQN----NKSNRG--RRNVVKSMQGADLTERLPEPPKAPKNGLRIYAL  125

SEQ ID NO:3   161  GGISEIGRNMTVFEYNNRLLIVDCGVLFPSSGEPGVDLILPDFGPIEDHLHRVDALVVTHGHEDHIGAIPWLLKLRNDIP  240
WP_011014791  161  GGISEIGRNMTVFEYNNRLLIVDCGVLFPSSGEPGVDLILPDFGPIEDHLHRVDALVVTHGHEDHIGAIPWLLKLRNDIP  240
WP_096456687  152  GGISEIGRNMTVFEYNNRLLIVDCGVLFPSSGEPGVDLILPDFGPIEDHLHRVDALVVTHGHEDHIGAIPWLLKLRHDIP  231
WP_023635875  126  GGISEIGRNMTVFEYNNKMLLVDCGVLFPSSGEPGVDLILPDFGPIEDKLDKVEALVVTHGHEDHIGAIPWLLKLRPDLP  205

SEQ ID NO:3   241  ILASRFTLALIAAKCKEHRQRPKLIEVNEQSNEDRGPFNIRFWAVNHSIPDCLGLAIKTPAGLVIHTGDIKLDQTPPDGR  320
WP_011014791  241  ILASRFTLALIAAKCKEHRQRPKLIEVNEQSNEDRGPFNIRFWAVNHSIPDCLGLAIKTPAGLVIHTGDIKLDQTPPDGR  320
WP_096456687  232  ILASRFTLALIAAKCKEHRQRPKLIEVNEKSSEDRGPFNIRFWAVNHSIPDCLGLAIKTPAGLVIHTGDIKLDQTPPDGR  311
WP_023635875  206  IYASKFTLALIAAKCREHRQRPKLIEVNEKSDINRGPFNIRFWAVNHSIPDCLGLAIKTGAGLVIHTGDIKLDQTPTDGR  285

SEQ ID NO:3   321  PTDLPALSRFGDEGVDLMLCDSTNATTPGVSGSEADVAPTLKRLVGDAKQRVILASFASNVYRVQAAVDAAVASNRKVAF  400
WP_011014791  321  PTDLPALSRFGDEGVDLMLCDSTNATTPGVSGSEADVAPTLKRLVGDAKQRVILASFASNVYRVQAAVDAAVASNRKVAF  400
WP_096456687  312  PTDLPALSRFGDEGVDLMLCDSTNATTPGVSGSEADVAPTLKRLVGDAKQRVILASFASNVYRVQAAVDAAVAANRKVAF  391
WP_023635875  286  PTDLPALSRFGDEGVDLMLCDSTNATTPGVSGSEADIAPTLKRLVGDAKQRVILASFASNVYRVQAAVDAAVASGRKVAF  365

SEQ ID NO:3   401  NGRSMIRNMEIAEKLGYLKAPRGTIISMDDASRMAPHKVMLITTGTQSEPMAALSRMARREHRQITVRDGDLIILSSSLV  480
WP_011014791  401  NGRSMIRNMEIAEKLGYLKAPRGTIISMDDASRMAPHKVMLITTGTQGEPMAALSRMARREHRQITVRDGDLIILSSSLV  480
WP_096456687  392  NGRSMIRNMEIAEKLGYLKAPRGTIISMDDASRMAPHKVMLITTGTQGEPMAALSRMARREHRQITVRDGDLIILSSSLV  471
WP_023635875  366  NGRSMIRNMEIAEKMGYLKAPRGTIVSMDDAAKMAPHKVMLITTGTQGEPMAALSRMARREHRQITVRDGDLIILSSSLV  445

SEQ ID NO:3   481  PGNEEAVFGVINMLAQIGATVVTGRDAKVHTSGHGYSGELLFLYNAARPKNAMPVHGEWRHLRANKELAISTGVNRDNVV  560
WP_011014791  481  PGNEEAVFGVINMLAQIGATVVTGRDAKVHTSGHGYSGELLFLYNAARPKNAMPVHGEWRHLRANKELAISTGVNRDNVV  560
WP_096456687  472  PGNEEAVFGVINMLAQIGATVVTGRDAKVHTSGHGYSGELLFLYNAARPKNAMPVHGEWRHLRANKELAISTGVNRDNVV  551
WP_023635875  446  PGNEEAVFGVINMLAQIGATVVTSRDAKVHTSGHGYSGELLFLYNAARPVNAMPVHGEWRHLRANKELAISTGVERDRVV  525
```

Figure 1A

```
SEQ ID NO:3    561  LAQNGVVVDMVNGRAQVVGQIPVGNLYVDGVTMGDIDADILADRTSLGEGGLISITAVIDNRTGRLLERPTVQTSGFSED  640
WP_011014791   561  LAQNGVVVDMVNGRAQVVGQIPVGNLYVDGVTMGDIDADILADRTSLGEGGLISITAVIDNRTGRLLERPTVQTSGFSED  640
WP_096456687   552  LAQNGVVVDLVNGRAQVVGQIPVGNLYVDGVTMGDIDADILADRTSLGEGGLISITAVIDNRTGRLLERPTVQTSGFSED  631
WP_023635875   526  LAQNGVVVDLVDGRARVVGQIQIGNLYVDGVTMGDIDAGVLEERTSLGEGGLIAITAVIDNRTGRLLERPTVQAKGFSED  605

SEQ ID NO:3    641  AKSMMGEVTELSETTMNDLAAEGENDPYRMVQQLRRKLSRFVEQKWKRQPVIMPTVIPMTAETTHIGDDEVRASRESL  718
WP_011014791   641  AKSMMGEVTELSETTMNDLAAEGENDPYRMVQQLRRKLSRFVEQKWKRQPVIMPTVIPMTAETTHIGDDEVRASRESL  718
WP_096456687   632  AKSMMGEVTELAETTMNDLAAEGENDPYRMVQQMRRKLSRFVEQKWKRQPVIMPTVIPMTAETRHIDDDEVRASRESL  709
WP_023635875   606  AVAMMPEVTELVENTMTDLAGEGENDPYRMVQQLRRRVSRFVEQKWRRKPMIMPTVIPTTQTQVEADEEEIRATRESL  683
```

*Figure 1B*

```
SEQ ID NO:6    1    MVWGMEHTSALTLIDSVLDPDSFISWDETPQYDNLNQGYAETLERARSKAKCDESVITGEGTVEGIPVAVILSDFSFLGGS  81
WP_075348128   1    MVWGMEHTSALTLIDSVLDPDSFISWDETPQYDNLNQGYAETLERARSKAKCDESVITGEGTVEGIPVAVILSDFSFLGGS  81
AGT04828       1        MEHTSALTLIDSVLDPDSFISWNETPQYDNLNQGYAETLERARSKAKCDESVITGEGTVEGIPVAVILSDFSFLGGS  77
WP_066564978   1        MAYTSALSLIDTVLDSDSFASWDTPPRYGNIDPKYAETLAKARSKSECNESIITGEGTVDGIAVAVILSDFSFLGGS  77

SEQ ID NO:6    82   LGTVASVRIMKAIHRATELKLPLLVSPASGGARMQEDNRAFVMMVSITAAVQRHREAHLPFLVYLRNPTMGGAMASWGSS  161
WP_075348128   82   LGTVASVRIMKAIHRATELKLPLLVSPASGGARMQEDNRAFVMMVSITAAVQRHREAHLPFLVYLRNPTMGGAMASWGSS  161
AGT04828       78   LGTVASVRIMKAIHRATELKLPLLVSPASGGARMQEDNRAFVMMVSITAAVQRHREAHLPFLVYLRNPTMGGAMASWGSS  157
WP_066564978   78   LGTVASMRIMNAIHRATERKMPLLVSPASGGARMQEDNRAFVIMVSITAAVQRHREAHLPFLVYLRNPTMGGAMASWGSS  157

SEQ ID NO:6    162  GHLTFAEPGAQIGFLGPRVVELTTGRALPDGVQQAENLVKTGVIDGIVSPLQLRAAVAKTLKIIQPAEATDRFSPTTPGA  241
WP_075348128   162  GHLTFAEPGAQIGFLGPRVVELTTGRALPDGVQQAENLVKTGVIDGIVSPLQLRAAVAKTLKIIQPAEATDRFSPTTPGA  241
AGT04828       158  GHLTFAEPGAQIGFLGPRVVELTTGHALPDGVQQAENLVKTGVIDGIVSPLQLRAAVAKTLKVIQPVEATDRFSPTTPGV  237
WP_066564978   158  GHITFAEPGAQIGFLGPRVVELSTGKPLPEGVQQAENLVARGVIDGIVSPMQLRAAVSKTVKVLQPAVLGAHFPTTAPGS  237

SEQ ID NO:6    242  ALPVMEAIARSRDPHRPGIGEIMETLGADVVRLSGARAGALSSAVRVALARIGGRPVVLIGQDRRFTLEPQELRFARRGI  321
WP_075348128   242  ALPVMEAIARSRDPHRPGIGEIMETLGADVVRLSGARAGALSSAVRVALARIGGRPVVLIGQDRRFTLGPQELRFARRGI  321
AGT04828       238  ALPVMEAIARSRDPQRPGIGEIMETLGADVVKLSGARAGALSPAVRVALARIGGRPVVLIGQDRRFTLGPQELRFARRGI  317
WP_066564978   238  GLPVMEAIARSRDPRRPGIGEIIETLGEDVVKLSGARRGTAMRAVRVGLARLAGRPVVLIGQDRHFALGPQDLSFARRGI  317

SEQ ID NO:6    322  SLARELNLPIVSIIDTSGAELSQAAEELGIASSIARTLSKLIDAPLPTVSVIIGQGVGGGALAMLPADLVYAAENAWLSA  401
WP_075348128   322  SLARELNLPIVSIIDTSGAELSQAAEELGIASSIARTLSKLIDAPLPTVSVIIGQGVGGGALAMLPADLVYAAENAWLSA  401
AGT04828       318  SLARELNLPIVSIIDTSGAELSQAAEELGIASSIARTLSKLIDAPLPTVSVIIGQGVGGGALAMLPADLVYAAENAWLSA  397
WP_066564978   318  SLARELNLPIVSIIDTSGAELSQDAEELGIASSIARTLAKLIDAPLPTVSVILGQGVGGGALAMLPADKVYAAENAWLSA  397

SEQ ID NO:6    402  LPPEGASAILFRDTNHAAEIIERQGVQAHALLSQGLIDGIVAETEHFVEEILGTISNALSELDNNPERAGRDSRFTRFER  481
WP_075348128   402  LPPEGASAILFRDTNHAAEIIERQGVQAHALLSQGLIDGIVAETEHFVEEILGTISNALSELDNNPERAGRDSRFTRFER  481
AGT04828       398  LPPEGASAILFRDTNHAAEIIERQGVQAHALLSQGLIDGIVAETEHFVEEILGTISNALSELDNNPERAGRDSRFTRFER  477
WP_066564978   398  LPPEGASAILFRSTDHAAEIMERQGVQAQTLLSQGLIDGIISEAVPFVEEVLGTISNALSELASNPERAGRESRFKRFER  477

SEQ ID NO:6    482  LAQ  484
WP_075348128   482  LAQ  484
AGT04828       478  LAQ  480
WP_066564978   478  LAR  480
```

Figure 2

```
SEQ ID NO:9    1      MAFGFFSRRKKKNKDKNPNENSAVPAHSEDSPQEVFEGNGRQVGDPIEQQVDRDAKGRLTAADFLSDADLPQLNRS  76
WP_011897001   1      MAFGFFSRRKKKNKDKNPNENSAVPAHSEDSPQEVFEGNGRQVGDPIEQQVDRDARGRLTAADFLPDADLPQLNRS  76
WP_066565124   1      MAFGFFGR-KKERKDR----------HS---------------GDP-----ERDSKSRLTSADLLPDTDLPQLNRS  45
EEW49979       1      ----------------------------------------------MEQKVERDGNGILTPADFLPDTDLPQLNRS  30

SEQ ID NO:9    77   RANMLRRELEYRFSLQNAHINIDGNTAMIQRSDGGAAHVSLRTLAMNAAGLDNFDQLPELVESFVHGTLADATLNDLSTA  168
WP_011897001   77   RANMLRRELEYRFSLQNAHINIDGNTAMIQRSDGGAAHVSLRTLAMNAAGLDNFDQLPELVESFVHGTLADATLNDLSTA  156
WP_066565124   46   RANMLRQELEYRFALQDAHINIDGHSAMVQRADGGAAHVSLRTLAMNAAGLENFDQLPELVENFVHGTLADATLKDLSTA  125
EEW49979       31   RANMLRRELEYRFALKDAQITIDGASAMVHRPDGGAAHVSLRTLAMNAAGLDDLGQLPELVDNFVHGTLADATLSTLSTA  110

SEQ ID NO:9    157  DLYKALRLRLLPTPGEGDDLVEHGLDRESQIRDDSILRTFTSDMSIALVLDTEHAIRIQPLKELEEFDDLSALERAADRN  236
WP_011897001   157  DLYKALRLRLLPTPGEGDDLVEHGLDRESQIRDDSILRTFTSDMSIALVLDTEHAIRIQPLKELEEFDDLSALERAADRN  236
WP_066565124   126  DLYKALRLRLLPTPSENDELAEYGLTIESKIRDDSILRTFTSDMSIALVLDTEHAIRIQPLKELERFDDLGALERAADRN  205
EEW49979       111  DLYKSLRLRLLPNPEQGDSILETSDGVERQIRETSVLRDFTSDTSIALVLDTEHAIRIQPLHELEEFDSLDALERAADRN  190

SEQ ID NO:9    237  TWQELYDANVDASFVDAESDSEGSSFWAFESNSYYLGSAPLFLNDLLAKWAPDLDQSDGVIFAVPDRDLLIARPVTTGED  316
WP_011897001   237  TWQELYDANVDASFVDAESDSEGSSFWAFESNSYYLGSAPLFLNDLLAKWAPDLDQSDGVIFAVPDRDLLIARPVTTGED  316
WP_066565124   206  TWQELYDASVDVTFVDAESDSEGSSFWTFESNSYYLGSAPLFLGDLLAKWAPDLDQSDGVIFAVPDRDLLIARPISTGEN  285
EEW49979       191  TWQELLDADVDVTYFNNDEGGEGSDFWAFESSSYYLGSSPLFLTDLLHRWAPDLDQSRGVIFAVPDRDLLIARPVTTGEN  270

SEQ ID NO:9    317  LMNGITAMVRIAMRFGLGNPTSISPRLHLLRDNQVTTFTDFRVVSPEMEAEWEDSAFDAPPAGAIGIEVRPDPYLMERLQ  396
WP_011897001   317  LMNGITAMVRIAMRFGLGNPTSISPRLHLLRDNQVTTFTDFRVVSPEMEAEWEDSAFDAPPAGAIGIEVRPDPYLMERLQ  396
WP_066565124   286  LMNGITAMVRTAMRFGLGNPTSISPRLHMLHDNQVITFTDYRIVSPEMEAEWEENSFDAPPAGAIGIEVRPDPYLMERLQ  365
EEW49979       271  LMNGITSMVRIAMRFGLGNPTSISPRLHLLYDNQINTFTDYRIIEPTEDEEWAVPTADAPQPGSIGIEVRPDAYLMEMLQ  350

SEQ ID NO:9    397  QGGFGD-FGDFGKPRDLDM     414
WP_011897001   397  QGGFGD-FGDFGKPRDLDM     414
WP_066565124   366  QGGFGD-FGDFGKPRDLGM     383
EEW49979       351  QDGFGDSFDDFG-PRDLGP     373
```

Figure 3

SEQUENCE LISTING

```
<160> NUMBER OF SEQ ID NOS: 121

<210> SEQ ID NO 1
<211> LENGTH: 4101
<212> TYPE: DNA
<213> ORGANISM: C. glutamicum NRRL B-11474

<400> SEQUENCE: 1

aaaaactaga actgctcaag gccgttcgtg aggaagttgg ggatcgggcg aagctcatcg      60

ccggtgtcgg aaccaacaac acgcggacat ctgtggaact tgcggaagct gctgcttctg     120

ctggcgcaga cggcctttta gttgtaactc cttattactc caagccgagc caagagggat     180

tgctggcgca cttcggtgca attgctgcag caacagaggt tccaatttgt ctctatgaca     240

ttcctggtcg gtcaggtatt ccaattgaat ctgataccat gagacgcctg agtgaattac     300

ctacgatttt ggcggtcaag gacgccaagg gtgacctcgt tgcagccacg tcattgatca     360

aagaaacggg acttgcctgg tattcaggcg atgacccact aaaccttgtt tggcttgctt     420

tgggcggatc aggtttcatt tccgtaattg gacatgcagc ccccacagca ttacgtgagt     480

tgtacacaag cttcgaggaa ggcgacctcg tccgtgcgcg ggaaatcaac gccaaactat     540

caccgctggt agctgcccaa ggtcgcttgg gtggagtcag cttggcaaaa gctgctctgc     600

gtctgcaggg catcaacgta ggagatcctc gacttccaat tatggctcca aatgagcagg     660

aacttgaggc tctccgagaa gacatgaaaa aagctggagt tctataaata tgaatgattc     720

ccgaaatcgc ggccggaagg ttacccgcaa ggcgggccca ccagaagctg gtcaggaaaa     780

ccatctggat acccctgtct ttcaggcacc agatgcttcc tctaaccaga gcgctgtaaa     840

agctgagacc gccggaaacg acaatcggga tgctgcgcaa ggtgctcaag gatcccaaga     900

ttctcagggt tcccagaacg ctcaaggttc ccagaaccgc gagtccggaa ataacaaccg     960

caaccgttcc aacaacaacc gtcgcggtgg tcgtggacgt cgtggatccg gaaacgccaa    1020

tgagggcgcg aacaacaaca gtggtaacca gaaccgtcag ggcggaaacc gtggcaaccg    1080

cggtggcgga cgccgaaacg ttgttaagtc gatgcagggt gcggatctga cccagcgcct    1140

gccagagcca ccaaaggcac cggcaaacgg tctgcgtatt tacgcacttg gtggcatttc    1200

cgaaatcggt cgcaacatga ccgtgtttga gtacaacaac cgtctgctca tcgtggactg    1260

tggtgtgctc ttcccatctt caggtgagcc aggcgttgac ctgattcttc ctgacttcgg    1320

cccaattgag gatcacctgc accgcgtcga tgcattggtg gttactcacg gacacgaaga    1380

ccacattggt gctattccct ggctgctgaa gctgcgcaac gatatcccaa ttttggcatc    1440

ccgtttcacc ttggctctga ttgcagctaa gtgtaaggaa caccgtcagc gtccgaagct    1500

gatcgaggtc aacgagcagt ccaatgagga ccgcggaccg ttcaacattc gcttctgggc    1560

tgttaaccac tccatcccag actgccttgg tcttgctatc aagactcctg ctggtttggt    1620

catccacacc ggtgacatca agctggatca gactcctcct gatggacgcc caactgacct    1680

gcctgcattg tcccgtttcg gtgacgaggg cgtggacttg atgctgtgtg actccaccaa    1740
```

```
cgccaccacc cctggtgttt ctggatctga agctgatgtt gctccaaccc tgaagcgttt   1800

ggtcggcgat gctaagcagc gcgtcatttt ggcgtcgttt gcttccaacg tgtaccgcgt   1860

tcaggcagct gtggatgctg ctgttgcgtc caaccgtaag gttgcattca acggtcgttc   1920

catgattcgc aacatggaga tcgcggagaa gcttggttac ctgaaggcac ctcgcggaac   1980

cattatttcc atggatgatg cttctcgtat ggctcctcac aaggtcatgc tgattaccac   2040

tggtactcag ggtgagccta tggctgcgct gtctcgcatg gcgcgtcgtg agcaccgaca   2100

gatcactgtc cgtgatggag acttgattat cctttcttcc tccctggttc caggtaacga   2160

agaagcagtg ttcggtgtca tcaacatgct ggctcagatc ggtgcaactg ttgttaccgg   2220

tcgcgacgcc aaggtgcaca cctcgggcca cggctactcc ggagagctgt tgttcttgta   2280

caacgccgct cgtccgaaga acgctatgcc tgtccacggc gagtggcgcc acctgcgcgc   2340

caacaaggaa ctggctatct ccactggtgt taaccgcgac aacgttgtgc ttgcacaaaa   2400

cggtgttgtg gttgatatgg tcaacggtcg cgcacaggtt gttggtcaga ttccagttgg   2460

taacctttac gtcgacggtg tcaccatggg tgatattgac gcggacatcc ttgcagaccg   2520

tacctcgctt ggtgagggtg gcttgatctc gatcactgct gtcatcgaca accgcactgg   2580

ccgtctgttg gagcgcccaa ccgttcagac cagcggtttc tctgaggatg caaagtccat   2640

gatgggtgag gtcactgagc tgtccgaaac caccatgaat gatcttgcag ctgaaggtga   2700

aaacgatcct taccgcatgg ttcagcagct gcgccgcaag ctctctcgct tcgtcgagca   2760

gaagtggaag cgccagccgg tcatcatgcc aaccgtcatt ccgatgactg cggaaaccac   2820

gcacatcggt gacgatgagg ttcgcgcttc acgcgagtcc ctgtaaaagc atttcgcttt   2880

tcgacgtcgc gagcccgcag cacccaacct gggtgccgcg ggctcaacgc gtttctacac   2940

attgatctag tcttggttgc atgaatctcg cacaaacaga acgagcagca cttcaagcat   3000

cactgttgga aaaggggcca gacgcaccaa ccttgtgcgg cgaatggacc accaaagatc   3060

ttgcggcaca cctttatgtc cgtgagcaga agccaggagc agcgctgcgc agtatgcttc   3120

ccggcaagca ggatcctgca aaagaagagt ttgaagaagc gcttacccgc ccttacgtgg   3180

acgttgtcaa cgcgtgggct gaaggcccac aggggctgaa tccatggcga gcccttgact   3240

ctattggaaa tggcatggag catttcattc accatgaaga tgttctgcgt ggcgcgttgc   3300

agccaggcga tgaagtagaa gttcgtccca tggaccatgc gcacggcaaa gagctgcacc   3360

gcattttaaa acttctggct ccacgaatga tcaaatcacc gcgacccgtg gttctagctc   3420

cggtgggttt tccgaggatt gttcttcatg aaggtcgggg agtgtcggcc gatggtgaaa   3480

acgtctgtcg gattagcggt ggggtagggg agctgctgtt gtggctgtct ggccgtgatg   3540

ttgtgaaact aacatttgaa ggcaaccaag agggcgttgt tcggggaagt ttatagaaaa   3600

cttggacgaa tcgcgtggtg cttctgtgaa tagagttgtt tgagcgacta gagttaaggc   3660

catgactgtc agaaacggcg cacccaagcg gggaagctca cgatcatcgg gaaagtcgac   3720

ggggccaaaa accaccgcga cgaccaggcg aagcaaacca acaaccagca tctctcgggg   3780

tggccggtca gagactgctg cgtttacaac atcgatgacc gctcgacgcg ctgctgatac   3840

ttccgaagaa cggaccggca gcgcatttcg cgctgtggga tccggtatcg gaacgctatt   3900

tggtgccacc gcgagtggct tgggtaagat gacccgttcc attggtgaac ttggtcgtcg   3960

tcgaaacgaa gatgtactcg acgattttga tgatttcgag gaggagatcg caacgaaacc   4020

cgccacacga aaatcgcgga gcaaggctgt tgaacctgag ccggaattcg atgaggattt   4080
```

```
tgatgagcaa tcaggaaacc g                                              4101


<210> SEQ ID NO 2
<211> LENGTH: 2157
<212> TYPE: DNA
<213> ORGANISM: Artificial Sequence
<220> FEATURE:
<223> OTHER INFORMATION: coding sequence for altered RnaJ protein

<400> SEQUENCE: 2

atgaatgatt cccgaaatcg cggccggaag gttacccgca aggcgggccc accagaagct     60

ggtcaggaaa accatctgga taccccctgtc tttcaggcac cagatgcttc ctctaaccag    120

agcgctgtaa aagctgagac cgccggaaac gacaatcggg atgctgcgca aggtgctcaa    180

ggatcccaag attctcaggg ttcccagaac gctcaaggtt cccagaaccg cgagtccgga    240

aataacaacc gcaaccgttc caacaacaac cgtcgcggtg gtcgtggacg tcgtggatcc    300

ggaaacgcca atgagggcgc gaacaacaac agtggtaacc agaaccgtca gggcggaaac    360

cgtggcaacc gcggtggcgg acgccgaaac gttgttaagt cgatgcaggg tgcggatctg    420

acccagcgcc tgccagagcc accaaaggca ccggcaaacg gtctgcgtat ttacgcactt    480

ggtggcattt ccgaaatcgg tcgcaacatg accgtgtttg agtacaacaa ccgtctgctc    540

atcgtggact gtggtgtgct cttcccatct tcaggtgagc caggcgttga cctgattctt    600

cctgacttcg gcccaattga ggatcacctg caccgcgtcg atgcattggt ggttactcac    660

ggacacgaag accacattgg tgctattccc tggctgctga agctgcgcaa cgatatccca    720

attttggcat cccgtttcac cttggctctg attgcagcta agtgtaagga acaccgtcag    780

cgtccgaagc tgatcgaggt caacgagcag tccaatgagg accgcggacc gttcaacatt    840

cgcttctggg ctgttaacca ctccatccca gactgccttg gtcttgctat caagactcct    900

gctggtttgg tcatccacac cggtgacatc aagctggatc agactcctcc tgatggacgc    960

ccaactgacc tgcctgcatt gtcccgtttc ggtgacgagg gcgtggactt gatgctgtgt   1020

gactccacca acgccaccac ccctggtgtt tctggatctg aagctgatgt tgctccaacc   1080

ctgaagcgtt tggtcggcga tgctaagcag cgcgtcattt tggcgtcgtt tgcttccaac   1140

gtgtaccgcg ttcaggcagc tgtggatgct gctgttgcgt ccaaccgtaa ggttgcattc   1200

aacggtcgtt ccatgattcg caacatggag atcgcggaga agcttggtta cctgaaggca   1260

cctcgcggaa ccattatttc catggatgat gcttctcgta tggctcctca caaggtcatg   1320

ctgattacca ctggtactca gagtgagcct atggctgcgc tgtctcgcat ggcgcgtcgt   1380

gagcaccgac agatcactgt ccgtgatgga gacttgatta tcctttcttc ctccctggtt   1440

ccaggtaacg aagaagcagt gttcggtgtc atcaacatgc tggctcagat cggtgcaact   1500

gttgttaccg gtcgcgacgc caaggtgcac acctcgggcc acggctactc cggagagctg   1560

ttgttcttgt acaacgccgc tcgtccgaag aacgctatgc ctgtccacgg cgagtggcgc   1620

cacctgcgcg ccaacaagga actggctatc tccactggtg ttaaccgcga caacgttgtg   1680

cttgcacaaa acggtgttgt ggttgatatg gtcaacggtc gcgcacaggt tgttggtcag   1740

attccagttg gtaaccttta cgtcgacggt gtcaccatgg gtgatattga cgcggacatc   1800

cttgcagacc gtacctcgct tggtgagggt ggcttgatct cgatcactgc tgtcatcgac   1860

aaccgcactg gccgtctgtt ggagcgccca accgttcaga ccagcggttt ctctgaggat   1920

gcaaagtcca tgatgggtga ggtcactgag ctgtccgaaa ccaccatgaa tgatcttgca   1980

gctgaaggtg aaaacgatcc ttaccgcatg gttcagcagc tgcgccgcaa gctctctcgc   2040
```

```
ttcgtcgagc agaagtggaa gcgccagccg gtcatcatgc caaccgtcat tccgatgact   2100

gcggaaacca cgcacatcgg tgacgatgag gttcgcgctt cacgcgagtc cctgtaa      2157


<210> SEQ ID NO 3
<211> LENGTH: 718
<212> TYPE: PRT
<213> ORGANISM: Artificial Sequence
<220> FEATURE:
<223> OTHER INFORMATION: altered RnaJ protein

<400> SEQUENCE: 3

Met Asn Asp Ser Arg Asn Arg Gly Arg Lys Val Thr Arg Lys Ala Gly
1               5                   10                  15

Pro Pro Glu Ala Gly Gln Glu Asn His Leu Asp Thr Pro Val Phe Gln
            20                  25                  30

Ala Pro Asp Ala Ser Ser Asn Gln Ser Ala Val Lys Ala Glu Thr Ala
        35                  40                  45

Gly Asn Asp Asn Arg Asp Ala Ala Gln Gly Ala Gln Gly Ser Gln Asp
    50                  55                  60

Ser Gln Gly Ser Gln Asn Ala Gln Gly Ser Gln Asn Arg Glu Ser Gly
65                  70                  75                  80

Asn Asn Asn Arg Asn Arg Ser Asn Asn Asn Arg Arg Gly Gly Arg Gly
                85                  90                  95

Arg Arg Gly Ser Gly Asn Ala Asn Glu Gly Ala Asn Asn Asn Ser Gly
            100                 105                 110

Asn Gln Asn Arg Gln Gly Gly Asn Arg Gly Asn Arg Gly Gly Gly Arg
        115                 120                 125

Arg Asn Val Val Lys Ser Met Gln Gly Ala Asp Leu Thr Gln Arg Leu
    130                 135                 140

Pro Glu Pro Pro Lys Ala Pro Ala Asn Gly Leu Arg Ile Tyr Ala Leu
145                 150                 155                 160

Gly Gly Ile Ser Glu Ile Gly Arg Asn Met Thr Val Phe Glu Tyr Asn
                165                 170                 175

Asn Arg Leu Leu Ile Val Asp Cys Gly Val Leu Phe Pro Ser Ser Gly
            180                 185                 190

Glu Pro Gly Val Asp Leu Ile Leu Pro Asp Phe Gly Pro Ile Glu Asp
        195                 200                 205

His Leu His Arg Val Asp Ala Leu Val Val Thr His Gly His Glu Asp
    210                 215                 220

His Ile Gly Ala Ile Pro Trp Leu Leu Lys Leu Arg Asn Asp Ile Pro
225                 230                 235                 240

Ile Leu Ala Ser Arg Phe Thr Leu Ala Leu Ile Ala Ala Lys Cys Lys
                245                 250                 255

Glu His Arg Gln Arg Pro Lys Leu Ile Glu Val Asn Glu Gln Ser Asn
            260                 265                 270

Glu Asp Arg Gly Pro Phe Asn Ile Arg Phe Trp Ala Val Asn His Ser
        275                 280                 285

Ile Pro Asp Cys Leu Gly Leu Ala Ile Lys Thr Pro Ala Gly Leu Val
    290                 295                 300

Ile His Thr Gly Asp Ile Lys Leu Asp Gln Thr Pro Pro Asp Gly Arg
305                 310                 315                 320

Pro Thr Asp Leu Pro Ala Leu Ser Arg Phe Gly Asp Glu Gly Val Asp
                325                 330                 335

Leu Met Leu Cys Asp Ser Thr Asn Ala Thr Thr Pro Gly Val Ser Gly
```

-continued

```
            340                 345                 350

Ser Glu Ala Asp Val Ala Pro Thr Leu Lys Arg Leu Val Gly Asp Ala
        355                 360                 365

Lys Gln Arg Val Ile Leu Ala Ser Phe Ala Ser Asn Val Tyr Arg Val
    370                 375                 380

Gln Ala Ala Val Asp Ala Ala Val Ala Ser Asn Arg Lys Val Ala Phe
385                 390                 395                 400

Asn Gly Arg Ser Met Ile Arg Asn Met Glu Ile Ala Glu Lys Leu Gly
                405                 410                 415

Tyr Leu Lys Ala Pro Arg Gly Thr Ile Ile Ser Met Asp Asp Ala Ser
            420                 425                 430

Arg Met Ala Pro His Lys Val Met Leu Ile Thr Thr Gly Thr Gln Ser
        435                 440                 445

Glu Pro Met Ala Ala Leu Ser Arg Met Ala Arg Arg Glu His Arg Gln
    450                 455                 460

Ile Thr Val Arg Asp Gly Asp Leu Ile Ile Leu Ser Ser Ser Leu Val
465                 470                 475                 480

Pro Gly Asn Glu Glu Ala Val Phe Gly Val Ile Asn Met Leu Ala Gln
                485                 490                 495

Ile Gly Ala Thr Val Val Thr Gly Arg Asp Ala Lys Val His Thr Ser
            500                 505                 510

Gly His Gly Tyr Ser Gly Glu Leu Leu Phe Leu Tyr Asn Ala Ala Arg
        515                 520                 525

Pro Lys Asn Ala Met Pro Val His Gly Glu Trp Arg His Leu Arg Ala
    530                 535                 540

Asn Lys Glu Leu Ala Ile Ser Thr Gly Val Asn Arg Asp Asn Val Val
545                 550                 555                 560

Leu Ala Gln Asn Gly Val Val Val Asp Met Val Asn Gly Arg Ala Gln
                565                 570                 575

Val Val Gly Gln Ile Pro Val Gly Asn Leu Tyr Val Asp Gly Val Thr
            580                 585                 590

Met Gly Asp Ile Asp Ala Asp Ile Leu Ala Asp Arg Thr Ser Leu Gly
        595                 600                 605

Glu Gly Gly Leu Ile Ser Ile Thr Ala Val Ile Asp Asn Arg Thr Gly
    610                 615                 620

Arg Leu Leu Glu Arg Pro Thr Val Gln Thr Ser Gly Phe Ser Glu Asp
625                 630                 635                 640

Ala Lys Ser Met Met Gly Glu Val Thr Glu Leu Ser Glu Thr Thr Met
                645                 650                 655

Asn Asp Leu Ala Ala Glu Gly Glu Asn Asp Pro Tyr Arg Met Val Gln
            660                 665                 670

Gln Leu Arg Arg Lys Leu Ser Arg Phe Val Glu Gln Lys Trp Lys Arg
        675                 680                 685

Gln Pro Val Ile Met Pro Thr Val Ile Pro Met Thr Ala Glu Thr Thr
    690                 695                 700

His Ile Gly Asp Asp Glu Val Arg Ala Ser Arg Glu Ser Leu
705                 710                 715
```

<210> SEQ ID NO 4
<211> LENGTH: 4101
<212> TYPE: DNA
<213> ORGANISM: C. glutamicum NRRL B-11474

<400> SEQUENCE: 4

-continued

```
gctgcagaca ggtagtcacc tgcgatagcc agaccgttct gggttccgga gaaggaagca     60
ccaccggtgt agaagtcggt ggattcgctg gtgctcttgc ccacgcgaag caccacggtc    120
atcgtcacaa taatgaatac gacgaagaca ctgatgttaa gaatcggatt accgacgccc    180
tcagaaacag cgtcttgtgc aaggagaata gtggaattca tatctgatta accttccatc    240
ttctggcgaa tagcagcctg acgaggctcc aagttcctgt tcgcaaacat gacgtagacg    300
taagtaataa tgaatgtggt tacgaactga aggaagccga agattaggcc gatgttgatt    360
gcgccgaaaa ctggggttgc catccactct gatgcaaagg atgcaaccag aacgtagacg    420
acgtaccaca agaagaaggc aacggtcatt gggaaagcaa aggaacggaa cttgctgcgg    480
agctctccaa attctgggct cgcctgcatg tcccgaaact cttgagccgt cggctggcga    540
cgcccctggg tgatttgttc tgcattcact ggaaacttat ctcgctttca tatccctcga    600
gcgggagtcg gtgatcggcc actctttaag caatgccggc tttaaaataa agcaacttat    660
atgtttctca ccacatctgg ccgacgaccg ctaagtatgt tgtcgatcac agctaaacgt    720
gtgaatgtga agttacctaa ctcacattgc aatgcgatag cgatttggaa aactcactcc    780
ccccaatacc ttaacttgaa cttaaaaata gtggtttacc tgcatttata aaagttcccg    840
atctaccccc tctttacccc gaaatacccc ttttgcaaag attgcaaaca caacagtgca    900
atagttaacg ggcttcacac gtcacctttc tgtccggttt taggctatgt tcgggacgtc    960
taggcaaaag tagttttgtg agatgaaacg cataatccgt catttttttac gcaatcgata  1020
gcctaaattg ggcttagatc ttccgcctct aaataggtat gcaaagacat tcgaattaat   1080
taacaaagcc atttttcggc cgtggagaag cgttttccga ctatggtgtg gggcatggaa   1140
cacacttcag cattgacgct catagactcg gttttggacc ctgacagctt catttcttgg   1200
gatgaaactc cccaatatga caacctcaat caaggctatg cagagacctt ggagcgggct   1260
cgaagcaagg ccaaatgcga tgaatcggtg attactggag aaggcaccgt ggagggcatt   1320
ccggtagccg ttattttgtc cgattttttcc ttcctcggcg gttctttggg cacggtcgcg  1380
tcggtgcgca tcatgaaggc gattcaccgc gccacagagc tgaaactccc actgctggtc   1440
tcccctgctt ccggtggtgc gcgcatgcag gaagacaatc gagcctttgt catgatggtg   1500
tccataaccg cggctgtgca acgccaccgc gaagcacatt tgccgttcct ggtgtatttg   1560
cgcaatccca cgatgggtgg cgccatggcc tcgtggggtt catctgggca tctcactttt   1620
gcggaacccg gcgcgcagat cggtttcctg ggccctcgcg tggtggagtt gaccaccggg   1680
cgtgcgcttc cagacggtgt gcagcaggcg gagaatttgg tgaaaaactgg tgtgattgat  1740
ggcattgtgt cgccgctcca attgcgtgca gcggtggcaa aaacgctcaa gattattcag   1800
cctgcagagg caaccgatcg tttttctcca acaactcctg gcgcagcgct tccggtgatg   1860
gaggcgattg cgcgttctcg tgacccgcac aggcctggaa tcggggagat tatggaaacg   1920
ttgggggcag acgtcgtcag gctatctggt gcgcgtgctg gcgcgttgag ctcggctgtg   1980
cgcgttgccc tagcgcgcat cgggggccgg cctgtggtgc tgattggaca ggatcggcgc   2040
ttcacgcttg ggccgcagga gctgcgtttt gcgcgccgtg gcatttcgtt ggcgcgcgag   2100
ctgaacctgc cgatcgtgtc catcatcgac acctccggcg ccgaattgtc acaggcggct   2160
gaggagctcg gcatcgcaag ctcgattgcg cgcaccttgt ccaagcttat cgacgctccc   2220
ctccccaccg tttcggtcat tattggtcag ggcgttggcg gtggcgcgct ggccatgctg   2280
cccgccgatc tggtctacgc ggccgaaaac gcgtggctgt ccgcattgcc tccagagggc   2340
gcctcggcca tcctcttccg cgacaccaac cacgccgcgg aaatcataga gcgacaaggc   2400
```

```
gtgcaggcgc acgcactttt aagccaaggg cttatcgacg ggatcgtcgc cgaaaccgag   2460
cactttgttg aagaaattct cggcacaatc agcaacgccc tctccgaatt ggataacaat   2520
ccggagaggg caggacgcga cagtcgcttc acacgatttg agcgtttagc gcagtaaaga   2580
aaattatgcg ctgatcaaat cgatgatgaa caccagggta cggccagaca gtgggtggcc   2640
ggaaccctca gggccgtaag cagcctctgg cggaatggtc agctgacgac gtccgccgac   2700
cttcatgcct ggaattcctt cttgccaacc tgcaatgagg ccgttgagtg ggaactggct   2760
ggtctgtcca cgatcccagg aagagtcaaa ctcctcgccg gtttcaaggt caacgcccac   2820
atagtggacc tcaacttctc cgcctgggcg ggcttctgcg ccttcgccaa cgatgatgtc   2880
agagattacg agatcttccg gtgctggacc gaccggtagc tcaatctgtg gcttttccat   2940
gtgctgtaca tgctccttga aaatcgtatt ttttggtttc atgcaaaaac ggccgaaacc   3000
atccctgtca ttatgacaga cgaagtggct tcggccgaag ttgaacgaga atcatccgct   3060
aaatttagcg ctcctcgcga ggaaccaact tgcgggattc cttgccggtg tagacctggc   3120
gtgggcggtt gatcttgttg cctgctgcac cgagctgctc gcggtagtga gcgatccatc   3180
ctggcagacg accgattgcg aacaatacgg tgaagaagtc agttgggaag cccattgcgc   3240
ggtagatcag gccggtgtag aagtctacgt tcgggtagag cttgcgggag atgaagtaat   3300
catcagccag tgcaatttct tccagcttga ttgccagatc cagaagatcg tcgccaccga   3360
ggtgctcgag gatctcgtgt gcggtctcct tgacgattgc tgcacgtgga tcgtagttct   3420
tgtaaacgcg gtgtccgaag cccatgaggc ggacgccgtc ttccttgttc ttgaccttgt   3480
tcatgaacgc ggttgcgtcg ccaccgtggt tgttcttgat gtcttcgagc atctccagaa   3540
cagcctggtt tgcgccaccg tgcagtgggc cggacagagc gttgatgcca ccagcgatgg   3600
agacaaacat gttggcctgt gcggaaccga tcatacgaac ggtggaggtg gagcagttct   3660
gctcgtggtc agcgtgcagg atgagcagct tgtccagagc cttgaccatg attgggtcga   3720
tctcgtatgg ctcggttggg taaccgaaca tcatgcgcag gaagttctca cgcgcgttga   3780
gggagttgtc tgggtacatg taaggagcac ccttgcgtgc gcggtgtgcg tacgcagcca   3840
gcattggaac ctttgccatg aggcgaacgg ttgccttatc aagctgtgcc tcatcgagtg   3900
ggttcagctg atcctggtag taggtagaca aaatgttaac cgaggaagcc aaggttgcca   3960
ttgggtgagc gtcgcgtggg aacacgttga actgggactt gaagtcctcg tccagaaggg   4020
tgtggtggcg aatctcgtcg ttaaacttgt gaagctcatc tggggttggt agctcaccgt   4080
tgataagtag gtaagaaacc t                                             4101
```

<210> SEQ ID NO 5
<211> LENGTH: 1455
<212> TYPE: DNA
<213> ORGANISM: Artificial Sequence
<220> FEATURE:
<223> OTHER INFORMATION: coding sequence for altered accDA protein

<400> SEQUENCE: 5

```
atggtgtggg gcatggaaca cacttcagca ttgacgctca tagactcggt tttggaccct     60
gacagcttca tttcttggga tgaaactccc caatatgaca acctcaatca aggctatgca    120
gagaccttgg agcgggctcg aagcaaggcc aaatgcgatg aatcggtgat tactggagaa    180
ggcaccgtgg agggcattcc ggtagccgtt attttgtccg atttttcctt cctcggcggt    240
tctttgggca cggtcgcgtc ggtgcgcatc atgaaggcga ttcaccgcgc cacagagctg    300
```

```
aaactcccac tgctggtctc ccctgcttcc ggtggtgcgc gcatgcagga agacaatcga    360

gcctttgtca tgatggtgtc cataaccgcg gctgtgcaac gccaccgcga agcacatttg    420

ccgttcctgg tgtatttgcg caatcccacg atgggtggcg ccatggcctc gtggggttca    480

tctgggcatc tcacttttgc ggaacccggc gcgcagatcg gtttcctggg ccctcgcgtg    540

gtggagttga ccaccgggcg tgcgcttcca gacggtgtgc agcaggcgga gaatttggtg    600

aaaactggtg tgattgatgg cattgtgtcg ccgctccaat tgcgtgcagc ggtggcaaaa    660

acgctcaaga ttattcagcc tgcagaggca accgatcgtt tttctccaac aactcctggc    720

gcagcgcttc cggtgatgga ggcgattgcg cgttctcgtg acccgcacag gcctggaatc    780

ggggagatta tggaaacgtt gggggcagac gtcgtcaggc tatctggtgc gcgtgctggc    840

gcgttgagct cggctgtgcg cgttgcccta gcgcgcatcg gggccggcc tgtggtgctg    900

attggacagg atcggcgctt cacgcttgag ccgcaggagc tgcgttttgc gcgccgtggc    960

atttcgttgg cgcgcgagct gaacctgccg atcgtgtcca tcatcgacac ctccggcgcc   1020

gaattgtcac aggcggctga ggagctcggc atcgcaagct cgattgcgcg caccttgtcc   1080

aagcttatcg acgctcccct ccccaccgtt tcggtcatta ttggtcaggg cgttggcggt   1140

ggcgcgctgg ccatgctgcc cgccgatctg gtctacgcgg ccgaaaacgc gtggctgtcc   1200

gcattgcctc cagagggcgc ctcggccatc ctcttccgcg acaccaacca cgccgcggaa   1260

atcatagagc gacaaggcgt gcaggcgcac gcacttttaa gccaagggct tatcgacggg   1320

atcgtcgccg aaaccgagca ctttgttgaa gaaattctcg gcacaatcag caacgccctc   1380

tccgaattgg ataacaatcc ggagagggca ggacgcgaca gtcgcttcac acgatttgag   1440

cgtttagcgc agtaa                                                    1455
```

```
<210> SEQ ID NO 6
<211> LENGTH: 484
<212> TYPE: PRT
<213> ORGANISM: Artificial Sequence
<220> FEATURE:
<223> OTHER INFORMATION: altered accDA protein

<400> SEQUENCE: 6

Met Val Trp Gly Met Glu His Thr Ser Ala Leu Thr Leu Ile Asp Ser
1               5                   10                  15

Val Leu Asp Pro Asp Ser Phe Ile Ser Trp Asp Glu Thr Pro Gln Tyr
            20                  25                  30

Asp Asn Leu Asn Gln Gly Tyr Ala Glu Thr Leu Glu Arg Ala Arg Ser
        35                  40                  45

Lys Ala Lys Cys Asp Glu Ser Val Ile Thr Gly Glu Gly Thr Val Glu
    50                  55                  60

Gly Ile Pro Val Ala Val Ile Leu Ser Asp Phe Ser Phe Leu Gly Gly
65                  70                  75                  80

Ser Leu Gly Thr Val Ala Ser Val Arg Ile Met Lys Ala Ile His Arg
                85                  90                  95

Ala Thr Glu Leu Lys Leu Pro Leu Leu Val Ser Pro Ala Ser Gly Gly
            100                 105                 110

Ala Arg Met Gln Glu Asp Asn Arg Ala Phe Val Met Met Val Ser Ile
        115                 120                 125

Thr Ala Ala Val Gln Arg His Arg Glu Ala His Leu Pro Phe Leu Val
    130                 135                 140

Tyr Leu Arg Asn Pro Thr Met Gly Gly Ala Met Ala Ser Trp Gly Ser
145                 150                 155                 160
```

```
Ser Gly His Leu Thr Phe Ala Glu Pro Gly Ala Gln Ile Gly Phe Leu
                165                 170                 175

Gly Pro Arg Val Val Glu Leu Thr Thr Gly Arg Ala Leu Pro Asp Gly
            180                 185                 190

Val Gln Gln Ala Glu Asn Leu Val Lys Thr Gly Val Ile Asp Gly Ile
        195                 200                 205

Val Ser Pro Leu Gln Leu Arg Ala Ala Val Ala Lys Thr Leu Lys Ile
    210                 215                 220

Ile Gln Pro Ala Glu Ala Thr Asp Arg Phe Ser Pro Thr Thr Pro Gly
225                 230                 235                 240

Ala Ala Leu Pro Val Met Glu Ala Ile Ala Arg Ser Arg Asp Pro His
                245                 250                 255

Arg Pro Gly Ile Gly Glu Ile Met Glu Thr Leu Gly Ala Asp Val Val
            260                 265                 270

Arg Leu Ser Gly Ala Arg Ala Gly Ala Leu Ser Ser Ala Val Arg Val
        275                 280                 285

Ala Leu Ala Arg Ile Gly Gly Arg Pro Val Val Leu Ile Gly Gln Asp
    290                 295                 300

Arg Arg Phe Thr Leu Glu Pro Gln Glu Leu Arg Phe Ala Arg Arg Gly
305                 310                 315                 320

Ile Ser Leu Ala Arg Glu Leu Asn Leu Pro Ile Val Ser Ile Ile Asp
                325                 330                 335

Thr Ser Gly Ala Glu Leu Ser Gln Ala Ala Glu Glu Leu Gly Ile Ala
            340                 345                 350

Ser Ser Ile Ala Arg Thr Leu Ser Lys Leu Ile Asp Ala Pro Leu Pro
        355                 360                 365

Thr Val Ser Val Ile Ile Gly Gln Gly Val Gly Gly Gly Ala Leu Ala
    370                 375                 380

Met Leu Pro Ala Asp Leu Val Tyr Ala Ala Glu Asn Ala Trp Leu Ser
385                 390                 395                 400

Ala Leu Pro Pro Glu Gly Ala Ser Ala Ile Leu Phe Arg Asp Thr Asn
                405                 410                 415

His Ala Ala Glu Ile Ile Glu Arg Gln Gly Val Gln Ala His Ala Leu
            420                 425                 430

Leu Ser Gln Gly Leu Ile Asp Gly Ile Val Ala Glu Thr Glu His Phe
        435                 440                 445

Val Glu Glu Ile Leu Gly Thr Ile Ser Asn Ala Leu Ser Glu Leu Asp
    450                 455                 460

Asn Asn Pro Glu Arg Ala Gly Arg Asp Ser Arg Phe Thr Arg Phe Glu
465                 470                 475                 480

Arg Leu Ala Gln
```

<210> SEQ ID NO 7
<211> LENGTH: 4067
<212> TYPE: DNA
<213> ORGANISM: C. glutamicum NRRL B-11474

<400> SEQUENCE: 7

```
cacctgcgac aacaccgaga accgcgagga agagcaccac gcgcatgagg ccagtgatca      60

ggatgccggt gatagaggaa ttggcaacag ctttgacgct gttggggccg gttcgtccgg     120

agtccagcat gcggtgtgcg ccagcgtaag tgatgtatcc accgacggtt ccacccacaa     180

gtgtggtgat gacaagccag tcgatggtgt caggaagtac tgcattcttc agcgccgagc     240
```

```
caactggagg ttgggagacg aaagccacgt agacggtgag caggatcatc acgacgccga    300
ggaccacgag gaatttgtcc agagcagcac caagtcgctt gaacaagaag atcgcaatcg    360
cgatggccgc ggtgatcacg ccaccaactt tgacgtccca gccaagcaga gcgttaagcc    420
caaggccacc accggcgatg ttgccgatgt tgaatactat gccgccaata cagaccagta    480
cggccagcac ccaaccaaaa cctgggataa cagtattgcc gagttcttgg gcgcgcattt    540
cagagatgcc gatgatgcgc cacacattca gctgcaccgc gatgtcaatg aggatcgaca    600
ccaggatcgc aaatgcgaaa gctgcgccga gctggttggt gaagacagcg gtttgggtga    660
ggaaccctgg gccgatggca gaagttgcca tgaggaagat ggcacccatc agagcgcttc    720
ggccagaggc ggttactgca gcttgcttga gggatggcgc attggctttt gcaatgtcgc    780
caggcccagg ggttccagtg ctggctgaga ctagctggct gtcatcgaca tttttgttgt    840
cggccattgt cgcgctcctt tcgtgggggg ctttcaaaat gattggggta gcttgcacac    900
caatcgcaga ttgttgaaca atcttggtga gttgagagtg agtttagacc caatgtgtcc    960
tgtggcacaa tcccccatag ggattaatag tcattgcata cggccagacc acccccgcaa   1020
gtgcctaggt gtgtccccag tcctttaaga tcagtcacat gacgcaggca atagcagcat   1080
cccttgattt agcggctcga atcaccgcca aaattgatca aggagtgctc actccaggta   1140
ctcgactacc cgaggttgct ttggcagaag aacttggcgt ttcacggaac acgctgcgtg   1200
aagcttttcg ggtactcatg caagacggac tggtggatca tattcccaac cgtggggttt   1260
tcgtgcacac gttcaccaag tcggatgtgg aagatatcta tgcttaccgc acatttatcg   1320
aggttgctgc gattaggtcg gcgcggaaaa atcctcagtt gctggagcag tctttggggg   1380
taatgcgaga ggcctacgaa aggggtgctg cagccaatgc cgtgggtgat tggcaaactg   1440
tcggttctgc caacagtgct tttcacttgg cgattgtgga cctagcagga gtggctaggt   1500
tgtcagcaga cgctcgaaaa gtgttggcgc tggctcgcat cggattcatg gccacctaca   1560
acgtggagac attccatagc atttacgtgg aaaagaacca tcaaatcttg aagtatttgg   1620
ctgccggtga attcgaagag gcggaacaat acctccagaa atacttcgaa gattcgcgcg   1680
atgatttgtc tgcgcaccta ccggaatttt gaaattgcga tagcatagat gacttgacac   1740
tgttgcagca ggcggttttc acctggcctc ttaggatttg gtcaaatggt tgcaacgacg   1800
ccagggaagg aggcgcaccc catggcattt ggatttttta gtagacgtaa gaaaaagaac   1860
aaagacaaaa acccgaatga aaattcagca gtgcccgcac actctgaaga ttcacctcag   1920
gaggtttttg agggtaatgg tcgtcaggta ggcgaccccca ttgaacagca ggttgatcga   1980
gatgctaaag gtcgtctcac agcggcggat ttcttgccgg acgctgatct gccacagctg   2040
aatcgttcgc gtgcaaatat gctgcgccgt gaattggagt accgtttttc actccagaat   2100
gcccacatta atatcgatgg aaacacggcc atgattcagc gttcagatgg cggggcagca   2160
catgtctcgt tgcgcaccct cgcgatgaat gcagctggcc ttgataactt tgatcaactc   2220
cctgaactgg tggaaagctt cgttcacggc acgctggccg atgcaacatt aaacgatctt   2280
tctactgctg acctgtataa agcactgcgc cttcgcctgc tgccaacacc tggtgaaggc   2340
gacgatctag ttgagcatgg actcgaccgg gaaagccaga tccgcgacga ttcaatcctg   2400
cgcaccttca cctctgacat gtcgatcgcg ctggtgctcg ataccgagca tgccatccgc   2460
atccagccac tcaaagagct cgaggagttc gatgacctca gcgccctaga gcgggctgcg   2520
gaccgcaata cctggcaaga gctttacgac gcaaacgttg acgcttcctt cgtcgacgct   2580
gaatcagaca gcgaagggtc atcattttgg gctttcgaat ctaactcgta ctacctgggt   2640
```

```
agtgcaccac tgttcctcaa cgatttgttg gcaaagtggg cacctgacct ggaccaaagt   2700

gatggcgtca tctttgctgt ccctgatcgt gatctgttga ttgcgcgtcc tgtgaccacc   2760

ggcgaagatc tgatgaacgg aatcaccgcg atggtgagga tcgcgatgcg ctttggcctc   2820

gggaacccga cgtcgataag cccgcgcctg cacctgctgc gcgacaacca ggtgaccacc   2880

ttcaccgact tccgcgtcgt ctctcctgaa atggaagctg aatgggaaga cagcgcgttt   2940

gacgcgccac cggccggcgc gatcggcatt gaggtgcgcc cagatccgta tctgatggag   3000

cgcctccaac agggcggctt tggtgatttc ggagatttcg gcaagccccg cgatctagat   3060

atgtagcgaa aaaaggacct tcacttctta agaagtgaag gtccttattt atcgggttct   3120

agtgttagaa cttgttctcg cgctcggtgt gagccatagc aagaacgtcg aggcgcttgt   3180

ccagctcttc ctcggtgagc ttctcgccat caaccaagcc caaatcgatg acagtctggc   3240

ggatggtctt gccctcagcc aaagcagtct tagccacctt tgcagcagct tcgtagccga   3300

ttgcagagtt cagtggggta acgatggaag gtgaagactc agcgagctcc ttcatgtgtg   3360

cctcgtttgg ctcaatgcca tcaacgagac gggttgcgaa cacgcgggaa gtgttagcca   3420

gcaggcgagc ggactcaagc acgttgcgag ccatcactgg gatgaacacg ttgagctcga   3480

actggccctg ggtgccggag aacgcaacag ctgcgtcatt gccgataacc tgagcggaaa   3540

cctgggtagc ggtctcacag agaactgggt tgaccttgcc tggcatgatg gaggaacccg   3600

gctgcaggtc tgggagacgg atctcgccaa gaccggtcag tgggccggag cccatgaggc   3660

ggatatcgtt agcgatcttg tacaaggaga cagcgataac gcgcattgcg ccggagaact   3720

caacaagagc gtcgcgtgca gcctgagcct cgaagtggtt ctcagcttcc ttgagctcct   3780

tgacgtcggt caagttgatc agttcagcaa caaccttgcc gccgaaatca gcggaggtgt   3840

tgataccggt accagcagcg gtgccaccaa tagccagctc accaaggcga ggaagagtag   3900

cctcaacgcg ctcgatgccg agctggatct ggcgagcgta gccaccgaac tcctggccca   3960

gggttactgg aacagcgtcc atcaggtggg tgcggccgga cttaacaacc tcagaccact   4020

cgttagcctt cttcgccaaa gactcgtgca gaactttcag gcctggg                 4067
```

```
<210> SEQ ID NO 8
<211> LENGTH: 1245
<212> TYPE: DNA
<213> ORGANISM: Artificial Sequence
<220> FEATURE:
<223> OTHER INFORMATION: coding sequence for altered cg1144 protein

<400> SEQUENCE: 8

atggcatttg gatttttttag tagacgtaag aaaaagaaca aagacaaaaa cccgaatgaa     60

aattcagcag tgcccgcaca ctctgaagat tcacctcagg aggtttttga gggtaatggt    120

cgtcaggtag gcgaccccat tgaacagcag gttgatcgag atgctaaagg tcgtctcaca    180

gcggcggatt tcttgtcgga cgctgatctg ccacagctga atcgttcgcg tgcaaatatg    240

ctgcgccgtg aattggagta ccgtttttca ctccagaatg cccacattaa tatcgatgga    300

aacacggcca tgattcagcg ttcagatggc ggggcagcac atgtctcgtt gcgcaccctc    360

gcgatgaatg cagctggcct tgataacttt gatcaactcc ctgaactggt ggaaagcttc    420

gttcacggca cgctggccga tgcaacatta aacgatcttt ctactgctga cctgtataaa    480

gcactgcgcc ttcgcctgct gccaacacct ggtgaaggcg acgatctagt tgagcatgga    540

ctcgaccggg aaagccagat ccgcgacgat tcaatcctgc gcaccttcac ctctgacatg    600
```

```
tcgatcgcgc tggtgctcga taccgagcat gccatccgca tccagccact caaagagctc    660

gaggagttcg atgacctcag cgccctagag cgggctgcgg accgcaatac ctggcaagag    720

ctttacgacg caaacgttga cgcttccttc gtcgacgctg aatcagacag cgaagggtca    780

tcattttggg ctttcgaatc taactcgtac tacctgggta gtgcaccact gttcctcaac    840

gatttgttgg caaagtgggc acctgacctg gaccaaagtg atggcgtcat ctttgctgtc    900

cctgatcgtg atctgttgat tgcgcgtcct gtgaccaccg gcgaagatct gatgaacgga    960

atcaccgcga tggtgaggat cgcgatgcgc tttggcctcg ggaacccgac gtcgataagc   1020

ccgcgcctgc acctgctgcg cgacaaccag gtgaccacct tcaccgactt ccgcgtcgtc   1080

tctcctgaaa tggaagctga atgggaagac agcgcgtttg acgcgccacc ggccggcgcg   1140

atcggcattg aggtgcgccc agatccgtat ctgatggagc gcctccaaca gggcggcttt   1200

ggtgatttcg gagatttcgg caagccccgc gatctagata tgtag                   1245
```

```
<210> SEQ ID NO 9
<211> LENGTH: 414
<212> TYPE: PRT
<213> ORGANISM: Artificial Sequence
<220> FEATURE:
<223> OTHER INFORMATION: altered cg1144 protein

<400> SEQUENCE: 9

Met Ala Phe Gly Phe Phe Ser Arg Arg Lys Lys Lys Asn Lys Asp Lys
1               5                   10                  15

Asn Pro Asn Glu Asn Ser Ala Val Pro Ala His Ser Glu Asp Ser Pro
            20                  25                  30

Gln Glu Val Phe Glu Gly Asn Gly Arg Gln Val Gly Asp Pro Ile Glu
        35                  40                  45

Gln Gln Val Asp Arg Asp Ala Lys Gly Arg Leu Thr Ala Ala Asp Phe
    50                  55                  60

Leu Ser Asp Ala Asp Leu Pro Gln Leu Asn Arg Ser Arg Ala Asn Met
65                  70                  75                  80

Leu Arg Arg Glu Leu Glu Tyr Arg Phe Ser Leu Gln Asn Ala His Ile
                85                  90                  95

Asn Ile Asp Gly Asn Thr Ala Met Ile Gln Arg Ser Asp Gly Gly Ala
            100                 105                 110

Ala His Val Ser Leu Arg Thr Leu Ala Met Asn Ala Ala Gly Leu Asp
        115                 120                 125

Asn Phe Asp Gln Leu Pro Glu Leu Val Glu Ser Phe Val His Gly Thr
    130                 135                 140

Leu Ala Asp Ala Thr Leu Asn Asp Leu Ser Thr Ala Asp Leu Tyr Lys
145                 150                 155                 160

Ala Leu Arg Leu Arg Leu Leu Pro Thr Pro Gly Glu Gly Asp Asp Leu
                165                 170                 175

Val Glu His Gly Leu Asp Arg Glu Ser Gln Ile Arg Asp Asp Ser Ile
            180                 185                 190

Leu Arg Thr Phe Thr Ser Asp Met Ser Ile Ala Leu Val Leu Asp Thr
        195                 200                 205

Glu His Ala Ile Arg Ile Gln Pro Leu Lys Glu Leu Glu Glu Phe Asp
    210                 215                 220

Asp Leu Ser Ala Leu Glu Arg Ala Ala Asp Arg Asn Thr Trp Gln Glu
225                 230                 235                 240

Leu Tyr Asp Ala Asn Val Asp Ala Ser Phe Val Asp Ala Glu Ser Asp
                245                 250                 255
```

```
Ser Glu Gly Ser Ser Phe Trp Ala Phe Glu Ser Asn Ser Tyr Tyr Leu
            260                 265                 270

Gly Ser Ala Pro Leu Phe Leu Asn Asp Leu Leu Ala Lys Trp Ala Pro
        275                 280                 285

Asp Leu Asp Gln Ser Asp Gly Val Ile Phe Ala Val Pro Asp Arg Asp
    290                 295                 300

Leu Leu Ile Ala Arg Pro Val Thr Thr Gly Glu Asp Leu Met Asn Gly
305                 310                 315                 320

Ile Thr Ala Met Val Arg Ile Ala Met Arg Phe Gly Leu Gly Asn Pro
                325                 330                 335

Thr Ser Ile Ser Pro Arg Leu His Leu Leu Arg Asp Asn Gln Val Thr
            340                 345                 350

Thr Phe Thr Asp Phe Arg Val Val Ser Pro Glu Met Glu Ala Glu Trp
        355                 360                 365

Glu Asp Ser Ala Phe Asp Ala Pro Pro Ala Gly Ala Ile Gly Ile Glu
    370                 375                 380

Val Arg Pro Asp Pro Tyr Leu Met Glu Arg Leu Gln Gln Gly Gly Phe
385                 390                 395                 400

Gly Asp Phe Gly Asp Phe Gly Lys Pro Arg Asp Leu Asp Met
                405                 410
```

<210> SEQ ID NO 10
<211> LENGTH: 4210
<212> TYPE: DNA
<213> ORGANISM: C. glutamicum NRRL B-11474

<400> SEQUENCE: 10

```
cgcagtcatc cggtggagaa gacttctcgt ggtacctcga acacgtccca ggatcaatgg     60

cccggttggg ttgctggccg gggcacggac ccaagcaaga cctccatcaa agtgacctgg    120

ttgtggatga gcgagccatc ggagttggcg tcaggctctt tggctccctt gtgcagcagt    180

acagtagccg atctgaagct ttcttaaatt cctaatgggg gtagtgtgta gggctggctc    240

taaattgctg acacgtcacc caggctaatt cagcagtaat catttagact tggaatcgct    300

taccagtggt ttcaacaatg cattcaccca gctcacacgt gtggaggtgc cttaatggca    360

aagaggatcg taattatcgg cggtggacct gcaggctatg aagccgcact cgcaggcgct    420

aaatacggtg cagaagttac cgttattgaa gatgtcggag ttggcggatc cgcagtcacc    480

atggactgtg taccttcaaa gtccttcatc gctggtaccg gtatcaaaac cgacctccga    540

cgtgctgatg acatgggact taaccgtggg cttggaaaag cacacctaga aatcgatgca    600

ctgaacatcc gtgtgaagga ccttgcgaaa gcacagtccg aagatatctt gggccagctg    660

cagcgctcag atgtccgcat gattaacggt gtgggccgct ttgatgatta caacaccaag    720

caaaccaccc actacattaa agtcacccac agcgatggct ccgaagaaac cattgagtgc    780

gatctggtgc tggttgcaac tggtgcaacc ccccgcattc ttaaaggtgc agagccagac    840

ggcgagcgca tcttgacctg gcgtcaggtc tatgacattg aagaactccc cacccacctt    900

atcgtggttg gttccggtgt gaccggtgcg gaatttgtct ctgcgtttgc tgaactcggc    960

gtcaaagtca ccatggtggc atcccgtgac cgcattttgc ctcacgatga cgcagatgcc   1020

gcagacgtgc tggaaaccgt tctggctgag cgcggagtat ccctggaaaa gcatgcccgc   1080

gtggagtctg tcacccgcac cgaagacggt ggcgtgtgtg ttcgcactgc tgacggacgt   1140

gaaatctacg gttctcacgc gttgatgact gttggttcca ttccaaacac ggcagatctt   1200
```

```
ggcctggaga acatcggtgt tgagctggca ccatccggcc atatcaaggt tgaccgcgtc   1260
tcccgcacca acatccccgg tgtgtacgca gcaggtgact gtactgacct attcccactg   1320
gcgtccgttg cagcgatgca gggccgtatc gccatgtatc acgcactcgg tgaaggcgtg   1380
agccccatcc gtttgaagac tgttgccacc gcagtgttta cccgcccaga gatcgcagca   1440
gtaggtatca cccatgcaca ggttgattcc ggcgaagtgt ctgctcgcgt gattgtgctt   1500
cctttggcta ctaacccacg cgccaagatg cgttccctgc gccacggttt tgtgaagctg   1560
ttctgccgcc gtaactctgg cctgatcatc ggtggtgtcg tggtggcacc gaccgcgtct   1620
gagctgatcc taccgatcgc tgtggcagtg accaaccgtc tgacagttgc tgatctggct   1680
gataccttcg cggtgtaccc atcattgtca ggttcgatta ctgaagcagc acgtcagctg   1740
gttcaacatg atgatctagg ctaatttttc tgagtctcag attttaagaa aacccaggat   1800
tgctttgtgc actcctgggt tttcactttg ttaagcagtt ttggggaaaa gtgcaaagtt   1860
tgcaaagttt agaaatattt taagaggtaa gatgtctgca ggtggaagcg tttaaatgcg   1920
ttaaacttgg ccaaatgtgg caacctttgc aaggtgaaaa actggggcgg ggttagatcc   1980
tggggggttt atttcattca ctttggcttg aagtcgtgca ggtcagggga gtgttgcccg   2040
aaaacattga gaggaaaaca aaaaccgatg tttgattggg ggaatcgggg gttacgatac   2100
taggacgaag tgactgctat cacccttggc ggtctcttgt tgaaaggaat aattactcta   2160
gtgtcgactc acacatcttc aacgcttcca gcattcaaaa agatcttggt agcaaaccgc   2220
ggcgaaatcg cggtccgtgc tttccgtgca gcactcgaaa ccggtgcagc cacggtagct   2280
atttaccccc gtgaagatcg gggatcattc caccgctctt ttgcttctga agctgtccgc   2340
attggtactg aaggctcacc agtcaaggcg tacctggaca tcgatgaaat tatcggtgca   2400
gctaaaaaag ttaaagcaga tgctatttac ccgggatatg gcttcctgtc tgaaaatgcc   2460
cagcttgccc gcgagtgcgc ggaaaacggc attactttta ttggcccaac cccagaggtt   2520
cttgatctca ccggtgataa gtctcgtgcg gtaaccgccg cgaagaaggc tggtctgcca   2580
gttttggcgg aatccacccc gagcaaaaac atcgatgaca tcgttaaaag cgctgaaggc   2640
cagacttacc ccatctttgt aaaggcagtt gccggtggtg gcggacgcgg tatgcgcttt   2700
gtttcttcac ctgatgagct ccgcaaattg gcaacagaag catctcgtga agctgaagcg   2760
gcattcggcg acggttcggt atatgtcgaa cgtgctgtga ttaacccccca gcacattgaa   2820
gtgcagatcc ttggcgatcg cactggagaa gttgtacacc tttatgaacg tgactgctca   2880
ctgcagcgtc gtcaccaaaa agttgtcgaa attgcgccag cacagcattt ggatccagaa   2940
ctgcgtgatc gcatttgtgc ggatgcagta aagttctgcc gctccattgg ttaccagggc   3000
gcgggaaccg tggaattctt ggtcgatgaa aagggcaacc acgttttcat cgaaatgaac   3060
ccacgtatcc aggttgagca caccgtgact gaagaagtca ccgaggtgga cctggtgaag   3120
gcgcagatgc gcttggctgc tggtgcaacc ttgaaggaat tgggtctgac ccaagataag   3180
atcaagaccc acggtgcagc actgcagtgc cgcatcacca cggaagatcc aaacaacggc   3240
ttccgcccag ataccggaac tatcaccgcg taccgctcac caggcggagc tggcgttcgt   3300
cttgacggtg cagctcagct cggtggcgaa atcaccgcac actttgactc catgctggtg   3360
aaaatgacct gccgtggttc cgactttgaa actgctgttg ctcgtgcaca gcgcgcgttg   3420
gctgagttca ccgtgtctgg tgttgcaacc aacattggtt tcttgcgtgc gttgctgcgg   3480
gaagaggact tcacttccaa gcgcatcgcc accggattta tcggcgatca cccacacctc   3540
cttcaggctc cacctgcgga tgatgagcag ggacgcatcc tggattactt ggcagatgtc   3600
```

```
accgtgaaca agcctcatgg tgtgcgtcca aaggatgttg cagcaccaat cgataagctg   3660
cccaacatca aggatctgcc actgccacgc ggttcccgtg accgcctgaa gcagcttggc   3720
ccagccgcgt ttgctcgtga tctccgtgag caggacgcac tggcagttac tgataccacc   3780
ttccgcgatg cacaccagtc tttgcttgcg acccgagtcc gctcattcgc actgaagcct   3840
gcggcagagg ccgtcgcaaa gctgactcct gagcttttgt ccgtggaggc ctggggcggc   3900
gcgacctacg atgtggcgat gcgtttcctc tttgaggatc cgtgggacag gctcgacgag   3960
ctgcgcgagg cgatgccgaa tgtaaacatt cagatgctgc ttcgcggccg caacaccgtg   4020
ggatacaccc cgtacccaga ctccgtctgc cgcgcgtttg ttaaggaagc tgccacctcc   4080
ggcgtggaca tcttccgcat cttcgacgcg cttaacgacg tctcccagat gcgtccagca   4140
atcgacgcag tcctggagac caacaccgcg gtagccgagg tggctatggc ttattctggt   4200
gatctctctg                                                          4210
```

```
<210> SEQ ID NO 11
<211> LENGTH: 93
<212> TYPE: DNA
<213> ORGANISM: Artificial Sequence
<220> FEATURE:
<223> OTHER INFORMATION: promoter 1860

<400> SEQUENCE: 11

cttagctttg acctgcacaa atagttgcaa attgtcccac atacacataa agtagcttgc     60
gtatttaaaa ttatgaacct aaggggttta gca                                  93
```

```
<210> SEQ ID NO 12
<211> LENGTH: 3516
<212> TYPE: DNA
<213> ORGANISM: Artificial Sequence
<220> FEATURE:
<223> OTHER INFORMATION: promoter 1860 and pyc coding sequence

<400> SEQUENCE: 12

cttagctttg acctgcacaa atagttgcaa attgtcccac atacacataa agtagcttgc     60
gtatttaaaa ttatgaacct aaggggttta gcagtgtcga ctcacacatc ttcaacgctt    120
ccagcattca aaaagatctt ggtagcaaac cgcggcgaaa tcgcggtccg tgctttccgt    180
gcagcactcg aaaccggtgc agccacggta gctatttacc cccgtgaaga tcggggatca    240
ttccaccgct cttttgcttc tgaagctgtc cgcattggta ctgaaggctc accagtcaag    300
gcgtacctgg acatcgatga aattatcggt gcagctaaaa aagttaaagc agatgctatt    360
tacccgggat atggcttcct gtctgaaaat gcccagcttg cccgcgagtg cgcggaaaac    420
ggcattactt ttattggccc aaccccagag gttcttgatc tcaccggtga taagtctcgt    480
gcggtaaccg ccgcgaagaa ggctggtctg ccagttttgg cggaatccac cccgagcaaa    540
aacatcgatg acatcgttaa aagcgctgaa ggccagactt accccatctt tgtaaaggca    600
gttgccggtg gtggcggacg cggtatgcgc tttgtttctt cacctgatga gctccgcaaa    660
ttggcaacag aagcatctcg tgaagctgaa gcggcattcg gcgacggttc ggtatatgtc    720
gaacgtgctg tgattaaccc ccagcacatt gaagtgcaga tccttggcga tcgcactgga    780
gaagttgtac acctttatga acgtgactgc tcactgcagc gtcgtcacca aaaagttgtc    840
gaaattgcgc cagcacagca tttggatcca gaactgcgtg atcgcatttg tgcggatgca    900
gtaaagttct gccgctccat tggttaccag ggcgcgggaa ccgtggaatt cttggtcgat    960
```

-continued

```
gaaaagggca accacgtttt catcgaaatg aacccacgta tccaggttga gcacaccgtg   1020
actgaagaag tcaccgaggt ggacctggtg aaggcgcaga tgcgcttggc tgctggtgca   1080
accttgaagg aattgggtct gacccaagat aagatcaaga cccacggtgc agcactgcag   1140
tgccgcatca ccacggaaga tccaaacaac ggcttccgcc cagataccgg aactatcacc   1200
gcgtaccgct caccaggcgg agctggcgtt cgtcttgacg gtgcagctca gctcggtggc   1260
gaaatcaccg cacactttga ctccatgctg gtgaaaatga cctgccgtgg ttccgacttt   1320
gaaactgctg ttgctcgtgc acagcgcgcg ttggctgagt tcaccgtgtc tggtgttgca   1380
accaacattg gtttcttgcg tgcgttgctg cgggaagagg acttcacttc caagcgcatc   1440
gccaccggat ttatcggcga tcacccacac ctccttcagg ctccacctgc ggatgatgag   1500
cagggacgca tcctggatta cttggcagat gtcaccgtga acaagcctca tggtgtgcgt   1560
ccaaaggatg ttgcagcacc aatcgataag ctgcccaaca tcaaggatct gccactgcca   1620
cgcggttccc gtgaccgcct gaagcagctt ggcccagccg cgtttgctcg tgatctccgt   1680
gagcaggacg cactggcagt tactgatacc accttccgcg atgcacacca gtctttgctt   1740
gcgacccgag tccgctcatt cgcactgaag cctgcggcag aggccgtcgc aaagctgact   1800
cctgagcttt tgtccgtgga ggcctggggc ggcgcgacct acgatgtggc gatgcgtttc   1860
ctctttgagg atccgtggga caggctcgac gagctgcgcg aggcgatgcc gaatgtaaac   1920
attcagatgc tgcttcgcgg ccgcaacacc gtgggataca ccccgtaccc agactccgtc   1980
tgccgcgcgt ttgttaagga agctgccacc tccggcgtgg acatcttccg catcttcgac   2040
gcgcttaacg acgtctccca gatgcgtcca gcaatcgacg cagtcctgga gaccaacacc   2100
gcggtagccg aggtggctat ggcttattct ggtgatctct ctgatccaaa tgaaaagctc   2160
tacaccctgg attactacct aaagatggca gaggagatcg tcaagtctgg cgctcacatt   2220
ctggccatta aggatatggc tggtctgctt cgcccagctg cggtaaccaa gctggtcacc   2280
gcactgcgcc gtgaattcga tctgccagtg cacgtgcaca cccacgacac tgcgggtggc   2340
cagttggcta cctactttgc tgcagctcaa gctggtgcag atgctgttga cggtgcttcc   2400
gcaccactgt ctggcaccac ctcccagcca tccctgtctg ccattgttgc tgcattcgcg   2460
cacacccgtc gcgataccgg tttgagcctc gaggctgttt ctgacctcga gccgtactgg   2520
gaagctgtgc gcggactgta cctgccattt gagtctggaa ccccaggccc aaccggtcgc   2580
gtctaccgcc acgaaatccc aggcggacag ttgtccaacc tgcgtgcaca ggccaccgca   2640
ctgggccttg ctgatcgctt cgagctcatc gaagacaact acgcagccgt taatgagatg   2700
ctgggacgcc caaccaaggt caccccatcc tccaaggttg ttggcgacct cgcactccac   2760
ctggttggtg cgggtgtaga tccagcagac tttgctgcag acccacaaaa gtacgacatc   2820
ccagactctg tcatcgcgtt cctgcgcggc gagcttggta accctccagg tggctggcca   2880
gaaccactgc gcacccgcgc actggaaggc cgctccgaag gcaaggcacc tctgacggaa   2940
gttcctgagg aagagcaggc gcacctcgac gctgatgatt ccaaggaacg tcgcaacagc   3000
ctcaaccgcc tgctgttccc gaagccaacc gaagagttcc tcgagcaccg tcgccgcttc   3060
ggcaacacct ctgcgctgga tgatcgtgaa ttcttctacg gactggtcga gggccgcgag   3120
actttgatcc gcctgccaga tgtgcgcacc ccactgcttg ttcgcctgga tgcgatctct   3180
gagccagacg ataagggtat gcgcaatgtt gtggccaacg tcaacggcca gatccgccca   3240
atgcgtgtgc gtgaccgctc cgttgagtct gtcaccgcaa ccgcagaaaa ggcagattcc   3300
tccaacaagg gccatgttgc tgcaccattc gctggtgttg tcactgtgac tgttgctgaa   3360
```

```
ggtgatgagg tcaaggctgg agatgcagtc gcaatcatcg aggctatgaa gatggaagca   3420

acaatcactg cttctgttga cggcaagatt gaacgcgttg tggttcctgc tgcaacgaag   3480

gtggaaggtg gcgacttgat cgtcgtcgtt tcctaa                             3516
```

<210> SEQ ID NO 13
<211> LENGTH: 4101
<212> TYPE: DNA
<213> ORGANISM: C. glutamicum NRRL B-11474

<400> SEQUENCE: 13

```
catcgtctaa aaggcctggg cgaccacgta aagacgggca cgacgagaag atcatcgacg     60

caactttacg gctcatcgac agcaatcgtc ccgtcacggt caatgcagtt gtcaaagaaa    120

gcggagtggc acgtgcagcg gtttatcgac gctggcccag gctagtggat ctagtagcgg    180

aagctttaga tgccgggcga gctccagttg aaatagatac cccaggggac atcaaagaga    240

ccttgattga tgggctgttt acaaatcagg cgaaaaccac tggagtctcc tatcctcgtc    300

agcgatttcg caaacggctc gagttggtga tgtcagatca agaattacag ctcgcctaat    360

ggaattcaca tgtgaagaga cgtcgagaag caaatattcg cgcgctgcaa gtcgcgcaag    420

aaaaaggcca aatccgggcg gatctagaca tcgaggcgtg cctcgatgca atccttgggg    480

tgttttatta ccaatcggtc gcgcgtggag taaatttcac cgaccaaggt acaacgcaac    540

gatgcagaga agccttggag gtgatctggc atggaatgga accttaaatt caggttctga    600

cgaggtgcga agcaagttgt cgcgcgccgc acctcagtat ccggatcaac ttaatttcga    660

agtgctgggt tttctcgcgc atacccaatg cgtaccgatg tgctcatgag cgaaaaacag    720

gccacgataa gtttcttaaa acttatcgtg gcctgcttct atatttgtgc gccctgacgg    780

gctcgaaccg ccgacctgct gggtgtaaac cagctgctct tccagctgag ctaaaggcgc    840

gcacgtgctt ttctagaacc accttggtgg cctcgaaagc aacgagtgaa atactaacac    900

acaatctcca cagacctaaa atcgctgctc aggccgtgga aattagcgat tgttaaggct    960

tcttgtttcc acgctggacg aggcaagaac cttgccaatt accgagacgt tccgccttgg   1020

tctgcacgag acctgccagt tgtgctgatt cagagataac tccaggagcc agggctcctt   1080

ctttaccaat gccaggagtc aacacccaga tacgaccatt ctcagcgagg gagcggatgg   1140

aatccacaag tccgtcgacg agatcgccgt catcctcgcg ccaccagagc agcacgacat   1200

cgcacagctc gtcggtttct tcatcgagta gttcctcacc gattgcatct tcgatggact   1260

cgctgatcag cgtgtcggaa tcttcatccc atccaatttc ttgaacgata tgacccgatt   1320

gaatgccgag tagttgagca taatcctggg caccttgctt gactgcgccc ggagcgtcgg   1380

ccactttaat aatcctcctc gtgtgggccc cgatgtgttt ttcgattaca tggattcaac   1440

atgaaaccgc ggggctattg atatatccga attgcacatt accgtccaac cggtactttg   1500

aaccaccttt ccctggaatt ttttcctttt cctccccctt tacgctcaag aatcaatgaa   1560

ttcaatcact ggccagcgat taacttttcg agttttcagt cttggatttc cacaattctc   1620

ttcaaaataa tggtggctag atttttcatc aaaccctcac caaaaggaca tcagacctgt   1680

agttttatgc gattcgcgtc aaacgtgaga gaaacatcac atctcacggg aaactacccg   1740

ataattcttt gcaaaacttt gcaaagggta atgaacatgc agctagtttc cgtagaaatg   1800

ttctttaaaa aatccacaac aattgccagg aagcacaccg attgatggat acctgaaatc   1860

ccagtgagcg caccactccc cttacgtcac agtctgtaaa acaaatcttc ggtgttgcgt   1920
```

-continued

```
atccttgtta ataacttatg cgttgaccca ttcgtgcact tcggtgtgcc acaattaggt   1980
acgaccaaga atgggaccgg gaaaccggga cgtataaacg aaataaaaca ttccaacagg   2040
aggtgtggaa atggccgatc aagcaaaact tggtggtaag ccctcggatg actctaactt   2100
cgcgatgatc cgcgatggcg tggcatctta tttgaacgac tcagatccgg aggagaccaa   2160
cgagtggatg gattcactcg acggattact ccaggagtct tctccagaac gtgctcgtta   2220
cctcatgctt cgtttgcttg agcgtgcatc tgcaaagcgc gtatctcttc ccccaatgac   2280
gtcaaccgac tacgtcaaca ccattccaac ctctatggaa cctgaattcc caggcgatga   2340
ggaaatggag aagcgttacc gtcgttggat tcgctggaac gcagccatca tggttcaccg   2400
cgctcagcga ccaggcatcg gcgtcggcgg acacatttcc acttacgcag gcgcagcccc   2460
tctgtacgaa gttggcttca accacttctt ccgcggcaag gatcacccag gcggcggcga   2520
ccagatcttc ttccagggcc acgcatcacc aggtatgtac gcacgtgcat tcatggaggg   2580
tcgcctttct gaagacgatc tcgatggctt ccgtcaggaa gtttcccgtg agcagggtgg   2640
cattccgtcc taccctcacc cacacggtat gaaggacttc tgggagttcc caactgtgtc   2700
catgggtctt ggcccaatgg atgccattta ccaggcacgt ttcaaccgct acctcgaaaa   2760
ccgtggcatc aaggacacct ctgaccagca cgtctgggcc ttccttggcg acggcgaaat   2820
ggacgagcca gaatcacgtg gtctcatcca gcaggctgca ctgaacaacc tggacaacct   2880
gaccttcgtg gttaactgca acctgcagcg tctcgacgga cctgtccgcg gtaacaccaa   2940
gatcatccag gaactcgagt ccttcttccg tggcgcaggc tggtctgtga tcaaggttgt   3000
ttggggtcgc gagtgggatg aacttctgga gaaggaccag gatggtgcac ttgttgagat   3060
catgaacaac acctccgatg gtgactacca gaccttcaag gctaacgacg gcgcatatgt   3120
tcgtgagcac ttcttcggac gtgacccacg caccgcaaag ctcgttgaga acatgaccga   3180
cgaagaaatc tggaagctgc cacgtggcgg ccacgattac cgcaaggttt acgcagccta   3240
caagcgagct cttgagacca aggatcgccc aaccgtcatc cttgctcaca ccattaaggg   3300
ctacggactc ggccacaact tcgaaggccg taacgcaacc caccagatga agaagctgac   3360
gcttgatgat ctgaagttgt tccgcgacaa gcagggcatc ccaatcaccg atgagcagct   3420
ggagaaggat ccttaccttc ctccttacta ccacccaggt gaagacgctc ctgaaatcaa   3480
gtacatgaag gaacgtcgcg cagcgctcgg tggctacctg ccagagcgtc gtgagaacta   3540
cgatccaatt caggttccac cactggataa gcttcgctct gtccgtaagg gctccggcaa   3600
gcagcagatc gctaccacta tggcgactgt tcgtaccttc aaggaactga tgcgcgataa   3660
gggcttggct gatcgccttg tcccaatcat tcctgatgag gcacgtacct tcggtcttga   3720
ctcttggttc ccaaccttga agatctacaa cccgcacggt cagaactacg tgcctgttga   3780
ccacgacctg atgctctcct accgtgaggc acctgaagga cagatcctgc acgaaggcat   3840
caacgaggct ggttccgtgg catcgttcat cgctgcgggt acctcctacg ccacccacgg   3900
caaggccatg attccgctgt acatcttcta ctcgatgttc ggattccagc gcaccggtga   3960
ctccatctgg gcagcagccg atcagatggc acgtggcttc ctcttgggcg ctaccgcagg   4020
tcgcaccacc ctgaccggtg aaggcctcca gcacatggat ggacactccc ctgtcttggc   4080
ttccaccaac gagggtgtcg a                                              4101
```

<210> SEQ ID NO 14
<211> LENGTH: 2051
<212> TYPE: DNA
<213> ORGANISM: Artificial Sequence

```
<220> FEATURE:
<223> OTHER INFORMATION: altered aceE coding sequence

<400> SEQUENCE: 14

ttggccgatc aagcaaaact tggtggtaag ccctcggatg actctaactt cgcgatgatc      60

cgcgatggcg tggcatctta tttgaacgac tcagatccgg aggagaccaa cgagtggatg     120

gattcactcg acggattact ccaggagtct tctccagaac gtgctcgtta cctcatgctt     180

cgtttgcttg agcgtgcatc tgcaaagcgc gtatctcttc ccccaatgac gtcaaccgac     240

tacgtcaaca ccattccaac ctctatggaa cctgaattcc caggcgatga ggaaatggag     300

aagcgttacc gtcgttggat tcgctggaac gcagccatca tggttcaccg cgctcagcga     360

ccaggcatcg gcgtcggcgg acacatttcc acttacgcag gcgcagcccc tctgtacgaa     420

gttggcttca accacttctt ccgcggcaag gatcacccag gcggcggcga ccagatcttc     480

ttccagggcc acgcatcacc aggtatgtac gcacgtgcat tcatggaggg tcgccttttct    540

gaagacgatc tcgatggctt ccgtcaggaa gtttcccgtg agcagggtgg cattccgtcc     600

taccctcacc cacacggtat gaaggacttc tgggagttcc caactgtgtc catgggtctt     660

ggcccaatgg atgccattta ccaggcacgt ttcaaccgct acctcgaaaa ccgtggcatc     720

aaggacacct ctgaccagca cgtctgggcc ttccttggcg acggcgaaat ggacgagcca     780

gaatcacgtg gtctcatcca gcaggctgca ctgaacaacc tggacaacct gaccttcgtg     840

gttaactgca acctgcagcg tctcgacgga cctgtccgcg gtaacaccaa gatcatccag     900

gaactcgagt ccttcttccg tggcgcaggc tggtctgtga tcaaggttgt ttggggtcgc     960

gagtgggatg aacttctgga gaaggaccag gatggtgcac ttgttgagat catgaacaac    1020

acctccgatg gtgactacca gaccttcaag gctaacgacg gcgcatatgt tcgtgagcac    1080

ttcttcggac gtgacccacg caccgcaaag ctcgttgaga acatgaccga cgaagaaatc    1140

tggaagctgc cacgtggcgg ccacgattac cgcaaggttt acgcagccta caagcgagct    1200

cttgagacca aggatcgccc aaccgtcatc cttgctcaca ccattaaggg ctacggactc    1260

ggccacaact tcgaaggccg taacgcaacc caccagatga agaagctgac gcttgatgat    1320

ctgaagttgt tccgcgacaa gcagggcatc ccaatcaccg atgagcagct ggagaaggat    1380

ccttaccttc ctccttacta ccacccaggt gaagacgctc ctgaaatcaa gtacatgaag    1440

gaacgtcgcg cagcgctcgg tggctacctg ccagagcgtc gtgagaacta cgatccaatt    1500

caggttccac cactggataa gcttcgctct gtccgtaagg gctccggcaa gcagcagatc    1560

gctaccacta tggcgactgt tcgtaccttc aaggaactga tgcgcgataa gggcttggct    1620

gatcgccttg tcccaatcat tcctgatgag gcacgtacct tcggtcttga ctcttggttc    1680

ccaaccttga agatctacaa cccgcacggt cagaactacg tgcctgttga ccacgacctg    1740

atgctctcct accgtgaggc acctgaagga cagatcctgc acgaaggcat caacgaggct    1800

ggttccgtgg catcgttcat cgctgcgggt acctcctacg ccacccacgg caaggccatg    1860

attccgctgt acatcttcta ctcgatgttc ggattccagc gcaccggtga ctccatctgg    1920

gcagcagccg atcagatggc acgtggcttc ctcttgggcg ctaccgcagg tcgcaccacc    1980

ctgaccggtg aaggcctcca gcacatggat ggacactccc ctgtcttggc ttccaccaac    2040

gagggtgtcg a                                                         2051

<210> SEQ ID NO 15
<211> LENGTH: 4099
<212> TYPE: DNA
<213> ORGANISM: C. glutamicum NRRL B-11474
```

<400> SEQUENCE: 15

```
gaatcttatc ccatggctaa gaaagtagac acctcgaacg ctacccccgc tctagccctt     60
cttacggaga ggcaaattcc ttttgagctg gatgttcatg atgtagatcc aaaatcatca    120
aagggcttcg cattggatgc ctctgaagta atgggtgtgg agccggaagt ggtgtttaaa    180
acgctcatgg cagatattga tggtgaacac gtggtcgcga ttgttccagc cagcagcacg    240
ttgaatctca agcagttggc taaggctgga aaaggtaagc atgcaaacat gatggatcgc    300
agccgtgcac aggtagtcac ggggtatgtc cctggtggaa tctcaccgat agggcagaag    360
aataagcacc gcgtgttttt ggatgagtct gcaattctcc aggagcgaat ctacgtcagc    420
gcaggacgcc gaggctggtc actgattatc gccccggatg atgttcttct ggctaccgat    480
ggggtttacg cggatattgc tgatcattca taaaaggtaa aacccacccc cgcaggggtg    540
cgtcgtaaag caagctcctt ttcttagtac ggcgcgatag tggactcgtg cgcgtcgatg    600
ttgatgcggc cgtgcacgga cgggaatgcg cgctgcgcgc agttctcgcg ggtgcacact    660
cggcagccgg acccgatggg ggtggcggtg gataggtcct ggaggttgaa gccgcgggag    720
tacacggtgc ggtcggcgtg gcgcgcttcg cagccgagcc cgatggcgaa cattttgtcc    780
acttcgccga accgggcttc gtggtgtcgc acggtgcgtg agatccacag gtagttgcgt    840
ccgtcgggca tttgcgcgaa ttggcggagc acttggccgg ggttggtgaa ggtttcaaac    900
acgttccaca gggggcaggt gccgccgtag tgggtgaagt ggaagccggt ggcggattgg    960
cgtttggaca tgttgccggc gcggtcgacg cgcacgaagg taaacgggat gccgcgcagg   1020
ttgggacgct gcagggtgga caggcggtgg gcggtcgtct cgtagcccac gccgaaaagc   1080
tgacctaggt attcgatgtc gtagccggat tttcggcct  cggagtggaa gattttgtag   1140
ggcagcatta cggcggcggc gaagtaggag gcgacgccgc ggatggctag ggtgcgggct   1200
tcgggggtgg accagatgcc gtcgtcgacg atgccttcga tgaggtcgtt ggcttctagg   1260
tagccgagtt cggtggccat gcggaaggcg cgttgtccgg ggttgaggcg tgcgtggatt   1320
gtcagtaggc gcgtctcggg gtcaaagtgg tgcagcgtgc cggattcctc tttggaggag   1380
gtgatggtga catcgtgatc catttgcagg cgcctggcga tcgaatcttc catggcgcgg   1440
gaatcgtacg gctgccagcc cagttgcgcg gcgatggctt cggcgcggcg gtcgagcgca   1500
tcgaagtagt tttggcgggc gtaaatgaaa tcgcgcacct cttcgtgcgg catgctcacg   1560
gcctccgcga tggggcgacg ttcctcaggc gtgttggtgc gattgtccac tgcgatggag   1620
aacttgtcgc gtacgtttcg gtagcgctgg tgcatttcca ccatggcgcg cgccagctgc   1680
gggtggttgt acaccatctc cgatagctct tggagctcca cgttcgcggg gttgatctcc   1740
cggtccaaca tgacatcctg aacttcagct aaaaggcggg aatcatcgtc gcgggagaaa   1800
aacgttgcgt ctacgccgaa cgcctcggtg atgcgcaata acaccggtac ggtgagcggg   1860
cgtacgtcgt gctcaatctg atttacataa ctggcagata agccaagggt tgctgccaac   1920
gacgcctggc tcaggtctct ttcgcggcgc agttggcgca gcctggaccc cacatatgtc   1980
tttcccatgg cgcaactata gcgtgatcac catcacctta accactcttg gcattgaggt   2040
gttgcaaagt tgttgatttt cgcttttcga cgcagcccgc cgccatcggg tgcccggcgt   2100
ggtcaggcca catgcgcccc gggaactttt tgggcaccta cggtgcaaca gttgcgaaaa   2160
ttgtgtcacc tgcgcaaagc cttgcttcta ttcgggaaat tcgggtgtct aaactttttg   2220
gttgatacca aacggggtta gaaactgttc agatcggtat cctgtgagga agctcacctt   2280
```

```
ggttttagaa tgttgaaaaa gcctcacgtt tccgcaggta gagcacactc aattaaatga   2340

gcgtcaaacg acaataaagt aaggctaccc taataactgg ggttttatgc ctctaaacag   2400

tcagttgggg gcggtagggg agcgtcccat gactggttaa tgcctcgatc tgggacgtac   2460

agtaacagcg acactggagg tgccatgact gttagaaatc ccgaccgtga ggcaatccgt   2520

cacggaaaaa ttacgacgga ggcgctgcgt gagcgtcccg catacccgac ctgggcaatg   2580

aagctgacca tggccatcac tggcctaatc ttcggtggct tcgttcttgt tcacatgatc   2640

ggaaacctga aaatcttcat gccggactac gcagccgatt ctgcgcatcc gggtgaagca   2700

caagtagatg tctacggcga gttcctgcgt gagatcggat ccccgatcct cccacacggc   2760

tcagtcctct ggatcctacg tattatcctg ctggtcgcat tggttctgca catctactgt   2820

gcattcgcat tgaccggccg ttctcaccag tcccgcggaa agttccgccg taccaacctc   2880

gttggcggct tcaactcctt cgcgacccgc tccatgctgg tgaccggaat cgttctcctt   2940

gcgttcatta tcttccacat cctcgacctg accatgggtg ttgctccagc agccccaact   3000

tcattcgagc acggcgaagt atacgcaaat atggtggctt cctttagccg ctggcctgta   3060

gcaatttggt acatcattgc caacctggtc ctgttcgtcc acctgtctca cggcatctgg   3120

cttgcagtct ctgacctggg aatcaccgga cgtcgctgga gggcaatcct cctcgcagtt   3180

gcgtacatcg ttcctgcact ggtcctgatc ggcaacatca ccattccgtt cgccatcgct   3240

gttggctgga ttgcgtaaag gttaggaaga atttatgagc actcactctg aaaccacccg   3300

cccagagttc atccacccag tctcagtcct cccagaggtc tcagctggta cggtccttga   3360

cgctgctgag ccagcaggcg ttcccaccaa agatatgtgg gaataccaaa aagaccacat   3420

gaacctggtc tccccactga accgacgcaa gttccgcgtc ctcgtcgttg gcaccggcct   3480

gtccggtggc gctgcagcag cagccctcgg cgaactcgga tacgacgtca aggcgttcac   3540

ctaccacgac gcacctcgcc gtgcgcactc cattgctgca cagggtggcg ttaactccgc   3600

ccgcggcaag aaggtagaca acgacggcgc ataccgccac gtcaaggaca ccgtcaaggg   3660

cggcgactac cgtggccgcg agtccgactg ctggcgtctc gccgtcgagt ccgtccgcgt   3720

catcgaccac atgaacgcca tcggtgcacc attcgcccgc gaatacggtg gcgccttggc   3780

aacccgttcc ttcggtggtg tgcaggtctc ccgtacctac tacacccgtg gacaaaccgg   3840

acagcagctg cagctctcca ccgcatccgc actacagcgc cagatccacc tcggctccgt   3900

agagatcttc acccataacg aaatggttga cgtaattgtc accgaacgta atggtgaaaa   3960

gcgctgcgaa ggcctgatca tgcgcaacct gatcaccggc gagctcaccg cacacaccgg   4020

ccatgccgtt atcctggcaa ccggtggcta cggcaacgtg taccacatgt ccaccctggc   4080

gaagaactcc aacgcctcg                                                4099
```

<210> SEQ ID NO 16
<211> LENGTH: 1338
<212> TYPE: DNA
<213> ORGANISM: Artificial Sequence
<220> FEATURE:
<223> OTHER INFORMATION: codon-optimized lysA coding sequence

<400> SEQUENCE: 16

```
atggctaccg tagaaaactt caatgaacta cccgcgcatg tctggcctcg taatgcagtt     60

cgccaggaag atggcgttgt tacggtagcg ggagtgccgc ttcctgatct tgcagaagag    120

tacggtacac ctctctttgt tgttgacgaa gatgatttcc gttctcgatg tcgtgatatg    180

gctaccgcat ttgggggacc aggcaatgtg cattacgctt ccaaagcgtt ccttactaaa    240
```

```
actattgcac gctgggtaga cgaagaggga ctagcgttgg atatcgcgtc tattaatgaa    300

ctgggaattg cgttggcggc tggattcccg gcttcacgaa tcacggcaca tggtaataat    360

aaaggtgtcg agtttctgcg cgctcttgta cagaatggtg tgggtcatgt agtgcttgat    420

tctgctcaag aactagaact tcttgactat gttgcagcgg gcgaaggcaa gattcaagat    480

gttttgattc gtgttaagcc aggcattgaa gctcatactc atgaattcat cgcgacgagt    540

catgaagatc agaaatttgg attcagtctg gcgtcaggtt ccgctttcga agcggctaaa    600

gctgctaata acgctgagaa tcttaatctg gtagggctac attgtcatgt cggatcccag    660

gtttttgatg ctgagggttt caaacttgcg gctgaacgcg ttttgggttt gtatagtcaa    720

attcatagtg agcttggtgt agctctacca gaacttgatc ttggtggggg atatggtatt    780

gcgtatactg cggctgaaga accgcttaat gtagctgaag ttgcgtccga tttgcttacg    840

gctgtcggta aaatggcagc agaattgggt atcgatgcgc caactgttct tgtggaaccg    900

ggacgggcta ttgcgggtcc atctacagtt actatttacg aggtcggaac gactaaagat    960

gtgcatgtcg atgatgataa gactcgtcgc tatattgctg tcgacggtgg aatgtccgat   1020

aacattcgtc ctgcgctcta tggatctgag tatgatgcac gcgtcgtatc tcgttttgct   1080

gagggtgacc cggtttcaac tcgcatcgtg ggatctcatt gtgaatctgg agacattctg   1140

atcaatgacg aaatttatcc gtctgatatt acgagtggtg attttcttgc tttggctgcg   1200

actggcgcat attgttacgc aatgtctagt cgttataacg cttttactcg tccagctgtt   1260

gtatccgtgc gggcgggatc atctcgcctt atgcttagac gtgaaacctt ggacgacatt   1320

ctttcccttg aggcgtag                                                 1338
```

<210> SEQ ID NO 17
<211> LENGTH: 1516
<212> TYPE: DNA
<213> ORGANISM: Artificial Sequence
<220> FEATURE:
<223> OTHER INFORMATION: promoter cg0007_39-codon-optimized lysA coding sequence-sod terminator

<400> SEQUENCE: 17

```
tgccgtttct cgcgttgtgt gtggtactac gtggggacct aagcgtgtat tatggaaacg     60

tctgtatcgg ataagtagcg aggagtgttc gttaaaaatg gctaccgtag aaaacttcaa    120

tgaactaccc gcgcatgtct ggcctcgtaa tgcagttcgc caggaagatg gcgttgttac    180

ggtagcggga gtgccgcttc ctgatcttgc agaagagtac ggtacacctc tctttgttgt    240

tgacgaagat gatttccgtt ctcgatgtcg tgatatggct accgcatttg gggggaccagg    300

caatgtgcat tacgcttcca aagcgttcct tactaaaact attgcacgct gggtagacga    360

agagggacta gcgttggata tcgcgtctat taatgaactg ggaattgcgt tggcggctgg    420

attcccggct tcacgaatca cggcacatgg taataataaa ggtgtcgagt ttctgcgcgc    480

tcttgtacag aatggtgtgg gtcatgtagt gcttgattct gctcaagaac tagaacttct    540

tgactatgtt gcagcgggcg aaggcaagat tcaagatgtt ttgattcgtg ttaagccagg    600

cattgaagct catactcatg aattcatcgc gacgagtcat gaagatcaga aatttggatt    660

cagtctggcg tcaggttccg ctttcgaagc ggctaaagct gctaataacg ctgagaatct    720

taatctggta gggctacatt gtcatgtcgg atcccaggtt tttgatgctg agggtttcaa    780

acttgcggct gaacgcgttt tgggtttgta tagtcaaatt catagtgagc ttggtgtagc    840

tctaccagaa cttgatcttg gtgggggata tggtattgcg tatactgcgg ctgaagaacc    900
```

```
gcttaatgta gctgaagttg cgtccgattt gcttacggct gtcggtaaaa tggcagcaga    960

attgggtatc gatgcgccaa ctgttcttgt ggaaccggga cgggctattg cgggtccatc   1020

tacagttact atttacgagg tcggaacgac taaagatgtg catgtcgatg atgataagac   1080

tcgtcgctat attgctgtcg acggtggaat gtccgataac attcgtcctg cgctctatgg   1140

atctgagtat gatgcacgcg tcgtatctcg ttttgctgag ggtgacccgg tttcaactcg   1200

catcgtggga tctcattgtg aatctggaga cattctgatc aatgacgaaa tttatccgtc   1260

tgatattacg agtggtgatt ttcttgcttt ggctgcgact ggcgcatatt gttacgcaat   1320

gtctagtcgt tataacgctt ttactcgtcc agctgttgta tccgtgcggg cgggatcatc   1380

tcgccttatg cttagacgtg aaaccttgga cgacattctt tcccttgagg cgtagtaggc   1440

atttttagta cgtgcaataa ccactctggt tttccaggg tggtttttg atgccctttt   1500

tggagtcttc aactgg                                                   1516


<210> SEQ ID NO 18
<211> LENGTH: 445
<212> TYPE: PRT
<213> ORGANISM: C. glutamicum NRRL B-11474

<400> SEQUENCE: 18

Met Ala Thr Val Glu Asn Phe Asn Glu Leu Pro Ala His Val Trp Pro
1               5                   10                  15

Arg Asn Ala Val Arg Gln Glu Asp Gly Val Val Thr Val Ala Gly Val
            20                  25                  30

Pro Leu Pro Asp Leu Ala Glu Glu Tyr Gly Thr Pro Leu Phe Val Val
        35                  40                  45

Asp Glu Asp Asp Phe Arg Ser Arg Cys Arg Asp Met Ala Thr Ala Phe
    50                  55                  60

Gly Gly Pro Gly Asn Val His Tyr Ala Ser Lys Ala Phe Leu Thr Lys
65                  70                  75                  80

Thr Ile Ala Arg Trp Val Asp Glu Glu Gly Leu Ala Leu Asp Ile Ala
                85                  90                  95

Ser Ile Asn Glu Leu Gly Ile Ala Leu Ala Ala Gly Phe Pro Ala Ser
            100                 105                 110

Arg Ile Thr Ala His Gly Asn Asn Lys Gly Val Glu Phe Leu Arg Ala
        115                 120                 125

Leu Val Gln Asn Gly Val Gly His Val Val Leu Asp Ser Ala Gln Glu
    130                 135                 140

Leu Glu Leu Leu Asp Tyr Val Ala Ala Gly Glu Gly Lys Ile Gln Asp
145                 150                 155                 160

Val Leu Ile Arg Val Lys Pro Gly Ile Glu Ala His Thr His Glu Phe
                165                 170                 175

Ile Ala Thr Ser His Glu Asp Gln Lys Phe Gly Phe Ser Leu Ala Ser
            180                 185                 190

Gly Ser Ala Phe Glu Ala Ala Lys Ala Ala Asn Asn Ala Glu Asn Leu
        195                 200                 205

Asn Leu Val Gly Leu His Cys His Val Gly Ser Gln Val Phe Asp Ala
    210                 215                 220

Glu Gly Phe Lys Leu Ala Ala Glu Arg Val Leu Gly Leu Tyr Ser Gln
225                 230                 235                 240

Ile His Ser Glu Leu Gly Val Ala Leu Pro Glu Leu Asp Leu Gly Gly
                245                 250                 255
```

```
Gly Tyr Gly Ile Ala Tyr Thr Ala Ala Glu Glu Pro Leu Asn Val Ala
            260                 265                 270

Glu Val Ala Ser Asp Leu Leu Thr Ala Val Gly Lys Met Ala Ala Glu
        275                 280                 285

Leu Gly Ile Asp Ala Pro Thr Val Leu Val Glu Pro Gly Arg Ala Ile
    290                 295                 300

Ala Gly Pro Ser Thr Val Thr Ile Tyr Glu Val Gly Thr Thr Lys Asp
305                 310                 315                 320

Val His Val Asp Asp Asp Lys Thr Arg Arg Tyr Ile Ala Val Asp Gly
                325                 330                 335

Gly Met Ser Asp Asn Ile Arg Pro Ala Leu Tyr Gly Ser Glu Tyr Asp
            340                 345                 350

Ala Arg Val Val Ser Arg Phe Ala Glu Gly Asp Pro Val Ser Thr Arg
        355                 360                 365

Ile Val Gly Ser His Cys Glu Ser Gly Asp Ile Leu Ile Asn Asp Glu
    370                 375                 380

Ile Tyr Pro Ser Asp Ile Thr Ser Gly Asp Phe Leu Ala Leu Ala Ala
385                 390                 395                 400

Thr Gly Ala Tyr Cys Tyr Ala Met Ser Ser Arg Tyr Asn Ala Phe Thr
                405                 410                 415

Arg Pro Ala Val Val Ser Val Arg Ala Gly Ser Ser Arg Leu Met Leu
            420                 425                 430

Arg Arg Glu Thr Leu Asp Asp Ile Leu Ser Leu Glu Ala
        435                 440                 445
```

<210> SEQ ID NO 19
<211> LENGTH: 4508
<212> TYPE: DNA
<213> ORGANISM: C. glutamicum NRRL B-11474

<400> SEQUENCE: 19

```
cttctccgac tacatgcgtc ctgcagttcg tcttgcagct ctcatggaga ccgacgctta      60

ctacgtctgg acccacgact ccatcggtct gggcgaagat ggcccaaccc accagcctgt     120

tgaaaccttg gctgcactgc gcgccatccc aggtctgtcc gtcctgcgtc ctgcagatgc     180

gaacgagacc gcccaggctt gggctgcagc acttgagtac aaggaaggcc ctaagggtct     240

tgcactaacc cgccagaaca ttcctgttct ggaaggcacc aaggagaagg ctgctgaagg     300

cgttcgccgc ggtggctacg tcctggttga gggttccaag gaaaccccag atgtgatcct     360

catgggctcc ggctccgagg ttcagcttgc agttaacgct gcgaaggctc tggaagctga     420

gggcgttgca gctcgcgttg tttccgttcc ttgcatggat tggttccagg agcaggacgc     480

agagtacatc gagtccgttc tgcctgcagc tgtgaccgct cgtgtgtctg ttgaagctgg     540

catcgcaatg ccttggtacc gcttcttggg cacccagggc cgtgctgtct cccttgagca     600

cttcggtgct tctgcggatt accagaccct gtttgagaag ttcggcatca ccaccgatgc     660

agtcgtggca gcggccaagg actccattaa cggttaattg ccctgctgtt tttagcttca     720

acccggggca atatgattct ccggaatttt attgccccgg gttgttgttg ttaatcggta     780

caaagggtct taagcacatc ccttacttgc ctgctctcct tgagcacagt tcaagaacaa     840

ttcttttaag gaaaatttag tttcatgtct cacattgatg atcttgcaca gctcggcact     900

tccacttggc tcgacgacct ctcccgcgag cgcattactt ccggcaatct cagccaggtt     960

attgaggaaa agtctgtagt cggtgtcacc accaacccag ctattttcgc agcagcaatg    1020

tccaagggcg attcctacga cgctcagatc gcagagctca aggccgctgg cgcatctgtt    1080
```

```
gaccaggctg tttacgccat gagcatcgac gatgttcgca atgcttgtga tctgttcacc   1140
ggcatcttcg agtcctccaa cggctacgac ggccgcgtgt ccatcgaggt tgacccacgt   1200
atctctgctg accgcgacgc aaccctggct caggccaagg agctgtgggc aaaggttgat   1260
cgtccaaacg tcatgatcaa gatccctgca accccaggtt ctttgccagc aatcaccgac   1320
gctttggctg agggcatcag cgttaacgtc accctgatct tctccgttgc tcgctaccgc   1380
gaagtcatcg ctgcgttcat cgagggcatc aagcaggctg ctgcaaacgg ccacgacgta   1440
tccaagattc actctgtggc ttccttcttc gtctcccgcg tcgacgttga gatcgacaag   1500
cgcctcgagg caatcggatc cgatgaggct ttggctctgc gcggcaaggc aggcgttgcc   1560
aacgctcagc gcgcttacgc tgtgtacatg gagcttttcg acgccgccga gctgcctgaa   1620
ggtgccaaca ctcagcgccc tctgtgggca tccaccggcg tgaagaaccc tgcgtacgct   1680
gcaactcttt acgtttccga gctggctggt ccaaacaccg tcaacaccat gccagaaggc   1740
accatcgacg cggttctgga gcagggcaac ctgcacggcg acaccctgtc caactccgcg   1800
gcagaagctg acgctgtgtt ctcccagctt gaggctctgg gcgttgactt ggcagatgtc   1860
ttccaggtcc tggagaccga gggtgtggac aagttcgttg cttcttggag cgaactgctt   1920
gagtccatgg aagctcgcct gaagtagaat cggcacgctg catcagtaac ggcgacataa   1980
aatcgaatca gttcgatctt gtgtggccgt tacacatctt tcattaaaga aaggatcgtg   2040
acgctaccat cgtgagcaca aacacgaccc ccaccagctg gacaaaccca ctgcgcgacc   2100
cgcaggataa acgactcccc cgcatcgctg gcccttccgg catggtgatc ttcggtgtca   2160
ctggcgactt ggctcgaaag aagctgcttc ccgccattta tgatctagca aaccgcggat   2220
tgctgccccc aggattctcg ttggtaggtt acggccgccg cgaatggtcc aaagaagact   2280
ttgaaaaata cgtacgcgat gccgcaagtg ctggtgctcg tacggaattt cgtgaaaatg   2340
tttgggagcg cctcgccgag ggtatggaat ttgttcgcgg caactttgat gatgatgcag   2400
ctttcgacaa cctcgctgca acactcaagc gcatcgacaa aacccgcggc accgccggca   2460
actgggctta ctacctgtcc attccaccag attccttcac agcggtctgc caccagctgg   2520
agcgttccgg catggctgaa tccaccgaag aagcatggcg ccgcgtgatc atcgagaagc   2580
ctttcggcca caacctcgaa tccgcacacg agctcaacca gctggtcaac gcagtcttcc   2640
cagaatcttc tgtgttccgc atcgaccact atttgggcaa ggaaacagtt caaaacatcc   2700
tggctctgcg ttttgctaac cagctgtttg agccactgtg gaactccaac tacgttgacc   2760
acgtccagat caccatggct gaagatatcg gcttgggtgg acgtgctggt tactacgacg   2820
gcatcggtgc agcccgcgac gtcatccaga accacctgat ccagctcttg gctctggttg   2880
ccatggaaga accaatttct ttcgtgccag cgcagctgca ggcagaaaag atcaaggtgc   2940
tctctgcgac aaagccatgc tacccattgg ataaaacctc cgctcgtggt cagtacgctg   3000
ccggttggca gggctctgag ttagtcaagg gacttcgcga agaagatggc ttcaaccctg   3060
agtccaccac tgagactttt gcggcttgta ccttagagat cacgtctcgt cgctgggctg   3120
gtgtgccgtt ctacctgcgc accggtaagc gtcttggtcg ccgtgttact gagattgccg   3180
tggtgtttaa agacgcacca caccagcctt tcgacggcga catgactgta tcccttggcc   3240
aaaacgccat cgtgattcgc gtgcagcctg atgaaggtgt gctcatccgc ttcggttcca   3300
aggttccagg ttctgccatg gaagtccgtg acgtcaacat ggacttctcc tactcagaat   3360
ccttcactga agaatcacct gaagcatacg agcgcctcat tttggatgcg ctgttggatg   3420
```

```
aatccagcct cttccccacc aacgaggaag tggaactgag ctggaagatt ctggatccaa   3480

ttcttgaagc atgggacgcc gatggagaac cagaggatta cccagcaggt acgtggggtc   3540

caaagagcgc tgatgaaatg ctttcccgca acggtcacac ctggcgcagg ccataattta   3600

ggggcaaaaa atgatctttg aacttccgga taccaccacc cagcaaattt ccaagaccct   3660

aactcgactg cgtgaatcgg gcacccaggt caccaccggc cgagtgctca ccctcatcgt   3720

ggtcactgac tccgaaagcg atgtcgctgc agttaccgag tccaccaatg aagcctcgcg   3780

cgagcaccca tctcgcgtga tcattttggt ggttggcgat aaaactgcag aaaacaaagt   3840

tgacgcagaa gtccgtatcg gtggcgacgc tggtgcttcc gagatgatca tcatgcatct   3900

caacggacct gtcgctgaca agctccagca tgtcgtcaca ccactgttgc ttcctgacac   3960

ccccatcgtt gcttggtggc caggtgaatc accaaagaat ccttcccagg atccaattgg   4020

acgcatcgca caacgacgca tcactgatgc tttgtacgac cgtgatgacg cactagaaga   4080

tcgtgttgag aactatcacc cccctgcgta cgctgcaact ctttacgttt ccgagctggc   4140

tggtccaaac accgtcaaca ccatgccaga aggcaccatc gacgcggttc tggagcaggg   4200

caacctgcac ggcgacaccc tgtccaactc cgcggcagaa gctgacgctg tgttctccca   4260

gcttgaggct ctgggcgttg acttggcaga tgtcttccag gtcctggaga ccgagggtgt   4320

ggacaagttc gttgcttctt ggagcgaact gcttgagtcc atggaagctc gcctgaagta   4380

gaatcggcac gctgcatcag taacggcgac ataaaatcga atcagttcga tcttgtgtgg   4440

ccgttacaca tctttcatta aagaaaggat cgtgacgcta ccattgccgt ttctcgcgtt   4500

gtgtgtgg                                                            4508
```

<210> SEQ ID NO 20
<211> LENGTH: 97
<212> TYPE: DNA
<213> ORGANISM: Artificial Sequence
<220> FEATURE:
<223> OTHER INFORMATION: Promoter cg0007_39

<400> SEQUENCE: 20

```
tgccgtttct cgcgttgtgt gtggtactac gtggggacct aagcgtgtat tatggaaacg     60

tctgtatcgg ataagtagcg aggagtgttc gttaaaa                              97
```

<210> SEQ ID NO 21
<211> LENGTH: 1643
<212> TYPE: DNA
<213> ORGANISM: Artificial Sequence
<220> FEATURE:
<223> OTHER INFORMATION: Promoter cg0007_39 insertion and zwf coding region

<400> SEQUENCE: 21

```
tgccgtttct cgcgttgtgt gtggtactac gtggggacct aagcgtgtat tatggaaacg     60

tctgtatcgg ataagtagcg aggagtgttc gttaaaagtg agcacaaaca cgacccccac    120

cagctggaca aacccactgc gcgacccgca ggataaacga ctcccccgca tcgctggccc    180

ttccggcatg gtgatcttcg gtgtcactgg cgacttggct cgaaagaagc tgcttcccgc    240

catttatgat ctagcaaacc gcggattgct gcccccagga ttctcgttgg taggttacgg    300

ccgccgcgaa tggtccaaag aagactttga aaaatacgta cgcgatgccg caagtgctgg    360

tgctcgtacg gaatttcgtg aaaatgtttg ggagcgcctc gccgagggta tggaatttgt    420

tcgcggcaac tttgatgatg atgcagcttt cgacaacctc gctgcaacac tcaagcgcat    480
```

```
cgacaaaacc cgcggcaccg ccggcaactg ggcttactac ctgtccattc caccagattc    540

cttcacagcg gtctgccacc agctggagcg ttccggcatg gctgaatcca ccgaagaagc    600

atggcgccgc gtgatcatcg agaagccttt cggccacaac ctcgaatccg cacacgagct    660

caaccagctg gtcaacgcag tcttcccaga atcttctgtg ttccgcatcg accactattt    720

gggcaaggaa acagttcaaa acatcctggc tctgcgtttt gctaaccagc tgtttgagcc    780

actgtggaac tccaactacg ttgaccacgt ccagatcacc atggctgaag atatcggctt    840

gggtggacgt gctggttact acgacggcat cggtgcagcc cgcgacgtca tccagaacca    900

cctgatccag ctcttggctc tggttgccat ggaagaacca atttctttcg tgccagcgca    960

gctgcaggca gaaaagatca aggtgctctc tgcgacaaag ccatgctacc cattggataa   1020

aacctccgct cgtggtcagt acgctgccgg ttggcagggc tctgagttag tcaagggact   1080

tcgcgaagaa gatggcttca accctgagtc caccactgag acttttgcgg cttgtacctt   1140

agagatcacg tctcgtcgct gggctggtgt gccgttctac ctgcgcaccg gtaagcgtct   1200

tggtcgccgt gttactgaga ttgccgtggt gtttaaagac gcaccacacc agcctttcga   1260

cggcgacatg actgtatccc ttggccaaaa cgccatcgtg attcgcgtgc agcctgatga   1320

aggtgtgctc atccgcttcg gttccaaggt tccaggttct gccatggaag tccgtgacgt   1380

caacatggac ttctcctact cagaatcctt cactgaagaa tcacctgaag catacgagcg   1440

cctcattttg gatgcgctgt tggatgaatc cagcctcttc cccaccaacg aggaagtgga   1500

actgagctgg aagattctgg atccaattct tgaagcatgg gacgccgatg gagaaccaga   1560

ggattaccca gcaggtacgt ggggtccaaa gagcgctgat gaaatgcttt cccgcaacgg   1620

tcacacctgg cgcaggccat aat                                           1643
```

<210> SEQ ID NO 22
<211> LENGTH: 5082
<212> TYPE: DNA
<213> ORGANISM: C. glutamicum NRRL B-11474

<400> SEQUENCE: 22

```
ccctgcgtac gctgcaactc tttacgtttc cgagctggct ggtccaaaca ccgtcaacac     60

catgccagaa ggcaccatcg acgcggttct ggagcagggc aacctgcacg gcgacaccct    120

gtccaactcc gcggcagaag ctgacgctgt gttctcccag cttgaggctc tgggcgttga    180

cttggcagat gtcttccagg tcctggagac cgagggtgtg gacaagttcg ttgcttcttg    240

gagcgaactg cttgagtcca tggaagctcg cctgaagtag aatcggcacg ctgcatcagt    300

aacggcgaca taaaatcgaa tcagttcgat cttgtgtggc cgttacacat ctttcattaa    360

agaaaggatc gtgacgctac cattgccgtt tctcgcgttg tgtgtggtac tacgtgggga    420

cctaagcgtg tattatggaa acgtctgtat cggataagta gcgaggagtg ttcgttaaaa    480

gtgagcacaa acacgacccc caccagctgg acaaacccac tgcgcgaccc gcaggataaa    540

cgactccccc gcatcgctgg cccttccggc atggtgatct tcggtgtcac tggcgacttg    600

gctcgaaaga agctgcttcc cgccatttat gatctagcaa accgcggatt gctgccccca    660

ggattctcgt tggtaggtta cggccgccgc gaatggtcca aagaagactt tgaaaaatac    720

gtacgcgatg ccgcaagtgc tggtgctcgt acggaatttc gtgaaaatgt ttgggagcgc    780

ctcgccgagg gtatggaatt tgttcgcggc aactttgatg atgatgcagc tttcgacaac    840

ctcgctgcaa cactcaagcg catcgacaaa acccgcggca ccgccggcaa ctgggcttac    900

tacctgtcca ttccaccaga ttccttcaca gcggtctgcc accagctgga gcgttccggc    960
```

```
atggctgaat ccaccgaaga agcatggcgc cgcgtgatca tcgagaagcc tttcggccac   1020
aacctcgaat ccgcacacga gctcaaccag ctggtcaacg cagtcttccc agaatcttct   1080
gtgttccgca tcgaccacta tttgggcaag gaaacagttc aaaacatcct ggctctgcgt   1140
tttgctaacc agctgtttga gccactgtgg aactccaact acgttgacca cgtccagatc   1200
accatggctg aagatatcgg cttgggtgga cgtgctggtt actacgacgg catcggtgca   1260
gcccgcgacg tcatccagaa ccacctgatc cagctcttgg ctctggttgc catggaagaa   1320
ccaatttctt tcgtgccagc gcagctgcag gcagaaaaga tcaaggtgct ctctgcgaca   1380
aagccatgct acccattgga taaaacctcc gctcgtggtc agtacgctgc cggttggcag   1440
ggctctgagt tagtcaaggg acttcgcgaa gaagatggct tcaaccctga gtccaccact   1500
gagacttttg cggcttgtac cttagagatc acgtctcgtc gctgggctgg tgtgccgttc   1560
tacctgcgca ccggtaagcg tcttggtcgc cgtgttactg agattgccgt ggtgtttaaa   1620
gacgcaccac accagccttt cgacggcgac atgactgtat cccttggcca aaacgccatc   1680
gtgattcgcg tgcagcctga tgaaggtgtg ctcatccgct tcggttccaa ggttccaggt   1740
tctgccatgg aagtccgtga cgtcaacatg gacttctcct actcagaatc cttcactgaa   1800
gaatcacctg aagcatacga gcgcctcatt ttggatgcgc tgttggatga atccagcctc   1860
ttccccacca acgaggaagt ggaactgagc tggaagattc tggatccaat tcttgaagca   1920
tgggacgccg atggagaacc agaggattac ccagcaggta cgtggggtcc aaagagcgct   1980
gatgaaatgc tttcccgcaa cggtcacacc tggcgcaggc cataatttag gggcaaaaaa   2040
tgatctttga acttccggat accaccaccc agcaaatttc caagacccta actcgactgc   2100
gtgaatcggg cacccaggtc accaccggcc gagtgctcac cctcatcgtg gtcactgact   2160
ccgaaagcga tgtcgctgca gttaccgagt ccaccaatga agcctcgcgc gagcacccat   2220
ctcgcgtgat cattttggtg gttggcgata aaactgcaga aaacaaagtt gacgcagaag   2280
tccgtatcgg tggcgacgct ggtgcttccg agatgatcat catgcatctc aacggacctg   2340
tcgctgacaa gctccagcat gtcgtcacac cactgttgct tcctgacacc cccatcgttg   2400
cttggtggcc aggtgaatca ccaaagaatc cttcccagga tccaattgga cgcatcgcac   2460
aacgacgcat cactgatgct ttgtacgacc gtgatgacgc actagaagat cgtgttgaga   2520
actatcaccc aggtgatacc gacatgacgt gggcgcgcct tacccagtgg cggggacttg   2580
ttgcctcctc attggatcac ccaccacaca gcgaaatcac ttccgtgagg ctgaccggcg   2640
caagcggcag tacctcggtg gatttggctg caggctggtt ggcgcgcagg ctgaacgtgc   2700
ctgtgatccg cgaggtgaca gatgctccca ccgtgtcaac cgatgagttt ggtactccac   2760
tgctggctat ccagcgcctg gagatcgttc gcaccaccgg ctcgatcatc atcaccatcc   2820
atgacgctca tacccttcag gtagagatgc cggaatccgg caatgcccca tcgctggtgg   2880
ctattggtcg tcgaagtgag tccgactgct tgtctgagga gcttcgccac atggatccag   2940
atttgggcta ccagcacgca ctatccggct tgtccagcgt caagctggaa accgtctaag   3000
gagaaataca acactatggt tgatgtagta cgcgcacgcg atactgaaga tttggttgca   3060
caggctgcct ccaaattcat tgaggttgtt gaagcagcaa ctgccaataa tagcaccgca   3120
caggtagtgc tcaccggtgg tggcgccggc atcaagttgc tggaaaagct cagcgttgat   3180
gcggctgacc ttgcctggga tcgcattcat gtgttcttcg gcgatgagcg caatgtccct   3240
gtcagtgatt ctgagtccaa tgagggccag gctcgtgagg cactgttgtc caaggtttct   3300
```

```
atccctgaag ccaacattca cggatatggt ctcggcgacg tagatcttgc agaggcagcc   3360

cgcgcttacg aagctgtgtt ggatgaattc gcaccaaacg gctttgatct tcacctgctc   3420

ggcatgggtg gcgaaggcca tatcaactcc ctgttccctc acaccgatgc agtcaaggaa   3480

tcctccgcaa aggtcatcgc ggtgtttgat tcccctaagc ctccttcaga gcgtgcaact   3540

ctaacccttc ctgcggttca ctccgcaaag cgggtgtggt tgctggtttc tggtgcggag   3600

aaggctgagg cagctgcggc gatcgtcaac ggtgagcctg ctgttgagtg gcctgctgct   3660

ggagctaccg gatctgagga aacggtattg ttcttggctg atgatgctgc aggaaatctc   3720

taagtagcgc cagctctaac aagaagctct aacaagaagc ttcaacaaga agctctaacg   3780

aaaagcacta acaaactaat ccgggtgcga accttcatct gaatcgatgg aggttcgcac   3840

ccggattttt ggctcagcgt tagattctca ccctaaaacc gcgcacttaa aaaggttagc   3900

tttctatacg tgcaccgcct ctttgattgg ttcatgcgag gcgatccgaa agtcttcgct   3960

gtacagcggc gaggtgtttc cgaccgctag ttgtgctgcg agttcgccat aagctggaga   4020

gagcttgaag gcgtgtccgg atcctccggt gagcacaatg acattgtcca ccgcgtcgat   4080

aattggagat ttgtctgcag tgtaggtgtc atagtggacg ctgaaacggt tgggctctgg   4140

gttgacccct gggaagagtt cgtgggtttt ccgaccaaat tcagagactg cgtcccggtc   4200

gaggcggaga tcttcatctt ctacatgagc gcttaatgga acgcccact catccaatcc   4260

ggcaattttg atgctgtacc catcgacgca tggtgctcca aatacgtgga agccatcacg   4320

gtcacggatg aagcatggca gattttccgg ctggaagtcc actgggttgt tgggcaggaa   4380

ccaagtgagc actaggcgtc gcacttcaag cagtggcgcg atggagggca cgagctcgct   4440

tgtccagctg ccggtggtga cgataacgcg gtccacgatt gtggtttctt cgcctgcttg   4500

gatgactacg tgatcgccgt tgtcttcgat gctggtgatt ttttggtgat cgcgtacttg   4560

ggcaccattt gccttggctg tttcgattgc actgaacact gctagttcgg ggcgcagggc   4620

tccaccttga agatcaacaa ttccagcttc atcatcgcgg aagtctagac ctgggtaacg   4680

cttgcgcatc tgcgcggcgg taagtcgttc atgtggcagc tcataacgtt ccactgattc   4740

caccaggcgt tggaagggtg cttcgtcttc cttgccggtg cttaagacac cgaagttgtg   4800

gaagagttcg cgtccggaaa tctcgctcag tgatgaccat agtgctcgtg cgcgtttgag   4860

caacggaacg taggtgctgc cttcgtggta ggccatgcga aacagtcggg actcccctgt   4920

gaatgcgccg tagccatggg agatgccgaa ttgttcaaag ccgatggcct ctacacctgg   4980

gatgttactt aagtgccaca gtgccatgga gccggttgat ccaaggccga ttaccgcaat   5040

tttcattgtt gtttcttctc tcaagccagt gcgggtgatt cc                       5082
```

<210> SEQ ID NO 23
<211> LENGTH: 951
<212> TYPE: DNA
<213> ORGANISM: C. humireducens

<400> SEQUENCE: 23

```
atgaagatcg aattgcctga caccgatacc cgcaacattg cagcctccct gttggaagcc     60

cgcgaacaca actcccagac gactggtcgt gtactcaccc tgatcgtagt ggccgcattg    120

gatgatgacg tcgaccatat catctccgtc acccgtgacg cgagccatga gcacccagct    180

cgcgttctcg tgctccttac aggccgtgaa gacgcggact ctcgcctcga tgctgaagtt    240

cgcgttggag gtcacgccgg cgcgtcagaa atggtaatta tgcgcatcac cggagaaatg    300

gtgaaccact tggcggccgt cgtcacccca cttctgctgc ctgacactcc tgtagtggcg    360
```

```
tggtggccta ccactgcccc ggaaaaccca tcaggacacc ctctgggaca gctcgcccag    420

cgacgtatca caaacgcaga tcatccggat tccgaatctg tactccgtct tcgtcgagcg    480

acttacgctc cgggtgattc tgacatggtg tggtccaaga tcactgcctg gcgtggtatc    540

gtcgcttctt ctctcgatcg ccatccacat gaagacgtgg aggcggccgt gctcactgga    600

cctgctgatg aaccacaaat cgatatcgca gcgggttggc tggcagatcg cctgggtgtc    660

ccggtgcgcc gcgaggtctg tgagcccggc aacgatgccc gcctgttccc gattcgccgt    720

cttaagtttg agcgcgcttc aggtcctgtt cgtgtagagg tactcgacca tcgcactgtg    780

ttggtggccc ttccaggccg accagaatcg ctcgtggcca tgaacgaacg ctccgacgct    840

gattgcctca gcgaggaatt gcgccacctg gaccccgatc tggcatacgc caacgccttg    900

cgcggactca cccgcgtgaa gggcatcaat ggccacccag cgtcgtcctg a             951
```

<210> SEQ ID NO 24
<211> LENGTH: 1048
<212> TYPE: DNA
<213> ORGANISM: Artificial Sequence
<220> FEATURE:
<223> OTHER INFORMATION: promoter cg0007_39-C. humireducense opcA coding sequence

<400> SEQUENCE: 24

```
tgccgtttct cgcgttgtgt gtggtactac gtggggacct aagcgtgtat tatggaaacg     60

tctgtatcgg ataagtagcg aggagtgttc gttaaaaatg aagatcgaat tgcctgacac    120

cgatacccgc aacattgcag cctccctgtt ggaagcccgc gaacacaact cccagacgac    180

tggtcgtgta ctcaccctga tcgtagtggc cgcattggat gatgacgtcg accatatcat    240

ctccgtcacc cgtgacgcga gccatgagca cccagctcgc gttctcgtgc tccttacagg    300

ccgtgaagac gcggactctc gcctcgatgc tgaagttcgc gttggaggtc acgccggcgc    360

gtcagaaatg gtaattatgc gcatcaccgg agaaatggtg aaccacttgg cggccgtcgt    420

caccccactt ctgctgcctg acactcctgt agtggcgtgg tggcctacca ctgccccgga    480

aaacccatca ggacaccctc tgggacagct cgcccagcga cgtatcacaa acgcagatca    540

tccggattcc gaatctgtac tccgtcttcg tcgagcgact tacgctccgg gtgattctga    600

catggtgtgg tccaagatca ctgcctggcg tggtatcgtc gcttcttctc tcgatcgcca    660

tccacatgaa gacgtggagg cggccgtgct cactggacct gctgatgaac cacaaatcga    720

tatcgcagcg ggttggctgg cagatcgcct gggtgtcccg gtgcgccgcg aggtctgtga    780

gcccggcaac gatgcccgcc tgttcccgat tcgccgtctt aagtttgagc gcgcttcagg    840

tcctgttcgt gtagaggtac tcgaccatcg cactgtgttg gtggcccttc caggccgacc    900

agaatcgctc gtggccatga acgaacgctc cgacgctgat tgcctcagcg aggaattgcg    960

ccacctggac cccgatctgg catacgccaa cgccttgcgc ggactcaccc gcgtgaaggg   1020

catcaatggc cacccagcgt cgtcctga                                      1048
```

<210> SEQ ID NO 25
<211> LENGTH: 316
<212> TYPE: PRT
<213> ORGANISM: C. humireducens

<400> SEQUENCE: 25

```
Met Lys Ile Glu Leu Pro Asp Thr Asp Thr Arg Asn Ile Ala Ala Ser
1               5                   10                  15
```

```
Leu Leu Glu Ala Arg Glu His Asn Ser Gln Thr Thr Gly Arg Val Leu
            20                  25                  30

Thr Leu Ile Val Val Ala Ala Leu Asp Asp Asp Val Asp His Ile Ile
        35                  40                  45

Ser Val Thr Arg Asp Ala Ser His Glu His Pro Ala Arg Val Leu Val
    50                  55                  60

Leu Leu Thr Gly Arg Glu Asp Ala Asp Ser Arg Leu Asp Ala Glu Val
65                  70                  75                  80

Arg Val Gly Gly His Ala Gly Ala Ser Glu Met Val Ile Met Arg Ile
                85                  90                  95

Thr Gly Glu Met Val Asn His Leu Ala Ala Val Val Thr Pro Leu Leu
            100                 105                 110

Leu Pro Asp Thr Pro Val Val Ala Trp Trp Pro Thr Thr Ala Pro Glu
        115                 120                 125

Asn Pro Ser Gly His Pro Leu Gly Gln Leu Ala Gln Arg Arg Ile Thr
    130                 135                 140

Asn Ala Asp His Pro Asp Ser Glu Ser Val Leu Arg Leu Arg Arg Ala
145                 150                 155                 160

Thr Tyr Ala Pro Gly Asp Ser Asp Met Val Trp Ser Lys Ile Thr Ala
                165                 170                 175

Trp Arg Gly Ile Val Ala Ser Ser Leu Asp Arg His Pro His Glu Asp
            180                 185                 190

Val Glu Ala Ala Val Leu Thr Gly Pro Ala Asp Glu Pro Gln Ile Asp
        195                 200                 205

Ile Ala Ala Gly Trp Leu Ala Asp Arg Leu Gly Val Pro Val Arg Arg
    210                 215                 220

Glu Val Cys Glu Pro Gly Asn Asp Ala Arg Leu Phe Pro Ile Arg Arg
225                 230                 235                 240

Leu Lys Phe Glu Arg Ala Ser Gly Pro Val Arg Val Glu Val Leu Asp
                245                 250                 255

His Arg Thr Val Leu Val Ala Leu Pro Gly Arg Pro Glu Ser Leu Val
            260                 265                 270

Ala Met Asn Glu Arg Ser Asp Ala Asp Cys Leu Ser Glu Glu Leu Arg
        275                 280                 285

His Leu Asp Pro Asp Leu Ala Tyr Ala Asn Ala Leu Arg Gly Leu Thr
    290                 295                 300

Arg Val Lys Gly Ile Asn Gly His Pro Ala Ser Ser
305                 310                 315


<210> SEQ ID NO 26
<211> LENGTH: 4100
<212> TYPE: DNA
<213> ORGANISM: C. glutamicum NRRL B-11474

<400> SEQUENCE: 26

acacaaagaa gcaccaaccg atccggcgct tgcgcgtttg ctccctgatt ttcaacacga     60

gggcgatgag gaatacgacg gcgataattc tttcctccgt tcacttcatg aaggcgatat    120

cactcgcgcg aagctggaga atctgcgtgt gatcaatgat gcgctgggcc ccgacggcaa    180

tgttgcggtt accgcctctg aggaggaagc acacgcatgg ttggccgcgc tcaatgatat    240

ccgcctgtac gttgcctccg gtgatgcacg cggcggagaa gccgccgagg aagaccgcga    300

aaacctcgtg cagtggctgg cctacaatca agagtccttg ctggaagcga tgatgaatta    360

atgcttatcg acgtcccggg cttccttta ggccacgtca cgaaggggga tacgggttgc    420
```

-continued

```
tcagtggtca ttgcacctaa cggtgcattt gcgggcgtcg atgtccgtgg gggaggccca    480
ggcaccaggg aaaccgacct tctagaacca cacaattctg tgcagcaagc acatgccgtg    540
gtgttgtgtg gcggttcggc gttcgggttg gctgctgccg atggagtgat gacagcccta    600
gaaaaccgcg gtattggttt ccctgtccgt cccgaagggc ctatcgtgcc aatcgttcca    660
ggcgctgtga tttttgattt gttggtgggt gaccccaaaa ataggcccac cgcagctgat    720
ggggaacagg ctgtagaaaa cgctttcgct ggtacacaca acggttcggg cagtgtcggt    780
gcaggaaccg gcgctacggc aggtcggctg cgtggcggtt ttggccaaag ctcgcgccgg    840
gtcggaaagt acaccatcgc ggcaggtgtg gtggcgaatc ctgttgggga agtcgtggac    900
ctaaagactg ggctttgtt  tggtaggccc gaagtgatgg gggtgggcgt cgataagcta    960
aaaagcgcgg cagagacgct gaacacgacc atcggcgtcg tggcaactga cgcgccggtg   1020
acaaaagccc aggcgaagcg cttggcgctg gtggcccatg acggattggc gagggccgtg   1080
cggccgtcgc attcgccgat ggacggtgac acatttttg  ctatgtcatc gggtgatggt   1140
agtggcgtta ccccggttga gctgggggaa ttgtcggctc atgctgcaga ttgcgtacag   1200
gacgctatta tcgacgccat acttaccgcg agtccgggac tcgggctcaa aagcttcagg   1260
gaacttttac catgagttac aacagcccgt ataacaacac gaatttcagc accactggcg   1320
cgttccaacc tgctggtggg ccggtgaagc cgtggaataa gcctgatggc agcctgaatc   1380
agcagctgaa aaataaatcc cgtgtgcgca caggtcttac catcgccatc ggttatgttg   1440
tggtgatttg ggcggtgcat ttggcatcca tcgtgattgc gctgctcact ggcttcaacc   1500
tgaccaactt tggtattcat ccgctggata ccagtgcact gtggggtatt ttcgcctcac   1560
cgttgctgca tggaagcttc agtcacctca ttggaaatac cgttccaggc tttatattca   1620
gtttcctcat cggtatgagt ggcaagcgcg tgttctggga agtcacgatt atcgcaggtc   1680
tcatcggcgg tcttggtaca tggattttcg gtggaatcgg caccaaccac atcggtgcgt   1740
ccggcctgat ttatggctgg cttggctacc tgatcgtgcg tggaattttc aataaggata   1800
ttaaacagtt cctgcttggc atagttttgg cgttcattta ctccggtttg ttctggggtc   1860
tgctacctac tcaaatcggt gtgtcctggc agggccacct tttcggtgca cttggtggaa   1920
tcggtgcggg tgcttttatc gcctcggatg acccggcagc gttgaaagcg aagaagcagc   1980
agaagaaact agaaaagcaa caacgccaaa gaggcttgta gttttcacct agcgactaca   2040
cttaattgac atgacaagtg agaattccga atcccaggac atttggctaa ccgatgagca   2100
acaagatgtg tggctcgatg tgtggacaat gcgaatcggc ctgcctgctc gcttggatgc   2160
tcaactgaaa gaagctgcgg gtgtcagcca ctttgagtac ttcaccatgg cgcagatttc   2220
tatggccccg gaacatcggg tgcgcatgag tgagcttgct gagctgtccg atatgacgct   2280
atcgcatcta tctagagtgg ttactcgcct agaaaaggct ggctgggtga agcgtgttcc   2340
cgatcccgat gatggtcgcg ccaccgttgc tgtgctcacg gactctgggt gggagaaagt   2400
taaagcaaca gcccctggtc atgtgaagga agtgcgtcgt ttggtgtttg acgatctcac   2460
tccagaagaa ctcaaggtaa tgggcactgc aatgaagaag attgtgaacc gactcgatat   2520
gtccaacagg ctgccgcggg tgtagttaga agttttaaga aatgtagaca acggcgttgt   2580
caccacctgt gcaggtgaca tactcgccgt tgtcttcgca gttcatggtg tagtttccgc   2640
cagtgacagg gctggtggct gtcaccctgc cggatagttc attggtgtct aaatagtggt   2700
ttacaaaagc atctcggacg gcttgggcaa aacctgctga ggtggatgct gacccggtgt   2760
acacattgtt caaattgccg gcatcggtct gggtggcagc agcatcattg gctggtgatg   2820
```

```
ctcccgcagg aagtgatggt tgcgcagggc ggtttcgggg agtttccgtt gcactgcttg   2880

ggggctgatc ctctgtcgcg ctcggtgact caggggattc cgaaatagtt tgctccacag   2940

attcagaggt gcttggactt gccacagggc tcgaggaatt atttggtgca acgaggctgt   3000

tgaacaacaa gacaaacgca atcacgatga tggccaccaa gatcaagatc aacccaatga   3060

gactgccttt gggtgaacgt ttcgcgggcg ccacagctgt aggagagcca atagtctccg   3120

aagttgctcg caccgcagcg aatcgtctgg tttcttgatc aggtgaatca gccattgcca   3180

tattgtgaca catcttggac ggataaaaag ggaagcaacg cgaggtagct tatgatggca   3240

accgtgactg atttcagtgg atctatgatt gaacgccccg tgccaggtgc tgatgcgccg   3300

attggaattt ttgattctgg agttggcgga ttaaccgtag ctcgcacaat catcgatcaa   3360

ttgccacatg aatcagttat ttatatcggt gatactgcca atggccctta tggtccgttg   3420

cctatcgcta aggtccgtga gcacgccatc cgcattgccg atgagttggt ggaacgcgga   3480

tgcaagatga ttgtcattgc ctgtaacact gcgtccgctg cgtttctccg agatgcccgt   3540

gaacgataca gtgtgccagt cgtggaagtt attcttcccg cagtaaggcg tgcggtggca   3600

tccacccgca atggcaaagt gggcgtgatc ggcacagtgg gaaccattaa ctccggtgcg   3660

taccaggatc ttttctctgc aagcccctcc attgaggtca acgcagtggc atgcccacgg   3720

tttgtggatt tcgtggaacg cggaattacc agcggcaggc agatcctcaa cattgcgcag   3780

gattatttag agcctctgca agcagaaggg gtggacactc ttgtgcttgg atgcacccac   3840

tatccactgc tctccggtgt cattcagttg gcaatggggg accacgtaag tttggtctct   3900

agcgcggaag aaactgcgaa agacgtgctg agaatcttga gccagcaaga tcttttagcc   3960

gatccggaca tgcatcctga gccaagttat agctttgaat caacaggcga tccggaaatc   4020

tttgcacaat taagccgccg attccttgga ccaattgttt ccctagtgag acaaaacgag   4080

ggataacccc aggtgtgtgt                                                4100
```

<210> SEQ ID NO 27
<211> LENGTH: 595
<212> TYPE: DNA
<213> ORGANISM: Artificial Sequence
<220> FEATURE:
<223> OTHER INFORMATION: Promoter cg0007_39-cg2766

<400> SEQUENCE: 27

```
tgccgtttct cgcgttgtgt gtggtactac gtggggacct aagcgtgtat tatggaaacg     60

tctgtatcgg ataagtagcg aggagtgttc gttaaaaatg acaagtgaga attccgaatc    120

ccaggacatt tggctaaccg atgagcaaca agatgtgtgg ctcgatgtgt ggacaatgcg    180

aatcggcctg cctgctcgct tggatgctca actgaaagaa gctgcgggtg tcagccactt    240

tgagtacttc accatggcgc agatttctat ggccccggaa catcgggtgc gcatgagtga    300

gcttgctgag ctgtccgata tgacgctatc gcatctatct agagtggtta ctcgcctaga    360

aaaggctggc tgggtgaagc gtgttcccga tcccgatgat ggtcgcgcca ccgttgctgt    420

gctcacggac tctgggtggg agaaagttaa agcaacagcc cctggtcatg tgaaggaagt    480

gcgtcgtttg gtgtttgacg atctcactcc agaagaactc aaggtaatgg gcactgcaat    540

gaagaagatt gtgaaccgac tcgatatgtc caacaggctg ccgcgggtgt agtta         595
```

<210> SEQ ID NO 28
<211> LENGTH: 4283
<212> TYPE: DNA

<213> ORGANISM: C. glutamicum NRRL B-11474

<400> SEQUENCE: 28

```
cgcatgatgt gctgatgcag atcatccacc gcgtcatcgc ttttagccat ctctagggca     60
agatctggtt caggatcaat gaggatctga cgaatatgat ctgtcatgtc agctgcgagg    120
cgggccatct ccttgaaata gccacgcatg tcctccggga tcaccggatc ggggtaacgg    180
cgacgcacgg aattagctac gtgcattgcc agagcaccca tacgggtaat ttcctcgacg    240
atgtagatgg aggagacaac ctggcgaaga tcacgggcta caggagtttc aagcgccaaa    300
agttcgacgg cttgagactc gcatccagta cgaagctctt caagcttttc tgcattgcct    360
aaagcgcttt ctgccgatgc caaagaagtg cgcaggaggg catcagtcgc cttatccatg    420
cactccttag ttagatcaca caaaatgatt agatcgtgtg cgaattcatc caattgctgt    480
ctatatgcag tacgcatggc aacactataa ggcgataatg gtatttctgc agacctaaaa    540
caccccttta cggttgaatc acctaataat gggggatagc caactattgg cgggggtaag    600
tattaaatta actaccctcc ggagttttcc atttctgcgc ctttaggaac agtggcatcc    660
tcaggatcgt ccaaccagcc atctggaagt gccacctttg caggagcgcc ctgtcgacct    720
cgtgcacctt ccgcgtcctc tgccttggcg gtggagtcag cccatggtgc aaggagatcc    780
tcaagctcca cataggtgga aaccttggcc agattggagc ggaattcgcc gccaacaggg    840
aaaccgcgca ggtaccaacc catgtgctta cgcagatcgc gcagcccctt ggtttcgcca    900
tcatgctgca tgaggagttc tgcgtggcgc aggatgattt gggtaacttc gccgaaggta    960
ggctcctctg ggatttcttc tccacgaaca gcagcagaca gctcagcaaa gagccaaggc   1020
ctgcccaggc aaccacgccc aaccacgacg ccatcgcagc cagtttgctc catcatgcgc   1080
gttgcatcgg atgccgcgaa aatatcgcca ttgcccaaaa ctgggatgcc ggtatctgcc   1140
aaatgctcct tcaggcgcgc gatctcgttc caatcagcct caccggaata gcgctgcgcc   1200
gcagtgcggg cgtgaagcgc tacggacttg gcgcctgcgt cgacagcaat gcgtccagca   1260
tccaagtgag tatggtgctc atcatcaata ccaacgcgga acttcaccgt caccggaatg   1320
tccgtgcctt ccgtagcctt cacagccgcg gaaacgatgt tttcaaacaa acggcgcttg   1380
taaggaatcg cagaaccgcc accacggcgc gtgacctttg gaaccgggca gccaaagttc   1440
atatcaatat gatccgccaa gttttcatca acgatcatct tcgccgcttc gtaggtgtac   1500
ttcgggtcaa ccgtgtacag ctgcaagctt cggggatttt catccggcgc gaaggtggtc   1560
atgtgcatgg ttttctcatt gcgctcaaca agagcacgcg cagtcaccat ttcacagacg   1620
tacagccccg agattgttcc cgtgcgttgc atttcctgtt cgcggcacag cgtgcggaaa   1680
gcaacgttgg ttacaccagc catgggggct agaaccacag gggaggcaag gtcaaagggg   1740
ccgattttta gagtcaccta actattgtcc cccgtgaatc aggttgggca aaatatttga   1800
agcaaattgt gagcagggcg caactaggaa agtggtgtgc tttcactttt tgggggctgg   1860
ggttgggtta agcttcgcgg gctctagggt tggtctgagc tttattcctg agctttattc   1920
ctggtctttg ggaggcttgc aaacaggggg catgcaaatt tgggggtaat gctgggcctt   1980
gaaatcccac tatcacagat agtattcggg catttcctgt cacgatggtt tatccttggg   2040
acacaacatc aaagtggggt acatcatatg cttccggttg aagtgaccta tctgaaaaga   2100
ttggtcgaac cttgaagcaa tggtgtgaac tgcgttaacg aattttgtcg gacgttaaaa   2160
tggtcgcatt ctgcttgctg aagtggcaca cctatgtgtt ctgcttgggt atagcagtgc   2220
gggaaaaatt tgaaaaagtc cgattacctg aggaggtatt caatgtctga tcgcattgct   2280
```

```
tcagaaaagc tgcgctccaa gctcatgtcc gccgacgagg cggcacagtt tgttaaccac   2340

ggtgacaagg ttggtttctc tggcttcacc ggcgctggct acccaaaggc actgcctacg   2400

gcaatcgcta accgggctaa agaagcacac ggtgcaggca acgactacgc aatcgacctg   2460

ttcactggcg catcgaccgc ccctgactgc gatggcgtac ttgcagaagc tgacgctatc   2520

cgctggcgca tgccatacgc atctgatcca atcatgcgta acaagatcaa ctccggctcc   2580

atgggatact ccgatatcca cctgtcccac tccggccagc aggttgaaga gggcttcttc   2640

ggccagctca acgtagctgt cattgaagtc acccgcatca ctgaagacgg acacctcatc   2700

ccttcttcct ccgtgggtaa caacgttgag tggctcaacg ctgcagagaa ggtcatcctc   2760

gaggttaact cttggcagtc cgagaacctc gagggcatgc acgacatctg gtctgtacca   2820

gcactgccaa accgcatcgc tgtgccaatc aacaaggccg gcgaccgcat cggtaagacc   2880

tacatcgaat tcgacaccga caaggttgtc gcaattgttg aaaccaacac cccagaccgc   2940

aacgcaccat ttaagcctgt cgatgacatc tctaagaaga tcgccggtaa cttcctcgac   3000

ttcctcgaag gtgaagttgc agctggccgt ctttcctacg atggttacgt catgcagtcc   3060

ggcgtgggca acgtgcctaa tgctgtgatg gcaggcctgc tggagtccaa gtttgagaac   3120

atccaggctt acaccgaggt tatccaggac ggcatggttg accttatcga cgccggcaag   3180

atgaccgttg cttctgcaac ctccttctcc ttgtctcctg agtacgcaga gaagatgaac   3240

aacgacgcaa agcgttaccg tgagtccatc atcctgcgcc cacagcagat ctctaaccac   3300

ccagaggtga tccgtcgcgt cggcctgatc gccaccaacg gtcttatcga agctgacatc   3360

tatggcaacg ttaactccac caacgtttct ggctcccgcg tcatgaacgg catcggcggc   3420

tccggcgact tcacccgtaa cggctacatc tccagcttca tcaccccttc agaggcaaag   3480

ggcggcgcaa tctctgcgat cgttcctttc gcatcccaca tcgaccacac cgagcacgat   3540

gtcatggttg ttatctctga gtacggttac gcagaccttc gtggcctggc tccacgtgag   3600

cgcgttgcca agatgatcgg cctggcacac cctgattacc gcccactgct cgaggagtac   3660

tacgctcgcg caacctccgg tgacaacaag tacatgcaga cccctcatga tcttgcaacc   3720

gcgtttgatt tccacatcaa cctggctaag aacggctcca tgaaggcata agtttttttct   3780

tggtttagaa accgccgcct cgacaacatt tcgaggcggc ggtttctttt atcacctggg   3840

ttttgagcgt taaattagac caggtcaggc tagtgtttgg tagctaattg agggcgattt   3900

taataaggcc ggtgccatgt actaatatgg tctgagttgg gcctatagct cagttggtag   3960

agctacggac ttttaatccg caggtcttgg gttcgagtcc caatgggccc acatcttaag   4020

taccccctgtt ttggagaatg ctccgagcca ggggtacttt tcttttcctc acacacagta   4080

gctgctgaga aaaatgaaga ccttttgtta ggttgggagt atgaccaacc catacgaggc   4140

cttcataccg ctcaagcatc gtacggggat tgaacccgag cacacctttt gggaatggga   4200

aaacaaaagg gttcacattg caaggagacg tcgagaagcg cccgtccgcg ttatcgtggt   4260

gcatgggcta ggcacccata gtg                                              4283
```

```
<210> SEQ ID NO 29
<211> LENGTH: 1606
<212> TYPE: DNA
<213> ORGANISM: Artificial Sequence
<220> FEATURE:
<223> OTHER INFORMATION: promoter cg0007_39-actA

<400> SEQUENCE: 29
```

```
tgccgtttct cgcgttgtgt gtggtactac gtggggacct aagcgtgtat tatggaaacg     60
tctgtatcgg ataagtagcg aggagtgttc gttaaaaatg tctgatcgca ttgcttcaga    120
aaagctgcgc tccaagctca tgtccgccga cgaggcggca cagtttgtta accacggtga    180
caaggttggt ttctctggct tcaccggcgc tggctaccca aaggcactgc ctacggcaat    240
cgctaaccgg gctaaagaag cacacggtgc aggcaacgac tacgcaatcg acctgttcac    300
tggcgcatcg accgcccctg actgcgatgg cgtacttgca gaagctgacg ctatccgctg    360
gcgcatgcca tacgcatctg atccaatcat gcgtaacaag atcaactccg gctccatggg    420
atactccgat atccacctgt cccactccgg ccagcaggtt gaagagggct tcttcggcca    480
gctcaacgta gctgtcattg aagtcacccg catcactgaa gacggacacc tcatcccttc    540
ttcctccgtg ggtaacaacg ttgagtggct caacgctgca gagaaggtca tcctcgaggt    600
taactcttgg cagtccgaga acctcgaggg catgcacgac atctggtctg taccagcact    660
gccaaaccgc atcgctgtgc caatcaacaa ggccggcgac cgcatcggta agacctacat    720
cgaattcgac accgacaagg ttgtcgcaat tgttgaaacc aacaccccag accgcaacgc    780
accatttaag cctgtcgatg acatctctaa gaagatcgcc ggtaacttcc tcgacttcct    840
cgaaggtgaa gttgcagctg gccgtctttc ctacgatggt tacgtcatgc agtccggcgt    900
gggcaacgtg cctaatgctg tgatggcagg cctgctggag tccaagtttg agaacatcca    960
ggcttacacc gaggttatcc aggacggcat ggttgacctt atcgacgccg gcaagatgac   1020
cgttgcttct gcaacctcct tctccttgtc tcctgagtac gcagagaaga tgaacaacga   1080
cgcaaagcgt taccgtgagt ccatcatcct gcgcccacag cagatctcta accacccaga   1140
ggtgatccgt cgcgtcggcc tgatcgccac caacggtctt atcgaagctg acatctatgg   1200
caacgttaac tccaccaacg tttctggctc ccgcgtcatg aacggcatcg gcggctccgg   1260
cgacttcacc cgtaacggct acatctccag cttcatcacc ccttcagagg caaagggcgg   1320
cgcaatctct gcgatcgttc ctttcgcatc ccacatcgac cacaccgagc acgatgtcat   1380
ggttgttatc tctgagtacg gttacgcaga ccttcgtggc ctggctccac gtgagcgcgt   1440
tgccaagatg atcggcctgg cacaccctga ttaccgccca ctgctcgagg agtactacgc   1500
tcgcgcaacc tccggtgaca acaagtacat gcagacccct catgatcttg caaccgcgtt   1560
tgatttccac atcaacctgg ctaagaacgg ctccatgaag gcataa                  1606
```

```
<210> SEQ ID NO 30
<211> LENGTH: 35
<212> TYPE: DNA
<213> ORGANISM: Artificial Sequence
<220> FEATURE:
<223> OTHER INFORMATION: primer FarI 3p InfusF

<400> SEQUENCE: 30

atttcacacc gcatatgcgg catccttcag accgc                                35


<210> SEQ ID NO 31
<211> LENGTH: 43
<212> TYPE: DNA
<213> ORGANISM: Artificial Sequence
<220> FEATURE:
<223> OTHER INFORMATION: primer  FarI 3p InfusR AvrII

<400> SEQUENCE: 31

tgggatccgt cgacctgcag cctaggatct ctggaccgga atc                       43
```

<210> SEQ ID NO 32
<211> LENGTH: 34
<212> TYPE: DNA
<213> ORGANISM: Artificial Sequence
<220> FEATURE:
<223> OTHER INFORMATION: primer FarI 5p InfusF

<400> SEQUENCE: 32
gtccagagat cctaggatcc cgccgagaaa accg 34

<210> SEQ ID NO 33
<211> LENGTH: 34
<212> TYPE: DNA
<213> ORGANISM: Artificial Sequence
<220> FEATURE:
<223> OTHER INFORMATION: primer FarI 5p Infus R

<400> SEQUENCE: 33
aacagctcac tctagaagtg gaggtcatct gcac 34

<210> SEQ ID NO 34
<211> LENGTH: 71
<212> TYPE: DNA
<213> ORGANISM: Artificial Sequence
<220> FEATURE:
<223> OTHER INFORMATION: primer Pcg0007_39-zwf_P1

<400> SEQUENCE: 34
tttatgcttc cggctcgtat gttgtgtgga attgtgagcg gataacaatt cttctccgac 60
tacatgcgtc c 71

<210> SEQ ID NO 35
<211> LENGTH: 95
<212> TYPE: DNA
<213> ORGANISM: Artificial Sequence
<220> FEATURE:
<223> OTHER INFORMATION: primer Pcg0007_39-zwf_P2

<400> SEQUENCE: 35
tatccgatac agacgtttcc ataatacacg cttaggtccc cacgtagtac cacacacaac 60
gcgagaaacg gcaatggtag cgtcacgatc ctttc 95

<210> SEQ ID NO 36
<211> LENGTH: 92
<212> TYPE: DNA
<213> ORGANISM: Artificial Sequence
<220> FEATURE:
<223> OTHER INFORMATION: primer Pcg0007_39-zwf_P3

<400> SEQUENCE: 36
tactacgtgg ggacctaagc gtgtattatg gaaacgtctg tatcggataa gtagcgagga 60
gtgttcgtta aaagtgagca caaacacgac cc 92

<210> SEQ ID NO 37
<211> LENGTH: 76
<212> TYPE: DNA
<213> ORGANISM: Artificial Sequence
<220> FEATURE:
<223> OTHER INFORMATION: primer Pcg0007_39-zwf_P4

<400> SEQUENCE: 37
ctgcaaggcg attaagttgg gtaacgccag ggttttccca gtcacgacgt gggtgatagt 60
tctcaacacg atcttc 76

<210> SEQ ID NO 38
<211> LENGTH: 76
<212> TYPE: DNA
<213> ORGANISM: Artificial Sequence
<220> FEATURE:
<223> OTHER INFORMATION: primer SNP_084_P1

<400> SEQUENCE: 38
tttatgcttc cggctcgtat gttgtgtgga attgtgagcg gataacaatt cggtttcctg 60
attgctcatc aaaatc 76

<210> SEQ ID NO 39
<211> LENGTH: 50
<212> TYPE: DNA
<213> ORGANISM: Artificial Sequence
<220> FEATURE:
<223> OTHER INFORMATION: primer SNP_084_P2

<400> SEQUENCE: 39
catgctgatt accactggta ctcagagtga gcctatggct gcgctgtctc 50

<210> SEQ ID NO 40
<211> LENGTH: 50
<212> TYPE: DNA
<213> ORGANISM: Artificial Sequence
<220> FEATURE:
<223> OTHER INFORMATION: primer SNP_084_P3

<400> SEQUENCE: 40
gagacagcgc agccataggc tcactctgag taccagtggt aatcagcatg 50

<210> SEQ ID NO 41
<211> LENGTH: 73
<212> TYPE: DNA
<213> ORGANISM: Artificial Sequence
<220> FEATURE:
<223> OTHER INFORMATION: primer SNP_084_P4

<400> SEQUENCE: 41
ctgcaaggcg attaagttgg gtaacgccag ggttttccca gtcacgacgt aaaaactaga 60
actgctcaag gcc 73

<210> SEQ ID NO 42
<211> LENGTH: 76
<212> TYPE: DNA
<213> ORGANISM: Artificial Sequence
<220> FEATURE:
<223> OTHER INFORMATION: primer Pcg1860_pyc_P1

<400> SEQUENCE: 42
tttatgcttc cggctcgtat gttgtgtgga attgtgagcg gataacaatt cgcagtcatc 60
cggtggagaa gacttc 76

<210> SEQ ID NO 43
<211> LENGTH: 91
<212> TYPE: DNA
<213> ORGANISM: Artificial Sequence
<220> FEATURE:
<223> OTHER INFORMATION: primer Pcg1860_pyc_P2

<400> SEQUENCE: 43
attttaaata cgcaagctac tttatgtgta tgtgggacaa tttgcaacta tttgtgcagg 60
tcaaagctaa gtttcgggca acactcccct g 91

<210> SEQ ID NO 44
<211> LENGTH: 94
<212> TYPE: DNA
<213> ORGANISM: Artificial Sequence
<220> FEATURE:
<223> OTHER INFORMATION: primer Pcg1860_pyc_P3

<400> SEQUENCE: 44
agttgcaaat tgtcccacat acacataaag tagcttgcgt atttaaaatt atgaacctaa 60
ggggtttagc agtgtcgact cacacatctt caac 94

<210> SEQ ID NO 45
<211> LENGTH: 77
<212> TYPE: DNA
<213> ORGANISM: Artificial Sequence
<220> FEATURE:
<223> OTHER INFORMATION: primer Pcg1860_pyc_P4

<400> SEQUENCE: 45
ctgcaaggcg attaagttgg gtaacgccag ggttttccca gtcacgacgt cagagagatc 60
accagaataa gccatag 77

<210> SEQ ID NO 46
<211> LENGTH: 77
<212> TYPE: DNA
<213> ORGANISM: Artificial Sequence
<220> FEATURE:
<223> OTHER INFORMATION: primer SNP_033_P1

<400> SEQUENCE: 46
tttatgcttc cggctcgtat gttgtgtgga attgtgagcg gataacaatt aggtttctta 60
cctacttatc aacggtg 77

<210> SEQ ID NO 47
<211> LENGTH: 40
<212> TYPE: DNA
<213> ORGANISM: Artificial Sequence
<220> FEATURE:
<223> OTHER INFORMATION: primer SNP_033_P2

<400> SEQUENCE: 47
gatcggcgct tcacgcttga gccgcaggag ctgcgttttg 40

<210> SEQ ID NO 48
<211> LENGTH: 40
<212> TYPE: DNA
<213> ORGANISM: Artificial Sequence
<220> FEATURE:
<223> OTHER INFORMATION: primer SNP_033_P3

<400> SEQUENCE: 48
caaaacgcag ctcctgcggc tcaagcgtga agcgccgatc 40

<210> SEQ ID NO 49
<211> LENGTH: 70
<212> TYPE: DNA
<213> ORGANISM: Artificial Sequence
<220> FEATURE:
<223> OTHER INFORMATION: primer SNP_033_P4

<400> SEQUENCE: 49
ctgcaaggcg attaagttgg gtaacgccag ggttttccca gtcacgacgt gctgcagaca 60
ggtagtcacc 70

<210> SEQ ID NO 50
<211> LENGTH: 72
<212> TYPE: DNA
<213> ORGANISM: Artificial Sequence
<220> FEATURE:
<223> OTHER INFORMATION: primer SNP_316_P1

<400> SEQUENCE: 50
tttatgcttc cggctcgtat gttgtgtgga attgtgagcg gataacaatt cacctgcgac 60
aacaccgaga ac 72

<210> SEQ ID NO 51
<211> LENGTH: 40
<212> TYPE: DNA
<213> ORGANISM: Artificial Sequence
<220> FEATURE:
<223> OTHER INFORMATION: primer SNP_316_P2

<400> SEQUENCE: 51
ctgtggcaga tcagcgtccg acaagaaatc cgccgctgtg 40

<210> SEQ ID NO 52
<211> LENGTH: 40
<212> TYPE: DNA
<213> ORGANISM: Artificial Sequence
<220> FEATURE:
<223> OTHER INFORMATION: primer SNP_316_P3

<400> SEQUENCE: 52
cacagcggcg gatttcttgt cggacgctga tctgccacag 40

<210> SEQ ID NO 53
<211> LENGTH: 70
<212> TYPE: DNA
<213> ORGANISM: Artificial Sequence
<220> FEATURE:
<223> OTHER INFORMATION: primer SNP_316_P4

<400> SEQUENCE: 53
ctgcaaggcg attaagttgg gtaacgccag ggttttccca gtcacgacgt cccaggcctg 60
aaagttctgc 70

<210> SEQ ID NO 54
<211> LENGTH: 71
<212> TYPE: DNA
<213> ORGANISM: Artificial Sequence
<220> FEATURE:
<223> OTHER INFORMATION: primer SCS_aceE_P1

<400> SEQUENCE: 54
tttatgcttc cggctcgtat gttgtgtgga attgtgagcg gataacaatt catcgtctaa 60
aaggcctggg c 71

<210> SEQ ID NO 55
<211> LENGTH: 44
<212> TYPE: DNA
<213> ORGANISM: Artificial Sequence
<220> FEATURE:
<223> OTHER INFORMATION: primer SCS_aceE_P2

<400> SEQUENCE: 55
caagttttgc ttgatcggcc aattccacac ctcctgttgg aatg 44

<210> SEQ ID NO 56
<211> LENGTH: 44
<212> TYPE: DNA
<213> ORGANISM: Artificial Sequence
<220> FEATURE:
<223> OTHER INFORMATION: primer SCS_aceE_P3

<400> SEQUENCE: 56
cattccaaca ggaggtgtgg aattggccga tcaagcaaaa cttg 44

<210> SEQ ID NO 57
<211> LENGTH: 72
<212> TYPE: DNA
<213> ORGANISM: Artificial Sequence
<220> FEATURE:
<223> OTHER INFORMATION: primer SCS_aceE_P4

<400> SEQUENCE: 57
ctgcaaggcg attaagttgg gtaacgccag ggttttccca gtcacgacgt tcgacaccct 60
cgttggtgga ag 72

<210> SEQ ID NO 58
<211> LENGTH: 76
<212> TYPE: DNA
<213> ORGANISM: Artificial Sequence
<220> FEATURE:
<223> OTHER INFORMATION: primer opcA_P1

<400> SEQUENCE: 58
tttatgcttc cggctcgtat gttgtgtgga attgtgagcg gataacaatt ccctgcgtac 60
gctgcaactc tttacg 76

<210> SEQ ID NO 59
<211> LENGTH: 74
<212> TYPE: DNA
<213> ORGANISM: Artificial Sequence
<220> FEATURE:
<223> OTHER INFORMATION: primer opcA_P2

<400> SEQUENCE: 59
atacacgctt aggtccccac gtagtaccac acacaacgcg agaaacggca tttttgcccc 60
taaattatgg cctg 74

<210> SEQ ID NO 60
<211> LENGTH: 79
<212> TYPE: DNA
<213> ORGANISM: Artificial Sequence
<220> FEATURE:
<223> OTHER INFORMATION: primer opcA_P3

<400> SEQUENCE: 60
gcggactcac ccgcgtgaag ggcatcaatg gccacccagc gtcgtcctga ggagaaatac 60
aacactatgg ttgatgtag 79

<210> SEQ ID NO 61
<211> LENGTH: 75
<212> TYPE: DNA
<213> ORGANISM: Artificial Sequence
<220> FEATURE:
<223> OTHER INFORMATION: primer opcA_P4

<400> SEQUENCE: 61
ctgcaaggcg attaagttgg gtaacgccag ggttttccca gtcacgacgt ggaatcaccc 60
gcactggctt gagag 75

<210> SEQ ID NO 62
<211> LENGTH: 70
<212> TYPE: DNA
<213> ORGANISM: Artificial Sequence
<220> FEATURE:
<223> OTHER INFORMATION: primer pcg0007_39-cg2766_P1

<400> SEQUENCE: 62
tttatgcttc cggctcgtat gttgtgtgga attgtgagcg gataacaatt acacacacct 60
ggggttatcc 70

<210> SEQ ID NO 63
<211> LENGTH: 98
<212> TYPE: DNA
<213> ORGANISM: Artificial Sequence
<220> FEATURE:
<223> OTHER INFORMATION: primer pcg0007_39-cg2766_P2

<400> SEQUENCE: 63
tactacgtgg ggacctaagc gtgtattatg gaaacgtctg tatcggataa gtagcgagga 60
gtgttcgtta aaaatgacaa gtgagaattc cgaatccc 98

<210> SEQ ID NO 64
<211> LENGTH: 103
<212> TYPE: DNA
<213> ORGANISM: Artificial Sequence
<220> FEATURE:
<223> OTHER INFORMATION: primer pcg0007_39-cg2766_P3

<400> SEQUENCE: 64
tatccgatac agacgtttcc ataatacacg cttaggtccc cacgtagtac cacacacaac 60
gcgagaaacg gcagtcaatt aagtgtagtc gctaggtgaa aac 103

<210> SEQ ID NO 65
<211> LENGTH: 70
<212> TYPE: DNA
<213> ORGANISM: Artificial Sequence
<220> FEATURE:
<223> OTHER INFORMATION: primer pcg0007_39-cg2766_P4

<400> SEQUENCE: 65
ctgcaaggcg attaagttgg gtaacgccag ggttttccca gtcacgacgt acacaaagaa 60
gcaccaaccg 70

<210> SEQ ID NO 66
<211> LENGTH: 72
<212> TYPE: DNA
<213> ORGANISM: Artificial Sequence
<220> FEATURE:
<223> OTHER INFORMATION: primer 184f7primer pcg0007_39-actA_P1

<400> SEQUENCE: 66
tttatgcttc cggctcgtat gttgtgtgga attgtgagcg gataacaatt cactatgggt 60
gcctagccca tg 72

<210> SEQ ID NO 67
<211> LENGTH: 95
<212> TYPE: DNA
<213> ORGANISM: Artificial Sequence
<220> FEATURE:
<223> OTHER INFORMATION: primer 184f7primer pcg0007_39-actA_P2

<400> SEQUENCE: 67
tactacgtgg ggacctaagc gtgtattatg gaaacgtctg tatcggataa gtagcgagga 60
gtgttcgtta aaaatgtctg atcgcattgc ttcag 95

<210> SEQ ID NO 68
<211> LENGTH: 97
<212> TYPE: DNA
<213> ORGANISM: Artificial Sequence
<220> FEATURE:
<223> OTHER INFORMATION: primer 184f7primer pcg0007_39-actA_P3

<400> SEQUENCE: 68
tatccgatac agacgtttcc ataatacacg cttaggtccc cacgtagtac cacacacaac 60
gcgagaaacg gcagatgttg tgtcccaagg ataaacc 97

<210> SEQ ID NO 69
<211> LENGTH: 70
<212> TYPE: DNA
<213> ORGANISM: Artificial Sequence
<220> FEATURE:
<223> OTHER INFORMATION: primer 184f7primer pcg0007_39-actA_P4

<400> SEQUENCE: 69
ctgcaaggcg attaagttgg gtaacgccag ggttttccca gtcacgacgt cgcatgatgt 60
gctgatgcag 70

<210> SEQ ID NO 70
<211> LENGTH: 48
<212> TYPE: DNA
<213> ORGANISM: Artificial Sequence
<220> FEATURE:
<223> OTHER INFORMATION: primer 184f7

<400> SEQUENCE: 70
cggtatttca caccgcatac tagtaccatc cagaatcgtt tctaagcg 48

<210> SEQ ID NO 71
<211> LENGTH: 42
<212> TYPE: DNA
<213> ORGANISM: Artificial Sequence
<220> FEATURE:
<223> OTHER INFORMATION: primer 184F8

<400> SEQUENCE: 71
gggatccgtc gacctgcatc cacgaagcca cgagataatc tg 42

<210> SEQ ID NO 72
<211> LENGTH: 37
<212> TYPE: DNA
<213> ORGANISM: Artificial Sequence
<220> FEATURE:
<223> OTHER INFORMATION: primer 244-4Go F2 Inf SpeI

<400> SEQUENCE: 72
ggatcttggt actagtcgct gagacagttg agagaag 37

<210> SEQ ID NO 73
<211> LENGTH: 35
<212> TYPE: DNA
<213> ORGANISM: Artificial Sequence
<220> FEATURE:

<223> OTHER INFORMATION: primer 253-4Go R3

<400> SEQUENCE: 73
ggatcttggt actagtagga attcgatgcg gatcc 35

<210> SEQ ID NO 74
<211> LENGTH: 37
<212> TYPE: DNA
<213> ORGANISM: Artificial Sequence
<220> FEATURE:
<223> OTHER INFORMATION: primer 685

<400> SEQUENCE: 74
gaattcctgc agcccggggt accacactgt ttccttg 37

<210> SEQ ID NO 75
<211> LENGTH: 43
<212> TYPE: DNA
<213> ORGANISM: Artificial Sequence
<220> FEATURE:
<223> OTHER INFORMATION: primer 686

<400> SEQUENCE: 75
tcgagctcgg tacccgggac tagtccaagt gcgtggcgag ttt 43

<210> SEQ ID NO 76
<211> LENGTH: 46
<212> TYPE: DNA
<213> ORGANISM: Artificial Sequence
<220> FEATURE:
<223> OTHER INFORMATION: primer 687

<400> SEQUENCE: 76
ccaagcttgc atgcctgcag gactagtaac gggcggtgaa gggcaa 46

<210> SEQ ID NO 77
<211> LENGTH: 45
<212> TYPE: DNA
<213> ORGANISM: Artificial Sequence
<220> FEATURE:
<223> OTHER INFORMATION: primer 693

<400> SEQUENCE: 77
cttcgaaatg tttgacctgc aggacagcct ttaaacgctc ctttt 45

<210> SEQ ID NO 78
<211> LENGTH: 718
<212> TYPE: PRT
<213> ORGANISM: C. glutamicum

<400> SEQUENCE: 78

```
Met Asn Asp Ser Arg Asn Arg Gly Arg Lys Val Thr Arg Lys Ala Gly
1               5                   10                  15

Pro Pro Glu Ala Gly Gln Glu Asn His Leu Asp Thr Pro Val Phe Gln
            20                  25                  30

Ala Pro Asp Ala Ser Ser Asn Gln Ser Ala Val Lys Ala Glu Thr Ala
        35                  40                  45

Gly Asn Asp Asn Arg Asp Ala Ala Gln Gly Ala Gln Gly Ser Gln Asp
    50                  55                  60

Ser Gln Gly Ser Gln Asn Ala Gln Gly Ser Gln Asn Arg Glu Ser Gly
65                  70                  75                  80

Asn Asn Asn Arg Asn Arg Ser Asn Asn Asn Arg Arg Gly Gly Arg Gly
                85                  90                  95
```

```
Arg Arg Gly Ser Gly Asn Ala Asn Glu Gly Ala Asn Asn Asn Ser Gly
            100                 105                 110

Asn Gln Asn Arg Gln Gly Gly Asn Arg Gly Asn Arg Gly Gly Gly Arg
        115                 120                 125

Arg Asn Val Val Lys Ser Met Gln Gly Ala Asp Leu Thr Gln Arg Leu
    130                 135                 140

Pro Glu Pro Pro Lys Ala Pro Ala Asn Gly Leu Arg Ile Tyr Ala Leu
145                 150                 155                 160

Gly Gly Ile Ser Glu Ile Gly Arg Asn Met Thr Val Phe Glu Tyr Asn
                165                 170                 175

Asn Arg Leu Leu Ile Val Asp Cys Gly Val Leu Phe Pro Ser Ser Gly
            180                 185                 190

Glu Pro Gly Val Asp Leu Ile Leu Pro Asp Phe Gly Pro Ile Glu Asp
        195                 200                 205

His Leu His Arg Val Asp Ala Leu Val Val Thr His Gly His Glu Asp
    210                 215                 220

His Ile Gly Ala Ile Pro Trp Leu Leu Lys Leu Arg Asn Asp Ile Pro
225                 230                 235                 240

Ile Leu Ala Ser Arg Phe Thr Leu Ala Leu Ile Ala Ala Lys Cys Lys
                245                 250                 255

Glu His Arg Gln Arg Pro Lys Leu Ile Glu Val Asn Glu Gln Ser Asn
            260                 265                 270

Glu Asp Arg Gly Pro Phe Asn Ile Arg Phe Trp Ala Val Asn His Ser
        275                 280                 285

Ile Pro Asp Cys Leu Gly Leu Ala Ile Lys Thr Pro Ala Gly Leu Val
    290                 295                 300

Ile His Thr Gly Asp Ile Lys Leu Asp Gln Thr Pro Pro Asp Gly Arg
305                 310                 315                 320

Pro Thr Asp Leu Pro Ala Leu Ser Arg Phe Gly Asp Glu Gly Val Asp
                325                 330                 335

Leu Met Leu Cys Asp Ser Thr Asn Ala Thr Thr Pro Gly Val Ser Gly
            340                 345                 350

Ser Glu Ala Asp Val Ala Pro Thr Leu Lys Arg Leu Val Gly Asp Ala
        355                 360                 365

Lys Gln Arg Val Ile Leu Ala Ser Phe Ala Ser Asn Val Tyr Arg Val
    370                 375                 380

Gln Ala Ala Val Asp Ala Ala Val Ala Ser Asn Arg Lys Val Ala Phe
385                 390                 395                 400

Asn Gly Arg Ser Met Ile Arg Asn Met Glu Ile Ala Glu Lys Leu Gly
                405                 410                 415

Tyr Leu Lys Ala Pro Arg Gly Thr Ile Ile Ser Met Asp Asp Ala Ser
            420                 425                 430

Arg Met Ala Pro His Lys Val Met Leu Ile Thr Thr Gly Thr Gln Gly
        435                 440                 445

Glu Pro Met Ala Ala Leu Ser Arg Met Ala Arg Arg Glu His Arg Gln
    450                 455                 460

Ile Thr Val Arg Asp Gly Asp Leu Ile Ile Leu Ser Ser Ser Leu Val
465                 470                 475                 480

Pro Gly Asn Glu Glu Ala Val Phe Gly Val Ile Asn Met Leu Ala Gln
                485                 490                 495

Ile Gly Ala Thr Val Val Thr Gly Arg Asp Ala Lys Val His Thr Ser
            500                 505                 510
```

```
Gly His Gly Tyr Ser Gly Glu Leu Leu Phe Leu Tyr Asn Ala Ala Arg
        515                 520                 525

Pro Lys Asn Ala Met Pro Val His Gly Glu Trp Arg His Leu Arg Ala
    530                 535                 540

Asn Lys Glu Leu Ala Ile Ser Thr Gly Val Asn Arg Asp Asn Val Val
545                 550                 555                 560

Leu Ala Gln Asn Gly Val Val Val Asp Met Val Asn Gly Arg Ala Gln
                565                 570                 575

Val Val Gly Gln Ile Pro Val Gly Asn Leu Tyr Val Asp Gly Val Thr
            580                 585                 590

Met Gly Asp Ile Asp Ala Asp Ile Leu Ala Asp Arg Thr Ser Leu Gly
        595                 600                 605

Glu Gly Gly Leu Ile Ser Ile Thr Ala Val Ile Asp Asn Arg Thr Gly
    610                 615                 620

Arg Leu Leu Glu Arg Pro Thr Val Gln Thr Ser Gly Phe Ser Glu Asp
625                 630                 635                 640

Ala Lys Ser Met Met Gly Glu Val Thr Glu Leu Ser Glu Thr Thr Met
                645                 650                 655

Asn Asp Leu Ala Ala Glu Gly Glu Asn Asp Pro Tyr Arg Met Val Gln
            660                 665                 670

Gln Leu Arg Arg Lys Leu Ser Arg Phe Val Glu Gln Lys Trp Lys Arg
        675                 680                 685

Gln Pro Val Ile Met Pro Thr Val Ile Pro Met Thr Ala Glu Thr Thr
    690                 695                 700

His Ile Gly Asp Asp Glu Val Arg Ala Ser Arg Glu Ser Leu
705                 710                 715


<210> SEQ ID NO 79
<211> LENGTH: 709
<212> TYPE: PRT
<213> ORGANISM: C. glutamicum

<400> SEQUENCE: 79

Met Asn Asp Ser Arg Asn Arg Gly Arg Lys Val Thr Arg Lys Ala Gly
1               5                   10                  15

Pro Pro Glu Ala Gly Gln Glu Asn His Val Glu Thr Pro Val Phe Gln
            20                  25                  30

Ala Pro Asp Ala Ser Ser Asn Gln Ser Thr Val Lys Ala Glu Thr Ala
        35                  40                  45

Gly Asn Asp Asn Arg Asp Ser Ser Gln Gly Ser Gln Ala Gln Gly Ser
    50                  55                  60

Gln Ala Lys Glu Ser Gly Asp Ala Lys Ser Gly Asn Asn Asn Arg Asn
65                  70                  75                  80

Arg Ser Ser Asn Asn Arg Arg Gly Gly Arg Gly Arg Arg Gly Ser Gly
                85                  90                  95

Asn Ala Asn Glu Gly Ser Asn Asn Asn Gly Gly Asn Arg Gly Asn Arg
            100                 105                 110

Gly Asn Arg Gly Gly Gly Arg Arg Asn Val Val Lys Ser Met Gln Gly
        115                 120                 125

Ala Asp Leu Thr Gln Arg Leu Pro Glu Pro Pro Lys Ala Pro Ser Asn
    130                 135                 140

Gly Leu Arg Ile Tyr Ala Leu Gly Gly Ile Ser Glu Ile Gly Arg Asn
145                 150                 155                 160

Met Thr Val Phe Glu Tyr Asn Asn Arg Leu Leu Ile Val Asp Cys Gly
                165                 170                 175
```

```
Val Leu Phe Pro Ser Ser Gly Glu Pro Gly Val Asp Leu Ile Leu Pro
            180                 185                 190

Asp Phe Gly Pro Ile Glu Asp His Leu His Arg Val Asp Ala Leu Val
        195                 200                 205

Val Thr His Gly His Glu Asp His Ile Gly Ala Ile Pro Trp Leu Leu
    210                 215                 220

Lys Leu Arg His Asp Ile Pro Ile Leu Ala Ser Arg Phe Thr Leu Ala
225                 230                 235                 240

Leu Ile Ala Ala Lys Cys Lys Glu His Arg Gln Arg Pro Lys Leu Ile
                245                 250                 255

Glu Val Asn Glu Lys Ser Ser Glu Asp Arg Gly Pro Phe Asn Ile Arg
            260                 265                 270

Phe Trp Ala Val Asn His Ser Ile Pro Asp Cys Leu Gly Leu Ala Ile
        275                 280                 285

Lys Thr Pro Ala Gly Leu Val Ile His Thr Gly Asp Ile Lys Leu Asp
    290                 295                 300

Gln Thr Pro Pro Asp Gly Arg Pro Thr Asp Leu Pro Ala Leu Ser Arg
305                 310                 315                 320

Phe Gly Asp Glu Gly Val Asp Leu Met Leu Cys Asp Ser Thr Asn Ala
                325                 330                 335

Thr Thr Pro Gly Val Ser Gly Ser Glu Ala Asp Val Ala Pro Thr Leu
            340                 345                 350

Lys Arg Leu Val Gly Asp Ala Lys Gln Arg Val Ile Leu Ala Ser Phe
        355                 360                 365

Ala Ser Asn Val Tyr Arg Val Gln Ala Ala Val Asp Ala Ala Val Ala
    370                 375                 380

Ala Asn Arg Lys Val Ala Phe Asn Gly Arg Ser Met Ile Arg Asn Met
385                 390                 395                 400

Glu Ile Ala Glu Lys Leu Gly Tyr Leu Lys Ala Pro Arg Gly Thr Ile
                405                 410                 415

Ile Ser Met Asp Asp Ala Ser Arg Met Ala Pro His Lys Val Met Leu
            420                 425                 430

Ile Thr Thr Gly Thr Gln Gly Glu Pro Met Ala Ala Leu Ser Arg Met
        435                 440                 445

Ala Arg Arg Glu His Arg Gln Ile Thr Val Arg Asp Gly Asp Leu Ile
    450                 455                 460

Ile Leu Ser Ser Ser Leu Val Pro Gly Asn Glu Glu Ala Val Phe Gly
465                 470                 475                 480

Val Ile Asn Met Leu Ala Gln Ile Gly Ala Thr Val Val Thr Gly Arg
                485                 490                 495

Asp Ala Lys Val His Thr Ser Gly His Gly Tyr Ser Gly Glu Leu Leu
            500                 505                 510

Phe Leu Tyr Asn Ala Ala Arg Pro Lys Asn Ala Met Pro Val His Gly
        515                 520                 525

Glu Trp Arg His Leu Arg Ala Asn Lys Glu Leu Ala Ile Ser Thr Gly
    530                 535                 540

Val Asn Arg Asp Asn Val Val Leu Ala Gln Asn Gly Val Val Val Asp
545                 550                 555                 560

Leu Val Asn Gly Arg Ala Gln Val Val Gly Gln Ile Pro Val Gly Asn
                565                 570                 575

Leu Tyr Val Asp Gly Val Thr Met Gly Asp Ile Asp Ala Asp Ile Leu
            580                 585                 590
```

```
Ala Asp Arg Thr Ser Leu Gly Glu Gly Gly Leu Ile Ser Ile Thr Ala
        595                 600                 605

Val Ile Asp Asn Arg Thr Gly Arg Leu Leu Glu Arg Pro Thr Val Gln
    610                 615                 620

Thr Ser Gly Phe Ser Glu Asp Ala Lys Ser Met Met Gly Glu Val Thr
625                 630                 635                 640

Glu Leu Ala Glu Thr Thr Met Asn Asp Leu Ala Ala Glu Gly Glu Asn
                645                 650                 655

Asp Pro Tyr Arg Met Val Gln Gln Met Arg Arg Lys Leu Ser Arg Phe
            660                 665                 670

Val Glu Gln Lys Trp Lys Arg Gln Pro Val Ile Met Pro Thr Val Ile
        675                 680                 685

Pro Met Thr Ala Glu Thr Arg His Ile Asp Asp Asp Glu Val Arg Ala
    690                 695                 700

Ser Arg Glu Ser Leu
705
```

<210> SEQ ID NO 80
<211> LENGTH: 683
<212> TYPE: PRT
<213> ORGANISM: C. ulcerans

<400> SEQUENCE: 80

```
Met Thr Glu Pro Arg Asn Arg Ser Arg Lys Val Thr Arg Lys Ala Gly
1               5                   10                  15

Pro Pro Glu Thr Thr Glu Ala Pro Ala Phe Gln Ala Pro Asp Thr Ser
            20                  25                  30

Val Glu Val Ser Ala Lys Asp Glu Ala Glu Lys Lys Thr Ser Gly Glu
        35                  40                  45

Gly Ser Ser Asn Gln Glu Ala Ser Ser Lys Gly Asn Arg Gly Arg Ser
    50                  55                  60

Asn Ser Gly Arg Ala Gly Asn Gly Thr Arg Asn Gly Arg Ser Arg Arg
65                  70                  75                  80

Gly Gly Asn Pro Gln Asn Asn Lys Ser Asn Arg Gly Arg Arg Asn Val
                85                  90                  95

Val Lys Ser Met Gln Gly Ala Asp Leu Thr Glu Arg Leu Pro Glu Pro
            100                 105                 110

Pro Lys Ala Pro Lys Asn Gly Leu Arg Ile Tyr Ala Leu Gly Gly Ile
        115                 120                 125

Ser Glu Ile Gly Arg Asn Met Thr Val Phe Glu Tyr Asn Asn Lys Met
    130                 135                 140

Leu Leu Val Asp Cys Gly Val Leu Phe Pro Ser Ser Gly Glu Pro Gly
145                 150                 155                 160

Val Asp Leu Ile Leu Pro Asp Phe Gly Pro Ile Glu Asp Lys Leu Asp
                165                 170                 175

Lys Val Glu Ala Leu Val Val Thr His Gly His Glu Asp His Ile Gly
            180                 185                 190

Ala Ile Pro Trp Leu Leu Lys Leu Arg Pro Asp Leu Pro Ile Tyr Ala
        195                 200                 205

Ser Lys Phe Thr Leu Ala Leu Ile Ala Ala Lys Cys Arg Glu His Arg
    210                 215                 220

Gln Arg Pro Lys Leu Ile Glu Val Asn Glu Lys Ser Asp Ile Asn Arg
225                 230                 235                 240

Gly Pro Phe Asn Ile Arg Phe Trp Ala Val Asn His Ser Ile Pro Asp
                245                 250                 255
```

```
Cys Leu Gly Leu Ala Ile Lys Thr Gly Ala Gly Leu Val Ile His Thr
            260                 265                 270

Gly Asp Ile Lys Leu Asp Gln Thr Pro Thr Asp Gly Arg Pro Thr Asp
        275                 280                 285

Leu Pro Ala Leu Ser Arg Phe Gly Asp Glu Gly Val Asp Leu Met Leu
    290                 295                 300

Cys Asp Ser Thr Asn Ala Thr Thr Pro Gly Val Ser Gly Ser Glu Ala
305                 310                 315                 320

Asp Ile Ala Pro Thr Leu Lys Arg Leu Val Gly Asp Ala Lys Gln Arg
                325                 330                 335

Val Ile Leu Ala Ser Phe Ala Ser Asn Val Tyr Arg Val Gln Ala Ala
            340                 345                 350

Val Asp Ala Ala Val Ala Ser Gly Arg Lys Val Ala Phe Asn Gly Arg
        355                 360                 365

Ser Met Ile Arg Asn Met Glu Ile Ala Glu Lys Met Gly Tyr Leu Lys
    370                 375                 380

Ala Pro Arg Gly Thr Ile Val Ser Met Asp Asp Ala Ala Lys Met Ala
385                 390                 395                 400

Pro His Lys Val Met Leu Ile Thr Thr Gly Thr Gln Gly Glu Pro Met
                405                 410                 415

Ala Ala Leu Ser Arg Met Ala Arg Arg Glu His Arg Gln Ile Thr Val
            420                 425                 430

Arg Asp Gly Asp Leu Ile Ile Leu Ser Ser Ser Leu Val Pro Gly Asn
        435                 440                 445

Glu Glu Ala Val Phe Gly Val Ile Asn Met Leu Ala Gln Ile Gly Ala
    450                 455                 460

Thr Val Val Thr Ser Arg Asp Ala Lys Val His Thr Ser Gly His Gly
465                 470                 475                 480

Tyr Ser Gly Glu Leu Leu Phe Leu Tyr Asn Ala Ala Arg Pro Val Asn
                485                 490                 495

Ala Met Pro Val His Gly Glu Trp Arg His Leu Arg Ala Asn Lys Glu
            500                 505                 510

Leu Ala Ile Ser Thr Gly Val Glu Arg Asp Arg Val Val Leu Ala Gln
        515                 520                 525

Asn Gly Val Val Val Asp Leu Val Asp Gly Arg Ala Arg Val Val Gly
    530                 535                 540

Gln Ile Gln Ile Gly Asn Leu Tyr Val Asp Gly Val Thr Met Gly Asp
545                 550                 555                 560

Ile Asp Ala Gly Val Leu Glu Glu Arg Thr Ser Leu Gly Glu Gly Gly
                565                 570                 575

Leu Ile Ala Ile Thr Ala Val Ile Asp Asn Arg Thr Gly Arg Leu Leu
            580                 585                 590

Glu Arg Pro Thr Val Gln Ala Lys Gly Phe Ser Glu Asp Ala Val Ala
        595                 600                 605

Met Met Pro Glu Val Thr Glu Leu Val Glu Asn Thr Met Thr Asp Leu
    610                 615                 620

Ala Gly Glu Gly Glu Asn Asp Pro Tyr Arg Met Val Gln Gln Leu Arg
625                 630                 635                 640

Arg Arg Val Ser Arg Phe Val Glu Gln Lys Trp Arg Arg Lys Pro Met
                645                 650                 655

Ile Met Pro Thr Val Ile Pro Thr Thr Gln Thr Gln Val Glu Ala Asp
            660                 665                 670
```

```
Glu Glu Glu Ile Arg Ala Thr Arg Glu Ser Leu
        675                 680


<210> SEQ ID NO 81
<211> LENGTH: 484
<212> TYPE: PRT
<213> ORGANISM: C. glutamicum

<400> SEQUENCE: 81

Met Val Trp Gly Met Glu His Thr Ser Ala Leu Thr Leu Ile Asp Ser
1               5                   10                  15

Val Leu Asp Pro Asp Ser Phe Ile Ser Trp Asp Glu Thr Pro Gln Tyr
            20                  25                  30

Asp Asn Leu Asn Gln Gly Tyr Ala Glu Thr Leu Glu Arg Ala Arg Ser
        35                  40                  45

Lys Ala Lys Cys Asp Glu Ser Val Ile Thr Gly Glu Gly Thr Val Glu
    50                  55                  60

Gly Ile Pro Val Ala Val Ile Leu Ser Asp Phe Ser Phe Leu Gly Gly
65                  70                  75                  80

Ser Leu Gly Thr Val Ala Ser Val Arg Ile Met Lys Ala Ile His Arg
                85                  90                  95

Ala Thr Glu Leu Lys Leu Pro Leu Leu Val Ser Pro Ala Ser Gly Gly
            100                 105                 110

Ala Arg Met Gln Glu Asp Asn Arg Ala Phe Val Met Met Val Ser Ile
        115                 120                 125

Thr Ala Ala Val Gln Arg His Arg Glu Ala His Leu Pro Phe Leu Val
    130                 135                 140

Tyr Leu Arg Asn Pro Thr Met Gly Gly Ala Met Ala Ser Trp Gly Ser
145                 150                 155                 160

Ser Gly His Leu Thr Phe Ala Glu Pro Gly Ala Gln Ile Gly Phe Leu
                165                 170                 175

Gly Pro Arg Val Val Glu Leu Thr Thr Gly Arg Ala Leu Pro Asp Gly
            180                 185                 190

Val Gln Gln Ala Glu Asn Leu Val Lys Thr Gly Val Ile Asp Gly Ile
        195                 200                 205

Val Ser Pro Leu Gln Leu Arg Ala Ala Val Ala Lys Thr Leu Lys Ile
    210                 215                 220

Ile Gln Pro Ala Glu Ala Thr Asp Arg Phe Ser Pro Thr Thr Pro Gly
225                 230                 235                 240

Ala Ala Leu Pro Val Met Glu Ala Ile Ala Arg Ser Arg Asp Pro His
                245                 250                 255

Arg Pro Gly Ile Gly Glu Ile Met Glu Thr Leu Gly Ala Asp Val Val
            260                 265                 270

Arg Leu Ser Gly Ala Arg Ala Gly Ala Leu Ser Ser Ala Val Arg Val
        275                 280                 285

Ala Leu Ala Arg Ile Gly Gly Arg Pro Val Val Leu Ile Gly Gln Asp
    290                 295                 300

Arg Arg Phe Thr Leu Gly Pro Gln Glu Leu Arg Phe Ala Arg Arg Gly
305                 310                 315                 320

Ile Ser Leu Ala Arg Glu Leu Asn Leu Pro Ile Val Ser Ile Ile Asp
                325                 330                 335

Thr Ser Gly Ala Glu Leu Ser Gln Ala Ala Glu Glu Leu Gly Ile Ala
            340                 345                 350

Ser Ser Ile Ala Arg Thr Leu Ser Lys Leu Ile Asp Ala Pro Leu Pro
        355                 360                 365
```

```
Thr Val Ser Val Ile Ile Gly Gln Gly Val Gly Gly Gly Ala Leu Ala
    370                 375                 380

Met Leu Pro Ala Asp Leu Val Tyr Ala Ala Glu Asn Ala Trp Leu Ser
385                 390                 395                 400

Ala Leu Pro Pro Glu Gly Ala Ser Ala Ile Leu Phe Arg Asp Thr Asn
                405                 410                 415

His Ala Ala Glu Ile Ile Glu Arg Gln Gly Val Gln Ala His Ala Leu
            420                 425                 430

Leu Ser Gln Gly Leu Ile Asp Gly Ile Val Ala Glu Thr Glu His Phe
        435                 440                 445

Val Glu Glu Ile Leu Gly Thr Ile Ser Asn Ala Leu Ser Glu Leu Asp
    450                 455                 460

Asn Asn Pro Glu Arg Ala Gly Arg Asp Ser Arg Phe Thr Arg Phe Glu
465                 470                 475                 480

Arg Leu Ala Gln


<210> SEQ ID NO 82
<211> LENGTH: 480
<212> TYPE: PRT
<213> ORGANISM: C. glutamicum MB001

<400> SEQUENCE: 82

Met Glu His Thr Ser Ala Leu Thr Leu Ile Asp Ser Val Leu Asp Pro
1               5                   10                  15

Asp Ser Phe Ile Ser Trp Asn Glu Thr Pro Gln Tyr Asp Asn Leu Asn
            20                  25                  30

Gln Gly Tyr Ala Glu Thr Leu Glu Arg Ala Arg Ser Lys Ala Lys Cys
        35                  40                  45

Asp Glu Ser Val Ile Thr Gly Glu Gly Thr Val Glu Gly Ile Pro Val
    50                  55                  60

Ala Val Ile Leu Ser Asp Phe Ser Phe Leu Gly Gly Ser Leu Gly Thr
65                  70                  75                  80

Val Ala Ser Val Arg Ile Met Lys Ala Ile His Arg Ala Thr Glu Leu
                85                  90                  95

Lys Leu Pro Leu Leu Val Ser Pro Ala Ser Gly Gly Ala Arg Met Gln
            100                 105                 110

Glu Asp Asn Arg Ala Phe Val Met Met Val Ser Ile Thr Ala Ala Val
        115                 120                 125

Gln Arg His Arg Glu Ala His Leu Pro Phe Leu Val Tyr Leu Arg Asn
    130                 135                 140

Pro Thr Met Gly Gly Ala Met Ala Ser Trp Gly Ser Ser Gly His Leu
145                 150                 155                 160

Thr Phe Ala Glu Pro Gly Ala Gln Ile Gly Phe Leu Gly Pro Arg Val
                165                 170                 175

Val Glu Leu Thr Thr Gly His Ala Leu Pro Asp Gly Val Gln Gln Ala
            180                 185                 190

Glu Asn Leu Val Lys Thr Gly Val Ile Asp Gly Ile Val Ser Pro Leu
        195                 200                 205

Gln Leu Arg Ala Ala Val Ala Lys Thr Leu Lys Val Ile Gln Pro Val
    210                 215                 220

Glu Ala Thr Asp Arg Phe Ser Pro Thr Thr Pro Gly Val Ala Leu Pro
225                 230                 235                 240

Val Met Glu Ala Ile Ala Arg Ser Arg Asp Pro Gln Arg Pro Gly Ile
                245                 250                 255
```

```
Gly Glu Ile Met Glu Thr Leu Gly Ala Asp Val Val Lys Leu Ser Gly
            260                 265                 270

Ala Arg Ala Gly Ala Leu Ser Pro Ala Val Arg Val Ala Leu Ala Arg
        275                 280                 285

Ile Gly Gly Arg Pro Val Val Leu Ile Gly Gln Asp Arg Arg Phe Thr
    290                 295                 300

Leu Gly Pro Gln Glu Leu Arg Phe Ala Arg Arg Gly Ile Ser Leu Ala
305                 310                 315                 320

Arg Glu Leu Asn Leu Pro Ile Val Ser Ile Ile Asp Thr Ser Gly Ala
                325                 330                 335

Glu Leu Ser Gln Ala Ala Glu Glu Leu Gly Ile Ala Ser Ser Ile Ala
            340                 345                 350

Arg Thr Leu Ser Lys Leu Ile Asp Ala Pro Leu Pro Thr Val Ser Val
        355                 360                 365

Ile Ile Gly Gln Gly Val Gly Gly Gly Ala Leu Ala Met Leu Pro Ala
    370                 375                 380

Asp Leu Val Tyr Ala Ala Glu Asn Ala Trp Leu Ser Ala Leu Pro Pro
385                 390                 395                 400

Glu Gly Ala Ser Ala Ile Leu Phe Arg Asp Thr Asn His Ala Ala Glu
                405                 410                 415

Ile Ile Glu Arg Gln Gly Val Gln Ala His Ala Leu Leu Ser Gln Gly
            420                 425                 430

Leu Ile Asp Gly Ile Val Ala Glu Thr Glu His Phe Val Glu Glu Ile
        435                 440                 445

Leu Gly Thr Ile Ser Asn Ala Leu Ser Glu Leu Asp Asn Asn Pro Glu
    450                 455                 460

Arg Ala Gly Arg Asp Ser Arg Phe Thr Arg Phe Glu Arg Leu Ala Gln
465                 470                 475                 480


<210> SEQ ID NO 83
<211> LENGTH: 480
<212> TYPE: PRT
<213> ORGANISM: C. crudilactis

<400> SEQUENCE: 83

Met Ala Tyr Thr Ser Ala Leu Ser Leu Ile Asp Thr Val Leu Asp Ser
1               5                   10                  15

Asp Ser Phe Ala Ser Trp Asp Thr Pro Pro Arg Tyr Gly Asn Ile Asp
            20                  25                  30

Pro Lys Tyr Ala Glu Thr Leu Ala Lys Ala Arg Ser Lys Ser Glu Cys
        35                  40                  45

Asn Glu Ser Ile Ile Thr Gly Glu Gly Thr Val Asp Gly Ile Ala Val
    50                  55                  60

Ala Val Ile Leu Ser Asp Phe Ser Phe Leu Gly Gly Ser Leu Gly Thr
65                  70                  75                  80

Val Ala Ser Met Arg Ile Met Asn Ala Ile His Arg Ala Thr Glu Arg
                85                  90                  95

Lys Met Pro Leu Leu Val Ser Pro Ala Ser Gly Gly Ala Arg Met Gln
            100                 105                 110

Glu Asp Asn Arg Ala Phe Val Ile Met Val Ser Ile Thr Ala Ala Val
        115                 120                 125

Gln Arg His Arg Glu Ala His Leu Pro Phe Leu Val Tyr Leu Arg Asn
    130                 135                 140

Pro Thr Met Gly Gly Ala Met Ala Ser Trp Gly Ser Ser Gly His Ile
```

```
145                 150                 155                 160

Thr Phe Ala Glu Pro Gly Ala Gln Ile Gly Phe Leu Gly Pro Arg Val
                165                 170                 175

Val Glu Leu Ser Thr Gly Lys Pro Leu Pro Glu Gly Val Gln Gln Ala
            180                 185                 190

Glu Asn Leu Val Ala Arg Gly Val Ile Asp Gly Ile Val Ser Pro Met
        195                 200                 205

Gln Leu Arg Ala Ala Val Ser Lys Thr Val Lys Val Leu Gln Pro Ala
    210                 215                 220

Val Leu Gly Ala His Phe Pro Thr Thr Ala Pro Gly Ser Gly Leu Pro
225                 230                 235                 240

Val Met Glu Ala Ile Ala Arg Ser Arg Asp Pro Arg Arg Pro Gly Ile
                245                 250                 255

Gly Glu Ile Ile Glu Thr Leu Gly Glu Asp Val Val Lys Leu Ser Gly
            260                 265                 270

Ala Arg Arg Gly Thr Ala Met Arg Ala Val Arg Val Gly Leu Ala Arg
        275                 280                 285

Leu Ala Gly Arg Pro Val Val Leu Ile Gly Gln Asp Arg His Phe Ala
    290                 295                 300

Leu Gly Pro Gln Asp Leu Ser Phe Ala Arg Arg Gly Ile Ser Leu Ala
305                 310                 315                 320

Arg Glu Leu Asn Leu Pro Ile Val Ser Ile Ile Asp Thr Ser Gly Ala
                325                 330                 335

Glu Leu Ser Gln Asp Ala Glu Glu Leu Gly Ile Ala Ser Ser Ile Ala
            340                 345                 350

Arg Thr Leu Ala Lys Leu Ile Asp Ala Pro Leu Pro Thr Val Ser Val
        355                 360                 365

Ile Leu Gly Gln Gly Val Gly Gly Gly Ala Leu Ala Met Leu Pro Ala
    370                 375                 380

Asp Lys Val Tyr Ala Ala Glu Asn Ala Trp Leu Ser Ala Leu Pro Pro
385                 390                 395                 400

Glu Gly Ala Ser Ala Ile Leu Phe Arg Ser Thr Asp His Ala Ala Glu
                405                 410                 415

Ile Met Glu Arg Gln Gly Val Gln Ala Gln Thr Leu Leu Ser Gln Gly
            420                 425                 430

Leu Ile Asp Gly Ile Ile Ser Glu Ala Val Pro Phe Val Glu Glu Val
        435                 440                 445

Leu Gly Thr Ile Ser Asn Ala Leu Ser Glu Leu Ala Ser Asn Pro Glu
    450                 455                 460

Arg Ala Gly Arg Glu Ser Arg Phe Lys Arg Phe Glu Arg Leu Ala Arg
465                 470                 475                 480


<210> SEQ ID NO 84
<211> LENGTH: 414
<212> TYPE: PRT
<213> ORGANISM: C. glutamicum

<400> SEQUENCE: 84

Met Ala Phe Gly Phe Phe Ser Arg Arg Lys Lys Lys Asn Lys Asp Lys
1               5                   10                  15

Asn Pro Asn Glu Asn Ser Ala Val Pro Ala His Ser Glu Asp Ser Pro
            20                  25                  30

Gln Glu Val Phe Glu Gly Asn Gly Arg Gln Val Gly Asp Pro Ile Glu
        35                  40                  45
```

```
Gln Gln Val Asp Arg Asp Ala Arg Gly Arg Leu Thr Ala Ala Asp Phe
    50                  55                  60

Leu Pro Asp Ala Asp Leu Pro Gln Leu Asn Arg Ser Arg Ala Asn Met
65                  70                  75                  80

Leu Arg Arg Glu Leu Glu Tyr Arg Phe Ser Leu Gln Asn Ala His Ile
                85                  90                  95

Asn Ile Asp Gly Asn Thr Ala Met Ile Gln Arg Ser Asp Gly Gly Ala
            100                 105                 110

Ala His Val Ser Leu Arg Thr Leu Ala Met Asn Ala Ala Gly Leu Asp
        115                 120                 125

Asn Phe Asp Gln Leu Pro Glu Leu Val Glu Ser Phe Val His Gly Thr
    130                 135                 140

Leu Ala Asp Ala Thr Leu Asn Asp Leu Ser Thr Ala Asp Leu Tyr Lys
145                 150                 155                 160

Ala Leu Arg Leu Arg Leu Leu Pro Thr Pro Gly Glu Gly Asp Asp Leu
                165                 170                 175

Val Glu His Gly Leu Asp Arg Glu Ser Gln Ile Arg Asp Asp Ser Ile
            180                 185                 190

Leu Arg Thr Phe Thr Ser Asp Met Ser Ile Ala Leu Val Leu Asp Thr
        195                 200                 205

Glu His Ala Ile Arg Ile Gln Pro Leu Lys Glu Leu Glu Glu Phe Asp
    210                 215                 220

Asp Leu Ser Ala Leu Glu Arg Ala Ala Asp Arg Asn Thr Trp Gln Glu
225                 230                 235                 240

Leu Tyr Asp Ala Asn Val Asp Ala Ser Phe Val Asp Ala Glu Ser Asp
                245                 250                 255

Ser Glu Gly Ser Ser Phe Trp Ala Phe Glu Ser Asn Ser Tyr Tyr Leu
            260                 265                 270

Gly Ser Ala Pro Leu Phe Leu Asn Asp Leu Leu Ala Lys Trp Ala Pro
        275                 280                 285

Asp Leu Asp Gln Ser Asp Gly Val Ile Phe Ala Val Pro Asp Arg Asp
    290                 295                 300

Leu Leu Ile Ala Arg Pro Val Thr Thr Gly Glu Asp Leu Met Asn Gly
305                 310                 315                 320

Ile Thr Ala Met Val Arg Ile Ala Met Arg Phe Gly Leu Gly Asn Pro
                325                 330                 335

Thr Ser Ile Ser Pro Arg Leu His Leu Leu Arg Asp Asn Gln Val Thr
            340                 345                 350

Thr Phe Thr Asp Phe Arg Val Val Ser Pro Glu Met Glu Ala Glu Trp
        355                 360                 365

Glu Asp Ser Ala Phe Asp Ala Pro Pro Ala Gly Ala Ile Gly Ile Glu
    370                 375                 380

Val Arg Pro Asp Pro Tyr Leu Met Glu Arg Leu Gln Gln Gly Gly Phe
385                 390                 395                 400

Gly Asp Phe Gly Asp Phe Gly Lys Pro Arg Asp Leu Asp Met
                405                 410
```

<210> SEQ ID NO 85
<211> LENGTH: 383
<212> TYPE: PRT
<213> ORGANISM: C. crudilactis

<400> SEQUENCE: 85

```
Met Ala Phe Gly Phe Phe Gly Arg Lys Lys Glu Arg Lys Asp Arg His
1               5                   10                  15
```

```
Ser Gly Asp Pro Glu Arg Asp Ser Lys Ser Arg Leu Thr Ser Ala Asp
            20                  25                  30

Leu Leu Pro Asp Thr Asp Leu Pro Gln Leu Asn Arg Ser Arg Ala Asn
        35                  40                  45

Met Leu Arg Gln Glu Leu Glu Tyr Arg Phe Ala Leu Gln Asp Ala His
    50                  55                  60

Ile Asn Ile Asp Gly His Ser Ala Met Val Gln Arg Ala Asp Gly Gly
65                  70                  75                  80

Ala Ala His Val Ser Leu Arg Thr Leu Ala Met Asn Ala Ala Gly Leu
                85                  90                  95

Glu Asn Phe Asp Gln Leu Pro Glu Leu Val Glu Asn Phe Val His Gly
            100                 105                 110

Thr Leu Ala Asp Ala Thr Leu Lys Asp Leu Ser Thr Ala Asp Leu Tyr
        115                 120                 125

Lys Ala Leu Arg Leu Arg Leu Leu Pro Thr Pro Ser Glu Asn Asp Glu
    130                 135                 140

Leu Ala Glu Tyr Gly Leu Thr Ile Glu Ser Lys Ile Arg Asp Asp Ser
145                 150                 155                 160

Ile Leu Arg Thr Phe Thr Ser Asp Met Ser Ile Ala Leu Val Leu Asp
                165                 170                 175

Thr Glu His Ala Ile Arg Ile Gln Pro Leu Lys Glu Leu Glu Arg Phe
            180                 185                 190

Asp Asp Leu Gly Ala Leu Glu Arg Ala Ala Asp Arg Asn Thr Trp Gln
        195                 200                 205

Glu Leu Tyr Asp Ala Ser Val Asp Val Thr Phe Val Asp Ala Glu Ser
    210                 215                 220

Asp Ser Glu Gly Ser Ser Phe Trp Thr Phe Glu Ser Asn Ser Tyr Tyr
225                 230                 235                 240

Leu Gly Ser Ala Pro Leu Phe Leu Gly Asp Leu Leu Ala Lys Trp Ala
                245                 250                 255

Pro Asp Leu Asp Gln Ser Asp Gly Val Ile Phe Ala Val Pro Asp Arg
            260                 265                 270

Asp Leu Leu Ile Ala Arg Pro Ile Ser Thr Gly Glu Asn Leu Met Asn
        275                 280                 285

Gly Ile Thr Ala Met Val Arg Thr Ala Met Arg Phe Gly Leu Gly Asn
    290                 295                 300

Pro Thr Ser Ile Ser Pro Arg Leu His Met Leu His Asp Asn Gln Val
305                 310                 315                 320

Ile Thr Phe Thr Asp Tyr Arg Ile Val Ser Pro Glu Met Glu Ala Glu
                325                 330                 335

Trp Glu Glu Asn Ser Phe Asp Ala Pro Pro Ala Gly Ala Ile Gly Ile
            340                 345                 350

Glu Val Arg Pro Asp Pro Tyr Leu Met Glu Arg Leu Gln Gln Gly Gly
        355                 360                 365

Phe Gly Asp Phe Gly Asp Phe Gly Lys Pro Arg Asp Leu Gly Met
    370                 375                 380


<210> SEQ ID NO 86
<211> LENGTH: 373
<212> TYPE: PRT
<213> ORGANISM: C. efficiens YS-314

<400> SEQUENCE: 86

Met Glu Gln Lys Val Glu Arg Asp Gly Asn Gly Ile Leu Thr Pro Ala
```

-continued

```
1               5                   10                  15

Asp Phe Leu Pro Asp Thr Asp Leu Pro Gln Leu Asn Arg Ser Arg Ala
            20                  25                  30

Asn Met Leu Arg Arg Glu Leu Glu Tyr Arg Phe Ala Leu Lys Asp Ala
        35                  40                  45

Gln Ile Thr Ile Asp Gly Ala Ser Ala Met Val His Arg Pro Asp Gly
    50                  55                  60

Gly Ala Ala His Val Ser Leu Arg Thr Leu Ala Met Asn Ala Ala Gly
65                  70                  75                  80

Leu Asp Asp Leu Gly Gln Leu Pro Glu Leu Val Asp Asn Phe Val His
                85                  90                  95

Gly Thr Leu Ala Asp Ala Thr Leu Ser Thr Leu Ser Thr Ala Asp Leu
            100                 105                 110

Tyr Lys Ser Leu Arg Leu Arg Leu Leu Pro Asn Pro Glu Gln Gly Asp
        115                 120                 125

Ser Ile Leu Glu Thr Ser Asp Gly Val Glu Arg Gln Ile Arg Glu Thr
    130                 135                 140

Ser Val Leu Arg Asp Phe Thr Ser Asp Thr Ser Ile Ala Leu Val Leu
145                 150                 155                 160

Asp Thr Glu His Ala Ile Arg Ile Gln Pro Leu His Glu Leu Glu Glu
                165                 170                 175

Phe Asp Ser Leu Asp Ala Leu Glu Arg Ala Ala Asp Arg Asn Thr Trp
            180                 185                 190

Gln Glu Leu Leu Asp Ala Asp Val Asp Val Thr Tyr Phe Asn Asn Asp
        195                 200                 205

Glu Gly Gly Glu Gly Ser Asp Phe Trp Ala Phe Glu Ser Ser Ser Tyr
    210                 215                 220

Tyr Leu Gly Ser Ser Pro Leu Phe Leu Thr Asp Leu Leu His Arg Trp
225                 230                 235                 240

Ala Pro Asp Leu Asp Gln Ser Arg Gly Val Ile Phe Ala Val Pro Asp
                245                 250                 255

Arg Asp Leu Leu Ile Ala Arg Pro Val Thr Thr Gly Glu Asn Leu Met
            260                 265                 270

Asn Gly Ile Thr Ser Met Val Arg Ile Ala Met Arg Phe Gly Leu Gly
        275                 280                 285

Asn Pro Thr Ser Ile Ser Pro Arg Leu His Leu Leu Tyr Asp Asn Gln
    290                 295                 300

Ile Asn Thr Phe Thr Asp Tyr Arg Ile Ile Glu Pro Thr Glu Asp Glu
305                 310                 315                 320

Glu Trp Ala Val Pro Thr Ala Asp Ala Pro Gln Pro Gly Ser Ile Gly
                325                 330                 335

Ile Glu Val Arg Pro Asp Ala Tyr Leu Met Glu Met Leu Gln Gln Asp
            340                 345                 350

Gly Phe Gly Asp Ser Phe Asp Asp Phe Gly Pro Arg Asp Leu Gly Pro
        355                 360                 365

Asp Asp Phe Arg Tyr
    370
```

<210> SEQ ID NO 87
<211> LENGTH: 316
<212> TYPE: PRT
<213> ORGANISM: C. vitaeruminis DSM 20294

<400> SEQUENCE: 87

```
Met Ile Phe Glu Leu Pro Asp Ser Ser Thr Arg Asp Ile Ala Lys Thr
1               5                   10                  15

Leu Val Arg Ile Arg Asp Thr Gly Gly Gln Val Thr Thr Ser Arg Val
            20                  25                  30

Leu Ser Leu Ile Val Ile Ala Arg Lys Glu Asp Asp Val Glu Ala Val
        35                  40                  45

Ile Arg Ala Thr Asn Glu Ala Ser Arg Glu His Pro Ser Arg Val Ile
    50                  55                  60

Val Leu Ile Gln Gly Asp Pro Thr Val Pro Ser Ser Arg Leu Asp Ala
65                  70                  75                  80

Glu Val Arg Ile Gly Gly Asp Ala Gly Ala Ser Glu Leu Ile Leu Ile
                85                  90                  95

Asn Leu Asp Gly Glu Val Ala Asn Asn Leu Val His Val Val Thr Pro
            100                 105                 110

Leu Leu Leu Pro Asp Thr Pro Ile Val Thr Trp Trp Ala Tyr Ala Ala
        115                 120                 125

Pro Val Asp Pro Ser Ser Asp Pro Met Gly Ile Ile Ala Gln Arg Arg
    130                 135                 140

Ile Thr Asp Ser Leu Phe Asp Pro Pro Gln Asp Ala Leu Tyr Asn Arg
145                 150                 155                 160

Arg Asn His Tyr Val Pro Gly Asp Ser Asp Ile Ala Trp Ala Arg Leu
                165                 170                 175

Thr Pro Trp Arg Gly Val Leu Ala Ser Thr Leu Asp Gln Pro Pro His
            180                 185                 190

Glu Met Val Gln Glu Val Arg Val Val Gly Pro Gln Asp Ser Pro Ser
        195                 200                 205

Val Asp Leu Ala Ala Gly Trp Leu Ile Asp Arg Leu Gly Val Pro Val
    210                 215                 220

Ser Arg Leu Val Asp Glu His Ala Gln Ala Cys Asp Ala Asp Thr Ile
225                 230                 235                 240

Pro Val Asn Arg Val Glu Leu Asp Arg Pro Ser Gly Thr Val Val Leu
                245                 250                 255

Glu Val Leu Pro Asp Gln Asp Thr Leu Ser Val Thr Phe Pro Gly Lys
            260                 265                 270

Glu Val Ala Leu Val Ala Ile Ser Arg Arg Ser Thr Ser Asp Cys Leu
        275                 280                 285

Ala Glu Glu Leu Arg His Leu Asp Pro Asp Val Ala Tyr Gln Arg Ala
    290                 295                 300

Leu Ser Gly Leu Ala His Val Asp Tyr Pro Gln Gly
305                 310                 315
```

<210> SEQ ID NO 88
<211> LENGTH: 317
<212> TYPE: PRT
<213> ORGANISM: C. matruchotii ATCC 33806

<400> SEQUENCE: 88

```
Met Ile Phe Thr Leu Ser Asp Thr Asp Thr His Glu Ile Ala Arg Thr
1               5                   10                  15

Leu Val Glu Ile Arg Asp Asp Gly Ser Gln Gly Thr Thr Ser Arg Val
            20                  25                  30

Leu Thr Leu Ile Ala Val Ala Lys Asp Thr Asp Asn Ile Arg Ser Val
        35                  40                  45

Ile Ser Ala Ser Lys Asp Ala Ser Arg Glu His Pro Cys Arg Val Ile
    50                  55                  60
```

```
Val Leu Val Thr Gly Asp Pro Asp Arg Asn Thr Arg Ile Asp Ala Glu
65                  70                  75                  80

Val Arg Ile Gly Gly Asp Ala Gly Ala Ser Glu Ile Ile Val Ile Asp
                85                  90                  95

Leu Glu Gly Glu Val Thr Arg His Leu Val His Val Val Thr Pro Leu
            100                 105                 110

Leu Leu Pro Asp Thr Pro Ile Val Val Trp Trp Pro Tyr Thr Ala Pro
        115                 120                 125

Val Asn Pro Ala Glu Asp Pro Leu Gly Arg Ile Ala Gln Arg Arg Ile
    130                 135                 140

Thr Asp Ser Gln Lys Asp Pro Leu Val Asp Ala Leu Tyr Asn Arg Arg
145                 150                 155                 160

Asn Ser Tyr Thr Asp Gly Asp Ser Asp Leu Ala Trp Ala Arg Ile Thr
                165                 170                 175

Pro Trp Arg Gly Val Val Ala Ser Ala Leu Asp Gln Pro Pro Phe Glu
            180                 185                 190

Pro Val Ile Glu Ala Lys Val Tyr Gly Ala Thr Asn Cys Pro Ser Val
        195                 200                 205

Asp Leu Ala Ala Gly Trp Leu Ala Ala Arg Leu Gly Val Pro Val Thr
    210                 215                 220

Arg Ile Ala Val Asp Asp Pro Ser Val Lys Lys Gln Ala Ser Leu Asn
225                 230                 235                 240

Val Thr Pro Val Glu Arg Val Glu Leu Val Arg Pro Ser Gly Ala Thr
                245                 250                 255

Val Leu Glu Ala Leu Asp Ser Gln Thr Ile Gly Val Ser Val Pro Asn
            260                 265                 270

Arg Glu Pro Ala Arg Val Ala Val Asn Leu Arg Thr Asp Ala Asp Cys
        275                 280                 285

Leu Ala Glu Glu Leu Arg His Leu Asp Pro Asp His Ala Tyr Asp Glu
    290                 295                 300

Val Leu Arg Gly Leu Asn Gln Val Ser Tyr Pro Val Val
305                 310                 315


<210> SEQ ID NO 89
<211> LENGTH: 353
<212> TYPE: PRT
<213> ORGANISM: C. falsenii DSM 44353

<400> SEQUENCE: 89

Met Ile Ile Asp Leu Pro Asn Thr Ser Thr His Ile Ile Ser Gln Lys
1               5                   10                  15

Leu Ser Ala Leu Arg Glu Glu Arg Gly Glu Val Ala Thr Gly Arg Val
            20                  25                  30

Leu Thr Leu Ile Val Val Ala Ser Ser Glu Asp Asp Leu Pro Arg Ile
        35                  40                  45

Ile Asp Ala Thr His Glu Ala Ser Arg Glu His Pro Ala Arg Val Leu
    50                  55                  60

Ile Leu Val Asn His Arg Lys Ser Asp Glu Val His Leu Asp Ala Glu
65                  70                  75                  80

Ile Arg Leu Gly Gly Asp Ala Gly Ala Ser Glu Ile Ile Val Met His
                85                  90                  95

Asn His Gly Glu Leu Val Ala His Arg Ala Ser Val Val Thr Pro Leu
            100                 105                 110

Leu Leu Pro Asp Thr Pro Ile Val Ala Trp Trp Pro Thr Asn Gly Pro
```

```
        115                 120                 125

Arg Asn Pro Ala Ala Asp Ala Ile Gly Met Leu Ala Thr Arg Arg Ile
    130                 135                 140

Thr Asp Ser Leu His Asp Asp Asp Thr Asp Ala Leu Phe Arg Arg Arg
145                 150                 155                 160

Met Thr Tyr Thr Arg Gly Asp Ser Asp Met Ala Trp Ser Arg Ile Thr
                165                 170                 175

Leu Trp Arg Gly Leu Leu Ala Ser Ser Leu Asp Gln Pro Pro Tyr Glu
            180                 185                 190

Pro Ile Asp Ser Val Glu Leu Thr Gly Pro Ala Asp Asp Pro Ser Thr
        195                 200                 205

Asp Ile Ala Ala Gly Trp Leu Ala Glu Lys Leu Gln Val Pro Val Thr
    210                 215                 220

Arg His Asn Ser Gly Thr Asp Ala Ile Pro Arg Asp Asp Lys Gly Asn
225                 230                 235                 240

Lys Thr Ile Ser Ile Glu Lys Ala Val Leu His Arg Glu Ser Ala Thr
                245                 250                 255

Val Glu Val Thr Val Val Asp Ser Glu Thr Val Ser Met Lys Val Gly
            260                 265                 270

Asp Lys Glu Ser Leu Val Thr Leu Gly Arg Arg Pro Leu Ala Asp Cys
        275                 280                 285

Leu Ala Glu Glu Leu Arg His Leu Asp Pro Asp Tyr Ala Phe Gly His
    290                 295                 300

Ala Leu Arg Gly Leu Val Arg Val Asn Arg Pro Glu Arg Thr Asn Arg
305                 310                 315                 320

Leu Pro Asn Tyr Arg Gly Ala Ser Ile Pro Asp Glu Ala Pro Asp Arg
                325                 330                 335

Trp Ser Ala Ser Val Ala Asp Asp His Phe Ala Glu Gln Glu Ser Arg
            340                 345                 350

Arg


<210> SEQ ID NO 90
<211> LENGTH: 310
<212> TYPE: PRT
<213> ORGANISM: C. halotolerans YIM 70093

<400> SEQUENCE: 90

Met Ile Ile Thr Leu Pro Asp Thr Asp Ser Arg Glu Val Ala Ala Ser
1               5                   10                  15

Leu Leu Glu Ala Arg Glu Gln Asn Ser Arg Thr Thr Gly Arg Val Leu
            20                  25                  30

Thr Leu Ile Val Ala Ala Asn Leu Asn Asp Asn Val Asp Ala Ile Ile
        35                  40                  45

Ser Ala Ala Arg Gly Ala Ser His Glu His Pro Ala Arg Val Leu Val
    50                  55                  60

Phe Ile Thr Gly Glu Thr Ser Gly Lys Ala Gln Leu Asp Ala Glu Val
65                  70                  75                  80

Arg Val Gly Gly Asp Ala Gly Ala Ser Glu Met Val Ile Met Arg Val
                85                  90                  95

Ser Gly Glu Leu Ala Gly His Leu Glu Ser Val Val Thr Pro Leu Leu
            100                 105                 110

Leu Pro Asp Thr Pro Ile Val Thr Trp Trp Pro Thr Glu Ala Pro Glu
        115                 120                 125

Asn Pro Ser Ala His Pro Leu Gly Arg Leu Ser Gln Arg Arg Ile Thr
```

```
    130                 135                 140

Asn Ala Gln Arg Asp Gly Gly Glu Asp Ile Leu Asp Arg Leu Arg Ala
145                 150                 155                 160

Ala Tyr Thr Pro Gly Asp Ser Asp Met Met Trp Ser Arg Ile Thr Ala
                165                 170                 175

Trp Arg Gly Ile Val Ala Ser Ser Leu Asp Gln His Pro His Gly Ala
            180                 185                 190

Val Glu Ser Ala Thr Leu Val Gly Pro Pro Glu Asp Pro Ser Val Asp
        195                 200                 205

Ile Ala Ala Gly Trp Leu Ala Asp Arg Leu Gly Val Glu Ile Ile Arg
    210                 215                 220

Glu Asp Cys Glu Pro Ala Glu Asp Pro Thr Leu Phe Pro Ile Arg Ser
225                 230                 235                 240

Leu Arg Phe Asn Arg Ala Pro Gly Pro Leu Lys Val Asp Val Ile Asp
                245                 250                 255

His Arg Thr Val Gln Val Thr Leu Pro Gly Arg Pro Glu Ser Leu Val
            260                 265                 270

Ala Met Ser Val Arg Ser Asp Ser Glu Cys Leu Ser Glu Glu Leu Arg
        275                 280                 285

His Leu Asp Pro Asp Thr Ala Tyr Ala Gln Ala Leu Arg Ala Leu Asn
    290                 295                 300

Arg Val Thr His Arg Ser
305                 310


<210> SEQ ID NO 91
<211> LENGTH: 325
<212> TYPE: PRT
<213> ORGANISM: C. pyruviciproducens ATCC BAA-1742

<400> SEQUENCE: 91

Met His Gln Leu Arg Asn Thr Ser Thr Lys Glu Ile Ala Ser Lys Leu
1               5                   10                  15

Glu Gln Ile Glu Thr Ser Gly Met Gln Pro Arg Thr Asn His Val Leu
            20                  25                  30

Thr Leu Ile Val Val Ile Asn Gly Lys Thr Asn Lys Asp Arg Leu Phe
        35                  40                  45

His Thr Ile Ser Ser Ser Ser Lys Glu His Pro Ser Arg Val Leu Val
    50                  55                  60

Leu Glu Pro Leu Ala Glu Glu His Ser Leu Gly Phe His Ala Ser Ser
65                  70                  75                  80

Val Ile Asp Ala Glu Leu His Val Gly Gly Asp Ala Gly Ala Ser Glu
                85                  90                  95

Ile Ile Trp Met Gln Leu Arg Gly Glu Val Thr Glu His Leu Asp Ser
            100                 105                 110

Val Val Thr Pro Leu Leu Leu Pro Asp Thr Pro Ile Val Val Trp Trp
        115                 120                 125

Pro Ala Ser Ala Pro Val Asn Pro Ser His Asp Pro Leu Gly Lys Leu
    130                 135                 140

Ala Met Arg Arg Ile Thr Asp Ser Phe Phe Asp Pro Ala Glu Asp Ala
145                 150                 155                 160

Ile Tyr Arg Arg Arg Ser Asn Tyr Thr Pro Gly Asp Ser Asp Leu Cys
                165                 170                 175

Trp Ser Arg Leu Thr Pro Trp Arg Gly Ile Leu Ala Ser Ala Leu Asp
            180                 185                 190
```

Gln Pro Pro Phe Glu Pro Val Arg Ser Ala Lys Val Phe Gly Leu Ala
195 200 205

Val Ser Pro Thr Val Asp Leu Ala Ala Gly Trp Leu Ala Asp Val Leu
210 215 220

Gly Val Pro Val Tyr Arg Glu Val Arg Gly Thr Ala Asp Arg Pro Val
225 230 235 240

Asp His Asn Gly Asn Pro Ala Thr Pro Val Ala Glu Val Ile Leu Glu
245 250 255

Arg Asp Thr Gly Ser Val Arg Leu Val Val Ala Asp Ser Glu Thr Ile
260 265 270

Glu Leu Thr Ile Gly Asp Gly Pro Ala Thr Lys Ile Ala Gln Gly Arg
275 280 285

Arg Pro Asp Val Asp Cys Leu Ser Glu Glu Met Arg His Leu Val Pro
290 295 300

Asp Gln Ala Tyr Ala Gly Ala Leu Asp Gly Leu Ser Lys Val Thr Tyr
305 310 315 320

Leu Glu Ala Asp Gln
325

<210> SEQ ID NO 92
<211> LENGTH: 303
<212> TYPE: PRT
<213> ORGANISM: C. casei UCMA 3821

<400> SEQUENCE: 92

Met Ile Thr Pro Met Pro Asn Thr Thr Thr Ser Lys Ile Ala Arg Gly
1 5 10 15

Leu Val Glu Ala Gln Glu His Tyr Thr Leu Thr Thr Ser Arg Val Leu
20 25 30

Thr Leu Ile Val Val Val Asn Val Asp Asp Glu Val Asp Ala Val Leu
35 40 45

Asp Ser Val Arg Asp Ala Ser His Glu His Pro Ser Arg Val Leu Val
50 55 60

Val Ile Thr Gly Ser Arg Asp Ala Glu Pro Leu Leu Asn Ala Glu Leu
65 70 75 80

Arg Val Gly Gly Glu Ala Gly Ala Ser Glu Ile Val Val Met His Leu
85 90 95

Phe Gly Pro Leu Ala Asp Asn Ala Glu Ser Val Val Thr Pro Leu Leu
100 105 110

Leu Pro Asp Thr Pro Ile Val Val Trp Trp Pro Thr Ala Ala Pro Glu
115 120 125

Gly Pro Ser Lys Thr Pro Ile Gly Lys Leu Gly Gln Arg Arg Ile Thr
130 135 140

Tyr Ala Ala Ala Lys Gly Asp Leu Arg Arg Leu Ser Ser Gly Tyr Ala
145 150 155 160

Pro Gly Asp Thr Asp Met Ala Trp Gly Glu Ile Thr Gln Trp Arg Gly
165 170 175

Ile Val Ala Ser Ser Leu Asp Arg Leu Pro His Glu Pro Val Lys Arg
180 185 190

Val Glu Ile Ser Gly Pro Ser Asp Ser Leu Ala Val Asp Leu Ala Ala
195 200 205

Ala Trp Met Leu Asp Arg Leu Ala Val Pro Val Lys Arg Val Val Ser
210 215 220

Asp Ala Pro Gly Glu Lys Phe Thr Ile His Ser Val Arg Phe Phe Arg
225 230 235 240

```
Glu Thr Ser Asp Ile Ile Ile Asp Ala Ser Glu Glu Gly Ser Val Arg
                245                 250                 255

Val Asn Val Pro Gly Ser Pro Glu Ser Met Val Ala Leu Asn Thr Arg
            260                 265                 270

Ser Arg Ala Glu Ile Leu Ser Glu Glu Leu Arg His Leu Asp Ala Asp
        275                 280                 285

Glu Ala Tyr Ala His Thr Leu Arg Gly Leu Ala Gln Val Asp Tyr
    290                 295                 300


<210> SEQ ID NO 93
<211> LENGTH: 350
<212> TYPE: PRT
<213> ORGANISM: C. terpenotabidum Y-11

<400> SEQUENCE: 93

Met Thr Thr Pro Glu Ser Thr Gly Val Gly Ser Ser Gly Val Gly Gln
1               5                   10                  15

Leu Asp Gly Arg Met Asn Leu Gly Arg Thr Thr Thr His Arg Ile Thr
            20                  25                  30

Arg Ala Leu Arg Ser Leu Arg Glu Lys Arg Gly Glu Val Thr Thr Gly
        35                  40                  45

Arg Val Leu Thr Leu Ile Val Ser Ala Arg Ser Glu Glu Asp Leu Asp
    50                  55                  60

Ser Val Val Arg Gly Ala Asn Glu Ala Ser Arg Glu His Pro Ala Arg
65                  70                  75                  80

Val Ile Val Val Ile His Asp Arg Ser Thr Asp Glu Val Ser Leu Asp
                85                  90                  95

Ala Glu Leu Ile Val Gly Gly Gln Ala Gly Ala Ala Glu Ile Ile Phe
            100                 105                 110

Met Arg Leu His Gly Glu Leu Ala Asp His Ala Asp Ser Val Val Met
        115                 120                 125

Pro Leu Leu Leu Pro Asp Thr Pro Val Val Val Trp Trp Pro Phe Thr
    130                 135                 140

Ser Pro Arg Asn Pro Ala Gly Asp Ser Leu Gly Arg Leu Ala Ser Arg
145                 150                 155                 160

Arg Ile Thr Asp Ser Phe Ser Asp Ala Ala Ala Gly Lys Gly Ala Lys
                165                 170                 175

Ala Ile Phe Arg Arg Arg Ile Gly Tyr Thr Pro Gly Asp Ser Asp Leu
            180                 185                 190

Val Trp Ser Arg Ile Thr Pro Trp Arg Gly Leu Leu Ser Ser Ala Val
        195                 200                 205

Glu Gln His Ala Gly Asp Thr Val Thr Gly Val Asp Ile Thr Gly Pro
    210                 215                 220

Ala Glu Asp Pro Ala Val Asp Ile Ala Ala Gly Trp Leu Ala Asp Arg
225                 230                 235                 240

Phe Ser Val Pro Val Thr Arg Tyr Ala Gly Thr Ser Pro Ala Val Pro
                245                 250                 255

Ile Asp Asp Glu Gly Leu Ala Thr Ala Pro Val Glu Arg Val Val Leu
            260                 265                 270

His Phe Thr Gly Gly Asp Leu Val Met Glu Val Leu Asp His Arg Ser
        275                 280                 285

Val Arg Ile Leu Asp Gly Glu Thr Asp Asn Ile Val Thr Leu His Arg
    290                 295                 300

Arg Thr Leu Gly Glu Cys Leu Ala Glu Glu Leu Arg His Leu Glu Pro
```

```
305                 310                 315                 320

Asp Ala Ala Phe Gly Asp Ala Leu His Gly Leu Pro Arg Val Arg Val
                325                 330                 335

Ala Arg Glu Pro Ala Pro Ala Pro Val Glu Glu Ser His Arg
            340                 345                 350


<210> SEQ ID NO 94
<211> LENGTH: 319
<212> TYPE: PRT
<213> ORGANISM: C. glutamicum NRRL B-11474

<400> SEQUENCE: 94

Met Ile Phe Glu Leu Pro Asp Thr Thr Thr Gln Gln Ile Ser Lys Thr
1               5                   10                  15

Leu Thr Arg Leu Arg Glu Ser Gly Thr Gln Val Thr Thr Gly Arg Val
            20                  25                  30

Leu Thr Leu Ile Val Val Thr Asp Ser Glu Ser Asp Val Ala Ala Val
        35                  40                  45

Thr Glu Ser Thr Asn Glu Ala Ser Arg Glu His Pro Ser Arg Val Ile
    50                  55                  60

Ile Leu Val Val Gly Asp Lys Thr Ala Glu Asn Lys Val Asp Ala Glu
65                  70                  75                  80

Val Arg Ile Gly Gly Asp Ala Gly Ala Ser Glu Met Ile Ile Met His
                85                  90                  95

Leu Asn Gly Pro Val Ala Asp Lys Leu Gln His Val Val Thr Pro Leu
            100                 105                 110

Leu Leu Pro Asp Thr Pro Ile Val Ala Trp Trp Pro Gly Glu Ser Pro
        115                 120                 125

Lys Asn Pro Ser Gln Asp Pro Ile Gly Arg Ile Ala Gln Arg Arg Ile
    130                 135                 140

Thr Asp Ala Leu Tyr Asp Arg Asp Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro Pro His Ser Glu
            180                 185                 190

Ile Thr Ser Val Arg Leu Thr Gly Ala Ser Gly Ser Thr Ser Val Asp
        195                 200                 205

Leu Ala Ala Gly Trp Leu Ala Arg Arg Leu Asn Val Pro Val Ile Arg
    210                 215                 220

Glu Val Thr Asp Ala Pro Thr Val Ser Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile His Asp Ala His Thr Leu Gln Val Glu Met Pro Glu
            260                 265                 270

Ser Gly Asn Ala Pro Ser Leu Val Ala Ile Gly Arg Arg Ser Glu Ser
        275                 280                 285

Asp Cys Leu Ser Glu Glu Leu Arg His Met Asp Pro Asp Leu Gly Tyr
    290                 295                 300

Gln His Ala Leu Ser Gly Leu Ser Ser Val Lys Leu Glu Thr Val
305                 310                 315


<210> SEQ ID NO 95
<211> LENGTH: 87
```

<212> TYPE: DNA
<213> ORGANISM: Artificial Sequence
<220> FEATURE:
<223> OTHER INFORMATION: promoter 3121

<400> SEQUENCE: 95
gtggctaaaa cttttggaaa cttaagttac ctttaatcgg aaacttattg aattcgggtg 60
aggcaactgc aactctggac ttaaagc 87

<210> SEQ ID NO 96
<211> LENGTH: 98
<212> TYPE: DNA
<213> ORGANISM: Artificial Sequence
<220> FEATURE:
<223> OTHER INFORMATION: promoter 0755

<400> SEQUENCE: 96
aataaattta taccacacag tctattgcaa tagaccaagc tgttcagtag ggtgcatggg 60
agaagaattt cctaataaaa actcttaagg acctccaa 98

<210> SEQ ID NO 97
<211> LENGTH: 86
<212> TYPE: DNA
<213> ORGANISM: Artificial Sequence
<220> FEATURE:
<223> OTHER INFORMATION: promoter 3381

<400> SEQUENCE: 97
cgccggataa atgaattgat tattttaggc tcccagggat taagtctagg gtggaatgca 60
gaaatatttc ctacggaagg tccgtt 86

<210> SEQ ID NO 98
<211> LENGTH: 4093
<212> TYPE: DNA
<213> ORGANISM: C. glutamicum

<400> SEQUENCE: 98
gtgatggcat cgcgcacctc aaactgtgca cccgcttcta agccaagcgc tccaagatca 60
aggcgaacag tagcctcacg agcactacgt ggatccaagt tgaccacaat caacacggta 120
tttccggtca aagcatcaac cttggagtag gcgatgatct gatcattgtc tgcttcgtgg 180
aagtggatgt tgcgtagctg ctgcaaggca gggttcgcgc gacggatctg gttgagcaga 240
gcgatgtaat cctcgaggga atcgccacgc tccagagcgc cctcgaaatc gcggggacgc 300
agctcgtact tctcagaatc caagtactct tccgaaccag gcttgacggc ctcgtgctca 360
aagagctcat atccggaata tacgccccac acaggagaca tcgtggcggc caatgcggcg 420
cggatagcga acattgcgcg tccaccatgc tgcagagacg catgcaaaat gtcgggagtg 480
ttcacaaaca ggttcggacg agaaatatcc gccatgcggg cgatctcagt agcgaactcg 540
gtgagctcct ccttggtgac cttccacgtg aagtaggtgt aagactggga gaaaccaatc 600
ttggccaagc catacagacg tgccgggcga gtaaacgcct ccgctaggaa aatgacctca 660
gggtttgatt tatggatggc agaaataagc cactgccaga aattagcggg cttagtgtgc 720
gggttgtcca cgcggaatgt ggtcacaccc aaatccaccc agaacttcac cacacgatag 780
acctcttcat agatcttcgg agcagcatta tcaaagttga tgggataaat atcctggtac 840
ttcttcggtg ggttttctgc atacgcaatg gtgccatcag ccaacaccgt gaaaaactcg 900
cggtgttcct gcgcccatgg atgatcaggg gcagcctgca gagctagatc gagtgcaact 960

-continued

```
tccaaattga gttcccgtgc gcgagccaac aacgcctgga aatcttcaat ggtgcccaac   1020
cgcggatgcg ttgcatcatg cccaccatct ttagaaccaa tagcccacgg cgaacccaca   1080
tcatgaggtt ccggggtcag cgtattattg cggcccttgc ggttgacctc gccaatcgga   1140
tggatcggcg ggaagtaaac agtatcgaag cccatcttcg cgacacgctc caacgcctga   1200
gcagtggtag cgaaagtgcc atgaacgggg gtgccggact catcccaacc acctgtggaa   1260
cgagggaaaa gctcatacca agagttgacc aaagcggcac gacgctcgac acgaacctgc   1320
aggttttcac ccatcgtgac caactcacgc aacgggttaa gttctaaaag atgagtgaca   1380
ctcgcggtga gcgctggggc gagacgtgcg cgtacatcgc cgccacgccg cagagaggag   1440
gcgacgtcga aaagcgcagt cctatcctct ttagacaaat tctccgcagc ccgttcaaac   1500
agctgagccc cgtgctcaaa gtcgttatac aactcatctg aaccctggcc tgcctcaatt   1560
ttagtggtaa tcgcatgacg ccacgtagac ataggatccg accacgcatc cacacgaaat   1620
gtccaattac cagggacatc aggaacgaaa aatgcattcg actgatcctg attatcagga   1680
gtggggcgca tatgaatctg aataggctca gccgccactg aagaatcctc cggaccggac   1740
acattcaacg tcgcggcaat tgcatcatgg ccttcacgcc acacaacagc cgagacagga   1800
acaatctcac ccactactgc tttcgctgga tttccatcca aaatccgggg acgaacatca   1860
tcgataccga gacggccagt cacagttttc tcctcaacat gcagtgtgaa gtgcgaacaa   1920
acgcacacaa gcttaaaagt tcgatcaagc agacacaccg gcaattagcc gggggtatgt   1980
ctccattatg aaagcttaac ggagctgtgt cacttccaca cggaaccgga gaaatcagtc   2040
aagatgggag atgtgactaa ctctataaaa aactctgcag ctgcatcttt tccctctgat   2100
tcgagtgaac tcaatgacga attcaatgaa gacctcctca tcgatttcca aggagtcttc   2160
tttaagaggg atggtcgaaa cctcgtcggc cccgtcgact ggcaagtaga actagatgaa   2220
cgctgggtaa ttatcggacc aaacggagcc ggcaaaacca cactcatccg catggcatcc   2280
gccgaagaat tcccctccgg aggaatggca cgcctcatgg gagaacgcat cggcaaaact   2340
gacatgcgcg acctccgctc catgatcggc gtcagctcct ccgcattagg caaccgaatc   2400
ccctccgaag aaaaagtctc tgacctagtc atctccgcag gctacgcaat cctcggccgc   2460
tggcgcgaag actacgacga aatggacttc ggacaagcca ccgaaatcct cgaacaagtc   2520
ggagccatgc acctagccga ccgcacctgg ggaaccctct ccgaaggcga acgcaaacga   2580
gtcctggtcg cacgcgcact catgaccaac ccggaactcc tcatccttga cgaaccaacc   2640
gcaggaatgg acctcggcgg acgcgaagac ctcgtcggct acctcggaga actcgccatg   2700
gacccagacg cacctgccat cgtcatgatc acccaccacg tcgaagaaat ccccgccgga   2760
ttcacccacg caatgctcct cgacgaaggt gaaatcgtag cccaaggctt gatcaacacc   2820
gtcatgacaa acgagaacct atccaaagca ttccaccagc caatccaagt agaccgcatc   2880
ggggaacgct actttgcccg ccgtgtgaga accgccagga gtcatagggc tcagtaggtt   2940
ttttggagtt gtgggccggt gttggagggg tggttgttta ataggcgact tcacgtatgc   3000
ggacttcatg tgcactgact tcttgcgctc aacttctcat gtgctgactt cactccggat   3060
tgctggcatt tggtagtgat gtcgtgcgat gagaagttga gtatgcgaag tcggtaccga   3120
gaagtcgacc tttaggacat ttttagagga gtccacgcag agactctgtc tccgtaagtt   3180
cgatttcacg gttacgattt cgaactgtcg atatcccggg tgcggtttct caattacaat   3240
ttcgcacttc caatttctca agagcgatac cactaggaaa agtgccattt tccgattgaa   3300
atcgccgttg agaaattgag cgcaaggtat cgagtttgcg aaatcggtaa taagaaatcg   3360
```

gtaatgagaa atcgtaaccg tgaaatcgaa ctttaaaccc aaatgaccga aaaagttcaa 3420
accaacaagc atcaagtgac atattctcgt gcggactgcg cacggaatcc atagactggt 3480
ctgcagaagt tttacgtgtg ggtttgcttc ggatggggct ttaacaagct tcacagatgt 3540
tggtttttca taggcaagct atccagaagc aggctttaca gaaagtcagg gtgtggcaat 3600
ggtgatgcag ggcattggtg gtaggaagct ggcggcgacg gtgctgttgg ttcgggatgg 3660
gatcatcaat gggcgtcctg atgtggaggt ttacattcag gagcgtgtgt ctactatggc 3720
taattttcct cgggcgacgg tgtttccggg tgggggtgtt gattctcggg attttgcgga 3780
tggtcacggt aaggaagtgt ggaggggacc tagcgcggag gagtggggtg tgcgtttagg 3840
cgtggagcct catgttgcgt atgcgttggt ttttgctgcg gttcgtgagt tgtttgaaga 3900
ggccggtacg ttgcttgcgg agcatacgga tggttctggt ttggtgaaga atgctggtca 3960
gtatcacgga tatcgggagt tgttggagac tcatgagatg tcgctgacgg atatgttgca 4020
gagtgagaat ttggcgattc gtagtgattt gattgtgcct tttgccaggt gggcgagccc 4080
tgagggtaat agg 4093

<210> SEQ ID NO 99
<211> LENGTH: 74
<212> TYPE: DNA
<213> ORGANISM: Artificial Sequence
<220> FEATURE:
<223> OTHER INFORMATION: primer Pcg0007_39-cg1383_P1

<400> SEQUENCE: 99
tttatgcttc cggctcgtat gttgtgtgga attgtgagcg gataacaatt gtgatggcat 60
cgcgcacctc aaac 74

<210> SEQ ID NO 100
<211> LENGTH: 96
<212> TYPE: DNA
<213> ORGANISM: Artificial Sequence
<220> FEATURE:
<223> OTHER INFORMATION: primer Pcg0007_39-cg1383_P2

<400> SEQUENCE: 100
tatccgatac agacgtttcc ataatacacg cttaggtccc cacgtagtac cacacacaac 60
gcgagaaacg gcacttgact gatttctccg gttccg 96

<210> SEQ ID NO 101
<211> LENGTH: 103
<212> TYPE: DNA
<213> ORGANISM: Artificial Sequence
<220> FEATURE:
<223> OTHER INFORMATION: primer Pcg0007_39-cg1383_P3

<400> SEQUENCE: 101
tactacgtgg ggacctaagc gtgtattatg gaaacgtctg tatcggataa gtagcgagga 60
gtgttcgtta aaaatgggag atgtgactaa ctctataaaa aac 103

<210> SEQ ID NO 102
<211> LENGTH: 70
<212> TYPE: DNA
<213> ORGANISM: Artificial Sequence
<220> FEATURE:
<223> OTHER INFORMATION: primer Pcg0007_39-cg1383_P4

<400> SEQUENCE: 102

```
ctgcaaggcg attaagttgg gtaacgccag ggttttccca gtcacgacgt cctattaccc     60

tcagggctcg                                                            70


<210> SEQ ID NO 103
<211> LENGTH: 991
<212> TYPE: DNA
<213> ORGANISM: Artificial Sequence
<220> FEATURE:
<223> OTHER INFORMATION: Pcg0007_39 promoter inserted in front of cg1383
      start codon

<400> SEQUENCE: 103

tgccgtttct cgcgttgtgt gtggtactac gtggggacct aagcgtgtat tatggaaacg     60

tctgtatcgg ataagtagcg aggagtgttc gttaaaaatg ggagatgtga ctaactctat    120

aaaaaactct gcagctgcat cttttccctc tgattcgagt gaactcaatg acgaattcaa    180

tgaagacctc ctcatcgatt tccaaggagt cttctttaag agggatggtc gaaacctcgt    240

cggccccgtc gactggcaag tagaactaga tgaacgctgg gtaattatcg gaccaaacgg    300

agccggcaaa accacactca tccgcatggc atccgccgaa gaattcccct ccggaggaat    360

ggcacgcctc atgggagaac gcatcggcaa aactgacatg cgcgacctcc gctccatgat    420

cggcgtcagc tcctccgcat taggcaaccg aatcccctcc gaagaaaaag tctctgacct    480

agtcatctcc gcaggctacg caatcctcgg ccgctggcgc gaagactacg acgaaatgga    540

cttcggacaa gccaccgaaa tcctcgaaca agtcggagcc atgcacctag ccgaccgcac    600

ctggggaacc ctctccgaag gcgaacgcaa acgagtcctg gtcgcacgcg cactcatgac    660

caacccggaa ctcctcatcc ttgacgaacc aaccgcagga atggacctcg gcggacgcga    720

agacctcgtc ggctacctcg gagaactcgc catggaccca gacgcacctg ccatcgtcat    780

gatcacccac cacgtcgaag aaatccccgc cggattcacc cacgcaatgc tcctcgacga    840

aggtgaaatc gtagcccaag gcttgatcaa caccgtcatg acaaacgaga acctatccaa    900

agcattccac cagccaatcc aagtagaccg catcggggaa cgctactttg cccgccgtgt    960

gagaaccgcc aggagtcata gggctcagta g                                   991


<210> SEQ ID NO 104
<211> LENGTH: 4044
<212> TYPE: DNA
<213> ORGANISM: C. glutamicum

<400> SEQUENCE: 104

gacaggtgga tatcggagta tcccatggag ccggagttga tcttgttacg catgattgga     60

tcagatgcgt atggcatgcg ccagcggata gcgtcagctt ctgcaagtac gccatcgcag    120

tcaggggcgg tcgatgcgcc agtgaacagg tcgattgcgt agtcgttgcc tgcaccgtgt    180

gcttctttag cccggttagc gattgccgta ggcagtgcct ttgggtagcc agcgccggtg    240

aagccagaga aaccaacctt gtcaccgtgg ttaacaaact gtgccgcctc gtcggcggac    300

atgagcttgg agcgcagctt ttctgaagca atgcgatcag acatttttaa cgaacactcc    360

tcgctactta tccgatacag acgtttccat aatacacgct taggtcccca cgtagtacca    420

cacacaacgc gagaaacggc agatgttgtg tcccaaggat aaaccatcgt gacaggaaat    480

gcccgaatac tatctgtgat agtgggattt caaggcccag cattaccccc aaatttgcat    540

gccccctgtt tgcaagcctc ccaaagacca ggaataaagc tcaggaataa agctcagacc    600

aaccctagag cccgcgaagc ttaacccaac cccagccccc aaaaagtgaa agcacaccac    660
```

```
tttcctagtt gcgccctgct cacaatttgc ttcaaatatt ttgcccaacc tgattcacgg    720
gggacaatag ttaggtgact ctaaaaatcg gcccctttga ccttgcctcc cctgtggttc    780
tagccccccat ggctggtgta accaacgttg ctttccgcac gctgtgccgc gaacaggaaa    840
tgcaacgcac gggaacaatc tcggggctgt acgtctgtga aatggtgact gcgcgtgctc    900
ttgttgagcg caatgagaaa accatgcaca tgaccacctt cgcgccggat gaaaatcccc    960
gaagcttgca gctgtacacg gttgacccga agtacaccta cgaagcggcg aagatgatcg   1020
ttgatgaaaa cttggcggat catattgata tgaactttgg ctgcccggtt ccaaaggtca   1080
cgcgccgtgg tggcggttct gcgattcctt acaagcgccg tttgtttgaa aacatcgttt   1140
ccgcggctgt gaaggctacg gaaggcacgg acattccggt gacggtgaag ttccgcgttg   1200
gtattgatga tgagcaccat actcacttgg atgctggacg cattgctgtc gacgcaggcg   1260
ccaagtccgt agcgcttcac gcccgcactg cggcgcagcg ctattccggt gaggctgatt   1320
ggaacgagat cgcgcgcctg aaggagcatt tggcagatac cggcatccca gttttgggca   1380
atggcgatat tttcgcggca tccgatgcaa cgcgcatgat ggagcaaact ggctgcgatg   1440
gcgtcgtggt tgggcgtggt tgcctgggca ggccttggct ctttgctgag ctgtctgctg   1500
ctgttcgtgg agaagaaatc ccagaggagc ctaccttcgg cgaagttacc caaatcatcc   1560
tgcgccacgc agaactcctc atgcagcatg atggcgaaac caaggggctg cgcgatctgc   1620
gtaagcacat gggttggtac ctgcgcggtt tccctgttgg cggcgaattc cgctccaatc   1680
tggccaaggt ttccacctat gtggagcttg aggatctcct tgcaccatgg gctgactcca   1740
ccgccaaggc agaggacgcg gaaggtgcac gaggtcgaca gggcgctcct gcaaaggtgg   1800
cacttccaga tggctggttg gacgatcctg aggatgccac tgttcctaaa ggcgcagaaa   1860
tggaaaactc cggagggtag ttaatttaat acttaccccc gccaatagtt ggctatcccc   1920
cattattagg tgattcaacc gtaaaggggt gttttaggtc tgcagaaata ccattatcgc   1980
cttatagtgt tgccatgcgt actgcatata gacagcaatt ggatgaattc gcacacgatc   2040
taatcatttt gtgtgatcta actaaggagt gcatggataa ggcgactgat gccctcctgc   2100
gcacttcttt ggcatcggca gaaagcgctt taggcaatgc agaaaagctt gaagagcttc   2160
gtactggatg cgagtctcaa gccgtcgaac ttttggcgct tgaaactcct gtagcccgtg   2220
atcttcgcca ggttgtctcc tccatctaca tcgtcgagga aattacccgt atgggtgctc   2280
tggcaatgca cgtagctaat tccgtgcgtc gccgttaccc cgatccggtg atcccggagg   2340
acatgcgtgg ctatttcaag gagatggccc gcctcgcagc tgacatgaca gatcatattc   2400
gtcagatcct cattgatcct gaaccagatc ttgccctaga gatggctaaa agcgatgacg   2460
cggtggatga tctgcatcag cacatcatgc gtattctcac gctgcgtcct tggcctcacg   2520
acaccaagag cgcggttgat ctgacgctgc tttcccgctt ctacgagcgt tacgccgatc   2580
acacggtaaa cgtggccgcc cgtatcattt acctgtccac cgggctgcac ccggaggagt   2640
acatggaaaa gcgcgagcaa caaagggccg atgccgacat ggagaagcgc tgggccgagc   2700
tggagcggca gttccgcacc agcgagtaaa aagctgcttc tcgacgctaa aagccactac   2760
ccaccatctg aaattaatca ggtggtgggt agtggcttta attcttcgat ttatccgaag   2820
cggccggaga tgtaatcttc ggtttccttc tgatctgggt tttcgaagat cttcttggta   2880
ggtccgattt caaccagacg acctggccta ccggtcgcct ccagggagta gaacgcggtc   2940
tgatcggaca cacgtgcagc ctgctgcatg ttgtgggtca cgatgacgat ggtgaactct   3000
tccttcagct cgtggataag gtcctccaca gccagggttg agattgggtc aagcgcggag   3060
```

caaggctcgt ccatgaggag gatttctggc tcaaccgcga tcgcgcgagc gatgcacaga 3120
cgctgctgct gaccaccgga gaggccgccg cctggcttgt ccagacgatc cttaacctct 3180
tcccacaggt ttgcgccacg aagagacttc tcagcaactt ccttgagctt cttcttgttc 3240
ttctcgccgg aaagcttcag acctgcaacc acgttgtcct caatggacat ggttgggaat 3300
gggttagcct tctggaagac catgccgatg gtgttacgga ctgcaactgg gtcgatcttg 3360
gagccgtaga tgttctcgcc gtcgagaagg atctcaccct tgacgtatgc acctggggtg 3420
acctcgtgca tacggttgat ggagcgaaga actgtggact tgccacagcc ggatggtccg 3480
atgaatgcgg tgacagagcg tgcgggaact tcgaggttca cgttctgcac tgcgtggaaa 3540
tcaccgtagt agatgttgac atcattgagc ttgagcttcg acatcgcttt agatactcct 3600
gttgtatttt ctgagattgt tattgcttga cagagaactt ggcggagatg attcgtgcgc 3660
caatgttcag gacagcgatg atgagcacca gggtgagggc tgcgccccac agcttgtcca 3720
gcgttgctgg tgcggtgccg gccttgtaca tatcaagcat catcagtgga agggaagcct 3780
gcggaccgct gaatgggttc cagttgatgg cctgggagga accgaccaag accagaactg 3840
gtgcggactc acccatgaca cgtgcgactg cgagcatgac gccggtgacg ataccggaca 3900
gtgcggttgg gagaacgatc tttgcgatgg tcttccactt tggcacgccc agtgcgtagg 3960
acgcttcacg cagatcctga ggaacaacgc ggagcatttc ttcggtgttt cggatgatca 4020
ctggaaccat cagaatcacc agtg 4044

<210> SEQ ID NO 105
<211> LENGTH: 73
<212> TYPE: DNA
<213> ORGANISM: Artificial Sequence
<220> FEATURE:
<223> OTHER INFORMATION: primer Pcg0007_39-phoU_P1

<400> SEQUENCE: 105
tttatgcttc cggctcgtat gttgtgtgga attgtgagcg gataacaatt gacaggtgga 60
tatcggagta tcc 73

<210> SEQ ID NO 106
<211> LENGTH: 98
<212> TYPE: DNA
<213> ORGANISM: Artificial Sequence
<220> FEATURE:
<223> OTHER INFORMATION: primer Pcg0007_39-phoU_P2

<400> SEQUENCE: 106
tatccgatac agacgtttcc ataatacacg cttaggtccc cacgtagtac cacacacaac 60
gcgagaaacg gcaaatcacc taataatggg ggatagcc 98

<210> SEQ ID NO 107
<211> LENGTH: 100
<212> TYPE: DNA
<213> ORGANISM: Artificial Sequence
<220> FEATURE:
<223> OTHER INFORMATION: primer Pcg0007_39-phoU_P3

<400> SEQUENCE: 107
tactacgtgg ggacctaagc gtgtattatg gaaacgtctg tatcggataa gtagcgagga 60
gtgttcgtta aaaatgcgta ctgcatatag acagcaattg 100

<210> SEQ ID NO 108

<211> LENGTH: 72
<212> TYPE: DNA
<213> ORGANISM: Artificial Sequence
<220> FEATURE:
<223> OTHER INFORMATION: primer Pcg0007_39-phoU_P4

<400> SEQUENCE: 108
ctgcaaggcg attaagttgg gtaacgccag ggttttccca gtcacgacgt cactggtgat 60
tctgatggtt cc 72

<210> SEQ ID NO 109
<211> LENGTH: 832
<212> TYPE: DNA
<213> ORGANISM: Artificial Sequence
<220> FEATURE:
<223> OTHER INFORMATION: Pcg0007_39 promoter in front of phoU start codon

<400> SEQUENCE: 109
tgccgtttct cgcgttgtgt gtggtactac gtggggacct aagcgtgtat tatggaaacg 60
tctgtatcgg ataagtagcg aggagtgttc gttaaaaatg cgtactgcat atagacagca 120
attggatgaa ttcgcacacg atctaatcat tttgtgtgat ctaactaagg agtgcatgga 180
taaggcgact gatgccctcc tgcgcacttc tttggcatcg gcagaaagcg ctttaggcaa 240
tgcagaaaag cttgaagagc ttcgtactgg atgcgagtct caagccgtcg aacttttggc 300
gcttgaaact cctgtagccc gtgatcttcg ccaggttgtc tcctccatct acatcgtcga 360
ggaaattacc cgtatgggtg ctctggcaat gcacgtagct aattccgtgc gtcgccgtta 420
ccccgatccg gtgatcccgg aggacatgcg tggctatttc aaggagatgg cccgcctcgc 480
agctgacatg acagatcata ttcgtcagat cctcattgat cctgaaccag atcttgccct 540
agagatggct aaaagcgatg acgcggtgga tgatctgcat cagcacatca tgcgtattct 600
cacgctgcgt ccttggcctc acgacaccaa gagcgcggtt gatctgacgc tgctttcccg 660
cttctacgag cgttacgccg atcacacggt aaacgtggcc gcccgtatca tttacctgtc 720
caccgggctg cacccggagg agtacatgga aaagcgcgag caacaaaggg ccgatgccga 780
catggagaag cgctgggccg agctggagcg gcagttccgc accagcgagt aa 832

<210> SEQ ID NO 110
<211> LENGTH: 4137
<212> TYPE: DNA
<213> ORGANISM: C. glutamicum

<400> SEQUENCE: 110
cggcgtcggc aaatttgtag agggcttctt cggtgaaggt tccggcaggc cccaaatagg 60
ccacaacaat tggtgcgtcg ctcatggtta cacagcttaa cccgccgaac taaggtgggt 120
gtccatgtct gttgctcaat tagcgaaccg cttggcccaa ctctccccg ccgagcatgg 180 ttttgcatgg ttcgaccctg aaatcaccgc tggccatggc gttggcccgt tgcatggcat 240
ggtgattcca gccaaggacc tcaacgatgt cgtgggcatg cccaccgcgt tcggaaatgc 300
atctcggcgc aaggtagcaa cagacaccga tccgttcatc caaaatctca tcgaccgcgg 360
cgcgatcatc gctggcaaaa cccaaaccag cgagctcggc atgacggcgt attgcgagcc 420
catcggcatg gacgcaccca gcaacccggt tttacctggt cacacgcctg gaggttcgtc 480
cggtggtgcg gccgttgctg ttgccaggtc gcttgtcgac gccgcccacg cctcagacgg 540
tggcggctcg atccgggttc cagccgccgc gtgtggcctg gtcgggttta aacccgccca 600

-continued

```
cgattcccga ggtggaaacc cctccacgca ggggtttatc acccgcgacg tggccaccca    660
agtgcgtttg cacgcacttc aaccacgcac cagacgcctg cgcatcggcg ttctcgctga    720
gcccatccat gctaattcgc ttgtcgacgc ccccttcctg agcatcctcg aatccaccgc    780
ccacctcctg gagaaagctg gccacgaaat agtgtccgta cccctccctt atgacgcttg    840
ggcttttgac gcttatacag aagttttcat gatgaaatcc gctggactaa ccaacctggg    900
tagccccatt acaagatggt tgagtgaaca aggccgtagt ctttctcctt ctgatagaca    960
atcatgtgtc aaggcttttg attccgtggc tgagactgta cacggagcat gggacatcga   1020
tgttttatta acccctacct tggcttatgc acctcccaag attgggtact tttcatccat   1080
gccacctgaa gaagacttcc ttgcacaaac caaatggacg ccgtgggcaa cgctgttcaa   1140
catgaccggt ggtgcagcca tcagcgtgcc tgttgaaggt gtcggcattc atcttggtgg   1200
gatacgcgta cgagatgaag acctcttagg attagcagca tttcttgaag gagctgtggc   1260
atgagtagtt cagtaatgtc accgcgtcga ataaaggcgg aaatacttat cgttttagcc   1320
atcacctttg gcatgagcgg tctgcgatca atcctgcgcc tcatcgacga tctcctcgca   1380
ccggttgcgc tcaacgacca gcaagttgca ctgaatgcct caatggcaaa ctccgcatgg   1440
ctggatctcg ccttgcaatt gtgttccgcc ggtgtgctgt tttcctgggg agcgctagcg   1500
atctatctgc ttggcgaacg attccgctgg ataaaaccca aagattggac atggggtgca   1560
ggccttgcag cgctcatcgg cattcccggg ctgatcttct atgcgagtgc cgttcatctg   1620
ggtctttcca aacaggtcgt gcccaccact ttggaaacct ggtgggaaat cccagtgctg   1680
cttatatggt cagccgccaa cgcatttggt gaagagatcg tggtggtcat gtggttcttc   1740
accagactgc gccaactgaa gtggagcgtg ccagcagtca ttgtggcatc ttcagttttg   1800
cgcggttcct accacctcta ccagggaatc tctgcgggtt ttggcaacat catcatggga   1860
gtagcgttcg catatttctt tcaccgcacg ggcaaaatct ggccactggt aatcgctcac   1920
ttcttgattg atgcggtggc ttttgtgggc tactccgcaa ttggcgggaa tttaagctgg   1980
ttagggcttt aaactgaagt tcctatttta ttgggattag aaaaacacga gagatttaag   2040
gcaaatccgc taaatacatc tgtcccgcct aggcgctact ctattaacca tggattcacc   2100
aggacagggc gaaatagccc gcgatagtca aggacgcccg atactggacc ggtatggtcg   2160
gccggttcgg gttcgtccgc aaccgcggca aactccccg actcctcgaa cccctcccgt   2220
gaatgaaaca agggtctatc agccaaggca aacgccaccg cgccagactc ctccaaggca   2280
gacacctcca cgacaaatgc ctcctaggca aaccccaccg aggcaggttc ccccacaaca   2340
gcagtaccag cagcctggtc agatcggaca ccttcgcccg cagccgccag tgattacaaa   2400
tggtggaggg agacgtcgaa aagcaatatc ttttaagccc cgtggctgcc ttggctcgct   2460
cgcgggcctg gttgctgtgg tgctggtgct cgcttttgtg gtcgcgctgt gggcggatgc   2520
caagctgaat cgcgtggatg cgacgcccgc gacgcaggtg gcgaataccg caggcacgaa   2580
ctggctgctg gtgggttcgg actcgcggca gggtttaagt gatgaggata ttgagcggct   2640
gggtaccggc ggagatatcg gtgtgggtcg tacggacacg atcatggtgt tgcatatgcc   2700
gcgtactggc gagccgacgc tgttgtcgat tccgcgtgat tcttatgtca atgtccctgg   2760
ctggggcatg gataaggcaa acgcggcgtt cactgtgggt ggcccgcagc tgctcacgca   2820
gaccgtggag gaggcgactg gtctgcgaat tgatcactat gcggaaatcg gcatgggtgg   2880
tttggcgaac atggttgatg ccgtgggcgg cgtggaaatg tgtcctgctg agccgatgta   2940
tgatccgctg gccaacctgg atattcaagc cggctgccag gaatttgatg ggcgaccgc   3000
```

```
gctgggatac gtgcgcactc gtgccacatc cctgggtgat ctggaccgcg tggtgcgcca   3060

gcgggagttt ttctccgcgc tgctgagtac ggctacgtcc ccgggcacgt tgctgaatcc   3120

gttccgcacc ttcccgatga tctccaacgc ggtgggaaca ttcaccgtcg gcgagggcga   3180

tcacgtgtgg cacctggccc gattggcgct ggcgatgcgc ggaggaatcg tgacggagac   3240

cgtgccgatt gcctcattcg cagattacga tgtgggaaat gttgcgatct gggacgaagc   3300

tggagccgaa gcactattta gctccatgcg ctaaaacccc aggtaatcat tcacaggaag   3360

tgtccagtca actttttggt taattgatta tcttacctag agacttggat acttccctcc   3420

acggattgct aacgatccag ttttatcgtt ggactcatga aaaagatcca catgattcca   3480

gcggccctcc tcatcggttc cctcgcactt gtcagctgcg cgccttcaca acccacccag   3540

aacgcgcaga cggtttcttc tgcaatgatg gaaactccta cttatacttc atcatctagg   3600

tcggtggaat ctaccgcggg gacgatcgcc gccaccgagg aagccgcgat gacgctgctg   3660

gcgaatagtt cgggggatcc gggatctgat tctgggggtg cgcgctatag cctcaattcg   3720

ctcaaggttt ccgagcaagc cgcagcgaac gccgtattaa aggccgtgct taacgacgcc   3780

tcctaccaag agttcgcaga ctcctcctac ttagaaatca caggaacgcc ctccgccgac   3840

ggaacatggg gcatctcatt tggcggacct tccgaatcgg cctccgtgga attctccgac   3900

ggcagcgtca gcttctcccc cgtcgacatg acagtgcccg caacacgatt gcctcagatg   3960

ggcgcatttt atgaaaccct gaccgaagaa caattagaca tgctggagac tggcctcgcg   4020

gtttccacct tggattcgag ccaacaggaa atgcttctgg acttggtctc caactcgatc   4080

ggcctggcag atactgaaac cactgcgact gcaattagtg aaatccgagc aaaactt      4137
```

<210> SEQ ID NO 111
<211> LENGTH: 70
<212> TYPE: DNA
<213> ORGANISM: Artificial Sequence
<220> FEATURE:
<223> OTHER INFORMATION: Pcg0007_39-cg3210-p1

<400> SEQUENCE: 111

```
tttatgcttc cggctcgtat gttgtgtgga attgtgagcg gataacaatt cggcgtcggc     60

aaatttgtag                                                             70
```

<210> SEQ ID NO 112
<211> LENGTH: 103
<212> TYPE: DNA
<213> ORGANISM: Artificial Sequence
<220> FEATURE:
<223> OTHER INFORMATION: Pcg0007_39-cg3210-p2

<400> SEQUENCE: 112

```
tatccgatac agacgtttcc ataatacacg cttaggtccc cacgtagtac cacacacaac     60

gcgagaaacg gcatcgtgtt tttctaatcc caataaaata gga                       103
```

<210> SEQ ID NO 113
<211> LENGTH: 93
<212> TYPE: DNA
<213> ORGANISM: Artificial Sequence
<220> FEATURE:
<223> OTHER INFORMATION: Pcg0007_39-cg3210-p3

<400> SEQUENCE: 113

```
tactacgtgg ggacctaagc gtgtattatg gaaacgtctg tatcggataa gtagcgagga     60
```

gtgttcgtta aaaatggatt caccaggaca ggg 93

<210> SEQ ID NO 114
<211> LENGTH: 80
<212> TYPE: DNA
<213> ORGANISM: Artificial Sequence
<220> FEATURE:
<223> OTHER INFORMATION: Pcg0007_39-cg3210-p4

<400> SEQUENCE: 114
ctgcaaggcg attaagttgg gtaacgccag ggttttccca gtcacgacgt agttttgctc 60
ggatttcact aattgcagtc 80

<210> SEQ ID NO 115
<211> LENGTH: 1342
<212> TYPE: DNA
<213> ORGANISM: Artificial Sequence
<220> FEATURE:
<223> OTHER INFORMATION: Pcg0007_39 in front of cg3210

<400> SEQUENCE: 115
tgccgtttct cgcgttgtgt gtggtactac gtggggacct aagcgtgtat tatggaaacg 60
tctgtatcgg ataagtagcg aggagtgttc gttaaaaatg gattcaccag gacagggcga 120
aatagcccgc gatagtcaag gacgcccgat actggaccgg tatggtcggc cggttcgggt 180
tcgtccgcaa ccgcggcaaa ctccccccgac tcctcgaacc cctcccgtga atgaaacaag 240
ggtctatcag ccaaggcaaa cgccaccgcg ccagactcct ccaaggcaga cacctccacg 300
acaaatgcct cctaggcaaa ccccaccgag gcaggttccc ccacaacagc agtaccagca 360
gcctggtcag atcggacacc ttcgcccgca gccgccagtg attacaaatg gtggagggag 420
acgtcgaaaa gcaatatctt ttaagccccg tggctgcctt ggctcgctcg cgggcctggt 480
tgctgtggtg ctggtgctcg cttttgtggt cgcgctgtgg gcggatgcca agctgaatcg 540
cgtggatgcg acgcccgcga cgcaggtggc gaataccgca ggcacgaact ggctgctggt 600
gggttcggac tcgcggcagg gtttaagtga tgaggatatt gagcggctgg gtaccggcgg 660
agatatcggt gtgggtcgta cggacacgat catggtgttg catatgccgc gtactggcga 720
gccgacgctg ttgtcgattc cgcgtgattc ttatgtcaat gtccctggct ggggcatgga 780
taaggcaaac gcggcgttca ctgtgggtgg cccgcagctg ctcacgcaga ccgtggagga 840
ggcgactggt ctgcgaattg atcactatgc ggaaatcggc atgggtggtt tggcgaacat 900
ggttgatgcc gtgggcggcg tggaaatgtg tcctgctgag ccgatgtatg atccgctggc 960
caacctggat attcaagccg gctgccagga atttgatggg gcgaccgcgc tgggatacgt 1020
gcgcactcgt gccacatccc tgggtgatct ggaccgcgtg gtgcgccagc gggagttttt 1080
ctccgcgctg ctgagtacgg ctacgtcccc gggcacgttg ctgaatccgt tccgcacctt 1140
cccgatgatc tccaacgcgg tgggaacatt caccgtcggc gagggcgatc acgtgtggca 1200
cctggcccga ttggcgctgg cgatgcgcgg aggaatcgtg acggagaccg tgccgattgc 1260
ctcattcgca gattacgatg tgggaaatgt tgcgatctgg gacgaagctg gagccgaagc 1320
actatttagc tccatgcgct aa 1342

<210> SEQ ID NO 116
<211> LENGTH: 4233
<212> TYPE: DNA
<213> ORGANISM: C. glutamicum

<400> SEQUENCE: 116

```
cttttgccct cggtggccaa acatccgctg agtcctacct tgtcattgac aagatcatcg     60
atgcggcccg caagtccggc gccgacgcca tccaccctgg ctacggcttc ctcgcagaaa    120
acgctgactt cgcagaagca gtcatcaacg aaggcctgat ctggattgga ccttcacctg    180
agtccatccg cgccctcggc gacaaggtca ccgctcgcca catcgcagat accgccaagg    240
ctccaatggc tcctggcacc aaggaaccag taaaagacgc agcagaagtt gtggctttcg    300
ctgaagaatt cggtctccca atcgccatca aggcagcttt cggtggcggc ggacgtggca    360
tgaaggttgc ctacaagatg gaagaagtcg ctgacctctt cgagtccgca acccgtgaag    420
caaccgcagc gttcggccgc ggcgagtgct tcgtggagcg ctacctggac aaggcacgcc    480
acgttgaggc tcaggtcatc gccgataagc acggcaacgt tgttgtcgcc ggaacccgtg    540
actgctccct gcagcgccgt ttccagaagc tcgtcgaaga agcaccagca ccattcctca    600
ccgatgacca gcgcgagcgt ctccactcct ccgcgaaggc tatctgtaag gaagctggct    660
actacggtgc aggcaccgtt gagtacctcg ttggctccga cggactgatc tccttcctcg    720
aggtcaacac ccgcctccag gtggaacacc cagtcaccga agagaccacc ggcatcgacc    780
tggtccgcga aatgttccgc atcgcagaag gccacgagct ctccatcaag gaagatccag    840
ctccacgcgg ccacgcattc gagttccgca tcaacggcga agacgctggc tccaacttca    900
tgcctgcacc aggcaagatc accagctacc gcgagccaca gggcccaggc gtccgcatgg    960
actccggtgt cgttgaaggt tccgaaatct ccggacagtt cgactccatg ctggcaaagc   1020
tgatcgtttg gggcgacacc cgcgagcagg ctctccagcg ctcccgccgt gcacttgcag   1080
agtacgttgt cgagggcatg ccaaccgtta tcccattcca ccagcacatc gtggaaaacc   1140
cagcattcgt gggcaacgac gaaggcttcg agatctacac caagtggatc gaagaggttt   1200
gggataaccc aatcgcacct tacgttgacg cttccgagct cgacgaagat gaggacaaga   1260
ccccagcaca gaaggttatt gtggagatca acggccgtcg cgttgaggtt gcactcccag   1320
gcgatctggc actcggtggc accgctggtc ctaagaagaa ggccaagaag cgtcgcgcag   1380
gtggcgcaaa ggctggcgta tccggcgatg cagtggcagc tccaatgcag ggcactgtca   1440
tcaaggtcaa cgtcgaagaa ggcgctgaag tcaacgaagg cgacaccgtt gttgtcctcg   1500
aggctatgaa gatggaaaac cctgtgaagg ctcataagtc cggaaccgta accggcctta   1560
ctgtcgctgc aggcgagggt gtcaacaagg gcgttgttct cctcgagatc aagtaagttc   1620
ttggattcct gttagtcaaa aaccgggtcg catctgatgt tcagatgtgg cccggtttta   1680
ctatttgtga atacactctg cccctgttgt acattcgaca acaagatttc ggtaaaaagg   1740
tggtcaaaat caggaaatct tgttgtcgaa tgtacaccgc attgtgggct ttcacggttc   1800
gctgcgttga ttgttattta gccagcccgc tccccacact taaccggtga tcaacgagcc   1860
cacatacccg gcgcggtgct ggaacagccc gagaaattca agatcgtttg gggttggctg   1920
ctcgcccgct gatacttctc gttcaatgga gtggatgact gcttcgcgga ttgcggttcc   1980
atcggcgtag ccttgccagt tgatctcggt ggtgtctttc atggtgtgct ccccttgtgg   2040
tttttatttt tctttaacgc taatcggctg acggctttca atgcacaagg taaaatttgt   2100
gtaattgtgt cgtgtggatt tgaaggtttt tgtaaatcta gttaaatcat gaggtcataa   2160
gcttttcggg aggtggtcaa aagatgtcga agctttacgc gggggcaagg atcaatgcac   2220
tgcgccgaac ccaccaactg acccaatcag cattagccga caagcttgat ctctccacga   2280
gctatctcaa ccagttggaa aatgatggcc ggccgcttac tgccacggtg cttttgcaac   2340
```

```
tgatgaaagt ctttgatgtt gaggccagtt atttctcccc tgaccggggc acagccacgg   2400
ctacccgact ggcagaaacc ttggctatga atcaggggcc gacgatgtcg atggatgatc   2460
tgttagattt cgcggatcgt ttccctcagt tggcacagca tattatccag cctgctgagg   2520
tcgatcccgc acatagttct gcgcatgatt ttgttcggga ttattttgcc acccacaaga   2580
actacattga ttctcttgat cgccttggtg aggagttggc aaccgccatt ggtcagccgg   2640
ggcttcgggt taccaggctc gcgcagttgc ttgatgcgga gtacaacatc acggtgcgtt   2700
tccgggcgcc agatattact ggccggaggc actttgatcc ccaatcgcgt cagattctgc   2760
tgcggcaaga tctcagcgag gcgcagcagt gttttcagtt ggcggaggaa ttgacgtttc   2820
ttgctcatgc agagctcttg gataccctga ccacagatca accggatctc ccttatgagg   2880
cagctatccg cctggctaag gtgggtctct cccaatactt cgcggctgct gttgtcatgc   2940
cgtacacccg ctttttggaa ttcgcccagg acaagcacta tgacatcgag ttgatctctg   3000
aggcgtttgg agtgtctttc gagtccgcgt gccaccgctt gtctacgctg cagcgttcgg   3060
gggcgtcagg ggtgccgttt ttctttgtgc gctcggaccg ggcaggaaat atttccaaga   3120
ggcaatctgc agctacgttc catttctcgc gaacagacgg cacttgtcct ttgtgggcgc   3180
tgcatcgagc ttttgaacgt caaggaaaca tcacccgcca ggttgctcgc atgccggatg   3240
gccggaccta tttgtggctc gcacgcgcgg tgaaaggtcg aactcatggt ttcgggcatc   3300
ctgctgcgga attcgccatc ggcctgggct gcgatatcag cgaggcacca ggcttggtgt   3360
attcccaagg cctcaatttg gatccagagt ccgccgcaga gatcggccct ggttgtcgga   3420
tctgtcctcg ggagaactgt gtgcagcgtg cattcccacc atcgggtcaa gaatctatcc   3480
gcccagcccc tgtccaactc ctcaactaaa aaggcagcac ttaaaaaaca ctatggaacc   3540
catggaacta aacggcggtc gtttctacgc ccgcaagctc acctcagata atcggattga   3600
tgatgtcccg gcgctctcac tgatccttcc cgatgcggca cagttcatcg cggacgccac   3660
cacagcctgg cacgaggaca ccgaatacac ctgggctatc tgcgagcaga ccagtgttga   3720
actactggct ttggcacgcc ttgatcccaa gcagcgcaca ctcgaggtcg tgcccgcagg   3780
tgatcccgcc acccaattgc ccaatgatcc agtgctcgct ccgaaaacca tcggcgatgc   3840
tgtggcggag ggccgcgaca ccatcaccag atgggcacaa ggctatttag aaatcagcct   3900
cactgattag gttctctccg aaatgggcac cacctccctt tcttccactc cgttgtaggc   3960
agacaatggt cggatcagcg cattgttttc aaattgctcc acgatgtgtg ccgtccaccc   4020
tgacactcgg gccagcacaa acagcggtgt gaaaaagtcg acggggaatc ccagcatgta   4080
ataggcaggg ccggccggga agtcgaggtt gggtttaatg ccagtgcgag cctccatgac   4140
ttcctgcatc gactcataca tgtgcaccca tttttgacca cggtgacgag cagcaaggga   4200
gcgcatggat ttctccatgg aggggaccct gga                                4233
```

<210> SEQ ID NO 117
<211> LENGTH: 76
<212> TYPE: DNA
<213> ORGANISM: Artificial Sequence
<220> FEATURE:
<223> OTHER INFORMATION: Pcg0007_39-cg0800-p1

<400> SEQUENCE: 117

```
tttatgcttc cggctcgtat gttgtgtgga attgtgagcg gataacaatt tccagggtcc     60
cctccatgga gaaatc                                                     76
```

<210> SEQ ID NO 118
<211> LENGTH: 92
<212> TYPE: DNA
<213> ORGANISM: Artificial Sequence
<220> FEATURE:
<223> OTHER INFORMATION: Pcg0007_39-cg0800-p2

<400> SEQUENCE: 118
tactacgtgg ggacctaagc gtgtattatg gaaacgtctg tatcggataa gtagcgagga 60
gtgttcgtta aaaatgtcga agctttacgc gg 92

<210> SEQ ID NO 119
<211> LENGTH: 93
<212> TYPE: DNA
<213> ORGANISM: Artificial Sequence
<220> FEATURE:
<223> OTHER INFORMATION: Pcg0007_39-cg0800-p3

<400> SEQUENCE: 119
tatccgatac agacgtttcc ataatacacg cttaggtccc cacgtagtac cacacacaac 60
gcgagaaacg gcaaaaccac aaggggagca cac 93

<210> SEQ ID NO 120
<211> LENGTH: 72
<212> TYPE: DNA
<213> ORGANISM: Artificial Sequence
<220> FEATURE:
<223> OTHER INFORMATION: Pcg0007_39-cg0800-p4

<400> SEQUENCE: 120
ctgcaaggcg attaagttgg gtaacgccag ggttttccca gtcacgacgt cttttgccct 60
cggtggccaa ac 72

<210> SEQ ID NO 121
<211> LENGTH: 1423
<212> TYPE: DNA
<213> ORGANISM: Artificial Sequence
<220> FEATURE:
<223> OTHER INFORMATION: Pcg0007_39 in front of cg0800

<400> SEQUENCE: 121
tgccgtttct cgcgttgtgt gtggtactac gtggggacct aagcgtgtat tatggaaacg 60
tctgtatcgg ataagtagcg aggagtgttc gttaaaaatg tcgaagcttt acgcgggggc 120
aaggatcaat gcactgcgcc gaacccacca actgacccaa tcagcattag ccgacaagct 180
tgatctctcc acgagctatc tcaaccagtt ggaaaatgat ggccggccgc ttactgccac 240
ggtgcttttg caactgatga aagtctttga tgttgaggcc agttatttct cccctgaccg 300
gggcacagcc acggctaccc gactggcaga aaccttggct atgaatcagg ggccgacgat 360
gtcgatggat gatctgttag atttcgcgga tcgtttccct cagttggcac agcatattat 420
ccagcctgct gaggtcgatc ccgcacatag ttctgcgcat gattttgttc gggattattt 480
tgccacccac aagaactaca ttgattctct tgatcgcctt ggtgaggagt tggcaaccgc 540
cattggtcag ccggggcttc gggttaccag gctcgcgcag ttgcttgatg cggagtacaa 600
catcacggtg cgtttccggg cgccagatat tactggccgg aggcactttg atccccaatc 660
gcgtcagatt ctgctgcggc aagatctcag cgaggcgcag cagtgttttc agttggcgga 720
ggaattgacg tttcttgctc atgcagagct cttggatacc ctgaccacag atcaaccgga 780
tctcccttat gaggcagcta tccgcctggc taaggtgggt ctctcccaat acttcgcggc 840

-continued

```
tgctgttgtc atgccgtaca cccgcttttt ggaattcgcc caggacaagc actatgacat    900

cgagttgatc tctgaggcgt ttggagtgtc tttcgagtcc gcgtgccacc gcttgtctac    960

gctgcagcgt tcgggggcgt caggggtgcc gtttttcttt gtgcgctcgg accgggcagg   1020

aaatatttcc aagaggcaat ctgcagctac gttccatttc tcgcgaacag acggcacttg   1080

tcctttgtgg gcgctgcatc gagcttttga acgtcaagga aacatcaccc gccaggttgc   1140

tcgcatgccg gatggccgga cctatttgtg gctcgcacgc gcggtgaaag gtcgaactca   1200

tggtttcggg catcctgctg cggaattcgc catcggcctg ggctgcgata tcagcgaggc   1260

accaggcttg gtgtattccc aaggcctcaa tttggatcca gagtccgccg cagagatcgg   1320

ccctggttgt cggatctgtc ctcgggagaa ctgtgtgcag cgtgcattcc caccatcggg   1380

tcaagaatct atccgcccag cccctgtcca actcctcaac taa                     1423
```

ENGINEERED STRAINS OF *Corynebacteria*

CROSS-REFERENCE TO RELATED APPLICATIONS

This application is a national stage entry of International Application No. PCT/US19/49893, filed Sep. 6, 2019, which itself claims priority to U.S. Provisional Patent Application No. 62/728,384, filed Sep. 7, 2018, the contents of each are incorporated herein by reference.

Each reference, patent, and published patent application cited in this disclosure is incorporated herein by reference in its entirety.

This application incorporates by reference a 195 kb text file created on Sep. 1, 2021 and named "Ser. No. 17/274,093.txt," which is the sequence listing for this application.

TECHNICAL FIELD

This disclosure relates generally to lysine production.

BRIEF DESCRIPTION OF THE FIGURES

FIG. 1A-B is a multiple alignment of SEQ ID NO:3 with the amino acid sequences of three corynebacterial ribonuclease J (rnaJ) proteins identified by National Center for Biotechnology Information (NCBI) Reference Nos. WP_011014791.1 (SEQ ID NO:78), WP_096456687.1 (SEQ ID NO:79), and WP_023635875.1 (SEQ ID NO:80). A box identifies the amino acid in each sequence that alignments with amino acid 448 of SEQ ID NO:3. FIG. 1A, alignment with amino acids 1-560 of SEQ ID NO:3. FIG. 1B, alignment with amino acids 561-718 of SEQ ID NO:3.

FIG. 2 is a multiple alignment of SEQ ID NO:6 with the amino acid sequences of three corynebacterial accDA proteins identified by NCBI Reference Nos. WP_075348128 (SEQ ID NO:81), AGT04828.1 (SEQ ID NO:82), and WP_066564978.1 (SEQ ID NO:83). A box identifies the amino acid in each sequence that alignments with amino acid 310 of SEQ ID NO:6.

FIG. 3 is a multiple alignment of SEQ ID NO:9 with the amino acid sequences of three corynebacterial cg1144 proteins identified by NCBI Reference Nos. WP_011897001 (SEQ ID NO:84), WP_066565124 (SEQ ID NO:85), and EEW49979 (SEQ ID NO:86). A box identifies the amino acid in each sequence that alignments with amino acid 66 of SEQ ID NO:9.

DETAILED DESCRIPTION

This disclosure provides engineered strains of Corynebacteria for the cost-effective production of lysine, tools and methods used to produce the engineered strains, and methods of using the engineered strains to produce lysine.

Structural Alterations

This disclosure provides the following four structural alterations that can be engineered into Corynebacteria to improve lysine production: (a) insertion of a promoter in front of the cg1383 start codon, (b) replacement of the native phoU promoter; (c) replacement of the native cg3210 promoter; and (d) replacement of the native cg0800 promoter.

a. Insertion of a Promoter in Front of the cg1383 Start Codon cg1383 is also known as NCgl1179 and encodes an ATPase component of the ABC-type molybdenum transport system (e.g., WP_011014216.1). In some embodiments, a promoter is inserted in front of the cg1383 start codon. The inserted promoter can be a promoter from a different gene of the *Corynebacterium* species or strain being engineered or can be a heterologous promoter (i.e., a promoter of another *Corynebacterium* species or strain or an artificially constructed promoter). These promoters include, but are not limited to, promoters disclosed in Nešvera et al., 2012; Pátek et al., 2003(a); Pátek et al., 2003(b); Pátek et al., 2013; Rytter et al., 2014; Shang et al., 2017; Yim et al., 2013; US 2017/0159045; and WO 2017/00376. In some embodiments, the inserted promoter is promoter Pcg0007_39 (SEQ ID NO:20); see US 2017/0159045 and WO 2017/00376.

b. Replacement of the Native phoU Promoter phoU encodes a phosphate uptake regulator (e.g., BAB99964.1) and is also known as cgl2571 and NCgl2482. In some embodiments, the native phoU promoter is replaced with a phoU replacement promoter. The phoU replacement promoter can be a promoter from a different gene of the *Corynebacterium* species or strain being engineered or can be a heterologous promoter (i.e., a promoter of another *Corynebacterium* species or strain or an artificially constructed promoter). These promoters include, but are not limited to, promoters disclosed in Nešvera et al., 2012; Pátek et al., 2003(a); Pátek et al., 2003(b); Pátek et al., 2013; Rytter et al., 2014; Shang et al., 2017; Yim et al., 2013; US 2017/0159045; and WO 2017/00376. In some embodiments, the phoU replacement promoter is promoter Pcg0007_39 (SEQ ID NO:20); see US 2017/0159045 and WO 2017/00376.

c. Replacement of the Native Cg3210 Promoter cg3210 is also known as NCgl2802 and encodes a cell envelope-related transcriptional regulator (e.g., WP_011266029.1). In some embodiments, the native cg3210 promoter is replaced with a cg3210 replacement promoter. The cg3210 replacement promoter can be a promoter from a different gene of the *Corynebacterium* species or strain being engineered or can be a heterologous promoter (i.e., a promoter of another *Corynebacterium* species or strain or an artificially constructed promoter). These promoters include, but are not limited to, promoters disclosed in Nešvera et al., 2012; Pátek et al., 2003(a); Pátek et al., 2003(b); Pátek et al., 2013; Rytter et al., 2014; Shang et al., 2017; Yim et al., 2013; US 2017/0159045; and WO 2017/00376. In some embodiments, the cg3210 replacement promoter is promoter Pcg0007_39 (SEQ ID NO:20); see US 2017/0159045 and WO 2017/00376.

d. Replacement of the Native Cg0800 Promoter cg0800 is also known as NCg10668 or prpR and encodes a transcriptional regulatory of the MerR family (e.g., WP_011013825.1). In some embodiments, the native cg0800 promoter is replaced with a cg0800 replacement promoter. The cg0800 replacement promoter can be a promoter from a different gene of the *Corynebacterium* species or strain being engineered or can be a heterologous promoter (i.e., a promoter of another *Corynebacterium* species or strain or an artificially constructed promoter). These promoters include, but are not limited to, promoters disclosed in Nešvera et al., 2012; Pátek et al., 2003(a); Pátek et al., 2003(b); Pátek et al., 2013; Rytter et al., 2014; Shang et al., 2017; Yim et al., 2013; US 2017/0159045; and WO 2017/

00376. In some embodiments, the cg0800 replacement promoter is promoter Pcg0007_39 (SEQ ID NO:20); see US 2017/0159045 and WO 2017/00376.

Additional Structural Alterations

In some embodiments, engineered strains of Corynebacteria comprising one or more of the structural alterations described above may also comprise one or more of the additional structural alterations (e)-(o) described below.

e. Altered Corynebacterial Ribonuclease J Proteins

Engineered strains of Corynebacteria comprising any of the structural alterations described above can also comprise an altered corynebacterial ribonuclease (rnaJ) protein. Altered corynebacterial rnaJ proteins comprise a G448S substitution. One example of such a protein is shown in SEQ ID NO:3. "A corynebacterial rnaJ protein comprising a G448S substitution" as used herein means an rnaJ protein from a strain of *Corynebacterium* which, when compared with SEQ ID NO:3 using the NCBI's BLAST® alignment tool, has serine instead of glycine at the position that aligns with amino acid 448 of SEQ ID NO:3, as illustrated in FIG. 1A-B. Corynebacterial rnaJ proteins which can be altered to comprise the G448S substitution include, but are not limited to, proteins (regardless of how named) identified with the amino acid sequences provided by the NCBI Reference numbers in Table 1.

TABLE 1

NCBI Reference Numbers of Corynebacterial rnaJ Proteins

| Reference number | Species and/or Strain(s) |
|---|---|
| WP_011014791.1 | *C. glutamicum* 617, 1006, AJ1511, AS 1.299, ATCC 13032 (K051) and DSM 20300, ATCC 13869, ATCC 21831, C1, CP, MB001, TQ2223, XV, and ZL-; *B. flavum* ZL-1 |
| WP_003857476.1 | *C. glutamicum* AS 1.542, ATCC 13870, ATCC 14067, ATCC 21493, MT, S9114, SCgG1, SCgG2, SYPA 5-5, SYPS-062, SYPS-062-33a, T6-13, and Z188; *B. flavum* ATCC 15168 |
| WP_077312485.1 | *C. glutamicum* |
| WP_089158555.1 | *C. glutamicum* |
| WP_044030039.1 | *C. glutamicum* |
| WP_040967540.1 | *C. glutamicum* |
| WP_059289432.1 | *C. glutamicum* |
| WP_063967576.1 | *C. glutamicum* |
| WP_011897391.1 | *C. glutamicum* |
| WP_096456687.1 | *C. glutamicum* |
| WP_080794542.1 | *Corynebacterium* sp. Marseille-P2417 |
| WP_015651527.1 | *C. callunae* |
| WP_011075647.1 | *C. efficiens* |
| WP_095075511.1 | *C. ulcerans* |
| WP_014836513.1 | *C. ulcerans* |
| WP_087454146.1 | *C. ulcerans* |
| WP_013911733.1 | *C. ulcerans* |
| WP_014525921.1 | *C. ulcerans* |
| WP_023635875.1 | *C. ulcerans* |
| WP_014300762.1 | *C. pseudotuberculosis* |
| WP_013242122.1 | *C. pseudotuberculosis* |
| AJC14005.1 | *C. pseudotuberculosis* |
| WP_058832312.1 | *C. pseudotuberculosis* |
| WP_014523406.1 | *C. pseudotuberculosis* |
| WP_014558731.1 | *C. pseudotuberculosis* |
| OMH75460.1 | *C. pseudotuberculosis* |
| WP_014367221.1 | *C. pseudotuberculosis* |
| WP_092284332.1 | *C. spheniscorum* |
| WP_020976441.1 | *C. argentoratense* |
| WP_075726535.1 | *C. aquilae* |
| WP_027012113.1 | *C. freiburgense* |
| WP_034995241.1 | *C. matruchotii* |
| WP_005526573.1 | *C. matruchotii* |

TABLE 1-continued

NCBI Reference Numbers of Corynebacterial rnaJ Proteins

| Reference number | Species and/or Strain(s) |
|---|---|
| WP_018339963.1 | *C. caspium* |
| WP_018020369.1 | *C. ciconiae* |
| WP_023019341.1 | *Corynebacterium* sp. KPL1995 and KPL1989 |
| OUJ24662.1 | *C. kefirresidentii* |
| WP_018119731.1 | *C. propinquum* |
| ART21077.1 | *C. striatum* |
| ERS47112.1 | *Corynebacterium* sp. KPL1856 |
| WP_021352644.1 | *C. pseudodiphtheriticum* |
| WP_027017879.1 | *C. pseudodiphtheriticum* |
| WP_075691844.1 | *C. sphenisci* |
| WP_046202207.1 | *C. kroppenstedtii* |
| WP_012731758.1 | *C. kroppenstedtii* |
| WP_064833244.1 | *Corynebacterium* sp. EPI-003-04-2554_SCH2473622 |
| WP_070446719.1 | *Corynebacterium* sp. HMSC05D03, HMSC066C02, and HMSC072D12 |
| WP_070527124.1 | *Corynebacterium* sp. HMSC074E01 and HMSC074C01 |
| WP_010190304.1 | *C. aurimucosum* |
| WP_070719120.1 | *Corynebacterium* sp. HMSC069E04 |
| WP_070644981.1 | *Corynebacterium* sp. HMSC062A03 |
| WP_083303801.1 | *Corynebacterium* sp. HMSC072A02 |
| WP_070683378.1 | *Corynebacterium* sp. HMSC056E09 |
| WP_046649347.1 | *C. minutissimum* |
| WP_083299156.1 | *Corynebacterium* sp. HMSC055A01, HMSC065D07, and HMSC078C09 |
| WP_016829761.1 | *C. diphtheriae* |
| WP_010935082.1 | *C. diphtheriae* |
| WP_045143380.1 | *C. diphtheriae* |
| WP_003851901.1 | *C. diphtheriae* |
| WP_072574180.1 | *C. diphtheriae* |
| WP_071571681.1 | *C. diphtheriae* |
| OLN14990.1 | *C. diphtheriae* |
| WP_014319143.1 | *C. diphtheriae* |
| WP_071572121.1 | *C. diphtheriae* |
| WP_088246382.1 | *C. diphtheriae* |
| WP_088266276.1 | *C. diphtheriae* |
| WP_014302046.1 | *C. diphtheriae* |
| WP_071575574.1 | *C. diphtheriae* |
| WP_047262243.1 | *C. mustelae* |
| WP_048379222.1 | *C. renale* |
| WP_098389157.1 | *C. renale* |
| WP_079005470.1 | *C. stationis* |
| WP_083640700.1 | *C. stationis* |
| WP_082869553.1 | *C. stationis* |
| WP_054468244.1 | *C. ulcerans* |
| WP_015401129.1 | *C. halotolerans* |
| WP_014010148.1 | *C. variable* |
| WP_085548717.1 | *C. pollutisoli* |
| WP_047253276.1 | *C. testudinoris* |
| WP_040086051.1 | *C. humireducens* |
| EPD69865.1 | *C. pyruviciproducens* ATCC BAA-1742 |
| OFO43484.1 | *Corynebacterium* sp. HMSC073D01 |
| WP_046439708.1 | *C. kutscheri* |
| WP_006063636.1 | *C. durum* |
| WP_070434230.1 | *Corynebacterium* sp. HMSC28B08 |
| WP_025253035.1 | *C. vitaeruminis* |
| WP_035002300.1 | *C. jeikeium* |
| WP_025402845.1 | *C. falsenii* |
| WP_066566197.1 | *C. crudilactis* |
| WP_053545137.1 | *C. deserti* |
| WP_042621626.1 | *C. marinum* |
| WP_055121720.1 | *C. oculi* |
| WP_026165808.1 | *C. mastitidis* |
| WP_047240411.1 | *C. epidermidicanis* |
| WP_082099190.1 | *C. camporealensis* |
| EEW49517.1 | *C. efficiens* YS-314 |
| EEG27126.1 | *C. matruchotii* ATCC 33806 |
| WP_013888590.1 | *C. resistens* |
| WP_099298604.1 | *Corynebacterium* sp. Marseille-P4122 |
| WP_055176585.1 | *C. lowii* |

f. Altered Corynebacterial accDA Proteins

Engineered strains of Corynebacteria comprising any of the structural alterations described above can also comprise an altered corynebacterial accDA protein. Altered corynebacterial accDA proteins comprise a G310E substitution. One example of such a protein is shown in SEQ ID NO: 6. "A corynebacterial accDA protein comprising a G310E substitution" as used herein means an accDA protein from a strain of *Corynebacterium* which, when compared with SEQ ID NO:6 using the National Center for Biotechnology Information's BLAST® alignment tool, has glutamic acid instead of glycine at the position that aligns with amino acid 310 of SEQ ID NO:6, as illustrated in FIG. 2. Corynebacterial accDA proteins which can be altered to comprise the G310E substitution include, but are not limited to, proteins (regardless of how named) identified with the amino acid sequences provided by the NCBI Reference numbers in Table 2.

TABLE 2

NCBI Reference Numbers of Corynebacterial accDA Proteins

| Reference No. | Species and/or Strain(s) |
|---|---|
| WP_075348128.1 | *C. glutamicum* AJ1511, ZL-6, ATCC 13869, XV, CP, and WM001; *B. flavum* ZL-1 |
| WP_081099520.1 | *C. glutamicum* |
| WP_077311448.1 | *C. glutamicum* |
| WP_087061768.1 | *C. glutamicum* |
| ALP51538.1 | *C. glutamicum* |
| WP_074508465.1 | *C. glutamicum* |
| WP_080724089.1 | *C. glutamicum* |
| WP_003862368.1 | *C. glutamicum* ATCC 14067, SYPS-062, SYPS-062-33a, ATCC 21493; *B. flavum* ATCC 15168 |
| WP_074491484.1 | *C. glutamicum* |
| WP_011013915.1 | *C. glutamicum* |
| CAC42827.1 | *C. glutamicum* |
| WP_081253003.1 | *C. glutamicum* |
| WP_080506411.1 | *C. glutamicum* |
| BAF53919.1 | *C. glutamicum* |
| AMA01529.1 | *C. glutamicum* |
| SJM44016.1 | *C. glutamicum* |
| AIK87334.1 | *C. glutamicum* |
| KEI22570.1 | *C. glutamicum* ATCC 14067 |
| WP_074508304.1 | *C. glutamicum* |
| WP_003858326.1 | *C. glutamicum* SCgG1, SCgG2, S9114, Z188, AS 1.542, and T6; *C. crenatum* MT, and SYPA 5-5 |
| OKX89395.1 | *C. glutamicum* |
| AGT04828.1 | *C. glutamicum* MB001 |
| ANE09779.1 | *C. glutamicum* |
| OKX77810.1 | *C. glutamicum* |
| OKX76530.1 | *C. glutamicum* |
| WP_066564978.1 | *C. crudilactis* |
| BAU95211.1 | *C. glutamicum* |
| WP_096454843.1 | *C. glutamicum* |
| WP_006770129.1 | *C. efficiens* |
| WP_053544383.1 | *C. deserti* |
| WP_047261525.1 | *C. mustelae* |
| WP_027013104.1 | *C. freiburgense* |
| WP_075725271.1 | *C. aquilae* |
| WP_005527314.1 | *C. matruchotii* |
| WP_080796909.1 | *Corynebacterium* sp. Marseille-P2417 |
| WP_005523810.1 | *C. matruchotii* |
| WP_034651919.1 | *C. vitaeruminis* |
| WP_047239789.1 | *C. epidermidicanis* DSM 45586 |
| WP_020975778.1 | *C. argentoratense* |
| WP_084035934.1 | *C. glucuronolyticum* |
| WP_025252271.1 | *C. vitaeruminis* |
| WP_005395753.1 | *Corynebacterium* sp. HMSC073D01; *C. glucuronolyticum* ATCC 51866 |
| WP_005391688.1 | *C. glucuronolyticum* |
| WP_046095662.1 | *C. ulcerans* |
| WP_046693956.1 | *C. ulcerans* |
| WP_023635342.1 | *C. ulcerans* |
| WP_029975236.1 | *C. ulcerans* |
| WP_044032730.1 | *C. ulcerans* |
| WP_014525474.1 | *C. ulcerans* |
| WP_013911032.1 | *C. ulcerans* |
| WP_046649933.1 | *C. xerosis* |
| WP_095076119.1 | *C. ulcerans* |
| WP_038617892.1 | *C. ulcerans* |
| WP_087453611.1 | *C. ulcerans* |
| AKN76575.1 | *C. ulcerans* FRC58 |
| WP_014366686.1 | *C. pseudotuberculosis* |
| WP_048740779.1 | *C. halotolerans* |
| WP_014523140.1 | *C. pseudotuberculosis* |
| WP_032802070.1 | *C. pseudotuberculosis* |

TABLE 2-continued

NCBI Reference Numbers of Corynebacterial accDA Proteins

| Reference No. | Species and/or Strain(s) |
| --- | --- |
| WP_071307711.1 | *C. pseudotuberculosis* |
| WP_013241466.1 | *C. pseudotuberculosis* |
| WP_014558622.1 | *C. pseudotuberculosis* |
| WP_048588670.1 | *C. pseudotuberculosis* |
| WP_014800179.1 | *C. pseudotuberculosis* |
| WP_070834218.1 | *Corynebacterium* sp. HMSC073H12 |
| WP_070595314.1 | *Corynebacterium* sp. HMSC063G05 and HMSC064E08; *C. amycolatum* ICIS 9 |
| WP_040426984.1 | *C. pyruviciproducens* |
| EPD71091.1 | *C. pyruviciproducens* ATCC BAA-1742 |
| WP_070522630.1 | *Corynebacterium* sp. HMSC11E11 |
| WP_035120392.1 | *C. freneyi* |
| WP_070605452.1 | *C.* sp. HMSC055G02 |
| WP_070565960.1 | *Corynebacterium* sp. HMSC077G01 and HMSC072D01 |
| WP_070653141.1 | *Corynebacterium* sp. HMSC065H09 and HMSC072B08 |
| WP_049189720.1 | *C. jeikieum* 212_CJEI; *Corynebacterium* sp. HMSC064E07 |
| WP_070545912.1 | *Corynebacterium* sp. HMSC064H12, HMSC077C02, and HMSC070B05 |
| WP_070437593.1 | *Corynebacterium* sp. HMSC14H10 |
| WP_069359660.1 | *C. amycolatum* |
| WP_070601703.1 | *Corynebacterium* sp. HMSC063F04 and HMSC075F02 |
| WP_070642800.1 | *Corynebacterium* sp. HMSC076C10 |
| WP_070429963.1 | *Corynebacterium* sp. HMSC14B06 and HMSC077G07 |
| WP_018019334.1 | *C. ciconiae* |
| WP_016423306.1 | *Corynebacterium* sp. HFH0082 |
| AFM06966.2 | *C. pseudotuberculosis* Cp162 |
| WP_038626403.1 | *Corynebacterium* sp. ATCC 6931 and HMSC11H10 |
| WP_070862586.1 | *Corynebacterium* sp. HMSC072B09 and HMSC073B01 |
| WP_049171363.1 | *C. jeikeium* |
| WP_070851988.1 | *Corynebacterium* sp. HMSC074C03 |
| WP_049180908.1 | *C. jeikeium* 805_CJEI; *Corynebacterium* sp. HMSC074C11, HMSC063A05, and HMSC064E10 |
| WP_049193043.1 | *C. jeikeium* |
| WP_070855978.1 | *Corynebacterium* sp. HMSC074C05 |
| WP_088611726.1 | *C. jeikeium* |
| WP_005511812.1 | *C. amycolatum* |
| WP_088266872.1 | *C. diphtheriae* |
| WP_070858287.1 | *Corynebacterium* sp. HMSC061H03 |
| WP_048758709.1 | *C. vitaeruminis* |
| WP_072564663.1 | *C. diphtheriae* |
| WP_014303117.1 | *C. diphtheriae* |
| WP_014306652.1 | *C. diphtheriae* |
| WP_070794870.1 | *C. diphtheriae* |

g. Altered Corynebacterial cg1144 Proteins

Engineered strains of Corynebacteria comprising any of the structural alterations described above can also comprise an altered corynebacterial cg1144 protein. Altered corynebacterial cg1144 proteins comprise a P66S substitution. One example of such a protein is shown in SEQ ID NO:9. "A corynebacterial cg1144 protein comprising a P66S substitution" as used herein means a cg1144 protein from a strain of *Corynebacterium* which, when compared with SEQ ID NO:9 using the National Center for Biotechnology Information's BLAST® alignment tool, has serine instead of proline at the position that aligns with amino acid 66 of SEQ ID NO:9, as illustrated in FIG. 3. Corynebacterial cg1144 proteins which can be altered to comprise the P66S substitution include, but are not limited to, proteins (regardless of how named) identified with the amino acid sequences provided by the NCBI Reference numbers in Table 3.

TABLE 3

NCBI Reference Numbers of Corynebacterial cg1144 Proteins

| Reference No. | Species and/or Strains(s) |
| --- | --- |
| BAB98402.1 | *C. glutamicum* ATCC 13032 |
| WP_004568112.1 | *C. glutamicum* 617, ATCC 21493, B Co 03.31, ATCC 13032 (K051, DSM 20300), MB001, ATCC 14067, AJ1511, CS176, ZL-6, ATCC 21831, B253, CP, Y1, USDA-ARS-USMARC-56828, C1, XV, TQ2223, WM001, ATCC 14067, 1006, SYPS-062, SYPS-062-33a, and AS 1.299; *B. flavum* 15168 and ZL-1 |
| WP_011897001.1 | *C. glutamicum* |
| WP_044029870.1 | *C. glutamicum* |
| WP_074506400.1 | *C. glutamicum* |
| WP_003856809.1 | *C. glutamicum* AS 1.542, MT, S9114, SCgG1, SCgG2, SYPA 5-5, T6-13, and Z188 |

TABLE 3-continued

| NCBI Reference Numbers of Corynebacterial cg1144 Proteins | |
|---|---|
| Reference No. | Species and/or Strains(s) |
| WP_096455129.1 | *C. glutamicum* |
| WP_053544501.1 | *C. deserti* |
| WP_066565124.1 | *C. crudilactis* |
| WP_011075272.1 | *C. efficiens* |
| WP_015650827.1 | *C. callunae* |
| EEW49979.1 | *C. efficiens* YS-314 |
| WP_080795733.1 | *Corynebacterium* sp. Marseille-P2417 |
| WP_015400428.1 | *C. halotolerans* |
| WP_042621053.1 | *C. marinum* |
| AJK68412.1 | *C. marinum* DSM 44953 |
| WP_049168821.1 | *C. propinquum* |
| WP_027017701.1 | *C. pseudodiphtheriticum* |
| WP_049148216.1 | *C. propinquum* |
| WP_018119926.1 | *C. propinquum* |
| WP_023019702.1 | *Corynebacterium* sp. KPL1995, KPL1989, and EPI-003-04-2554_SCH2473622 |
| WP_085550290.1 | *C. pollutisoli* |
| WP_040085436.1 | *C. humireducens* |
| EKX88113.1 | *C. durum* F0235 |
| WP_051033899.1 | *C. durum* |
| WP_020934330.1 | *C. maris* |
| WP_075814724.1 | *Corynebacterium* sp. CNJ-954 |
| WP_021353009.1 | *C. pseudodiphtheriticum* |
| WP_014008877.1 | *C. variable* |
| WP_052540339.1 | *C. glyciniphilum* |
| AHW65364.1 | *C. glyciniphilum* AJ 3170 |
| WP_015400429.1 | *C. halotolerans* |
| WP_075814720.1 | *Corynebacterium* sp. CNJ-954 |
| SNV91221.1 | *C. urealyticum* |
| CUU66362.1 | *C. variable* |
| WP_020934331.1 | *C. maris* |
| WP_012361047.1 | *C. urealyticum* |
| WP_015381984.1 | *C. urealyticum* |
| WP_071055926.1 | *C. jeikeium* |
| SCX01561.1 | *C. jeikeium* |
| WP_049050177.1 | *C. jeikeium* 931_CJEI; *Corynebacterium* sp. HMSC08A12 |
| EEW16595.1 | *C. jeikeium* ATCC 43734 |
| WP_034965445.1 | *C. jeikeium* |
| WP_034986706.1 | *C. jeikeium* |
| WP_011272910.1 | *C. jeikeium* |
| WP_038550379. | *C. glyciniphilum* |
| WP_070760374.1 | *Corynebacterium* sp. HMSC27B11 |
| WP_035004904.1 | *C. jeikeium* |
| WP_070759388.1 | *Corynebacterium* sp. HMSC22B11 |
| WP_020440292.1 | *C. terpenotabidum* |
| WP_066586577.1 | *C. provencense* |
| WP_013887703.1 | *C. resistens* |
| WP_010120483.1 | *C. nuruki* |
| WP_034981842.1 | *C. jeikeium* |
| WP_034971855.1 | *C. jeikeium* |
| WP_043012061.1 | *C. jeikeium* Cj19409; *Corynebacterium* sp. HMSC058E07 |
| WP_034969387.1 | *C. jeikeium* |
| WP_025401902.1 | *C. falsenii* |
| WP_034974957.1 | *C. jeikeium* |
| WP_034992651.1 | *C. jeikeium* |
| WP_035007616.1 | *C. jeikeium* |
| WP_035002809.1 | *C. jeikeium* |
| WP_048737023.1 | *C. falsenii* |
| WP_099298200.1 | *Corynebacterium* sp. Marseille-P4122 |
| WP_018021816.1 | *C. doosanense* |
| WP_049168823.1 | *C. propinquum* |
| WP_049148215.1 | *C. propinquum* |
| WP_018119927.1 | *C. propinquum* |
| WP_029157673.1 | *C. bovis* |
| WP_021353010.1 | *C. pseudodiphtheriticum* 090104 and DSM 44287; *Corynebacterium* sp. KPL1995, KPL1989, and EPI-003-04-2554_SCH2473622 |
| WP_048737018.1 | *C. falsenii* |
| WP_047262329.1 | *C. mustelae* |

h. Insertion of a Promoter in Front of the cg2766 Start Codon

Engineered strains of Corynebacteria comprising any of the structural alterations described above can also comprise a promoter inserted in front of the cg2766 start codon. The inserted promoter can be a promoter from a different gene of the *Corynebacterium* species or strain being engineered or can be a heterologous promoter (i.e., a promoter of another *Corynebacterium* species or strain or an artificially constructed promoter). These promoters include, but are not limited to, promoters disclosed in Nešvera et al., 2012; Pátek et al., 2003(a); Pátek et al., 2003(b); Pátek et al., 2013; Rytter et al., 2014; Shang et al., 2017; Yim et al., 2013; US 2017/0159045; and WO 2017/00376. In some embodiments, the inserted promoter is promoter Pcg0007_39 (SEQ ID NO:20); see US 2017/0159045 and WO 2017/00376.

i. Replacement of the Native actA Promoter

Engineered strains of Corynebacteria comprising any of the structural alterations described above can also comprise a replacement actA promoter in place of the native actA promoter. The actA replacement promoter can be a promoter from a different gene of the *Corynebacterium* species or strain being engineered or can be a heterologous promoter (i.e., a promoter of another *Corynebacterium* species or strain or an artificially constructed promoter). These promoters include, but are not limited to, promoters disclosed in Nešvera et al., 2012; Pátek et al., 2003(a); Pátek et al., 2003(b); Pátek et al., 2013; Rytter et al., 2014; Shang et al., 2017; Yim et al., 2013; US 2017/0159045; and WO 2017/00376. In some embodiments, the actA replacement promoter is promoter Pcg0007_39 (SEQ ID NO:20).

j. Replacement of the Native opcA Coding Sequence

Engineered strains of Corynebacteria comprising any of the structural alterations described above can also comprise a coding sequence for an opcA protein of a different *Corynebacterium* species or strain in place of the native opcA coding sequence. Suitable opcA proteins are listed in Table 4A and Table 4B. Using the NCBI's BLAST® alignment tool, the amino acid sequences of the opcA proteins in Table 4A are less than 75% identical to the amino acid sequence of the opcA protein of NRRL B-11474 (SEQ ID NO:94), and the amino acid sequences of the opcA proteins in Table 4B are more than 75% identical to the amino acid sequence of the opcA protein of NRRL B-11474 (SEQ ID NO:94).

In some embodiments the replacement opcA coding sequence is under the control of a promoter that drives expression of both zwf and opcA. In some embodiments, the replacement opcA coding sequence is under the control of an inserted opcA promoter. The inserted opcA promoter can be a promoter from a different gene of the *Corynebacterium* species or strain being engineered or can be a heterologous promoter (i.e., a promoter of another *Corynebacterium* species or strain or an artificially constructed promoter). These promoters include, but are not limited to, promoters disclosed in Nešvera et al., 2012; Pátek et al., 2003(a); Pátek et al., 2003(b); Pátek et al., 2013; Rytter et al., 2014; Shang et al., 2017; Yim et al., 2013; US 2017/0159045; and WO 2017/00376. In some embodiments, the inserted opcA promoter is promoter Pcg0007_39 (SEQ ID NO:20).

TABLE 4A

NCBI Reference Numbers for Corynebacterial opcA Proteins

| Reference Number | Species and/or Strain(s) |
|---|---|
| WP_046439480.1 | *C. kutscheri* |
| WP_099298719.1 | *Corynebacterium* sp. Marseille-P22 |
| WP_006823740.1 | *C. casei* UCMA 3821 (GenBank Accession No. CCE56308.1), LMG S-19264; *Corynebacterium* sp. JB4; SEQ ID NO: 92 |
| WP_095661089.1 | *C. glaucum* |
| WP_095276461.1 | *Corynebacterium* sp. NBT06-6, NML99-0020, and NML92-0415 |
| WP_095553723.1 | *Corynebacterium* sp. NML 150383 |
| WP_095548171.1 | *Corynebacterium* sp. NML00-0156 |
| WP_095545764.1 | *Corynebacterium* sp. NML 120412 |
| WP_095536183.1 | *Corynebacterium* sp. NML93-0607 |
| SNV73072.1 | *C. imitans* |
| WP_092286146.1 | *C. spheniscorum* |
| WP_092255258.1 | *C. cystitidis* |
| WP_092148525.1 | *C. mycetoides* |
| WP_088266936.1 | *C. diphtheriae* |
| WP_088265045.1 | *C. diphtheriae* |
| WP_088246432.1 | *C. diphtheriae* |
| WP_087454020.1 | *C. ulcerans* |
| WP_087117967.1 | *C. urinapleomorphum* |
| WP_049360793.1 | *C. aurimucosum* 1237_CAUR; *C. kefirresidentii* SB |
| WP_086891441.1 | *C. striatum* |
| WP_085958015.1 | *C. fournierii* |
| WP_085713610.1 | *C. diphtheriae* |
| WP_085549995.1 | *C. pollutisoli* |
| SLM96782.1 | *C. xerosis* |
| WP_084759291.1 | *C. phoceense* |
| WP_084168239.1 | *C. atypicum* |
| WP_084082961.1 | *C. freneyi* |
| WP_082796495.1 | *C. variabile* |
| WP_081920634.1 | *C. variabile* |
| WP_081803842.1 | *C. glyciniphilum* |
| WP_078057488.1 | *C. provencense* |

TABLE 4A-continued

NCBI Reference Numbers for Corynebacterial opcA Proteins

| Reference Number | Species and/or Strain(s) |
|---|---|
| WP_076598597.1 | *C. appendicis* |
| WP_075816106.1 | *Corynebacterium* sp. CNJ-954 |
| WP_075734014.1 | *C. phocae* |
| WP_075729852.1 | *C. flavescens* |
| WP_075726270.1 | *C. aquilae* |
| WP_075722895.1 | *C. stationis* |
| WP_075691979.1 | *C. sphenisci* |
| WP_075663775.1 | *C. frankenforstense* |
| WP_072590090.1 | *C. diphtheriae* |
| WP_071575625.1 | *C. diphtheriae* |
| WP_071572602.1 | *Corynebacterium* sp. NML120713 |
| WP_071571645.1 | *C. diphtheriae* |
| WP_071570066.1 | *C. diphtheriae* |
| WP_071568288.1 | *Corynebacterium* sp. NML140438 |
| WP_071566266.1 | *Corynebacterium* sp. NML130628 |
| WP_071056558.1 | *C. jeikeium* |
| WP_070976878.1 | *Corynebacterium* sp. MC3 |
| WP_070832090.1 | *Corynebacterium* sp. HMSC073H12 and HMSC074C03 |
| WP_070681225.1 | *Corynebacterium* sp. HMSC072A04, HMSC074H12, and HMSC035E02 |
| WP_070653088.1 | *Corynebacterium* sp. HMSC065H09 and HMSC072B08 |
| WP_070451416.1 | *C. coyleae* DSM 44184; *Corynebacterium* sp. HMSC11D10 and HMSC034E211 |
| WP_070866373.1 | *Corynebacterium* sp. HMSC072D01 |
| WP_070856734.1 | *Corynebacterium* sp. HMSC074C05 |
| WP_070843904.1 | *Corynebacterium* sp. HMSC034A01 |
| WP_070839048.1 | *Corynebacterium* sp. HMSC070H05 |
| WP_070828994.1 | *Corynebacterium* sp. HMSC036E10 |
| WP_070822776.1 | *Corynebacterium* sp. HMSC036D03 |
| WP_070816208.1 | *Corynebacterium* sp. HMSC034B08 |
| WP_070799051.1 | *C. diphtheriae* |
| WP_070770986.1 | *Corynebacterium* sp. HMSC075D04 |
| WP_070768006.1 | *Corynebacterium* sp. HMSC04H06 |
| WP_070761406.1 | *Corynebacterium* sp. HMSC27B11 |
| WP_070758918.1 | *Corynebacterium* sp. HMSC22B11 |
| WP_070738933.1 | *Corynebacterium* sp. HMSC073D01 |
| WP_070732205.1 | *Corynebacterium* sp. HMSC076D02 |
| WP_070683023.1 | *Corynebacterium* sp. HMSC056E09 |
| WP_070671164.1 | *Corynebacterium* sp. HMSC078H07 |
| WP_070643476.1 | *Corynebacterium* sp. HMSC062A03 and HMSC072D12 |
| WP_070642957.1 | *Corynebacterium* sp. HMSC076C10 |
| WP_070615011.1 | *Corynebacterium* sp. HMSC067D03 |
| WP_070570372.1 | *Corynebacterium* sp. HMSC055D05 |
| WP_070567126.1 | *C. jeikeium* FDAARGOS_328; *Corynebacterium* sp. HMSC077G01, HMSC063F04, HMSC064E07, HMSC072B09, and HMSC073B01 |
| WP_070564456.1 | *Corynebacterium* sp. HMSC072A02 and HMSC078A10 |
| WP_070549602.1 | *Corynebacterium* sp. HMSC077G07 |
| WP_070547341.1 | *Corynebacterium* sp. HMSC070E08 |
| WP_070536503.1 | *Corynebacterium* sp. HMSC05E07 |
| WP_070528425.1 | *Corynebacterium* sp. HMSC074E01, HMSC074C01, and HMSC036D02 |
| WP_070524283.1 | *Corynebacterium* sp. HMSC055A01, HMSC065D07, and HMSC078C09 |
| WP_070522356.1 | *Corynebacterium* sp. HMSC11E11 |
| WP_070494917.1 | *Corynebacterium* sp. HMSC30G07 |
| WP_070487506.1 | *Corynebacterium* sp. HMSC08A12 |
| WP_070484826.1 | *Corynebacterium* sp. HMSC08F01 |
| WP_070473987.1 | *Corynebacterium* sp. HMSC05H05 |
| WP_070462224.1 | *Corynebacterium* sp. HMSC29G08 |
| WP_070444875.1 | *Corynebacterium* sp. HMSC055A01, HMSC065D07, and HMSC078C09 |
| WP_070435059.1 | *Corynebacterium* sp. HMSC28B08 |
| WP_070423128.1 | *Corynebacterium* sp. HMSC05C01 |
| WP_070420257.1 | *Corynebacterium* sp. HMSC06C06 |
| WP_070362427.1 | *Corynebacterium* sp. NML98-0116 and HMSC08D02 |
| WP_062035107.1 | *C. simulans* PES1; *Corynebacterium* sp. HMSC06G04 |
| WP_061922333.1 | *C. simulans* Wattiau and 1B08; *Corynebacterium* sp. HMSC06D04, HMSC08C04, HMSC077D03, HMSC071F07; *Corynebacterium accolens* AH4003 |
| WP_049193712.1 | *C. jeikeium* 401_CJE1; *Corynebacterium* sp. HMSC055G02 |
| WP_046649108.1 | *C. aurimucosum* 944_CAUR; *Corynebacterium* sp. HMSC068G04 and HMSC056F09; *C. minutissimum* 1941 |
| WP_043015176.1 | *C. jeikeium* Cj30184; *Corynebacterium* sp. HMSC058E07 |

TABLE 4A-continued

| NCBI Reference Numbers for Corynebacterial opcA Proteins | |
|---|---|
| Reference Number | Species and/or Strain(s) |
| WP_005531605.1 | *C. striatum* 216, ATCC 6940, 797_CAUR, 587_CAUR, 542_CAUR, 1329_CAUR, 1327_CAUR, 2230, 2245, 2023, and 2247; *Corynebacterium* sp. HMSC05D08 |
| OHF39428.1 | *Corynebacterium* sp. HMSC074A01 |
| WP_066493224.1 | *Corynebacterium* sp. DNF00584, CMW7794, HMSC072G08, HMSC077B05, HMSC077D10, and HMSC0665A05 |
| WP_066839768.1 | *C. stationis* |
| WP_066794092.1 | *C. stationis* |
| WP_066525378.1 | *C. bouchesdurhonense* |
| WP_049167646.1 | *C. propinquum* |
| WP_049158908.1 | *C. striatum* |
| WP_049148304.1 | *C. propinquum* |
| WP_065421559.1 | *C. halotolerans* |
| WP_064833329.1 | *Corynebacterium* sp. EPI-003-04-2554_SCH2473622 |
| WP_063936745.1 | *C. afermentans* |
| WP_058832265.1 | *C. pseudotuberculosis* |
| WP_006063324.1 | *C. durum* |
| WP_058093366.1 | *C. pseudotuberculosis* |
| WP_055178564.1 | *C. lowii* |
| WP_055121854.1 | *C. oculi* |
| AKK06005.1 | *C. mustelae* |
| WP_053412142.1 | *C. lactis* |
| WP_052204189.1 | *C. riegelii* |
| WP_038628980.1 | *C. jeikeium* 805_CJEI; *Corynebacterium* sp. ATCC 6931, HMSC11H10, HMSC074C11, HMSC063A05, HMSC064E10, and HMSC074C04 |
| WP_049049964.1 | *C. jeikeium* |
| WP_049378186.1 | *C. aurimucosum* |
| WP_048758558.1 | *C. vitaeruminis* |
| WP_048737982.1 | *C. falsenii* |
| WP_016422736.1 | *C. jeikeium* 239_CJEI and 212_CJEI; *C. urealyticum* 1055_CURE; *Corynebacterium* sp. HFH0082, HMSC14H10, HMSC064H12, HMSC063G05, HMSC077C02, HMSC064E08, HMSC070B05, HMSC061H03, HMSC075F02; *C. amycolatum*_ICIS 53 and ICIS 9 |
| WP_048381636.1 | *C. renale* |
| WP_047263492.1 | *C. mustelae* |
| WP_047259618.1 | *C. uterequi* |
| WP_047253131.1 | *C. testudinoris* |
| WP_047240275.1 | *C. epidermidicanis* |
| WP_005526431.1 | *C. matruchotii* |
| WP_046650939.1 | *C. xerosis* |
| WP_046645947.1 | *C. striatum* |
| WP_046204153.1 | *C. argentoratense* |
| WP_046202297.1 | *C. kroppenstedtii* |
| WP_046095943.1 | *C. ulcerans* |
| AHW64140.1 | *C. glyciniphilum* AJ 3170 |
| WP_042621478.1 | *C. marinum* |
| WP_042530750.1 | *C. singulare* |
| WP_042404782.1 | *C. jeddahense* |
| WP_040354603.1 | *C. ammoniagenes* |
| WP_040085900.1 | *C. humireducens* (GenBank Accession No. AJE33249.1, SEQ ID NO: 25) |
| WP_039675253.1 | *C. minutissimum* |
| WP_038620584.1 | *C. ulcerans* |
| WP_038611699.1 | *C. ureicelerivorans* |
| WP_035113157.1 | *C. auriscanis* |
| WP_035104698.1 | *C. camporealensis* |
| WP_035012334.1 | *C. jeikeium* |
| WP_035010427.1 | *C. jeikeium* |
| WP_035008179.1 | *C. jeikeium* |
| WP_035003885.1 | *C. jeikeium* |
| WP_035001868.1 | *C. jeikeium* |
| WP_034998920.1 | *C. ihumii* |
| WP_034987985.1 | *C. jeikeium* |
| WP_034981960.1 | *C. jeikeium* |
| WP_034974411.1 | *C. jeikeium* |
| WP_034967970.1 | *C. jeikeium* |
| WP_034663424.1 | *C. tuscaniense* |
| WP_027020497.1 | *C. sputi* |
| WP_027012302.1 | *C. freiburgense* |
| WP_025402713.1 | *C. falsenii* (GenBank Accession No. AHI03141.1), SEQ ID NO: 89 |
| WP_025252883.1 | *C. vitaeruminis* (GenBank Accession No. AHI22863.1); SEQ ID NO: 87 |
| WP_023022439.1 | *Corynebacterium* sp. KPL1859, KPL1855, and KPL1814 |

TABLE 4A-continued

| NCBI Reference Numbers for Corynebacterial opcA Proteins | |
|---|---|
| Reference Number | Species and/or Strain(s) |
| WP_023021500.1 | *Corynebacterium* sp. KPL1860, KPL1857, KPL1856, KPL1821, KPL1817, and KPL1856 |
| WP_023019439.1 | *Corynebacterium* sp. KPL1995 and KPL1989 |
| WP_023017462.1 | *Corynebacterium* sp. KPL2004, KPL1998, KPL1996, KPL1986, KPL1824, and KPL1996 |
| WP_005279118.1 | *C. accolens* ATCC 49725; *Corynebacterium* sp. KPL1818 |
| WP_022862033.1 | *C. massiliense* |
| WP_021353956.1 | *C. pseudodiphtheriticum* |
| WP_020976309.1 | *C. argentoratense* |
| WP_005324852.1 | *C. tuberculostearicum* SK141; *C. pseudogenitalium* ATCC 33035 |
| WP_020934820.1 | *C. maris* |
| WP_020441165.1 | *C. terpenotabidum* (GenBank Accession No. AGP30804.1), SEQ ID NO: 93 |
| WP_019194592.1 | *C. timonense* |
| WP_018582009.1 | *C. pilosum* |
| WP_018339807.1 | *C. caspium* |
| WP_018295562.1 | *C. lubricantis* |
| WP_018119593.1 | *C. propinquum* |
| WP_018118857.1 | *C. mastitidis* |
| WP_018023988.1 | *C. ulceribovis* |
| WP_018021704.1 | *C. doosanense* |
| WP_018019762.1 | *C. ciconiae* |
| WP_018017013.1 | *C. capitovis* |
| WP_016457552.1 | *C. pyruviciproducens* (GenBank Accession No. EPD70204.1), SEQ ID NO: 91 |
| WP_010265064.1 | *C. bovis* |
| WP_010186759.1 | *C. aurimucosum* |
| EFG82419.1 | *C. ammoniagenes* DSM 20306 |
| WP_006840267.1 | *C. lipophiloflavum* |
| WP_005521071.1 | *C. matruchotii* (GenBank Accession No. EEG26974.1), SEQ ID NO: 88 |
| WP_005510779.1 | *C. amycolatum* |
| WP_005389976.1 | *C. glucuronolyticum* |
| WP_005294809.1 | *C. jeikeium* |
| WP_005290056.1 | *C. genitalium* |
| WP_005283075.1 | *C. accolens* |
| WP_015400950.1 | *C. halotolerans* (GenBank Accession No. AGF72531.1), SEQ ID NO: 90 |
| WP_014525815.1 | *C. ulcerans* |
| WP_014367098.1 | *C. pseudotuberculosis* |
| WP_014306922.1 | *C. diphtheriae* |
| WP_014009994.1 | *C. variabile* |
| WP_013911577.1 | *C. ulcerans* |
| WP_013888447.1 | *C. resistens* |
| WP_013241959.1 | *C. pseudotuberculosis* |
| WP_012731602.1 | *C. kroppenstedtii* |
| WP_012360244.1 | *C. urealyticum* |
| WP_011273572.1 | *C. jeikeium* |
| WP_003851588.1 | *C. diphtheriae* |

TABLE 4B

| NCBI Reference Numbers for Corynebacterial OpcA Proteins | |
|---|---|
| Reference Number | Species and/or Strain |
| WP_075348233.1 | *C. glutamicum* XV |
| WP_003862265.1 | *C. glutamicum* ATCC 14067, ATCC 21831, AR1, USDA-ARS-USMARC-56828, YI, SYPS-062, SYPS-062-33a, and ATCC 21493; *B. flavum* ATCC 15168 |
| WP_040967467.1 | *C. glutamicum* |
| WP_003856048.1 | *C. glutamicum* SCgG1, SCgG2, S9114, Z118, CS176, AS 1.542, TG-13; *C. crenatum* MT |
| WP_074508163.1 | *C. glutamicum* |
| WP_011897297.1 | *C. glutamicum* |
| WP_011014458.1 | *C. glutamicum* |
| WP_087497587.1 | *C. glutamicum* |
| WP_066565817.1 | *C. crudilactis* |
| WP_096456023.1 | *C. glutamicum* |
| WP_053544982.1 | *C. deserti* |

TABLE 4B-continued

| NCBI Reference Numbers for Corynebacterial OpcA Proteins | |
|---|---|
| Reference Number | Species and/or Strain |
| WP_015651366.1 | *C. callunae* |
| WP_080794830.1 | *Corynebacterium* sp. Marseille-P2417 |
| WP_006767698.1 | *C. efficiens* |

k. Insertion of at Least One Additional Copy of lysA, ask, asd, ddh, and/or dapB Engineered strains of Corynebacteria comprising any of the structural alterations described above can also comprise at least one additional copy of at least one gene selected from the group consisting of lysA, ask, asd, ddh, and dapB. The additional copies can be provided using one or more vectors. Example 1 describes two integration vectors that can be used to insert copies of ask, asd, ddh, and dapB.

In some embodiments, the engineered *Corynebacterium* contains at least one additional copy of lysA, ask, asd, ddh, and dapB.

In some embodiments, the engineered *Corynebacterium* contains at least one additional copy of ask, asd, ddh, and dapB. In other embodiments, the engineered *Corynebacterium* contains at least one additional copy of lysA, asd, ddh, and dapB. In other embodiments, the engineered *Corynebacterium* contains at least one additional copy of lysA, ask, ddh, and dapB. In other embodiments, the engineered *Corynebacterium* contains at least one additional copy of lysA, ask, asd, and dapB. In other embodiments, the engineered *Corynebacterium* contains at least one additional copy of lysA, ask, asd, and ddh.

In some embodiments, the engineered *Corynebacterium* contains at least one additional copy of asd, ddh, and dapB. In other embodiments, the engineered *Corynebacterium* contains at least one additional copy of ask, ddh, and dapB. In other embodiments, the engineered *Corynebacterium* contains at least one additional copy of ask, asd, and dapB. In other embodiments, the engineered *Corynebacterium* contains at least one additional copy of ask, asd, and ddh. In other embodiments, the engineered *Corynebacterium* contains at least one additional copy of lysA, ddh, and dapB. In other embodiments, the engineered *Corynebacterium* contains at least one additional copy of lysA, asd, and dapB. In other embodiments, the engineered *Corynebacterium* contains at least one additional copy of lysA, asd, and ddh. In other embodiments, the engineered *Corynebacterium* contains at least one additional copy of lysA, ask, and dapB. In other embodiments, the engineered *Corynebacterium* contains at least one additional copy of lysA, ask, and ddh.

In some embodiments, the engineered *Corynebacterium* contains at least one additional copy of ddh and dapB. In other embodiments, the engineered *Corynebacterium* contains at least one additional copy of asd and dapB. In other embodiments, the engineered *Corynebacterium* contains at least one additional copy of asd and ddh. In other embodiments, the engineered *Corynebacterium* contains at least one additional copy of lysA and dapB. In other embodiments, the engineered *Corynebacterium* contains at least one additional copy of lysA and ddh. In other embodiments, the engineered *Corynebacterium* contains at least one additional copy of lysA, and ask.

In other embodiments, the engineered *Corynebacterium* contains at least one additional copy of lysA. In other embodiments, the engineered *Corynebacterium* contains at least one additional copy of ask. In other embodiments, the engineered *Corynebacterium* contains at least one additional copy of asd. In other embodiments, the engineered *Corynebacterium* contains at least one additional copy of ddh. In other embodiments, the engineered *Corynebacterium* contains at least one additional copy of dapB.

In any of the embodiments described above in which the engineered *Corynebacterium* contains at least one additional copy of lysA, the additional copy of lysA is a codon-optimized version described below.

l. Replacement of the Start Codon of aceE

In some embodiments, the start codon of the native aceE gene in the genome of any of the engineered strains of Corynebacteria described above is replaced. In some of these embodiments, the start codon is replaced with GTG, CTG, or TTG. In some embodiments, the start codon is replaced with TTG.

m. Replacement of the Native pyc Gene Promoter

Engineered strains of Corynebacteria comprising any of the structural alterations described above can also comprise a pyc replacement promoter in place of the native pyc gene promoter. The pyc replacement promoter can be a promoter from a different gene of the *Corynebacterium* species or strain being engineered or can be a heterologous promoter (i.e., a promoter of another *Corynebacterium* species or strain or an artificially constructed promoter). These promoters include, but are not limited to, promoters disclosed in Nešvera et al., 2012; Pátek et al., 2003(a); Pátek et al., 2003(b); Pátek et al., 2013; Rytter et al., 2014; Shang et al., 2017; Yim et al., 2013; US 2017/0159045; and WO 2017/00376. In some embodiments, the pyc replacement promoter is promoter Pcg1860 (SEQ ID NO:11; see US 2017/0159045).

n. Insertion of a Promoter in Front of the zwf Open Reading Frame

Engineered strains of Corynebacteria comprising any of the structural alterations described above can also comprise a promoter inserted in front of the zwf open reading frame. The inserted promoter can be a promoter from a different gene of the *Corynebacterium* species or strain being engineered or can be a heterologous promoter (i.e., a promoter of another *Corynebacterium* species or strain or an artificially constructed promoter). These promoters include, but are not limited to, promoters disclosed in Nešvera et al., 2012; Pátek et al., 2003(a); Pátek et al., 2003(b); Pátek et al., 2013; Rytter et al., 2014; Shang et al., 2017; Yim et al., 2013; US 2017/0159045; and WO 2017/00376. In some embodiments, the additional promoter is promoter Pcg0007_39 (SEQ ID NO:20).

o. Insertion of a Codon-Optimized lysA Coding Sequence

Engineered strains of Corynebacteria comprising any of the structural alterations described above can comprise a codon-optimized lysA coding sequence under the control of a promoter and including terminator sequence. The promoter can be a promoter from a different gene of the *Corynebacterium* species or strain being engineered or can be a heterologous promoter (i.e., a promoter of another *Corynebacterium* species or strain or an artificially constructed promoter). These promoters include, but are not limited to, promoters disclosed in Nešvera et al., 2012; Pátek et al., 2003(a); Pátek et al., 2003(b); Pátek et al., 2013; Rytter et al., 2014; Shang et al., 2017; Yim et al., 2013; US 2017/0159045; and WO 2017/00376. Terminator sequences include, but are not limited to, those disclosed in Pfeifer-Sancar et al., 2013.

In some embodiments, the promoter is Pcg0007_39 (SEQ ID NO:20). In some of these embodiments, the codon-optimized sequence is SEQ ID NO:16. In some of these embodiments, the terminator is the sod terminator (nucleotides 1436-1516 of SEQ ID NO:17). In some embodiments, the genome of the engineered *Corynebacterium* contains the nucleotide sequence SEQ ID NO:17, which is codon-optimized lysA sequence SEQ ID NO:16 under the control of promoter Pcg0007_39 (SEQ ID NO:20) and having a sod terminator (nucleotides 1436-1516 of SEQ ID NO:17).

Nucleic Acids and Vectors

Vectors can be used to engineer a *Corynebacterium* having one or more of the structural alterations described above, resulting in improved lysine production compared with the corresponding native *Corynebacterium* (i.e., the *Corynebacterium* which has not been engineered to include the structural alterations). Such corynebacteria include, but are not limited to, the *Corynebacterium* deposited as NRRL B-11474, the *Corynebacterium* deposited as NRRL B-67439, and the corynebacterial species and strains in Tables 1, 2, 3, 4A, and 4B. Methods of delivering vectors to Corynebacteria are well known and include, for example, calcium phosphate transfection, DEAE-dextran mediated transfection, microinjection, lipid-mediated transfection, electroporation, conjugation, and infection.

Nucleic acids that can be used to engineer the alterations described above are well known and are described, for example, in U.S. Pat. Nos. 7,368,276, 6,927,046, US 2017/0159045, and WO 2017/00376 and in the Examples, below. Nucleic acids encoding the altered corynebacterial rnaJ, accDA, and cg1144 proteins described above can be included in vectors in which a coding sequence is operably linked to a suitable regulatory sequence for expression in a *Corynebacterium*. SEQ ID NO:2, SEQ ID NO:5, and SEQ ID NO:8 are examples of nucleotide sequences encoding SEQ ID NO:3, SEQ ID NO:6, and SEQ ID NO:9, respectively, but any nucleotide sequence that encodes the altered corynebacterial protein can be used. The nucleotide sequences can be optimized for expression in various species or strains of Corynebacteria as is well known in the art.

The regulatory sequence includes a suitable mRNA ribosome binding site and a sequence for regulating the termination of transcription and translation and may include other elements, such as a promoter or operator. Once transformed into a host *Corynebacterium*, the vector may replicate or function independently of the host genome or may integrate into the genome itself. The vector that is used is not specifically limited and may be any vector known in the art, as long as it can replicate in a *Corynebacterium* host. See, for example, Lee, 2014; Knoppová et al., 2007; and Pátek & Nešvera, 2013.

A vector can include at least one selectable marker, such as an antibiotic resistance gene. Suitable antibiotics include, e.g., amikacin, ampicillin, augmentin (amoxicillin plus clavulonic acid), cefazolin, cefoxitin, ceftazidime, ceftiofur, cephalothin, chloramphenicol, enrofloxacin, florfenicol, gentamicin, imipenem, kanamycin, penicillin, sarafloxicin, spectinomycin, streptomycin, tetracycline, ticarcillin, and tilmicosin.

Engineered Strains of Corynebacteria

This disclosure provides strains of Corynebacteria engineered to contain at least one of the four alterations described above—i.e., (a) insertion of a replacement promoter in front of the cg1383 start codon; (b) replacement of the native phoU promoter; (c) replacement of the native cg3210 promoter; and (d) replacement of the native cg0800 promoter—as well as at least one of the following alterations:

(e) alteration of the rnaJ coding sequence to encode a ribonuclease J protein comprising a G448S substitution;
(f) alteration of the native accDA coding sequence to encode an acetyl-CoA carboxylase carboxyl transferase subunit alpha/beta protein comprising a G310E substitution;
(g) alteration of the native cg1144 coding sequence to encode a cg1144 protein comprising a P66S substitution;
(h) insertion of a promoter in front of the cg2766 start codon;
(i) replacement of the native actA promoter;
(j1) replacement of the native opcA coding sequence by coding sequence for an opcA protein of a different *Corynebacterium* species or strain;
(j2) replacement of the native opcA coding sequence by coding sequence for an opcA protein of a different *Corynebacterium* species or strain under the control of an inserted opcA promoter;
(k) insertion of at least one additional copy of at least one gene selected from the group consisting ask, asd, ddh, and dapB;
(l) replacement of the start codon of the native aceE gene;
(m) replacement of the native pyc gene promoter;
(n) insertion of an additional promoter in front of the zwf open reading frame; and
(o) insertion of a codon-optimized lysA coding sequence.

The following non-limiting embodiments of engineered Corynebacteria fall within the description above.

Embodiment 1. The *Corynebacterium* deposited with the Agriculture Research Culture Collection (NRRL) International Depository Authority, 1815 N. University Street, Peoria, IL 61604 on Dec. 22, 2017, under the provisions of the Budapest Treaty and assigned Accession No. NRRL B-67535.

Embodiment 2. A *Corynebacterium* having a bacterial genome consisting essentially of the genome of the bacterium deposited as NRRL B-67439 but for up to 4 structural alterations selected from the group consisting of:

(a) insertion of a promoter in front of the cg1383 start codon;
(b) replacement of the native phoU promoter;
(c) replacement of the native cg3210 promoter; and (d) replacement of the native cg0800 promoter.

Embodiment 3. A *Corynebacterium* having a bacterial genome consisting essentially of the genome of the bacterium deposited as NRRL B-11474 but for

- (i) at least one structural alteration selected from the group consisting of:
  - (a) insertion of a promoter in front of the cg1383 start codon;
  - (b) replacement of the native phoU promoter;
  - (c) replacement of the native cg3210 promoter; and
  - (d) replacement of the native cg0800 promoter; and
- (ii) at least one additional structural alteration selected from the group consisting of:
  - (e) alteration of the rnaJ coding sequence to encode a corynebacterial rnaJ protein comprising a G448S substitution;
  - (f) alteration of the native accDA coding sequence to encode a corynebacterial accDA protein comprising a G310E substitution;
  - (g) alteration of the native cg1144 coding sequence to encode a corynebacterial cg1144 protein comprising a P66S substitution;
  - (h) insertion of a promoter in front of the cg2766 start codon;
  - (i) replacement of the native actA promoter;
  - (j1) replacement of the native opcA coding sequence by a replacement opcA coding sequence for an opcA protein of a different *Corynebacterium;*
  - (j2) replacement of the native opcA coding sequence by a replacement opcA coding sequence for an opcA protein of a different *Corynebacterium* under the control of an inserted opcA promoter;
  - (k) insertion of at least one additional copy of at least one gene selected from the group consisting of lysA, ask, asd, ddh, and dapB;
  - (l) replacement of the native start codon of aceE by GTG, CTG, or TTG;
  - (m) replacement of the native pyc gene promoter by promoter Pcg1860 (SEQ ID NO:11);
  - (n) insertion of promoter Pcg0007_39 (SEQ ID NO:20) in front of the zwf open reading frame; and
  - (o) insertion of a codon-optimized lysA coding sequence.

Embodiment 4. The *Corynebacterium* of Embodiment 2 or 3, wherein the promoter in front of the cg1383 start codon is promoter Pcg0007_39 (SEQ ID NO:20).

Embodiment 5. The *Corynebacterium* of any of Embodiments 2-4, wherein the native phoU promoter is replaced by promoter Pcg0007_39 (SEQ ID NO:20).

Embodiment 6. The *Corynebacterium* of any of Embodiments 2-5, wherein the native cg3210 promoter is replaced by promoter Pcg0007_39 (SEQ ID NO:20).

Embodiment 7. The *Corynebacterium* of any of Embodiments 2-6, wherein the native cg0800 promoter is replaced by promoter Pcg0007_39 (SEQ ID NO:20).

Embodiment 8. The *Corynebacterium* of any of Embodiments 3-7, in which (e) the native rnaJ coding sequence is altered to encode the corynebacterial rnaJ protein comprising a G448S substitution.

Embodiment 9. The *Corynebacterium* of any of Embodiments 3-8, in which (e) the native rnaJ coding sequence is altered to encode the amino acid sequence SEQ ID NO:3.

Embodiment 10. The *Corynebacterium* of any of Embodiments 3-9, in which (f) the native accDA coding sequence is altered to encode the corynebacterial accDA protein comprising the G310E substitution.

Embodiment 11. The *Corynebacterium* bacterium of any of Embodiments 3-10, in which (f) the native accDA coding sequence is altered to encode the amino acid sequence SEQ ID NO:6.

Embodiment 12. The *Corynebacterium* of any of Embodiments 3-11, in which (g) the native cg1144 coding sequence is altered to encode the corynebacterial cg1144 protein comprising the P66S substitution.

Embodiment 13. The *Corynebacterium* bacterium of any of Embodiments 3-12, in which (g) the native cg1144 coding sequence is altered to encode the amino acid sequence SEQ ID NO:9.

Embodiment 14. The *Corynebacterium* bacterium of any of Embodiments 3-13, in which (h) the promoter is inserted in front of the cg2766 start codon.

Embodiment 15. The *Corynebacterium* of any of Embodiments 3-14, in which (h) the promoter inserted in front of the cg2766 start codon is promoter Pcg0007_39 (SEQ ID NO:20).

Embodiment 16. The *Corynebacterium* bacterium of any of Embodiments 3-15, in which (i) the native actA promoter is replaced.

Embodiment 17. The *Corynebacterium* of any of Embodiments 3-16 in which (i) the native actA promoter is replaced by promoter Pcg0007_39 (SEQ ID NO:20).

Embodiment 18. The *Corynebacterium* bacterium of any of Embodiments 3-17, in which (j) the native opcA coding sequence is replaced by a replacement opcA coding sequence for an opcA protein of a different *Corynebacterium.*

Embodiment 19. The *Corynebacterium* of any of Embodiments 3-18, in which the native opcA coding sequence is replaced by a replacement opcA coding sequence for an opcA protein of a *Corynebacterium* selected from the group consisting of *Corynebacterium vitaeruminis* DSM 20294, *Corynebacterium matruchotii* ATCC 33806*, Corynebacterium falsenii* DSM 44353, *Corynebacterium halotolerans* YIM 70093, *Corynebacterium pyruviciproducens* ATCC BAA-1742, *Corynebacterium casei* UCMA 3821, *Corynebacterium terpenotabidum* Y-11, and *C. humireducens* NBRC 106098.

Embodiment 20. The *Corynebacterium* of any of Embodiments 3-19, in which the native opcA coding sequence is replaced by a replacement opcA coding sequence for an opcA protein of *C. humireducens* NBRC 106098.

Embodiment 21. The *Corynebacterium* of any of Embodiments 3-20, in which the replacement opcA coding sequence is under control of an inserted opcA promoter.

Embodiment 22. The *Corynebacterium* of Embodiment 21, in which the inserted opcA promoter is promoter Pcg0007_39 (SEQ ID NO:20).

Embodiment 23. The *Corynebacterium* bacterium of any of Embodiments 3-22, in which (k) the genome of the bacterium contains the at least one additional copy of the at least one gene selected from the group consisting of lysA, ask, asd, ddh, and dapB.

Embodiment 24. The *Corynebacterium* bacterium of Embodiment 23, in which the genome of the bacterium contains (a) at least one additional copy of lysA, ask, asd, ddh, and dapB.

Embodiment 24. The *Corynebacterium* bacterium of Embodiment 23, in which the genome of the bacterium contains:

- (b) at least one additional copy of ask, asd, ddh, and dapB;
- (c) at least one additional copy of lysA, asd, ddh, and dapB;

(d) at least one additional copy of lysA, ask, ddh, and dapB;
(e) at least one additional copy of lysA, ask, asd, and dapB; or
(f) at least one additional copy of lysA, ask, asd, and ddh.

Embodiment 25. The *Corynebacterium* bacterium of Embodiment 23, in which the genome of the bacterium contains:

(g) at least one additional copy of asd, ddh, and dapB;
(h) at least one additional copy of ask, ddh, and dapB;
(i) at least one additional copy of ask, asd, and dapB;
(j) at least one additional copy of ask, asd, and ddh;
(k) at least one additional copy of lysA, ddh, and dapB;
(l) at least one additional copy of lysA, asd, and dapB;
(m) at least one additional copy of lysA, asd, and ddh;
(n) at least one additional copy of lysA, ask, and dapB; or
(o) at least one additional copy of lysA, ask, and ddh.

Embodiment 26. The *Corynebacterium* bacterium of Embodiment 23, in which the genome of the bacterium contains:

(p) at least one additional copy of ddh and dapB;
(q) at least one additional copy of asd and dapB;
(r) at least one additional copy of asd and ddh;
(s) at least one additional copy of lysA and dapB;
(t) at least one additional copy of lysA and ddh;
(u) at least one additional copy of lysA, and ask.

Embodiment 27. The *Corynebacterium* bacterium of Embodiment 23, in which the genome of the bacterium contains:

(v) at least one additional copy of lysA;
(w) at least one additional copy of ask;
(x) at least one additional copy of asd;
(y) at least one additional copy of ddh; or
(z) at least one additional copy of dapB.

Embodiment 28. The *Corynebacterium* bacterium of any of Embodiments 3-27, in which the start codon of aceE is replaced by TTG, GTG, or CTG.

Embodiment 29. The *Corynebacterium* bacterium of any of Embodiments 3-28, in which the start codon of aceE is replaced by TTG.

Embodiment 30. The *Corynebacterium* bacterium of any of Embodiments 3-29, in which the native pyc gene promoter is replaced.

Embodiment 31. The *Corynebacterium* bacterium of any of Embodiments 3-30, in which the native pyc gene promoter is replaced by promoter Pcg1860 (SEQ ID NO:11).

Embodiment 32. The *Corynebacterium* bacterium of any of Embodiments 3-31, in which a promoter is inserted in front of the zwf open reading frame.

Embodiment 33. The *Corynebacterium* bacterium of any of Embodiments 3-32, in which promoter Pcg0007_39 (SEQ ID NO:20) is inserted in front of the zwf open reading frame.

Embodiment 34. The *Corynebacterium* of any of Embodiments 3-33, which contains (o) a codon-optimized lysA coding sequence.

Embodiment 35. The *Corynebacterium* of Embodiment 34, in which the codon-optimized lysA coding sequence is under control of Pcg0007_39 (SEQ ID NO:20).

Embodiment 36. The *Corynebacterium* of Embodiment 34 or 35, which comprises a heterologous terminator for the codon-optimized lysA coding sequence.

Embodiment 37. The *Corynebacterium* bacterium of any of Embodiments 34-36, which comprises the nucleotide sequence SEQ ID NO:17.

Production of Lysine

Methods of using Corynebacteria to produce lysine are well known in the art, and the engineered Corynebacteria provided in this disclosure can be used with any of these methods. See, for example, U.S. Pat. Nos. 8,048,649, 7,635,579, 7,504,242, 7,300,777, 7,267,967, 7,160,711, 7,141,388, 7,122,369, 6,927,046, 6,830,903, US 2002/0086371, US 2004/0043458, US 2009/0325244, EP 1246921, and EP 1619252.

Those skilled in the art will appreciate that there are numerous variations and permutations of the above described embodiments that fall within the scope of the appended claims.

Example 1. Preparation of L-Lysine Pathway Four-Gene Constructs

Example 1A. Construction of an Integration Vector Containing Lysine Biosynthesis Genes ask-asd-dapB-ddh in the bioD Region pBKMS vector is a pBR322 derivative unable to replicate in *C. glutamicum* and which contains a kanamycin resistance gene marker and a levansucrase sacB gene from *Bacillus subtilis* under the control of a strong synthetic promoter for sucrose counter-selection. The 5.4 kb ask-asd-ddh-dapB-orj2' cassette (4Go) was digested from pFC3-ask-asd-dapB-ddh plasmid (U.S. Pat. No. 7,368,276) with PmeI and XmaI and ligated into pDElia11 (U.S. Pat. No. 6,927,046) linearized with HincII and XmaI to construct pD11-KBDH.

To generate a 9.4 kb homology region containing a SpeI site, a DNA fragment was amplified from NRRL B-11474 genomic DNA using primers 18417 (SEQ ID NO:70) and 184F8 (SEQ ID NO:71) and cloned into the pBKMS vector NdeI/PstI sites by IN-FUSION® (Clontech). The resulting plasmid pBKMS 184 3p was digested with SpeI and a second PCR product similarly obtained from NRRL B-11474 genomic DNA using primers 161-184f5 and 162-184r6 was inserted by IN-FUSION® reaction to generate pBKMS184. The 5.4 kb 4Go cassette was amplified from pD11-KDBH with primers 244-4Go F2 Inf SpeI (SEQ ID NO:72) and 253-4Go R3 (SEQ ID NO:73), digested with SpeI and cloned by ligation into pBKMS 184 SpeI site.

Example 1B. Construction of a Vector Containing the Lysine Biosynthesis Genes ask-asd-dapB-ddh and a FarI Homology Region for Targeted Integration The 3' FarI homology region from a NRRL B-11474 derived strain was amplified by PCR using primers FarI 3P InfusF (SEQ ID NO:30) and FarI 3P InfusR AvrII (SEQ ID NO:31). The purified PCR fragment was cloned by IN-FUSION® reaction (Clontech) into pBKMS digested with NdeI and PstI to generate pBKMS FarI 3p. Similarly, the 5' FarI homology region from a NRRL B-11474-derived strain was PCR amplified with primers FarI 5p InfusF (SEQ ID NO:32) and FarI 5p InfusR (SEQ ID NO:33) and cloned into the XbaI/AvrII sites of pBKMS FarI 3p to generate pBKMS FarI.

The 5.4 kb ask-asd-ddh-dapB-orj2' cassette (4Go) was digested from pFC3-ask-asd-dapB-ddh plasmid (U.S. Pat. No. 7,368,276) with PmeI and XmaI and ligated into pDElia11 (U.S. Pat. No. 6,927,046) linearized with HincII and XmaI. The resulting vector pD11-KBDH was digested with NruI and SwaI to eliminate a ddh-dapB 2.9-kb fragment to generate pD11KD. pD11KD was then digested with SmaI and a 1.36 kb PCR fragment amplified from pD11KDBH using primers 685 (SEQ ID NO:74) and 686 (SEQ ID NO:75) was inserted using IN-FUSION® (Clontech) to generate pD11KDH. A 986-bp dapB fragment was then amplified from pD11KDBH with primers 687 (SEQ ID NO:76) and 693 (SEQ ID NO:77) and cloned into the pD11KDH SbfI site by IN-FUSION® (Clontech) reaction. The KBDH fragment was excised from the resulting pD11KBDH R plasmid by restriction with SpeI and cloned into the AvrII site of pBKMS FarI to generate pBKMSFarI4GRA.

Example 2. Allelic Replacement in *C. glutamicum*

This examples describes the methods used for allelic replacement in Example 4, below. Strains were cultured in Medium B (Table 5) or BHI broth (BD Biosciences) at 30° C. until OD 660 nm reached 0.5. Cells were harvested at 4° C. by centrifugation, washed twice in ice-cold deionized water, and resuspended in ice-cold 10% glycerol to generate electrocompetent *C. glutamicum* cells. Plasmid and cells were mixed together, transformed by electroporation, plated on BHI agar plates with 10 μg/ml kanamycin, and incubated until transformants (kanamycin resistant, sucrose sensitive) which have integrated the plasmid appeared. Transformants were further cultivated overnight at 30° C. in Medium B (Table 5) supplemented with an additional 5% sucrose (final concentration 10% sucrose) and plated on Medium B to select for strains that excised the plasmid through a second recombination event and thus were sucrose resistant and kanamycin sensitive. Clones were further screened by PCR and sequencing to verify the presence of the desired mutation.

TABLE 5

Media used in Examples 2 and 3.

| | Medium B | Medium C | Medium D | Medium E | Medium F | Medium G | units |
|---|---|---|---|---|---|---|---|
| Volume | 1000 | 1000 | 1000 | 1000 | 1000 | 1000 | ml |
| glucose | | | 30 | 75 | 35 | 50 | g |
| Sucrose | 50 | 50 | | | | | g |
| L-alanine | 0.5 | | | | | | mg |
| L-methionine | 0.5 | | | | | | mg |
| l-threonine | 0.25 | | | | | | mg |
| $KH_2PO_4$ | | | | | | 1 | g |
| $K_2HPO_4$ | 3 | 3 | | 0.75 | 1 | | g |
| Urea | 3 | 3 | | | | | g |
| $MgSO_4*7H_2O$ | 0.5 | 0.5 | | 0.3 | 0.4 | 0.4 | g |
| yeast extract | | 35 | | | | | g |
| Polypeptone peptone (BBL) | 20 | | | | | | g |
| Beef Extract (BBL) | 5 | | | | | | g |
| d-Biotin | 0.756 | 0.756 | 3.024 | 0.225 | 0.3 | 0.3 | mg |
| Thiamine*HCl | 3 | 3 | 3 | | | | mg |
| Niacinamide | 0.125 | 0.125 | 0.125 | | | | g |
| pH (KOH) | 7.3 | 7.3 | | 7.4 | 7.4 | 7.3 | |
| $MnSO_4*H_2O$ | | | 0.01 | 0.0075 | 0.01 | 0.01 | g |
| FeSO4*7$H_2O$ | | | | | 0.1 | 0.01 | g |
| $(NH_4)_2SO_4$ | | | | 37.5 | 50 | 50 | g |
| CSL Roquette | | | 20 | 15 | 20 | 20 | g |
| Raffinae[1] | | | 5 | | | | g |
| $CaCO_3$ | | | 50 | 50 | 50 | 50 | g |

Example 3. Genomic DNA Extraction

For the extraction of genomic DNA, the selected strains were grown overnight in Medium B (Table 5) at 30° C. Cultures were precipitated by centrifugation at 5000×g (4° C.) for 10 minutes. The pellets were suspended in 10 ml of a solution containing 25 mM Tris-HCl pH 8.0, 10 mM EDTA, 50 mM glucose, and 20 mg/ml lysozyme and incubated for 2 hours at 37° C. The incubation was extended for an additional 2 hours following addition of 1.3 ml 10% SDS, 67 μl 10 mg/ml RNAse A, and 167 μl of Proteinase K (20 mg/ml stock). Genomic DNA was further purified by phenol-chloroform extraction and precipitation by addition of two volumes of ice cold ethanol and 0.1 volume of 3M sodium acetate (pH 5.2). After incubation at −80° C. for 1 hour, the DNA pellet was separated by centrifugation at 14,000 rpm (4° C.) for 1 hour, washed with 70% ethanol, air dried, and dissolved in nuclease-free water.

Example 4. Assembly of Insertion Fragments into a pK18mobsacB-Derived Vector and Transformation into *C. glutamicum* Strains

Example 4A. Assembly of Plasmids for Integration and Allelic Replacement

All DNA fragments used in the generation of upstream or downstream homologous recombination regions, as well as inserts, were either amplified from purified genomic DNA extracted from strain NRRL B-11474 or from plasmids containing sequences derived from this strain as described in Example 2 using the polymerase chain reaction (PCR), or were chemically synthesized (DNA 2.0). A pZ vector derived from pK18mobsacB (Schaffer et al., Gene 145: 69-73, 1994; Accession FJ437239) containing an URA3 gene for selection in yeast was used as the vector backbone for introducing the changes into *C. glutamicum*. Homology arms and inserts were assembled into the vector backbone by homologous recombination in yeast (Ma et al., Gene (58): 201-16, 1987). Each DNA fragment contained a 50-bp overlap on each side to ensure correct assembly with its adjacent parts. For assembly, the linearized vector backbone, the two homology arms, and optionally the inserted DNA fragment were simultaneously transformed into *Saccharomyces cerevisiae* CEN.PK (Entian & Kotter, Methods in Microbiology 36: 629-66, 2007) and plated on synthetic complete agar plates without uracil (Sigma). The assembled plasmids were extracted from yeast using a ZYMOPREP™ I yeast plasmid miniprep kit (Zymo Research) and propagated in *E. coli* 10-Beta cells (New England Biolabs) with 50 μg/ml kanamycin selection before transformation into *C. glutamicum* as described in Example 2.

Example 4B. Construction of Transformation Vector to Introduce rnaJ$_{G448S}$ Allele Two homology arms were amplified using PCR from NRRL B-11474 genomic DNA obtained as described in Example 3.

The approximately 2.1 kb downstream homology arm (nucleotides 2026 to 4101 from SEQ ID NO:1) was amplified using primers SNP_084_P1 (SEQ ID NO:38) and SNP_084_P2 (SEQ ID NO:39). Primer SNP_084_P1 includes a 50-nucleotide 5' extension that overlaps with the pZ backbone described in Example 4A. Primer SNP_084_P2 contains a G to A substitution at position 25 to introduce the G448S substitution. Similarly, the approximately 2.1 kb upstream homology arm (nucleotides 1 to 2075 from SEQ ID NO:1) was amplified using primers SNP_084_P3 (SEQ ID NO:40) and SNP_084_P4 (SEQ ID NO:41). Primer SNP_084_P3 contains a C to T substitution at position 20 to introduce the G448S substitution. SNP_084_P4 includes a 50-base 5' extension that overlaps with the pZ described in Example 4A. Alignment of the two homology arms results in a 50-bp overlap defined by primers SNP_084_P2 and SNP_084_P3. The two homology arms were then assembled into pZ as described in Example 4A and transformed into *C. glutamicum* NRRL B-11474 and its derived strains as described in Example 2. Resulting strains carry the altered rnaJ coding sequence (SEQ ID NO:2), encoding the rnaJ amino acid sequence with the G448S substitution (SEQ ID NO:3).

Example 4C. Construction of Transformation Vector to Introduce accDA$_{G310E}$ Allele Two homology arms were amplified from NRRL B-11474 genomic DNA by PCR. The 2070 bp downstream homology arm (nucleotides 2032 to 4101 from SEQ ID NO:4) was amplified using primers SNP_033_P1 (SEQ ID NO:46) and SNP_033_P2 (SEQ ID NO:47). Primer SNP_033_P1 includes a 50-nucleotide 5' extension that overlaps with the pZ vector backbone described in Example 4A. Primers SNP_033_P2 contains a G to A substitution at position 20 to introduce the G310E mutation. Similarly, the approximately 2.1 kb upstream homology arm (nucleotides 1 to 2071 from SEQ ID NO:4) was amplified using primers SNP_084_P3 (SEQ ID NO:48) and SNP_084_P4 (SEQ ID NO:49). Primer SNP_033_P3 contains a C to T substitution at position 21 to introduce the G310E mutation. SNP_033_P4 includes a 50-base 5' extension that overlaps with the pZ backbone described in Example 4A. Alignment of the two homology arms results in a 40-bp overlap defined by primers SNP_033_P2 and SNP_033_P3. The two homology arms were then assembled into pZ as described in Example 4A and transformed into *C. glutamicum* NRRL B-11474 and its derived strains as described in Example 2. Resulting strains carry the altered accDA coding sequence (SEQ ID NO:5), encoding the accDA amino acid sequence with the G310E substitution (SEQ ID NO:6).

Example 4D. Construction of Transformation Vector to Introduce cg1144$_{P66S}$ Allele Two homology arms were amplified from NRRL B-11474 genomic DNA by PCR. The 2037 bp upstream homology arm (nucleotides 1 to 2037 from SEQ ID NO:7) was amplified using primers SNP_316_P1 (SEQ ID NO:50) and SNP_316_P2 (SEQ ID NO:51). Primer SNP_316_P1 includes a 50-nucleotide 5' extension that overlaps with the pZ vector backbone described in Example 4A. Primer SNP_316_P2 contains a G to A substitution at position 21 to introduce the P66S mutation. Similarly, the 2070 bp downstream homology arm (nucleotides 1998 to 4067 from SEQ ID NO:7) was amplified using primers SNP_316_P3 (SEQ ID NO:52) and SNP_316_P4 (SEQ ID NO:53). Primer SNP_316_P3 contains a C to T substitution at position 20 to introduce the P66S mutation. SNP_316_P4 includes a 50-base 5' extension that overlaps with the pZ backbone described in Example 4A. Alignment of the two homology arms results in a 40-bp overlap defined by primers SNP_316_P2 and SNP_316_P3. The two homology arms were then assembled into pZ as described in Example 4A and transformed into *C. glutamicum* NRRL B-11474 and its derived strains as described in Example 2. Resulting strains carry the altered cg1144 coding sequence (SEQ ID NO:8), encoding the cg1144 amino acid sequence with the P66S substitution (SEQ ID NO:9).

Example 4E. Construction of Transformation Vector to Replace the Native pyc Promoter by Promoter Pcg1860

Two homology arms were amplified from NRRL B-11474 genomic DNA by PCR. The 2043 bp upstream homology arm (nucleotides 1 to 2043 from SEQ ID NO:10) was amplified using primers Pcg1860_pyc_P1 (SEQ ID NO:42) and Pcg1860_pyc_P2 (SEQ ID NO:43). Similarly, the 2050 bp downstream homology arm (nucleotides 2161 to 4210 from SEQ ID NO:10) was amplified using primers Pcg1860_pyc_P3 (SEQ ID NO:44) and Pcg1860_pyc_P4 (SEQ ID NO:45). The 93-bp Pcg1860 nucleotide sequence (SEQ ID NO:11) was obtained by overlap of the 5' extensions of primers Pcg1860_pyc_P2 and Pcg1860-pyc_P3. The two homology arms were then assembled into pZ as described in Example 4A and transformed into *C. glutamicum* NRRL B-11474 and its derived strains as described in Example 2. Resulting strains carry the promoter Pcg1860 (SEQ ID NO:11) instead of the pyc promoter (SEQ ID NO:12).

Example 4F. Construction of Transformation Vector to Introduce aceE$_{atg>ttg}$ Allele Two homology arms were amplified from NRRL B-11474 genomic DNA by PCR. The 2072 bp upstream homology arm (nucleotides 1 to 2072 from SEQ ID NO:13) was amplified using primers SNP_aceE_P1 (SEQ ID NO:54) and SNP_aceE_P2 (SEQ ID NO:55). Primer SNP_aceE_P1 includes a 50-nucleotide 5' extension that overlaps with the pZ vector backbone described in Example 4A. Primer SNP_aceE_P2 contains a T to A substitution at position 22 to introduce the A mutation. Similarly, the 2073 bp downstream homology arm (nucleotides 2029 to 4101 from SEQ ID NO:13) was amplified using primers SNP_aceE_P3 (SEQ ID NO:56) and SNP_aceE_P4 (SEQ ID NO:57). Primer SNP_aceE_P3 contains an A to T substitution at position 23 to introduce the T mutation. SNP_aceE_P4 includes a 50-base 5' extension that overlaps with the pZ backbone described in Example 4. Alignment of the two homology arms results in a 44-bp overlap defined by primers SNP_aceE_P2 and SNP_aceE_P3. The two homology arms were then assembled into pZ as described in Example 4A and transformed into *C. glutamicum* NRRL B-11474 and its derived strains as described in Example 2. Resulting strains carry the TTG start codon in the aceE open reading frame (SEQ ID NO:14).

Example 4G. Insertion of a Codon-Optimized lysA Coding Sequence

A cassette containing the codon optimized lysA fragment of SEQ ID NO:16 was inserted between nucleotides 2048 and 2049 of SEQ ID NO:15 and synthetically assembled (DNA 2.0) into the pZ vector described in Example 4A. The final plasmid contains two ~2 kb homology arms (nucleotides 1 to 2048, and nucleotides 2049 to 4099 of SEQ ID NO:15) flanking a Pcg0007_39-lysA$^{CO}$-sodT (SEQ ID NO:17). The lysA$^{CO}$ containing plasmid was transformed into *C. glutamicum* NRRL B-11474 and its derived strains as described in Example 2. Resulting strains carry an additional copy of the codon-optimized lysA coding sequence under the control of promoter Pcg0007_39.

Example 4H. Insertion of a Promoter Upstream of the zwf Coding Sequence

Two homology arms were amplified from a NRRL B-11474 genomic DNA by PCR. The 2050 bp upstream homology arm (nucleotides 1 to 2050 from SEQ ID NO:19) was amplified using primers Pcg0007_39-zwf_P1 (SEQ ID NO:34) and Pcg0007_39-zwf_P2 (SEQ ID NO:35) Similarly, the 2050 bp downstream homology arm (nucleotides 2052 to 4101 from SEQ ID NO:19) was amplified using primers Pcg0007_39-zwf_P3 (SEQ ID NO:36) and Pcg0007_39-zwf_P4 (SEQ ID NO:37). The 93-bp Pcg0007_39 nucleotide sequence was obtained by overlap of the 5' extensions of primers Pcg0007_39-zwf_P2 and Pcg0007_39-pyc_P3. The two homology arms were then assembled into pZ as described in Example 4A and transformed into *C. glutamicum* NRRL B-11474 and its derived strains as described in Example 2. Resulting strains result in the replacement of nucleotide 2051 of SEQ ID NO:19 by the promoter Pcg0007_39 (SEQ ID NO:20). Resulting strains carry the promoter Pcg0007_39 upstream of the zwf ORF (SEQ ID NO:21).

Example 4I. Replacement of Native opcA Coding Sequence by the opcA Coding Sequence of *C. humireducens* NBRC 106098

Two homology arms were amplified from NRRL B-11474-derived strain BS2CZ genomic DNA (Example 3) by PCR. The 2039 bp upstream homology arm (nucleotides 1 to 2039 from SEQ ID NO:22) was amplified using primers opcA_P1 (SEQ ID NO:58) and opcA_P2 (SEQ ID NO:59). Similarly, the 2083 bp downstream homology arm (nucleotides 3000 to 5082 from SEQ ID NO:22) was amplified using primers opcA_P3 (SEQ ID NO:60) and opcA_P4 (SEQ ID NO:61). A gene cassette consisting of the 93-bp Pcg0007_39 nucleotide sequence (SEQ ID NO:20) and *C. humireducens* opcA (SEQ ID NO:23) carries sequence overlaps of the 5' extensions of primers opcA_P2 and opcA_P3. The two homology arms and the gene cassette were then assembled into pZ as described in Example 4A and transformed into *C. glutamicum* NRRL B-11474 and its derived strains as described in Example 2. Resulting strains result in the replacement of nucleotide 2040 to 2999 of SEQ ID NO:22 by the Pcg0007_39-opcA (SEQ ID NO:24).

Example 4J. Construction of Transformation Vector to Insert Promoter Pcg0007_39 in Front of the cg2766 Start Codon Two homology arms were amplified from NRRL B-11474 genomic DNA by PCR. The 2050 bp downstream homology arm (nucleotides 2051 to 4100 from SEQ ID NO:26) was amplified using primers Pcg0007_39-cg2766_P1 (SEQ ID NO:62) and Pcg0007_39-cg2766_P2 (SEQ ID NO:63). Similarly, the 2050 bp upstream homology arm (nucleotides 1 to 2050 from SEQ ID NO:26) was amplified using primers Pcg0007_39-cg2766_P3 (SEQ ID NO:64) and Pcg0007_39-cg2766_P4 (SEQ ID NO:65). The 93-bp Pcg0007_39 nucleotide sequence (SEQ ID NO:20) was obtained by overlap of the 5' extensions of primers Pcg0007_39-cg2766_P2 and Pcg0007_39-cg2766_P3. The two homology arms were then assembled into pZ as described in Example 4A and transformed into *C. glutamicum* NRRL B-11474 and its derived strains as described in Example 2. Resulting strains carry the promoter Pcg0007_39 inserted in front of cg2766 (SEQ ID NO:27).

Example 4K. Construction of Transformation Vector to Replace the actA Promoter with Promoter Pcg0007_39

Two homology arms were amplified from NRRL B-11474 genomic DNA (Example 3) by PCR.

The 2021 bp downstream homology arm (nucleotides 2263 to 4283 from SEQ ID NO:28) was amplified using primers Pcg0007_39-actA_P1 (SEQ ID NO:66) and Pcg0007_39-actA_P2 (SEQ ID NO:67). Similarly, the 2050 bp upstream homology arm (nucleotides 1 to 2050 from SEQ ID NO:28) was amplified using primers Pcg0007_39-actA_P3 (SEQ ID NO:68) and Pcg0007_39-actA_P4 (SEQ ID NO:69). The 93-bp Pcg0007_39 nucleotide sequence (SEQ ID NO:20) was obtained by overlap of the 5' extensions of primers Pcg0007_39-actA_P2 and Pcg0007_39-actA_P3. The two homology arms were then assembled into pZ as described in Example 4A and transformed into *C. glutamicum* NRRL B-11474 and its derived strains as described in Example 2. Resulting strains carry the promoter Pcg0007_39 in place of nucleotides 2051 to 2262 of SEQ ID NO:28 and inserted in front of actA (SEQ ID NO:29).

Example 4L. Construction of Transformation Vector to Insert Promoter Pcg0007_39 in Front of the cg1383 Start Codon Two homology arms were amplified from a NRRL B-11474 genomic DNA by PCR. The 2043 bp upstream homology arm (nucleotides 1 to 2043 of SEQ ID NO:98) was amplified using primers Pcg0007_39-cg1383_P1 (SEQ ID NO:99) and Pcg0007_39-cg1383_P2 (SEQ ID NO:100). Similarly, the 2050 bp downstream homology arm (nucleotides 2044 to 4093 of SEQ ID NO:98) was amplified using primers Pcg0007_39-cg1383_P3 (SEQ ID NO:101) and Pcg0007_39-cg1383_P4 (SEQ ID NO:102). The 93-bp Pcg0007_39 nucleotide sequence was obtained by overlap of the 5' extensions of primers Pcg0007_39-cg1383_P2 and Pcg0007_39-cg1383_P3. The two homology arms were then assembled into pZ as described in Example 4A and transformed into *C. glutamicum* NRRL B-11474 and its derived strains as described in Example 2. Resulting strains carry the Pcg0007_39 promoter inserted in front of cg1383 start codon (SEQ ID NO:103).

Example 4M. Construction of Transformation Vector to Replace the Native phoU Promoter with Promoter Pcg0007_39

Two homology arms were amplified from a NRRL B-11474 genomic DNA by PCR. The 1935 bp upstream homology arm (nucleotides 1 to 1935 of SEQ ID NO:104) was amplified using primers Pcg0007_39-phoU_P1 (SEQ ID NO:105) and Pcg0007_39-phoU_P2 (SEQ ID NO:106). Similarly, the 2050 bp downstream homology arm (nucleotides 1995 to 4044 of SEQ ID NO:104) was amplified using primers Pcg0007_39-phoU_P3 (SEQ ID NO:107) and Pcg0007_39-phoU_P4 (SEQ ID NO:108). The 93-bp Pcg0007_39 nucleotide sequence is obtained by overlap of the 5' extensions of primers Pcg0007_39-phoU_P2 and Pcg0007_39-phoU_P3. The two homology arms are then assembled into pZ as described in Example 4A and transformed into *C. glutamicum* NRRL B-11474 and its derived strains as described in Example 2. Resulting strains carry the Pcg0007_39 promoter in front of phoU start codon (SEQ ID NO:109) and replacing nucleotides 1936-1994 of SEQ ID NO:104.

Example 4N. Construction of Transformation Vector to Replace the Native Cg3210 Promoter with Promoter Pcg0007_39

Two homology arms were amplified from a NRRL B-11474 genomic DNA by PCR. The 1935 bp upstream homology arm (nucleotides 1 to 2030 of SEQ ID NO:110) were amplified using primers Pcg0007_39-cg3210_P1 (SEQ ID NO:111) and Pcg0007_39-cg3210_P2 (SEQ ID NO:112). Similarly, the 2047 bp downstream homology arm (nucleotides 2090 to 4136 of SEQ ID NO:110) were amplified using primers Pcg0007_39-cg3210_P3 (SEQ ID NO:113) and Pcg0007_39-3210_P4 (SEQ ID NO:114). The 93-bp Pcg0007_39 nucleotide sequence was obtained by overlap of the 5' extensions of primers Pcg0007_39-cg3210_P2 and Pcg0007_39-cg3210_P3. The two homology arms are then assembled into pZ as described in Example 4A and transformed into *C. glutamicum* NRRL B-11474 and its derived strains as described in Example 2. Resulting strains carry the Pcg0007_39 replacing nucleotides 2031 to 2089 of SEQ ID NO:110, and inserted in front of cg3210 start codon (SEQ ID NO:115).

Example 4O. Construction of Transformation Vector to Replace the Native Cg0800 Promoter with Promoter Pcg0007_39

Two homology arms were amplified from a NRRL B-11474 genomic DNA by PCR. The 2043 bp upstream homology arm (nucleotides 1 to 2043 of SEQ ID NO:116) was amplified using primers Pcg0007_39-cg0800_P3 (SEQ ID NO:117) and Pcg0007_39-cg0800_P4 (SEQ ID NO:118). Similarly, the 2050 bp downstream homology arm (nucleotides 2184 to 4233 of SEQ ID NO:116) was amplified using primers Pcg0007_39-cg0800_P1 (SEQ ID NO:119) and Pcg0007_39-0800_P2 (SEQ ID NO:120). The 93-bp Pcg0007_39 nucleotide sequence was obtained by overlap of the 5' extensions of primers Pcg0007_39-cg0800_P2 and Pcg0007_39-cg0800_P3. The two homology arms were then assembled into pZ as described in Example 4A and transformed into *C. glutamicum* NRRL B-11474 and its derived strains as described in Example 2. Resulting strains carry the Pcg0007_39 promoter inserted in front of cg0800 start codon (SEQ ID NO:121), and replacing nucleotides 2044-2183 of SEQ ID NO:116.

Example 5. Evaluation of Altered *C. glutamicum* Strains for Lysine Production in Microtiter Plates

Example 5A. Lysine Production by Altered *C. glutamicum* Strains

Each of the altered strains described in the previous examples as well as strains resulting from combining the different alterations were evaluated for lysine production by a three-stage fermentation in microtiter plates. Cells were grown in Medium C (Table 5). After 48 hours a 10% inoculum was transferred to Medium D (Table 5). Ten percent of the cell culture was transferred after 19 hours to Medium E (Table 5) and grown for an additional 24 hours or 96 hours. Culture conditions were 32° C., 1000 rpm (Infors HT).

The amount of lysine produced was determined using a coupled lysine oxidase assay. Culture supernatants were added to a lysine oxidase reaction solution (250 mM potassium phosphate buffer, pH 7.5, 824 mg/ml phenol, 76 mg/ml 4-amino antipyrene (Sigma), 0.03 mg/ml peroxidase (Sigma), 0.015 units/ml Lysine oxidase (Sigma). Samples were incubated at 25° C. for 40 min and absorbance was read at 490 nm. The amount of dextrose in the microtiter plates was determined by a couple glucose oxidase assay. Culture supernatants were added to a glucose oxidase reaction solution (275 mM sodium maleate buffer pH 5.5, 730 mg/ml phenol, 680 mg/ml 4-amino antipyrene (Sigma), 0.027 mg/ml peroxidase (Sigma), 56 mg/L glucose oxidase (Sigma). Samples were incubated at 25° C. for 40 min and absorbance was read at 490 nm.

The amount of lysine (mM) produced by each recombinant strain and its immediate parent strain is shown in the Table 6. Table 7A is a list of genomic alterations, and Table 7B identifies which alterations are present in the tested strains with respect to the native genome of the bacterium deposited as NRRL B-11474.

TABLE 6

| Parent | Modified | Change from Parent to | Lysine production (mM) - 24 hrs | | Lysine production (mM) - 96 hrs | |
|---|---|---|---|---|---|---|
| Strain ID | Strain ID | Modified Strain | Parent Strain | Modified Strain | Parent Strain | Modified Strain |
| 34507 | 88274 | 0007_39-cg0800 | 5.51 +/- 3.24 | 4.84 +/- 1.85 | 47.62 +/- 6.82 | 54.13 +/- 1.02 |
| 121645 | 139804 | 0007_39-cg0800 | 20.22 +/- 4.62 | 14.59 +/- 1.54 | 49.84 +/- 4.51 | 53.08 +/- 1.41 |
| 151834 | 174547 | 0007_39-cg0800 | 5.33 +/- 9.59 | 12.71 +/- 10.45 | 57.98 +/- 4.13 | 56.78 +/- 4.55 |
| 174205 | 182533 | 0007_39-cg0800 | 12.82 +/- 7.93 | 17.86 +/- 2.46 | 55.51 +/- 5.11 | 61.54 +/- 2.09 |
| 174275 | 182550 | 0007_39-cg0800 | 18.06 +/- 5.8 | 20.24 +/- 5.46 | 58.89 +/- 4.31 | 57.48 +/- 3.8 |
| 174275 | 182557 | 0007_39-cg0800 | 18.06 +/- 5.8 | 19.3 +/- 2.73 | 58.89 +/- 4.31 | 63.14 +/- 2.55 |

TABLE 6-continued

| Parent Strain ID | Modified Strain ID | Change from Parent to Modified Strain | Lysine production (mM) - 24 hrs Parent Strain | Lysine production (mM) - 24 hrs Modified Strain | Lysine production (mM) - 96 hrs Parent Strain | Lysine production (mM) - 96 hrs Modified Strain |
|---|---|---|---|---|---|---|
| 175088 | 182566 | 0007_39-cg0800 | 19.65 +/- 5.47 | 19.83 +/- 5.4 | 59.7 +/- 3.89 | 57.61 +/- 3.73 |
| 175093 | 182574 | 0007_39-cg0800 | 26.29 +/- 8.54 | 21.54 +/- 6.77 | 55.33 +/- 6.84 | 60.49 +/- 2.8 |
| 175109 | 182591 | 0007_39-cg0800 | 24.07 +/- 6.91 | 16.86 +/- 6.38 | 53.94 +/- 3.57 | 56.96 +/- 2.37 |
| 175109 | 182598 | 0007_39-cg0800 | 24.07 +/- 6.91 | 33.71 +/- 5.63 | 53.94 +/- 3.57 | 58.56 +/- 2.41 |
| 175784 | 182601 | 0007_39-cg0800 | 26.06 +/- 11.12 | 17.64 +/- 6.7 | 57.43 +/- 2.77 | 59.8 +/- 2.57 |
| 175784 | 182608 | 0007_39-cg0800 | 26.06 +/- 11.12 | 25.56 +/- 2.25 | 57.43 +/- 2.77 | 61.07 +/- 2.22 |
| 176538 | 182609 | 0007_39-cg0800 | 25.6 +/- 6.2 | 28.81 +/- 2.81 | 57.82 +/- 5.05 | 62.76 +/- 1.23 |
| 176538 | 182616 | 0007_39-cg0800 | 25.6 +/- 6.2 | 24.35 +/- 2.7 | 57.82 +/- 5.05 | 64.08 +/- 1.6 |
| 176509 | 182617 | 0007_39-cg0800 | 23.21 +/- 11.77 | 9.03 +/- 3.72 | 62.92 +/- 4.61 | 66.83 +/- 3.8 |
| 176509 | 182624 | 0007_39-cg0800 | 23.21 +/- 11.77 | 15.26 +/- 2.45 | 62.92 +/- 4.61 | 66.74 +/- 1.18 |
| 174547 | 183652 | 0007_39-cg0800 | 12.71 +/- 10.45 | 20.12 +/- 6.82 | 56.78 +/- 4.55 | 61.19 +/- 1.97 |
| 175155 | 183691 | 0007_39-cg0800 | 21.4 +/- 5.14 | 21.27 +/- 2.26 | 56.03 +/- 3.66 | 52.58 +/- 2.62 |
| 175174 | 183700 | 0007_39-cg0800 | 23.97 +/- 5.96 | 24.65 +/- 5.13 | 57.11 +/- 2.8 | 55.95 +/- 4.59 |
| 175776 | 183708 | 0007_39-cg0800 | 30.83 +/- 10.18 | 20.58 +/- 4.21 | 58.82 +/- 4.55 | 55.64 +/- 4.54 |
| 175785 | 183715 | 0007_39-cg0800 | 26.69 +/- 6.46 | 26.39 +/- 2.62 | 57.18 +/- 3.68 | 53.79 +/- 2.97 |
| 175785 | 183716 | 0007_39-cg0800 | 26.69 +/- 6.46 | 23.11 +/- 5.68 | 57.18 +/- 3.68 | 51.52 +/- 2.25 |
| 178745 | 187964 | 0007_39-cg0800 | 18.28 +/- 9.23 | 8.24 +/- 1.95 | 60.96 +/- 4.7 | 63.09 +/- 1.94 |
| 180398 | 187972 | 0007_39-cg0800 | 23.43 +/- 12.62 | 10.26 +/- 1.19 | 57.63 +/- 3.9 | 59.75 +/- 1.86 |
| 180402 | 187984 | 0007_39-cg0800 | 22.94 +/- 15.61 | 13.82 +/- 2.75 | 52.86 +/- 5.07 | 57.71 +/- 2.64 |
| 178726 | 188102 | 0007_39-cg0800 | 15.7 +/- 12.23 | 5.54 +/- 3.79 | 62.47 +/- 3.79 | 60.2 +/- 1.47 |
| 178726 | 188104 | 0007_39-cg0800 | 15.7 +/- 12.23 | 4.62 +/- 4.5 | 62.47 +/- 3.79 | 61.32 +/- 1.82 |
| 180390 | 188154 | 0007_39-cg0800 | 26.07 +/- 11.03 | 19.31 +/- 8.45 | 57.26 +/- 2.63 | 58.87 +/- 2.1 |
| 176538 | 188162 | 0007_39-cg0800 | 25.6 +/- 6.2 | 22.58 +/- 2.65 | 57.82 +/- 5.05 | 61.01 +/- 1.67 |
| 176538 | 188169 | 0007_39-cg0800 | 25.6 +/- 6.2 | 14.06 +/- 4.59 | 57.82 +/- 5.05 | 61.24 +/- 1.71 |
| 175229 | 188170 | 0007_39-cg0800 | 14.97 +/- 7.27 | 15.19 +/- 3.38 | 42.82 +/- 18.51 | 64.79 +/- 1.95 |
| 181567 | 188178 | 0007_39-cg0800 | 16.82 +/- 11.51 | 4.96 +/- 3.88 | 58.84 +/- 5.97 | 61.7 +/- 3.84 |
| 180384 | 188186 | 0007_39-cg0800 | 27.09 +/- 13.8 | 23.88 +/- 12.17 | 56.9 +/- 3.43 | 60.93 +/- 2.15 |
| 182562 | 190037 | 0007_39-cg0800 | 15.13 +/- 6.02 | 18.61 +/- 1.81 | 61.26 +/- 3.72 | 60.35 +/- 1.59 |
| 182563 | 190045 | 0007_39-cg0800 | 23.62 +/- 7.18 | 19.63 +/- 1.79 | 62.13 +/- 3.81 | 60.13 +/- 1.86 |
| 182612 | 190053 | 0007_39-cg0800 | 21.67 +/- 4.04 | 17.96 +/- 6.16 | 62.94 +/- 4.44 | 58.86 +/- 2.58 |
| 182620 | 190061 | 0007_39-cg0800 | 19.34 +/- 6.03 | 18.17 +/- 5.41 | 61.92 +/- 4.76 | 63.53 +/- 3.46 |
| 182623 | 190069 | 0007_39-cg0800 | 23.86 +/- 4.55 | 25.51 +/- 7.13 | 58.63 +/- 5.35 | 59.76 +/- 3.09 |
| 179967 | 191527 | 0007_39-cg0800 | 9.16 +/- 5.93 | 9.28 +/- 4.58 | 61.7 +/- 5.41 | 58.22 +/- 4.37 |
| 182566 | 192419 | 0007_39-cg0800 | 19.83 +/- 5.4 | 22.34 +/- 3.99 | 57.61 +/- 3.73 | 53.9 +/- 2.05 |
| 176538 | 193279 | 0007_39-cg0800 | 25.6 +/- 6.2 | 26.4 +/- 2.41 | 57.82 +/- 5.05 | 56.47 +/- 4.58 |
| 182612 | 193295 | 0007_39-cg0800 | 21.67 +/- 4.04 | 24.95 +/- 5.13 | 62.94 +/- 4.44 | 56.12 +/- 5.52 |
| 191541 | 197907 | 0007_39-cg0800 | 13.96 +/- 7.55 | 19.08 +/- 3.27 | 63.49 +/- 3.11 | 62.35 +/- 2.05 |
| 191520 | 206822 | 0007_39-cg0800 | 14.26 +/- 5.09 | 14.33 +/- 2.29 | 64.17 +/- 3.8 | 61.85 +/- 1.8 |
| 193318 | 213002 | 0007_39-cg0800 | 24 +/- 6.35 | 21.79 +/- 3.62 | 61.14 +/- 3.26 | 57.62 +/- 1.17 |
| 193318 | 213012 | 0007_39-cg0800 | 24 +/- 6.35 | 24.84 +/- 3.03 | 61.14 +/- 3.26 | 61.88 +/- 4.03 |
| 00000 | 219284 | 0007_39-cg0800 | 5.06 +/- 5.44 | 3.82 +/- 3.9 | 24.04 +/- 7.01 | 36.76 +/- 4.58 |
| 121645 | 219308 | 0007_39-cg0800 | 20.22 +/- 4.62 | 20.06 +/- 8.89 | 49.84 +/- 4.51 | 52.49 +/- 4.39 |
| 34507 | 87642 | 0007_39-cg1383 | 5.51 +/- 3.24 | 10.65 +/- 2.82 | 47.62 +/- 6.82 | 48.74 +/- 4.66 |
| 81651 | 121624 | 0007_39-cg 1383 | 9.15 +/- 2.55 | 9.27 +/- 2.27 | 43.53 +/- 2.69 | 47.46 +/- 2.64 |
| 99349 | 121638 | 0007_39-cg1383 | 16.22 +/- 3.6 | 17.45 +/- 1.02 | 53.98 +/- 3.54 | 52.36 +/- 1 |
| 99370 | 121643 | 0007_39-cg 1383 | 13.58 +/- 3.8 | 11.72 +/- 2.78 | 51.8 +/- 4.46 | 49.6 +/- 1.97 |
| 71075 | 132568 | 0007_39-cg 1383 | 23.93 +/- 5.69 | 27.33 +/- 3.66 | 51.37 +/- 5.54 | 56.21 +/- 2.84 |
| 112373 | 134579 | 0007_39-cg 1383 | 19.39 +/- 4.03 | 17.46 +/- 1.34 | 52.21 +/- 4.81 | 51.73 +/- 1.92 |
| 121645 | 134603 | 0007_39-cg1383 | 20.22 +/- 4.62 | 18.52 +/- 3.41 | 49.84 +/- 4.51 | 52.89 +/- 2.6 |
| 108568 | 144042 | 0007_39-cg1383 | 26.79 +/- 7.43 | 14.54 +/- 8.65 | 52.58 +/- 5.38 | 60.47 +/- 5.14 |
| 108569 | 144051 | 0007_39-cg 1383 | 13.76 +/- 8.08 | 20.82 +/- 0.97 | 58.16 +/- 6.61 | 64.88 +/- 2.74 |
| 132598 | 148418 | 0007_39-cg1383 | 25.69 +/- 4.05 | 23.55 +/- 1.52 | 50.53 +/- 3.56 | 53.64 +/- 1.32 |
| 132581 | 148431 | 0007_39-cg1383 | 10.81 +/- 3.05 | 9.17 +/- 1.73 | 48.17 +/- 9.27 | 54.36 +/- 1.53 |
| 134595 | 148999 | 0007_39-cg1383 | 10.48 +/- 3.33 | 13.14 +/- 1.15 | 50.76 +/- 2.94 | 53 +/- 0.93 |
| 132599 | 149034 | 0007_39-cg1383 | 19.33 +/- 4.23 | 23.52 +/- 1.53 | 52.51 +/- 5.41 | 49.83 +/- 0.84 |
| 134610 | 149042 | 0007_39-cg1383 | 18.73 +/- 4.67 | 19.1 +/- 3.06 | 48.27 +/- 2.83 | 48.46 +/- 1.81 |
| 102381 | 149058 | 0007_39-cg1383 | 26.82 +/- 8.13 | 33.01 +/- 3.67 | 49.78 +/- 3.59 | 49.01 +/- 1.14 |
| 148401 | 151595 | 0007_39-cg1383 | 19.21 +/- 5.8 | 9.29 +/- 7.05 | 52.95 +/- 4.06 | 54.43 +/- 2.93 |
| 148401 | 151611 | 0007_39-cg 1383 | 19.21 +/- 5.8 | −11.43 +/- 1.47 | 52.95 +/- 4.06 | 0 +/- 0 |
| 148936 | 151753 | 0007_39-cg1383 | 20.42 +/- 10.42 | 29.69 +/- 4.69 | 44.38 +/- 7.76 | 52.61 +/- 7.57 |
| 148409 | 151764 | 0007_39-cg1383 | 11.55 +/- 4.46 | 10.69 +/- 2.77 | 56.02 +/- 2.26 | 56.33 +/- 1.12 |
| 148416 | 151804 | 0007_39-cg 1383 | 19.71 +/- 5.15 | 10.16 +/- 1.63 | 52.61 +/- 2 | 51.87 +/- 1.61 |
| 148989 | 151840 | 0007_39-cg 1383 | 22.37 +/- 3.54 | 23.75 +/- 3.91 | 41.08 +/- 3.55 | 40.95 +/- 3.54 |
| 149046 | 151904 | 0007_39-cg1383 | 18.43 +/- 5.34 | 19.02 +/- 3.73 | 52.81 +/- 5.31 | 50.01 +/- 4.06 |
| 149046 | 151914 | 0007_39-cg1383 | 18.43 +/- 5.34 | 17.83 +/- 3.84 | 52.81 +/- 5.31 | 46.8 +/- 0.96 |
| 148930 | 151920 | 0007_39-cg 1383 | 23.07 +/- 3.68 | 15.93 +/- 5.26 | 50.11 +/- 3.78 | 55.57 +/- 5.07 |
| 138706 | 151965 | 0007_39-cg1383 | 26.08 +/- 4.76 | 18.24 +/- 6.28 | 50.84 +/- 4.61 | 54.03 +/- 5.93 |
| 108568 | 152452 | 0007_39-cg 1383 | 26.79 +/- 7.43 | 25.7 +/- 1.89 | 52.58 +/- 5.38 | 54.45 +/- 0.96 |
| 102381 | 152468 | 0007_39-cg 1383 | 26.82 +/- 8.13 | 29.39 +/- 4.95 | 49.78 +/- 3.59 | 49.8 +/- 3.74 |
| 132590 | 152500 | 0007_39-cg 1383 | 26.43 +/- 7.04 | 24.96 +/- 2.09 | 43.76 +/- 5.2 | 44.2 +/- 0.9 |
| 151863 | 154589 | 0007_39-cg1383 | 17.14 +/- 4.77 | 22.8 +/- 1.45 | 55.32 +/- 4.32 | 52.28 +/- 2.72 |
| 151867 | 154600 | 0007_39-cg1383 | 19.54 +/- 4.74 | 18.29 +/- 5.44 | 48.04 +/- 5.55 | 49.91 +/- 5.85 |
| 151834 | 155462 | 0007_39-cg 1383 | 5.33 +/- 9.59 | 16.23 +/- 0.93 | 57.98 +/- 4.13 | 49.11 +/- 1.17 |
| 151834 | 155466 | 0007_39-cg 1383 | 5.33 +/- 9.59 | 15.89 +/- 1.64 | 57.98 +/- 4.13 | 49.56 +/- 0.95 |
| 151834 | 155469 | 0007_39-cg1383 | 5.33 +/- 9.59 | 17.14 +/- 1.1 | 57.98 +/- 4.13 | 49.3 +/- 1.13 |
| 151906 | 162735 | 0007_39-cg 1383 | 19.77 +/- 3.91 | 20.74 +/- 1.45 | 54.38 +/- 4.77 | 49.16 +/- 0.76 |

TABLE 6-continued

| Parent Strain ID | Modified Strain ID | Change from Parent to Modified Strain | Lysine production (mM) - 24 hrs Parent Strain | Lysine production (mM) - 24 hrs Modified Strain | Lysine production (mM) - 96 hrs Parent Strain | Lysine production (mM) - 96 hrs Modified Strain |
|---|---|---|---|---|---|---|
| 152616 | 163111 | 0007_39-cg 1383 | 12.28 +/- 4.92 | 10.65 +/- 2.71 | 55.25 +/- 2.57 | 53.29 +/- 1.51 |
| 152672 | 163167 | 0007_39-cg1383 | 22.62 +/- 6.35 | 16.67 +/- 2.9 | 53.52 +/- 4.63 | 48.45 +/- 1.79 |
| 154572 | 172144 | 0007_39-cg 1383 | 21.71 +/- 6.13 | 15.03 +/- 2.39 | 39.85 +/- 4.03 | 40.41 +/- 2.88 |
| 154591 | 172152 | 0007_39-cg 1383 | 17.14 +/- 5.9 | 12.96 +/- 1.6 | 50.61 +/- 3.77 | 52.72 +/- 2.16 |
| 154599 | 172168 | 0007_39-cg1383 | 20.27 +/- 4.57 | 15.68 +/- 3.72 | 50.86 +/- 3 | 51.08 +/- 1.63 |
| 155481 | 174249 | 0007_39-cg1383 | 16.87 +/- 6.35 | 14.66 +/- 13.4 | 55.17 +/- 4.66 | 56.8 +/- 4.07 |
| 162769 | 175204 | 0007_39-cg1383 | 9.47 +/- 2.63 | 9.35 +/- 0.75 | 51.09 +/- 4.23 | 57.99 +/- 1.77 |
| 155479 | 175787 | 0007_39-cg1383 | 25.76 +/- 13.89 | 14.66 +/- 7.05 | 54.62 +/- 4.15 | 55.9 +/- 2.03 |
| 158120 | 175821 | 0007_39-cg1383 | 24.09 +/- 11.01 | 14.42 +/- 6.62 | 55.15 +/- 5.86 | 53.72 +/- 1.55 |
| 155470 | 176476 | 0007_39-cg1383 | 19.35 +/- 8.82 | 25.29 +/- 6.91 | 54.58 +/- 4.66 | 59.02 +/- 3.23 |
| 155475 | 176484 | 0007_39-cg 1383 | 8.82 +/- 10.28 | 15.14 +/- 7.35 | 57.55 +/- 4.53 | 55.73 +/- 1.1 |
| 155475 | 176485 | 0007_39-cg 1383 | 8.82 +/- 10.28 | 13.75 +/- 8.3 | 57.55 +/- 4.53 | 55.32 +/- 1.25 |
| 163159 | 176545 | 0007_39-cg 1383 | 11.22 +/- 9.89 | 8.07 +/- 6.14 | 56.13 +/- 2.65 | 57.41 +/- 1.5 |
| 163159 | 176546 | 0007_39-cg1383 | 11.22 +/- 9.89 | 7.11 +/- 4.97 | 56.13 +/- 2.65 | 57.38 +/- 1.61 |
| 174232 | 180360 | 0007_39-cg1383 | 15.11 +/- 8.67 | 0.76 +/- 6.4 | 55.05 +/- 5.29 | 57.54 +/- 3.5 |
| 174547 | 183641 | 0007_39-cg1383 | 12.71 +/- 10.45 | 27.95 +/- 4.06 | 56.78 +/- 4.55 | 58.42 +/- 1.32 |
| 182550 | 193331 | 0007_39-cg 1383 | 20.24 +/- 5.46 | 24.15 +/- 2.8 | 57.48 +/- 3.8 | 58.09 +/- 1.39 |
| 193318 | 210851 | 0007_39-cg 1383 | 24 +/- 6.35 | 20.06 +/- 2.12 | 61.14 +/- 3.26 | 62.29 +/- 3.93 |
| 71075 | 101738 | 0007_39-cg3210 | 23.93 +/- 5.69 | 18.26 +/- 0.81 | 51.37 +/- 5.54 | 55.17 +/- 2.13 |
| 121645 | 139570 | 0007_39-cg3210 | 20.22 +/- 4.62 | 21.73 +/- 2.3 | 49.84 +/- 4.51 | 47.31 +/- 1.93 |
| 151834 | 174360 | 0007_39-cg3210 | 5.33 +/- 9.59 | 15.7 +/- 5.87 | 57.98 +/- 4.13 | 59.32 +/- 5.04 |
| 212960 | 279235 | 0007_39-cg3210 | 19.01 +/- 7.66 | 8.94 +/- 4.87 | 65.29 +/- 2.97 | 66.82 +/- 2.72 |
| 242504 | 279255 | 0007_39-cg3210 | 8.19 +/- 8.46 | 18.38 +/- 6.79 | 46.34 +/- 21.04 | 68.67 +/- 2.51 |
| 224392 | 279327 | 0007_39-cg3210 | 17.04 +/- 7.51 | 15.54 +/- 9.31 | 62.15 +/- 4.39 | 63.25 +/- 2.23 |
| 212953 | 279352 | 0007_39-cg3210 | 22.18 +/- 7.38 | 16.91 +/- 9.64 | 66.66 +/- 4.4 | 66.6 +/- 1.73 |
| 176509 | 182623 | 0007_39-cg3210 | 23.21 +/- 11.77 | 23.86 +/- 4.55 | 62.92 +/- 4.61 | 58.63 +/- 5.35 |
| 148936 | 151762 | 0007_39-phoU | 20.42 +/- 10.42 | 26.53 +/- 2.19 | 44.38 +/- 7.76 | 56.79 +/- 3.2 |
| 148409 | 151773 | 0007_39-phoU | 11.55 +/- 4.46 | 10.75 +/- 1.81 | 56.02 +/- 2.26 | 59.85 +/- 1.48 |
| 148401 | 151832 | 0007_39-phoU | 19.21 +/- 5.8 | 14.31 +/- 10.23 | 52.95 +/- 4.06 | 56.79 +/- 1.82 |
| 149046 | 151913 | 0007_39-phoU | 18.43 +/- 5.34 | 18.56 +/- 4.04 | 52.81 +/- 5.31 | 48.29 +/- 3.71 |
| 148930 | 151929 | 0007_39-phoU | 23.07 +/- 3.68 | 16.8 +/- 3.51 | 50.11 +/- 3.78 | 47.53 +/- 2.28 |
| 138706 | 151969 | 0007_39-phoU | 26.08 +/- 4.76 | 23.62 +/- 3.26 | 50.84 +/- 4.61 | 48.12 +/- 1.63 |
| 149004 | 151978 | 0007_39-phoU | 14.69 +/- 3.98 | 12.23 +/- 2.18 | 50.89 +/- 2.53 | 47.9 +/- 0.94 |
| 132590 | 152448 | 0007_39-phoU | 26.43 +/- 7.04 | 25.78 +/- 5.19 | 43.76 +/- 5.2 | 34.64 +/- 11.84 |
| 108568 | 152464 | 0007_39-phoU | 26.79 +/- 7.43 | 21.13 +/- 4.3 | 52.58 +/- 5.38 | 49.87 +/- 3.36 |
| 102381 | 152480 | 0007_39-phoU | 26.82 +/- 8.13 | 21.83 +/- 3 | 49.78 +/- 3.59 | 46.3 +/- 2.46 |
| 134595 | 152496 | 0007_39-phoU | 10.48 +/- 3.33 | 8.37 +/- 6.33 | 50.76 +/- 2.94 | 53.53 +/- 2.61 |
| 151790 | 152592 | 0007_39-phoU | 6.73 +/- 3.54 | 6.04 +/- 2.46 | 38.81 +/- 6.33 | 39.33 +/- 5.41 |
| 151772 | 152616 | 0007_39-phoU | 15.86 +/- 5.08 | 12.28 +/- 4.92 | 54.33 +/- 2.55 | 55.25 +/- 2.57 |
| 151778 | 152628 | 0007_39-phoU | 17.31 +/- 1.59 | 16.09 +/- 1.57 | 47.45 +/- 2.14 | 49.53 +/- 2.67 |
| 151605 | 152636 | 0007_39-phoU | 18.94 +/- 5.76 | 19.7 +/- 4.58 | 54.45 +/- 3 | 55.89 +/- 2.5 |
| 151834 | 152648 | 0007_39-phoU | 5.33 +/- 9.59 | 23 +/- 3.03 | 57.98 +/- 4.13 | 52.13 +/- 1.52 |
| 151739 | 152672 | 0007_39-phoU | 26.26 +/- 4.46 | 22.62 +/- 6.35 | 45.11 +/- 2.72 | 53.52 +/- 4.63 |
| 151920 | 155490 | 0007_39-phoU | 15.93 +/- 5.26 | 17.69 +/- 4.34 | 55.57 +/- 5.07 | 48.22 +/- 2.57 |
| 151920 | 155510 | 0007_39-phoU | 15.93 +/- 5.26 | 17.55 +/- 2.09 | 55.57 +/- 5.07 | 47.51 +/- 2.64 |
| 151904 | 155525 | 0007_39-phoU | 19.02 +/- 3.73 | 18.57 +/- 1.27 | 50.01 +/- 4.06 | 50.17 +/- 2.74 |
| 151965 | 155545 | 0007_39-phoU | 18.24 +/- 6.28 | 21.53 +/- 5.21 | 54.03 +/- 5.93 | 54.69 +/- 3.12 |
| 151863 | 162721 | 0007_39-phoU | 17.14 +/- 4.77 | 22.19 +/- 3.3 | 55.32 +/- 4.32 | 0 +/- 0 |
| 151906 | 162743 | 0007_39-phoU | 19.77 +/- 3.91 | 21.93 +/- 1.14 | 54.38 +/- 4.77 | 49.46 +/- 1.14 |
| 152645 | 162789 | 0007_39-phoU | 25.2 +/- 7.97 | 16.31 +/- 1.1 | 51.26 +/- 2.62 | 46.29 +/- 2.06 |
| 152645 | 163154 | 0007_39-phoU | 25.2 +/- 7.97 | 0 +/- 0 | 51.26 +/- 2.62 | 48.62 +/- 1.16 |
| 154572 | 172143 | 0007_39-phoU | 21.71 +/- 6.13 | 17.81 +/- 2.22 | 39.85 +/- 4.03 | 42.4 +/- 2.67 |
| 154591 | 172151 | 0007_39-phoU | 17.14 +/- 5.9 | 14.07 +/- 1.89 | 50.61 +/- 3.77 | 50.45 +/- 2.24 |
| 154650 | 172199 | 0007_39-phoU | 26.32 +/- 3.56 | 0 +/- 0 | 50.5 +/- 2.27 | 50.32 +/- 1.7 |
| 154660 | 172228 | 0007_39-phoU | 22.3 +/- 7.62 | 23.55 +/- 1.24 | 60.29 +/- 4.52 | 53.48 +/- 3.04 |
| 155464 | 174199 | 0007_39-phoU | 16.27 +/- 5.92 | 0 +/- 0 | 50.22 +/- 2.48 | 52.48 +/- 1.7 |
| 155475 | 174232 | 0007_39-phoU | 8.82 +/- 10.28 | 15.11 +/- 8.67 | 57.55 +/- 4.53 | 55.05 +/- 5.29 |
| 155479 | 174240 | 0007_39-phoU | 25.76 +/- 13.89 | 0 +/- 0 | 54.62 +/- 4.15 | 53.38 +/- 2.96 |
| 155481 | 174248 | 0007_39-phoU | 16.87 +/- 6.35 | 0 +/- 0 | 55.17 +/- 4.66 | 53.97 +/- 1.38 |
| 155554 | 174264 | 0007_39-phoU | 23.09 +/- 7.12 | 17.48 +/- 3.64 | 54.58 +/- 4.71 | 52.23 +/- 1.66 |
| 159431 | 174281 | 0007_39-phoU | 22.48 +/- 6.07 | 19.72 +/- 1.98 | 51.6 +/- 3.61 | 47.51 +/- 2.1 |
| 155470 | 175029 | 0007_39-phoU | 19.35 +/- 8.82 | 12.01 +/- 6.57 | 54.58 +/- 4.66 | 50.94 +/- 3.23 |
| 155475 | 175046 | 0007_39-phoU | 8.82 +/- 10.28 | 0 +/-0 | 57.55 +/- 4.53 | 51.7 +/- 2.26 |
| 155479 | 175062 | 0007_39-phoU | 25.76 +/- 13.89 | 0 +/-0 | 54.62 +/- 4.15 | 53.76 +/- 1.99 |
| 155554 | 175086 | 0007_39-phoU | 23.09 +/- 7.12 | 15.63 +/- 2.23 | 54.58 +/- 4.71 | 52.66 +/- 1.56 |
| 159431 | 175102 | 0007_39-phoU | 22.48 +/- 6.07 | 17.03 +/- 2.67 | 51.6 +/- 3.61 | 50.82 +/- 1.13 |
| 161403 | 175165 | 0007_39-phoU | 19.67 +/- 3.35 | 21.39 +/- 3.92 | 52.14 +/- 2.96 | 57.3 +/- 2.23 |
| 162718 | 175181 | 0007_39-phoU | 20.15 +/- 3.26 | 17.88 +/- 0.5 | 55.8 +/- 3.85 | 58.37 +/- 1.64 |
| 162753 | 175183 | 0007_39-phoU | 14.14 +/- 3.34 | 16.72 +/- 3.58 | 52.11 +/- 5.03 | 58.46 +/- 1.78 |
| 162753 | 175184 | 0007_39-phoU | 14.14 +/- 3.34 | 17.1 +/- 3.23 | 52.11 +/- 5.03 | 55.09 +/- 1.33 |
| 162769 | 175200 | 0007_39-phoU | 9.47 +/- 2.63 | 12.16 +/- 1.03 | 51.09 +/- 4.23 | 57.07 +/- 1.7 |
| 158120 | 175816 | 0007_39-phoU | 24.09 +/- 11.01 | 13.14 +/- 7.43 | 55.15 +/- 5.86 | 52.89 +/- 1.62 |
| 155554 | 176509 | 0007_39-phoU | 23.09 +/- 7.12 | 23.21 +/- 11.77 | 54.58 +/- 4.71 | 62.92 +/- 4.61 |
| 163159 | 176542 | 0007_39-phoU | 11.22 +/- 9.89 | 10.93 +/- 9.9 | 56.13 +/- 2.65 | 59.53 +/- 1.93 |
| 174275 | 183629 | 0007_39-phoU | 18.06 +/- 5.8 | 18.36 +/- 1.97 | 58.89 +/- 4.31 | 59.27 +/- 5.68 |
| 174547 | 186920 | 0007_39-phoU | 12.71 +/- 10.45 | 18.02 +/- 6.25 | 56.78 +/- 4.55 | 54.57 +/- 2.8 |

TABLE 6-continued

| Parent Strain ID | Modified Strain ID | Change from Parent to Modified Strain | Lysine production (mM) - 24 hrs Parent Strain | Lysine production (mM) - 24 hrs Modified Strain | Lysine production (mM) - 96 hrs Parent Strain | Lysine production (mM) - 96 hrs Modified Strain |
|---|---|---|---|---|---|---|
| 182566 | 187910 | 0007_39-phoU | 19.83 +/- 5.4 | 10.81 +/- 2.17 | 57.61 +/- 3.73 | 64.1 +/- 2.74 |
| 182574 | 187918 | 0007_39-phoU | 21.54 +/- 6.77 | 15.3 +/- 3.93 | 60.49 +/- 2.8 | 60.85 +/- 2.78 |
| 182591 | 187926 | 0007_39-phoU | 16.86 +/- 6.38 | 14.86 +/- 4.26 | 56.96 +/- 2.37 | 58.1 +/- 2.44 |
| 182601 | 187934 | 0007_39-phoU | 17.64 +/- 6.7 | 6.77 +/- 4.44 | 59.8 +/- 2.57 | 61.9 +/- 1.68 |
| 182617 | 187942 | 0007_39-phoU | 9.03 +/- 3.72 | 7.02 +/- 1.84 | 66.83 +/- 3.8 | 65.52 +/- 2.46 |
| 182550 | 187990 | 0007_39-phoU | 20.24 +/- 5.46 | 10.05 +/- 1.68 | 57.48 +/- 3.8 | 65.34 +/- 1.65 |
| 175776 | 188149 | 0007_39-phoU | 30.83 +/- 10.18 | 20.56 +/- 2.06 | 58.82 +/- 4.55 | 65.39 +/- 1.41 |
| 180390 | 188159 | 0007_39-phoU | 26.07 +/- 11.03 | 19.93 +/- 2.96 | 57.26 +/- 2.63 | 57.94 +/- 1.42 |
| 183661 | 190101 | 0007_39-phoU | 25 +/- 6.72 | 17.15 +/- 5.25 | 55.74 +/- 3.95 | 58.42 +/- 3.41 |
| 175776 | 193273 | 0007_39-phoU | 30.83 +/- 10.18 | 19.93 +/- 3.32 | 58.82 +/- 4.55 | 61.28 +/- 4.94 |
| 182566 | 193289 | 0007_39-phoU | 19.83 +/- 5.4 | 25.28 +/- 3.47 | 57.61 +/- 3.73 | 56.86 +/- 3.79 |
| 182566 | 193293 | 0007_39-phoU | 19.83 +/- 5.4 | 22.06 +/- 3.24 | 57.61 +/- 3.73 | 59.08 +/- 4.96 |
| 183175 | 196697 | 0007_39-phoU | 25.54 +/- 6.32 | 25.38 +/- 2.97 | 59.81 +/- 3.17 | 58.08 +/- 1.95 |
| 187911 | 197877 | 0007_39-phoU | 23.32 +/- 7.65 | 23.58 +/- 2.87 | 59.21 +/- 2.88 | 60.42 +/- 1.91 |
| 187929 | 197885 | 0007_39-phoU | 6.36 +/- 5.48 | 4.56 +/- 4.95 | 60.03 +/- 3.8 | 63.01 +/- 3.09 |
| 191496 | 197954 | 0007_39-phoU | 23.88 +/- 6.7 | 24.32 +/- 2.9 | 56.21 +/- 3.28 | 55.7 +/- 2.66 |
| 188141 | 201612 | 0007_39-phoU | 20.98 +/- 6.13 | 27.79 +/- 8.07 | 57.51 +/- 4.3 | 56.12 +/- 1.65 |
| 191500 | 201628 | 0007_39-phoU | 27.42 +/- 5.91 | 19.4 +/- 4.61 | 52.16 +/- 3.99 | 51.01 +/- 2.82 |
| 191504 | 201644 | 0007_39-phoU | 17.11 +/- 5.12 | 7.49 +/- 1.61 | 58.22 +/- 4.58 | 61.16 +/- 2.28 |
| 191520 | 201660 | 0007_39-phoU | 14.26 +/- 5.09 | 14.07 +/- 4.87 | 64.17 +/- 3.8 | 62.95 +/- 2.53 |
| 190123 | 201676 | 0007_39-phoU | 13.81 +/- 3.49 | 9.42 +/- 7.47 | 63.37 +/- 3 | 62.34 +/- 1.92 |
| 191520 | 206820 | 0007_39-phoU | 14.26 +/- 5.09 | 13.92 +/- 1.51 | 64.17 +/- 3.8 | 62.34 +/- 3.9 |
| 191500 | 206860 | 0007_39-phoU | 27.42 +/- 5.91 | 28.84 +/- 2.6 | 52.16 +/- 3.99 | 53.4 +/- 1.89 |
| 199384 | 212930 | 0007_39-phoU | 15.95 +/- 5.44 | 12.93 +/- 0.97 | 64.3 +/- 3.56 | 63.47 +/- 1.84 |
| 190061 | 212954 | 0007_39-phoU | 18.17 +/- 5.41 | 17.23 +/- 2.08 | 63.53 +/- 3.46 | 61.59 +/- 2.24 |

TABLE 7A

| Abbreviation | Description |
|---|---|
| 4GoB | insertion of lysine biosynthesis genes ask, asd, dapB, and ddh in the bioD region (Example 1) |
| 4GR | insertion of lysine biosynthesis genes ask, asd, dapB, and ddh in a FarI homology region (Example 1) |
| 0007_39-zwf | insertion of promoter Pcg0007_39 in front of the zwf open reading frame |
| DSS_084 | replacement of native maJ coding sequence with maJG448S allele |
| 1860-pyc | replacement of native pyc promoter with promoter Pcg1860 |
| DSS_033 | replacement of native accDA coding sequence with accDAG310E allele |
| DSS_316 | replacement of native cg1144 coding sequence with cg1144P66S allele |
| aceE_ATG > TTG | replacement of aceE start codon with TTG |
| lisa68 | insertion of codon-optimized lysA coding sequence under the control of promoter Pcg0007_39 and including sod terminator (SEQ ID NO: 17) |
| 0007_39_opca_P4 | replacement of native opcA coding sequence with opcA coding sequence for *C. humireducens* under the control of promoter Pcg0007_39 |
| 0007_39-actA | replacement of native actA promoter with promoter Pcg0007_39 |
| 0007_39-cg1383 | insertion of promoter Pcg0007_39 in front of cg1383 start codon |
| 0007_39-cg2766 | insertion of promoter Pcg0007_39 in front of cg2766 start codon |
| 0007_39-phoU | replacement of native phoU promoter with promoter Pcg0007_39 |
| 0007_39-cg3210 | replacement of native cg3210 promoter with promoter Pcg0007_39 |
| 0007_39-cg0800 | replacement of native cg0800 promoter with promoter Pcg0007_39 |
| Vhb04 | nitric oxide dioxygenase [*Fischerella thermalis*] WP_009454354.1 under the control of Pcg0007_39 |
| fumC_atg > gtg | replacement of fumC start codon with GTG |
| 0007_39-lysA | insertion of codon-optimized lysA sequence under the control of promoter Pcg0007_39 and having a sod terminator |
| 0007_39-CAA | insertion of codon-optimized glcp sequence (accession CAA34119.1) under the control of promoter Pcg0007_39 and codon optimized ppgK sequence (accession cg2091) under the control of Pcg1860 |
| 1860-xerD | replacement of native xerD promoter with promoter Pcg1860 |
| 0007_39-lpd | replacement of native lpd promoter with promoter Pcg0007_39 |
| 1860-aceF | replacement of native aceF promoter by promoter Pcg1860 |
| 0007_39-cg0725 | replacement of native cg0725 promoter with promoter Pcg0007_39 |
| DSS_121 | replacement of native cg3092 coding sequence with cg3092D213N allele |
| DSS_422 | replacement of native cg3180 coding sequence with cg3180W297* allele |
| 0007_39-SCO | insertion of codon-optimized SCO5578 sequence (accession NP_629713.1) under the control of promoter Pcg0007_39 and codon optimized ppgK sequence (accession cg2091) under the control of Pcg1860 |
| 1860-cg1768 | replacement of native cg1768 promoter by promoter Pcg1860 |
| 0007_39-rpoB | replacement of native rpoB promoter with promoter Pcg0007_39 |
| 0007_39-rpoB gene-383 | same as 0007_39-rpoB |

TABLE 7A-continued

| Abbreviation | Description |
| --- | --- |
| 0007__39BL1631 | insertion of codon-optimized BL1631 sequence (accession NP__696783.1) under the control of promoter Pcg0007__39 and codon optimized ppgK sequence (accession cg2091) under the control of Pcg1860 |
| 0007__39-glf | replacement of native glf promoter with promoter Pcg0007__39 |
| glk | insertion of codon-optimized glf sequence (accession AAA27691.1) under the control of promoter Pcg0007__39 and codon optimized glk sequence (accession AHJ72364.1) under the control of Pcg1860 (at Ni487) |
| glk__2966 | same construct as above integrated at different insertion site (Ni2966) |
| 0007__39-NCgl1262 | replacement of native NCgl1262 promoter with promoter Pcg0007__39 |
| Pcg0007-amtB | replacement of native amtB promoter with Pcg0007 |
| Pcg0007__39-cg800 | replacement of native cg0800 promoter with Pcg0007__39 |
| 3121-mutM2 | replacement of native mutM promoter with promoter Pcg3121 |
| 1860-cg1144 | replacement of native cg1144 promoter with promoter Pcg1860 |
| 3121-gltD | replacement of native gltD promoter with promoter Pcg3121 |
| SCO__Ni2966 | same construct as 0007__39-SCO, integrated at Ni2966 |
| 1860-tkt | replacement of native tkt promoter with promoter Pcg1860 |
| 3381-cg1410 | replacement of native cg1410 promoter by promoter Pcg3381 (WO 2017/100376) |
| Pcg3121-prpB2 | replacement of the native promoter of cg0760 with Pcg0760 |
| 0007__39-nusG | replacement of native nusG promoter with promoter Pcg0007__39 |
| 0007__39-aroP | replacement of native aroP promoter with promoter Pcg0007__39 |
| 0007__39-rho | replacement of native rho promoter with promoter Pcg0007__39 |
| 0007__39-cg1503 | replacement of native cg1503 promoter with promoter Pcg0007__39 |
| 0007-39__ureR | replacement of native ureR promoter with promoter Pcg0007__39 |
| 0007__39-kgd | replacement of native kgd promoter with promoter Pcg0007__39 |
| 0007__39-cg2466 | replacement of native cg2466 promoter with promoter Pcg0007__39 |
| 0007__39-cg2899 | replacement of native cg2899 promoter with promoter Pcg0007__39 |
| 3121-cg1081 | replacement of native cg1081 promoter with promoter Pcg3121 |
| 0007__39-cg1486 | replacement of native cg1486 promoter with promoter Pcg0007__39 |
| 0007__39-Ncgl0304 | replacement of native Ncg10304 promoter with promoter Pcg0007__39 |
| 0007__39-Ncgl0304 | replacement of native Ncgl0304 promoter with promoter Pcg0007__39 |
| 0007__39-ncgl1511 | replacement of native Ncgl1511 promoter with promoter Pcg0007__39 |
| 0007__39-Ncgl0767 | replacement of native Ncgl0767 promoter with promoter Pcg0007__39 |
| 0755-dapA | replacement of native dapA promoter with promoter Pcg0755 |
| 0007__39-glpX | replacement of native glpX promoter with promoter Pcg0007__39 |

TABLE 7B

| Genotypes of Modified Strains | |
| --- | --- |
| Modified Strain | Changes with respect to genome of NRRL B-11474 |
| 88274 | 0007__39-zwf; DSS__084; 1860-pyc; DSS__033; fumC__atg > gtg; 0007__39-opca__P4; 0007__39-cg0800 |
| 139804 | 0007__39-zwf; DSS__084; 1860-pyc; DSS__033; DSS__316; 0007__39-lysA; 0007__39-opcA__P4; 0007__39-cg0800 |
| 174547 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg0800 |
| 182533 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg0725; 0007-__39-rho; 0007__39-cg0800 |
| 182550 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800 |
| 182557 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800 |
| 182566 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-rpoB; 0007__39-cg0800 |
| 182574 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-kgd; 0007__39-cg0800 |
| 182591 | 0007__39-zwf; DSS__084; 1860-pyc; DSS__033; DSS__316; aceE__ATG > TTG; lisa68; opcA__P4; 0007__39-actA; 0007__39-cg1383; Pcg0007-amtB; 0007__39-kgd; 0007__39-cg0800 |
| 182598 | 0007__39-zwf; DSS__084; 1860-pyc; DSS__033; DSS__316; aceE__ATG > TTG; lisa68; opcA__P4; 0007__39-actA; 0007__39-cg1383; Pcg0007-amtB; 0007__39-kgd; 0007__39-cg0800 |
| 182601 | 0007__39-zwf; DSS__084; 1860-pyc; DSS__033; DSS__316; aceE__ATG > TTG; lisa68; opcA__P4; 0007__39-cg2766; 0007__39-actA; glk__2966; 3121-cg1081; 0007__39-cg0800 |
| 182608 | 0007__39-zwf; DSS__084; 1860-pyc; DSS__033; DSS__316; aceE__ATG > TTG; lisa68; opcA__P4; 0007__39-cg2766; 0007__39-actA; glk__2966; 3121-cg1081; 0007__39-cg0800 |
| 182609 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-rpoB; 0007__39-kgd; 0007__39-cg0800 |
| 182616 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-rpoB; 0007__39-kgd; 0007__39-cg0800 |
| 182617 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU;0007__39-cg0800 |

TABLE 7B-continued

Genotypes of Modified Strains

| Modified Strain | Changes with respect to genome of NRRL B-11474 |
|---|---|
| 182624 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-cg0800 |
| 183652 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg800; Pcg0007__39-cg800 |
| 183691 | 0007__39-zwf; DSS__084; 1860-pyc; DSS__033; DSS__316; aceE__ATG > TTG; lisa68; opcA__P4; 0007__39-actA; 0007__39-cg1383; 0007__39-phoU; 0007__39-kgd; 0007__39-cg0800 |
| 183700 | 0007__39-zwf; DSS__084; 1860-pyc; DSS__033; DSS__316; 0007__39-lysA; 0007__39-lpd; opcA__P4; 1860-cg1768; glk; 0007__39-cg0725; 0007__39-cg2766; 0007__39-kgd; 0007__39-cg0800 |
| 183708 | 0007__39-zwf; DSS__084; 1860-pyc; DSS__033; DSS__316; 0007__39-lysA; 0007__39-lpd; opcA__P4; 0007__39-glf; 0007__39-cg1383; 0007__39-aroP; 0007__39-kgd; 0007__39-cg0800 |
| 183715 | 0007__39-zwf; DSS__084; 1860-pyc; DSS__033; DSS__316; aceE__ATG > TTG; lisa68; opcA__P4; 0007__39-cg2766; 0007__39-actA; glk__2966; 0007__39-cg2466; 0007__39-cg0800 |
| 183716 | 0007__39-zwf; DSS__084; 1860-pyc; DSS__033; DSS__316; aceE__ATG > TTG; lisa68; opcA__P4; 0007__39-cg2766; 0007__39-actA; glk__2966; 0007__39-cg2466; 0007__39-cg0800 |
| 187964 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-nusG; 0007__39-cg0800 |
| 187972 | 0007__39-zwf; DSS__084; 1860-pyc; DSS__033; DSS__316; aceE__ATG > TTG; lisa68; opcA__P4; 0007__39-actA; 0007__39-cg1383; Pcg0007-amtB; 0007__39-kgd; 0007__39-cg1503; 0007__39-cg0800 |
| 187984 | 0007__39-zwf; DSS__084; 1860-pyc; DSS__033; DSS__316; aceE__ATG > TTG; lisa68; opcA__P4; 0007__39-actA; 0007__39-cg1383; Pcg0007-amtB; 0007__39-kgd; 1860-xerD; 0007__39-cg0800 |
| 188102 | 0007__39-zwf; DSS__084; 1860-pyc; DSS__033; DSS__316; aceE__ATG > TTG; lisa68; opcA__P4; 0007__39-cg2766; 0007__39-actA; 3121-mutM2; 0007__39-aroP; 0007__39-ureR; 0007__39-cg0800 |
| 188104 | 0007__39-zwf; DSS__084; 1860-pyc; DSS__033; DSS__316; aceE__ATG > TTG; lisa68; opcA__P4; 0007__39-cg2766; 0007__39-actA; 3121-mutM2; 0007__39-aroP; 0007__39-ureR; 0007__39-cg0800 |
| 188154 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-kgd; 0007__39-cg0800 |
| 188162 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-rpoB; 0007__39-kgd; 0007__39-cg0800 |
| 188169 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-rpoB; 0007__39-kgd; 0007__39-cg0800 |
| 188170 | 0007__39-zwf; DSS__084; 1860-pyc; DSS__033; DSS__316; 0007__39-lysA; opcA__P4; lisa__68; 0007__39-rpoB; 0007__39-cg2766; 0007__39-aroP; 0007__39-cg0800 |
| 188178 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg2899; 0007__39-cg0800 |
| 188186 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-cg2899; 0007__39-kgd; 0007__39-cg0800 |
| 190037 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-rpoB; 0007__39-cg2899; 0007__39-cg0800 |
| 190045 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-rpoB; 0007__39-ureR; 0007__39-cg0800 |
| 190053 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-rpoB; 0007__39-kgd; 0007__39-cg1486; 0007__39-cg0800 |
| 190061 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU; 0007__39-cg1486; 0007__39-cg0800 |
| 190069 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU; 0007__39-cg3210; 0007__39-cg0800 |
| 191527 | 0007__39-zwf; DSS__084; 1860-pyc; DSS__033; DSS__316; aceE__ATG > TTG; lisa68; opcA__P4; 0007__39-cg2766; 0007__39-actA; glk__2960007__39-NCgl1262; 0007__39-cg0800 |
| 192419 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg1383; 0007__39-rpob; 0007__39-cg0800 |
| 193279 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-rpoB; 0007__39-kgd; 0007__39-cg0800 |
| 193295 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-rpoB; 0007__39-kgd; 0007__39-cg1486; 0007__39-cg0800 |
| 197907 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU; 0007__39-cg1486; 0007__39-Ncgl0304; 0007__39-cg0800 |

TABLE 7B-continued

| Genotypes of Modified Strains | |
|---|---|
| Modified Strain | Changes with respect to genome of NRRL B-11474 |
| 206822 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800; 0007__39-NCgl1262; 0007__39-cg0800 |
| 213002 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-rpoB; 0007__39-kgd; 0007__39-cg1486; 1860-xerD; 0007__39-cg0800 |
| 213012 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-rpoB; 0007__39-kgd; 0007__39-cg1486; 1860-xerD; 0007__39-cg0800 |
| 219284 | 0007__39-cg0800 |
| 219308 | 0007__39-zwf; DSS__084; 1860-pyc; DSS__033; DSS__316; 0007__39-lysA; opcA__P4; 0007__39-cg0800 |
| 87642 | 0007__39-zwf; DSS__084; 1860-pyc; DSS__033; fumC__atg > gtg; 0007__39-opca__P4; 0007__39-cg1383 |
| 121624 | 0007__39-zwf; DSS__084; 1860-pyc; DSS__033; fumC__ATG > TTG; opcA__P__4; Vhb04; 0007__39-cg1383 |
| 121638 | 0007__39-zwf; DSS__084; 1860-pyc; DSS__033; DSS__316; 0007__39-lysA; 0007__39-lpd; 0007__39-cg1383 |
| 121643 | 0007__39-zwf; DSS__084; 1860-pyc; DSS__033; fumC__ATG > GTG; opcA__P__4; 1860-aceF; 0007__39-lysA; 0007-39__BL1631; 0007__39-cg1383 |
| 132568 | 0007__39-zwf; DSS__084; 1860-pyc; DSS__033; DSS__316; 0007__39-lysA; 0007__39-cg1383 |
| 134579 | 0007__39-zwf; DSS__084; 1860-pyc; DSS__033; DSS__316; aceE__ATG > TTG; lisa68; opcA__P4; 0007__39-cg1383 |
| 134603 | 0007__39-zwf; DSS__084; 1860-pyc; DSS__033; DSS__316; 0007__39-lysA; opcA__P4; 0007__39-cg1383 |
| 144042 | 0007__39-zwf; DSS__084; 1860-pyc; DSS__033; DSS__316; aceE__ATG > TTG; lisa__68; DSS__121; 0007__39-cg1383 |
| 144051 | 0007__39-zwf; DSS__084; 1860-pyc; DSS__033; DSS__316; aceE__ATG > TTG; lisa__68; DSS__422; 0007__39-cg1383 |
| 148418 | 0007__39-zwf; DSS__084; 1860-pyc; DSS__033; fumC__ATG > GTG; opcA__P4; 1860-aceF; 0007__39-CAA; 0007__39-lysA; 0007__39-cg1383 |
| 148431 | 0007__39-zwf; DSS__084; 1860-pyc; DSS__033; fumC__ATG > GTG; opcA__P4; 1860-aceF; 0007__39-lysA; 0007__39-SCO; 0007__39-cg1383 |
| 148999 | 0007__39-zwf; DSS__084; 1860-pyc; DSS__033; DSS__316; 0007__39-lysA; 0007__39-lpd; opcA__P4; 0007__39-rpoB; 0007__39-cg1383 |
| 149034 | 0007__39-zwf; DSS__084; 1860-pyc; DSS__033; DSS__316; 0007__39-lysA; 0007__39-lpd; 0007__39-CAA; 0007__39-cg1383 |
| 149042 | 0007__39-zwf; DSS__084; 1860-pyc; DSS__033; DSS__316; 0007__39-lysA; opcA__P4; lisa__68; 0007__39-cg1383 |
| 149058 | 0007__39-zwf; DSS__084; 1860-pyc; DSS__033; DSS__316; 0007__39-lysA; 1860-xerD; 0007__39-cg1383 |
| 151595 | 0007__39-zwf; DSS__084; 1860-pyc; DSS__033; DSS__316; aceE__ATG > TTG; lisa68; opcA__P4; 0007__39-cg2766; 0007__39-cg1383 |
| 151611 | 0007__39-zwf; DSS__084; 1860-pyc; DSS__033; DSS__316; aceE__ATG > TTG; lisa68; opcA__P4; 0007__39-cg2766; 0007__39-cg1383 |
| 151753 | 0007__39-zwf; DSS__084; 1860-pyc; DSS__033; DSS__316; 0007__39-lysA; 0007__39-lpd; opcA__P4; 0007__39-glf; 0007__39-cg1383 |
| 151764 | 0007__39-zwf; DSS__084; 1860-pyc; DSS__033; DSS__316; 0007__39-lysA; 0007__39-lpd; opcA__P4; 0007__39-cg2766; 0007__39-cg1383 |
| 151804 | 0007__39-zwf; DSS__084; 1860-pyc; DSS__033; DSS__316; 0007__39-lysA; opcA__P4; 0007__39-cg2766; 0007__39-cg1383 |
| 151840 | 0007__39-zwf; DSS__084; 1860-pyc; DSS__033; DSS__316; aceE__ATG > TTG; 0007__39-lysA; 0007__39-SCO; opcA__P__4; 0007__39-cg1383 |
| 151904 | 0007__39-zwf; DSS__084; 1860-pyc; DSS__033; DSS__316; 0007__39-lysA; opcA__P4; lisa__68; 0007__39-rpoB-gene-383; 0007__39-cg1383 |
| 151914 | 0007__39-zwf; DSS__084; 1860-pyc; DSS__033; DSS__316; 0007__39-lysA; opcA__P4; lisa__68; 0007__39-rpoB-gene-383; 0007__39-cg1383 |
| 151920 | 0007__39-zwf; DSS__084; 1860-pyc; DSS__033; DSS__316; 0007__39-lysA; 0007__39-cg2766; opcA__P4; 0007__39-cg1383 |
| 151965 | 0007__39-zwf; DSS__084; 1860-pyc; DSS__033; DSS__316; aceE__ATG > TTG; lisa68; opcA__P4; 0007__39-actA; 0007__39-cg1383 |
| 152452 | 0007__39-zwf; DSS__084; 1860-pyc; DSS__033; DSS__316; aceE__ATG > TTG; lisa68; DSS__121; 0007__39-cg1383 |
| 152468 | 0007__39-zwf; DSS__084; 1860-pyc; DSS__033; DSS__316; 0007__39-lysA; 1860-xerD; 0007__39-cg1383 |
| 152500 | 0007__39-zwf; DSS__084; 1860-pyc; DSS__033; DSS__316; aceE__ATG > TTG; 0007__39-lysA; 0007__39-SCO; 0007__39-cg1383 |
| 154589 | 0007__39-zwf; DSS__084; 1860-pyc; DSS__033; DSS__316; 0007__39-lysA; 0007__39-lpd; opcA__P4; 1860-cg1768; glk; 0007__39-cg0725; 0007__39-cg1383 |
| 154600 | 0007__39-zwf; DSS__084; 1860-pyc; DSS__033; DSS__316; 0007__39-lysA; 0007__39-lpd; opcA__P4; 1860-cg1768; glk; 1860-cg1144; 0007__39-cg1383 |
| 155462 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg1383 |
| 155466 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg1383 |

TABLE 7B-continued

| Genotypes of Modified Strains | |
|---|---|
| Modified Strain | Changes with respect to genome of NRRL B-11474 |
| 155469 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg1383 |
| 162735 | 0007__39-zwf; DSS__084; 1860-pyc; DSS__033; DSS__316; 0007__39-lysA; opcA__P4; lisa__68; 0007__39-rpoB-gene-383; 0007__39-cg2766; 0007__39-cg1383 |
| 163111 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-cg1383 |
| 163167 | 0007__39-zwf; DSS__084; 1860-pyc; DSS__033; DSS__316; aceE__ATG > TTG; 0007__39-lysA; 0007__39-SCO; 0007__39-cg2766; opcA__P4; 0007__39-phoU; 0007__39-cg1383 |
| 172144 | 0007__39-zwf; DSS__084; 1860-pyc; DSS__033; DSS__316; aceE__ATG > TTG; 0007__39-lysA; 0007__39-SCO; opcA__P__4; 0007__39-cg0725; 0007__39-aroP; 0007__39-cg1383 |
| 172152 | 0007__39-zwf; DSS__084; 1860-pyc; DSS__033; DSS__316; 0007__39-lysA; 0007__39-lpd; opcA__P4; 1860-cg1768; glk; 0007__39-cg0725; 0007__39-cg2899; 0007__39-cg1383 |
| 172168 | 0007__39-zwf; DSS__084; 1860-pyc; DSS__033; DSS__316; 0007__39-lysA; 0007__39-lpd; opcA__P4; 1860-cg1768; glk; 1860-cg1144; 0007__39-cg2766; 0007__39-cg1383 |
| 174249 | 0007__39-zwf; DSS__084; 1860-pyc; DSS__033; DSS__316; aceE__ATG > TTG; lisa68; opcA__P4; 0007__39-cg2766; 0007__39-actA; 3121-mutM2; 0007__39-cg1383 |
| 175204 | 0007__39-zwf; DSS__084; 1860-pyc; DSS__033; DSS__316; 0007__39-lysA; 0007__39-cg0725; opcA__P4; lisa68; 0007__39-nusG; 1860-xerD; 0007__39-cg1383 |
| 175787 | 0007__39-zwf; DSS__084; 1860-pyc; DSS__033; DSS__316; aceE__ATG > TTG; lisa68; opcA__P4; 0007__39-cg2766; 0007__39-actA; 1860-tkt; 0007__39-cg1383 |
| 175821 | 0007__39-zwf; DSS__084; 1860-pyc; DSS__033; DSS__316; aceE__ATG > TTG; lisa68; opcA__P4; 0007__39-cg2766; 0007__39-actA; 3381-cg1410; 0007__39-cg1383 |
| 176476 | 0007__39-zwf; DSS__084; 1860-pyc; DSS__033; DSS__316; aceE__ATG > TTG; lisa68; opcA__P4; 0007__39-cg2766; 0007__39-actA; 0007-__39-rho; 0007__39-cg1383 |
| 176484 | 0007__39-zwf; DSS__084; 1860-pyc; DSS__033; DSS__316; aceE__ATG > TTG; lisa68; opcA__P4; 0007__39-cg2766; 0007__39-actA; glk__2966; 0007__39-cg1383 |
| 176485 | 0007__39-zwf; DSS__084; 1860-pyc; DSS__033; DSS__316; aceE__ATG > TTG; lisa68; opcA__P4; 0007__39-cg2766; 0007__39-actA; glk__2966; 0007__39-cg1383 |
| 176545 | 0007__39-zwf; DSS__084; 1860-pyc; DSS__033; DSS__316; aceE__ATG > TTG; lisa68; opcA__P4; 0007__39-cg2766; 0007__39-actA; 3121-gltD; 0007__39-cg1503; 0007__39-cg1383 |
| 176546 | 0007__39-zwf; DSS__084; 1860-pyc; DSS__033; DSS__316; aceE__ATG > TTG; lisa68; opcA__P4; 0007__39-cg2766; 0007__39-actA; 3121-gltD; 0007__39-cg1503; 0007__39-cg1383 |
| 180360 | 0007__39-zwf; DSS__084; 1860-pyc; DSS__033; DSS__316; aceE__ATG > TTG; lisa68; opcA__P4; 0007__39-cg2766; 0007__39-actA; glk__2966; 0007__39-phoU; 0007__39-cg1383 |
| 183641 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg800; 0007__39-cg1383 |
| 193331 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800; 0007__39-cg1383 |
| 210851 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU; 0007__39-rpoB; 0007__39-kgd; 0007__39-cg1486; 1860-xerD; 0007__39-cg1383 |
| 101738 | 0007__39-zwf; DSS__084; 1860-pyc; DSS__033; DSS__316; 0007__39-lysA; 0007__39-cg3210 |
| 139570 | 0007__39-zwf; DSS__084; 1860-pyc; DSS__033; DSS__316; 0007__39-lysA; 0007__39-opca__P4; 9: 0007__39-cg3210 |
| 174360 | 0007__39-zwf; DSS__084; 1860-pyc; DSS__033; DSS__316; 0007__39-lysA@ni487; 0007__39-opca__P4; 0007__39-acta; 0007__39-cg2766; 0007__39-cg3210 |
| 279235 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU; 0007__39-cg3210; 0007__39-cg0800; 1860-cg1768; 0007__39-cg3210 |
| 279255 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-0800; 0007__39-cg1486; 1860-NCgl1262; 0007__39-cg3210 |
| 279327 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-0800; 0007__39-cg1486; 0007__39-cg3210 |
| 279352 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU; 0007__39-0800; 0007__39-cg1486; 0007__39-cg3210 |
| 182623 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU; 0007__39-cg3210 |
| 151762 | 0007__39-zwf; DSS__084; 1860-pyc; DSS__033; DSS__316; 0007__39-lysA; 0007__39-lpd; opcA__P4; 0007__39-glf; 0007__39-phoU |
| 151773 | 0007__39-zwf; DSS__084; 1860-pyc; DSS__033; DSS__316; 0007__39-lysA; 0007__39-lpd; opcA__P4; 0007__39-cg2766; 0007__39-phoU |
| 151832 | 0007__39-zwf; DSS__084; 1860-pyc; DSS__033; DSS__316; aceE__ATG > TTG; lisa68; opcA__P4; 0007__39-cg2766; 0007__39-phoU |
| 151913 | 0007__39-zwf; DSS__084; 1860-pyc; DSS__033; DSS__316; 0007__39-lysA; opcA__P4; lisa__68; 0007__39-rpoB-gene-383; 0007__39-phoU |
| 151929 | 0007__39-zwf; DSS__084; 1860-pyc; DSS__033; DSS__316; 0007__39-lysA; 0007__39-cg2766; opcA__P4; 0007__39-phoU |
| 151969 | 0007__39-zwf; DSS__084; 1860-pyc; DSS__033; DSS__316; aceE__ATG > TTG; lisa68; opcA__P4; 0007__39-actA; 0007__39-phoU |
| 151978 | 0007__39-zwf; DSS__084; 1860-pyc; DSS__033; DSS__316; 0007__39-lysA; 0007__39-lpd; opcA__P4; 0007__39-rpoB; lisa__68; 0007__39-phoU |

TABLE 7B-continued

| Genotypes of Modified Strains | |
|---|---|
| Modified Strain | Changes with respect to genome of NRRL B-11474 |
| 152448 | 0007__39-zwf; DSS__084; 1860-pyc; DSS__033; DSS__316; aceE__ATG > TTG; 0007__39-lysA; 0007__39-SCO; 0007__39-phoU |
| 152464 | 0007__39-zwf; DSS__084; 1860-pyc; DSS__033; DSS__316; aceE__ATG > TTG; lisa68; DSS__121; 0007__39-phoU |
| 152480 | 0007__39-zwf; DSS__084; 1860-pyc; DSS__033; DSS__316; 0007__39-lysA; 1860-xerD; 0007__39-phoU |
| 152496 | 0007__39-zwf; DSS__084; 1860-pyc; DSS__033; DSS__316; 0007__39-lysA; 0007__39-lpd; opcA__P4; 0007__39-rpoB; 0007__39-phoU |
| 152592 | 0007__39-zwf; DSS__084; 1860-pyc; DSS__033; DSS__316; 0007__39-lysA; 0007__39-cg0725; opcA__P4; lisa68; 0007__39-phoU |
| 152616 | 0007__39-zwf; DSS__084; 1860-pyc; DSS__033; DSS__316; 0007__39-lysA; 0007__39-lpd; opcA__P4; 0007__39-cg2766; 0007__39-actA; 0007__39-phoU |
| 152628 | 0007__39-zwf; DSS__084; 1860-pyc; DSS__033; DSS__316; 0007__39-lysA; 0007__39-lpd; opcA__P4; 0007__39-cg2766; glk; 0007__39-phoU |
| 152636 | 0007__39-zwf; DSS__084; 1860-pyc; DSS__033; DSS__316; aceE__ATG > TTG; lisa68; opcA__P4; 0007__39-cg2766; glk__2966; 0007__39-phoU |
| 152648 | 0007__39-zwf; DSS__084; 1860-pyc; DSS__033; DSS__316; aceE__ATG > TTG; lisa68; opcA__P4; 0007__39-cg2766; 0007__39-actA; 0007__39-phoU |
| 152672 | 0007__39-zwf; DSS__084; 1860-pyc; DSS__033; DSS__316; aceE__ATG > TTG; 0007__39-lysA; 0007__39-SCO; 0007__39-cg2766; opcA__P4; 0007__39-phoU |
| 155490 | 0007__39-zwf; DSS__084; 1860-pyc; DSS__033; DSS__316; 0007__39-lysA; 0007__39-cg2766; opcA__P4; 0007__39-cg1383; 0007__39-phoU |
| 155510 | 0007__39-zwf; DSS__084; 1860-pyc; DSS__033; DSS__316; 0007__39-lysA; 0007__39-cg2766; opcA__P4; 0007__39-cg1383; 0007__39-phoU |
| 155525 | 0007__39-zwf; DSS__084; 1860-pyc; DSS__033; DSS__316; 0007__39-lysA; opcA__P4; lisa__68; 0007__39-rpoB-gene-383; 0007__39-cg1383; 0007__39-phoU |
| 155545 | 0007__39-zwf; DSS__084; 1860-pyc; DSS__033; DSS__316; aceE__ATG > TTG; lisa68; opcA__P4; 0007__39-actA; 0007__39-cg1383; 0007__39-phoU |
| 162721 | 0007__39-zwf; DSS__084; 1860-pyc; DSS__033; DSS__316; 0007__39-lysA; 0007__39-lpd; opcA__P4; 1860-cg1768; glk; 0007__39-cg0725; 0007__39-phoU |
| 162743 | 0007__39-zwf; DSS__084; 1860-pyc; DSS__033; DSS__316; 0007__39-lysA; opcA__P4; lisa__68; 0007__39-rpoB-gene-383; 0007__39-cg2766; 0007__39-phoU |
| 162789 | 0007__39-zwf; DSS__084; 1860-pyc; DSS__033; DSS__316; aceE__ATG > TTG; lisa68; opcA__P4; 0007__39-cg2766; 0007__39-actA; 3121-gltD; 0007__39-phoU |
| 163154 | 0007__39-zwf; DSS__084; 1860-pyc; DSS__033; DSS__316; aceE__ATG > TTG; lisa68; opcA__P4; 0007__39-cg2766; 0007__39-actA; 3121-gltD; 0007__39-phoU |
| 172143 | 0007__39-zwf; DSS__084; 1860-pyc; DSS__033; DSS__316; aceE__ATG > TTG; 0007__39-lysA; 0007__39-SCO; opcA__P__4; 0007__39-cg0725; 0007__39-aroP; 0007__39-phoU |
| 172151 | 0007__39-zwf; DSS__084; 1860-pyc; DSS__033; DSS__316; 0007__39-lysA; 0007__39-lpd; opcA__P4; 1860-cg1768; glk; 0007__39-cg0725; 0007__39-cg2899; 0007__39-phoU |
| 172199 | 0007__39-zwf; DSS__084; 1860-pyc; DSS__033; DSS__316; aceE__ATG > TTG; lisa68; opcA__P4; 0007__39-cg2766; 0007__39-actA; SCO__Ni2966; 0007__39-phoU |
| 172228 | 0007__39-zwf; DSS__084; 1860-pyc; DSS__033; DSS__316; 0007__39-lysA; 0007__39-lpd; opcA__P4; 0007__39-glf; 0007__39-cg1383; 0007__39-aroP; 0007__39-phoU |
| 174199 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg0725; 0007__39-phoU |
| 174232 | 0007__39-zwf; DSS__084; 1860-pyc; DSS__033; DSS__316; aceE__ATG > TTG; lisa68; opcA__P4; 0007__39-cg2766; 0007__39-actA; glk__2966; 0007__39-phoU |
| 174240 | 0007__39-zwf; DSS__084; 1860-pyc; DSS__033; DSS__316; aceE__ATG > TTG; lisa68; opcA__P4; 0007__39-cg2766; 0007__39-actA; 1860-tkt; 0007__39-phoU |
| 174248 | 0007__39-zwf; DSS__084; 1860-pyc; DSS__033; DSS__316; aceE__ATG > TTG; lisa68; opcA__P4; 0007__39-cg2766; 0007__39-actA; 3121-mutM2; 0007__39-phoU |
| 174264 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU |
| 174281 | 0007__39-zwf; DSS__084; 1860-pyc; DSS__033; DSS__316; aceE__ATG > TTG; lisa68; opcA__P4; 0007__39-actA; 0007__39-cg1383; Pcg0007-amtB; 0007__39-phoU |
| 175029 | 0007__39-zwf; DSS__084; 1860-pyc; DSS__033; DSS__316; aceE__ATG > TTG; lisa68; opcA__P4; 0007__39-cg2766; 0007__39-actA; 0007-__39-rho; 0007__39-phoU |
| 175046 | 0007__39-zwf; DSS__084; 1860-pyc; DSS__033; DSS__316; aceE__ATG > TTG; lisa68; opcA__P4; 0007__39-cg2766; 0007__39-actA; glk__2966; 0007__39-phoU |
| 175062 | 0007__39-zwf; DSS__084; 1860-pyc; DSS__033; DSS__316; aceE__ATG > TTG; lisa68; opcA__P4; 0007__39-cg2766; 0007__39-actA; 1860-tkt; 0007__39-phoU |
| 175086 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU |
| 175102 | 0007__39-zwf; DSS__084; 1860-pyc; DSS__033; DSS__316; aceE__ATG > TTG; lisa68; opcA__P4; 0007__39-actA; 0007__39-cg1383; Pcg0007-amtB; 0007__39-phoU |
| 175165 | 0007__39-zwf; DSS__084; 1860-pyc; DSS__033; DSS__316; aceE__ATG > TTG; lisa68; opcA__P4; 0007__39-actA; 0007__39-cg1383; 3121-prpB28; 0007__39-phoU |
| 175181 | 0007__39-zwf; DSS__084; 1860-pyc; DSS__033; DSS__316; 0007__39-lysA; 0007__39-lpd; opcA__P4; 1860-cg1768; glk; 0007__39-cg0725; 0007__39-cg2766; 0007__39-phoU |
| 175183 | 0007__39-zwf; DSS__084; 1860-pyc; DSS__033; DSS__316; 0007__39-lysA; 0007__39-cg0725; opcA__P4; lisa68; 0007__39-actA; 0007__39-nusG; 0007__39-phoU |
| 175184 | 0007__39-zwf; DSS__084; 1860-pyc; DSS__033; DSS__316; 0007__39-lysA; 0007__39-cg0725; opcA__P4; lisa68; 0007__39-actA; 0007__39-nusG; 0007__39-phoU |

TABLE 7B-continued

Genotypes of Modified Strains

| Modified Strain | Changes with respect to genome of NRRL B-11474 |
|---|---|
| 175200 | 0007__39-zwf; DSS__084; 1860-pyc; DSS__033; DSS__316; 0007__39-lysA; 0007__39-cg0725; opcA__P4; lisa68; 0007__39-nusG; 1860-xerD; 0007__39-phoU |
| 175816 | 0007__39-zwf; DSS__084; 1860-pyc; DSS__033; DSS__316; aceE__ATG > TTG; lisa68; opcA__P4; 0007__39-cg2766; 0007__39-actA; 3381-cg1410; 0007__39-phoU |
| 176509 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU |
| 176542 | 0007__39-zwf; DSS__084; 1860-pyc; DSS__033; DSS__316; aceE__ATG > TTG; lisa68; opcA__P4; 0007__39-cg2766; 0007__39-actA; 3121-gltD; 0007__39-cg1503; 0007__39-phoU |
| 183629 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-phoU |
| 186920 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg0800; 0007__39-phoU |
| 187910 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-rpoB; 0007__39-cg0800; 0007__39-phoU |
| 187918 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-kgd; 0007__39-cg0800; 0007__39-phoU |
| 187926 | 0007__39-zwf; DSS__084; 1860-pyc; DSS__033; DSS__316; aceE__ATG > TTG; lisa68; opcA__P4; 0007__39-actA; 0007__39-cg1383; Pcg0007-amtB; 0007__39-kgd; 0007__39-cg0800; 0007__39-phoU |
| 187934 | 0007__39-zwf; DSS__084; 1860-pyc; DSS__033; DSS__316; aceE__ATG > TTG; lisa68; opcA__P4; 0007__39-cg2766; 0007__39-actA; glk__2966; 3121-cg1081; 0007__39-cg0800; 0007__39-phoU |
| 187942 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-phoU;0007__39-cg0800; 0007__39-phoU |
| 187990 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800; 0007__39-phoU |
| 188149 | 0007__39-zwf; DSS__084; 1860-pyc; DSS__033; DSS__316; 0007__39-lysA; 0007__39-lpd; opcA__P4; 0007__39-glf; 0007__39-cg1383; 0007__39-aroP; 0007__39-kgd; 0007__39-phoU |
| 188159 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-kgd; 0007__39-phoU |
| 190101 | 0007__39-zwf; DSS__084; 1860-pyc; DSS__033; DSS__316; aceE__ATG > TTG; lisa68; opcA__P4; 0007__39-cg2766; 0007__39-actA; 0007__39-cg800; 0007__39-cg2899; 0007__39-phoU |
| 193273 | 0007__39-zwf; DSS__084; 1860-pyc; DSS__033; DSS__316; 0007__39-lysA; 0007__39-lpd; opcA__P4; 0007__39-glf; 0007__39-cg1383; 0007__39-aroP; 0007__39-kgd; 0007__39-phoU |
| 193289 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-rpoB; 0007__39-cg0800; 0007__39-phoU |
| 193293 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-rpoB; 0007__39-cg0800; 0007__39-phoU |
| 196697 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-phoU |
| 197877 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-rpoB; 0007__39-cg0800; 0007__39-cg1486; 0007__39-phoU |
| 197885 | 0007__39-zwf; DSS__084; 1860-pyc; DSS__033; DSS__316; aceE__ATG > TTG; lisa68; opcA__P4; 0007__39-cg2766; 0007__39-actA; glk__2966; 3121-cg1081; 0007__39-cg0800; 0007__39-ncgl1511; 0007__39-phoU |
| 197954 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800; 0007__39-Ncgl0304; 0007__39-phoU |
| 201612 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800; 0007__39-cg1486; 0007__39-phoU |
| 201628 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800; 0755-dapA; 0007__39-phoU |
| 201644 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800; 0007__39-Ncgl0767; 0007__39-phoU |
| 201660 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800; 0007__39-NCgl1262; 0007__39-phoU |
| 201676 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-rpoB; 0007__39-cg0800; 0007__39-NCgl1262; 0007__39-phoU |
| 206820 | 0007__39-zwf; DSS__084; 1860-pyc; DSS__033; DSS__316; aceE__ATG > TTG; lisa68; opcA__P4; 0007__39-actA; 0007__39-cg1383; 0007__39-cg2766; 0007__39-ureR; 0007__39-cg0800; 0007__39-NCgl1262; 0007__39-phoU |

TABLE 7B-continued

| Genotypes of Modified Strains | |
|---|---|
| Modified Strain | Changes with respect to genome of NRRL B-11474 |
| 206860 | 0007_39-zwf; DSS_084; 1860-pyc; DSS_033; DSS_316; aceE_ATG > TTG; lisa68; opcA_P4; 0007_39-actA; 0007_39-cg1383; 0007_39-cg2766; 0007_39-ureR; 0007_39-cg0800; 0755-dapA; 0007_39-phoU |
| 212930 | 0007_39-zwf; DSS_084; 1860-pyc; DSS_033; DSS_316; aceE_ATG > TTG; lisa68; opcA_P4; 0007_39-actA; 0007_39-cg1383; 0007_39-cg2766; 0007_39-rpoB; 0007_39-cg0800; 0007_39-cg1486; 0007_39-glpX; 0007_39-phoU |
| 212954 | 0007_39-zwf; DSS_084; 1860-pyc; DSS_033; DSS_316; aceE_ATG > TTG; lisa68; opcA_P4; 0007_39-actA; 0007_39-cg1383; 0007_39-cg2766; 0007_39-phoU; 0007_39-cg1486; 0007_39-cg0800; 0007_39-phoU |

TABLE 8

| Sequence Listing | |
|---|---|
| SEQ ID NO: | sequence |
| 1 | *C. glutamicum* NRRL B-11474, RnaJ homology region |
| 2 | coding sequence for altered RnaJ protein |
| 3 | altered RnaJ protein |
| 4 | *C. glutamicum* NRRL B-11474, accDA homology region |
| 5 | coding sequence for altered accDA protein |
| 6 | altered accDA protein |
| 7 | *C. glutamicum* NRRL B-11474, cg1144 homology region |
| 8 | coding sequence for altered cg1144 protein |
| 9 | altered cg1144 protein |
| 10 | *C. glutamicum* NRRL B-11474, pyc homology region |
| 11 | promoter 1860 |
| 12 | promoter 1860 and pyc coding sequence |
| 13 | *C. glutamicum* NRRL B-11474, aceE homology region |
| 14 | altered aceE coding sequence |
| 15 | *C. glutamicum* NRRL B-11474, lysA insertion homology region |
| 16 | codon-optimized lysA coding sequence |
| 17 | promoter cg0007_39-codon-optimized lysA coding sequence-sod terminator |
| 18 | *C. glutamicum* NRRL B-11474, lysA |
| 19 | *C. glutamicum* NRRL B-11474 zwf homology region |
| 20 | Promoter cg0007_39 |
| 21 | Promoter cg0007_39 insertion and zwf coding region |
| 22 | *C. glutamicum* NRRL B-11474, opcA homology region |
| 23 | *C. humireducens* opcA coding sequence |
| 24 | promoter cg0007_39-C. humireducense opcA coding sequence |
| 25 | *C. humireducens* opcA protein |
| 26 | *C. glutamicum* NRRL B-11474, cg2766 homology region |
| 27 | Promoter cg0007_39-cg2766 |
| 28 | *C. glutamicum* NRRL B-11474, actA homology region |
| 29 | promoter cg0007_39-actA |
| 30 | primer FarI 3p InfusF |
| 31 | primer FarI 3p InfusR AvrII |
| 32 | primer FarI 5p InfusF |
| 33 | primer FarI 5p Infus R |
| 34 | primer Pcg0007_39-zwf_P1 |
| 35 | primer Pcg0007_39-zwf_P2 |
| 36 | primer Pcg0007_39-zwf_P3 |
| 37 | primer Pcg0007_39-zwf_P4 |
| 38 | primer SNP_084_P1 |
| 39 | primer SNP_084_P2 |
| 40 | primer SNP_084_P3 |
| 41 | primer SNP_084_P4 |
| 42 | primer Pcg1860_pyc_P1 |
| 43 | primer Pcg1860_pyc_P2 |
| 44 | primer Pcg1860_pyc_P3 |
| 45 | primer Pcg1860_pyc_P4 |
| 46 | primer SNP_033_P1 |
| 47 | primer SNP_033_P2 |
| 48 | primer SNP_033_P3 |
| 49 | primer SNP_033_P4 |
| 50 | primer SNP_316_P1 |
| 51 | primer SNP_316_P2 |
| 52 | primer SNP_316_P3 |
| 53 | primer SNP_316_P4 |
| 54 | primer SCS_aceE_P1 |
| 55 | primer SCS_aceE_P2 |

TABLE 8-continued

| Sequence Listing | |
|---|---|
| SEQ ID NO: | sequence |
| 56 | primer SCS_aceE_P3 |
| 57 | primer SCS_aceE_P4 |
| 58 | primer opcA_P1 |
| 59 | primer opcA_P2 |
| 60 | primer opcA_P3 |
| 61 | primer opcA_P4 |
| 62 | primer pcg0007_39-cg2766_p1 |
| 63 | primer pcg0007_39-cg2766_P2 |
| 64 | primer pcg0007_39-cg2766_P3 |
| 65 | primer pcg0007_39-cg2766_P4 |
| 66 | primer pcg0007_39-actA_P1 |
| 67 | primer pcg0007_39-actA_P2 |
| 68 | primer pcg0007_39-actA_P3 |
| 69 | primer pcg0007_39-actA_P4 |
| 70 | primer 184f7 |
| 71 | primer 184F8 |
| 72 | primer 244-4Go F2 Inf SpeI |
| 73 | primer 253-4Go R3 |
| 74 | primer 685 |
| 75 | primer 686 |
| 76 | primer 687 |
| 77 | primer 693 |
| 78 | *C. glutamicum* RnaJ protein |
| 79 | *C. glutamicum* RnaJ protein |
| 80 | *C. ulcerans* RnaJ protein |
| 81 | *C. glutamicum* accDA protein |
| 82 | *C. glutamicum* MB001 accDA protein |
| 83 | *C. crudilactis* accDA protein |
| 84 | *C. glutamicum* cg1144 protein |
| 85 | *C. crudilactis* cg1144 protein |
| 86 | *C. efficiens* YS-314cg1144 protein |
| 87 | *C. vitaeruminis* DSM 20294 opcA protein |
| 88 | *C. matruchotii* ATCC 33806 opcA protein |
| 89 | *C. falsenii* DSM 44353 opcA protein |
| 90 | *C. halotolerans* YIM 70093 = DSM 44683 opcA protein |
| 91 | *C. pyruviciproducens* ATCC BAA-1742 opcA protein |
| 92 | *C. casei* UCMA 3821 opcA protein |
| 93 | *C. terpenotabidum* Y-11 opcA protein |
| 94 | *C. glutamicum* NRRL B-11474 opcA protein |
| 95 | promoter 3121 |
| 96 | promoter 0755 |
| 97 | promoter 3381 |
| 98 | *C. glutamicum* cg1383 homology region |
| 99 | primer Pcg0007_39-cg1383_P1 |
| 100 | primer Pcg0007_39-cg1383_P2 |
| 101 | primer Pcg0007_39-cg1383_P3 |
| 102 | primer Pcg0007_39-cg1383_P4 |
| 103 | Pcg0007_39 promoter inserted in front of cg1383 start codon |
| 104 | *C. glutamicum* phoU homology region |
| 105 | primer Pcg0007_39-phoU_P1 |
| 106 | primer Pcg0007_39-phoU_P2 |
| 107 | primer Pcg0007_39-phoU_P3 |
| 108 | primer Pcg0007_39-phoU_P4 |
| 109 | Pcg0007_39 promoter in front of phoU start codon |
| 110 | *C. glutamicum* cg3210 homology region |
| 111 | Pcg0007_39-cg3210-p1 |
| 112 | Pcg0007_39-cg3210-p2 |
| 113 | Pcg0007_39-cg3210-p3 |
| 114 | Pcg0007_39-cg3210-p4 |
| 115 | Pcg0007_39 in front of cg3210 |
| 116 | *C. glutamicum* cg0800 homology region |
| 117 | Pcg0007_39-cg0800-p1 |
| 118 | Pcg0007_39-cg0800-p2 |
| 119 | Pcg0007_39-cg0800-p3 |
| 120 | Pcg0007_39-cg0800-p4 |
| 121 | Pcg0007_39 in front of cg0800 |

REFERENCES

Becker et al., "Systems level engineering of *Corynebacterium glutamicum*—Reprogramming translational efficiency for superior production," Engineering in Life Sciences 10, 430-38, 2010

Buchholz et al., "Platform Engineering of *Corynebacterium glutamicum* with Reduced Pyruvate Dehydrogenase Complex Activity for Improved Production of 1-Lysine, 1-Valine, and 2-Ketoisovalerate," Applied Env. Microbiol. 79, 5566-75, 2013

Knoppová et al., Curr. Microbiol. 55, 234-39, 2007

Lee, J Microbiol Biotechnol. 2014 January; 24(1):70-9

Nešvera et al., Subcell. Biochem. 2012; 64:203-21

Pátek & Nešvera, "Promoters and Plasmid Vectors of *Corynebacterium glutamicum*," in *Corynebacterium glutamicum*, Yukawa & Inui, eds., Springer-Verlag, Berlin 2013, pp. 51-88

Pátek et al., J. Biotechnol. 104, 311-23, 2003(a)

Pátek et al., J. Biotechnol. 104, 325-34, 2003(b)

Pátek et al., Microb. Biotechnol. 2013 March; 6(2):103-17

Pfeifer-Sancar et al., BMC Genomics 14, 888, 2013

Rytter et al., Appl. Microbiol Biotechnol. 2014 March; 98(6):2617-23

Shang et al., Biotechnol. Lett. 2017 Nov. 21. doi: 10.1007/s10529-017-2479-y

Yim et al., Biotechnol. Bioeng. 2013 November; 110(11): 2959-69

The invention claimed is:

1. A *Corynebacterium* having a bacterial genome consisting essentially of the genome of the bacterium deposited as NRRL B-67439 but for structural alterations:

(a) insertion of a promoter in front of the cg1383 start codon;

(b) replacement of the native phoU promoter;

(c) replacement of the native cg3210 promoter; and (d) replacement of the native cg0800 promoter.

2. A method of producing lysine, comprising:

(a) culturing a Corynebacterium; and (b) recovering lysine produced by the Corynebacterium, wherein the Corynebacterium is a Corynebacterium having a bacterial genome consisting essentially of the genome of the bacterium deposited as NRRL B-67439 but for structural alterations:

(1) insertion of a promoter in front of the cg1383 start codon;

(2) replacement of the native phoU promoter;

(3) replacement of the native cg3210 promoter; and (4) replacement of the native cg0800 promoter.

3. The method of claim 2, wherein the Corynebacterium has the bacterial genome consisting essentially of the genome of the bacterium deposited as NRRL B-67439 but for the 4 structural alterations.

4. The Corynebacterium of claim 1, wherein the promoter in front of the cg1383 start codon is promoter Pcg0007_30 (SEQ ID NO:20).

* * * * *